US012480051B2

(12) United States Patent
Motooka et al.

(10) Patent No.: US 12,480,051 B2
(45) Date of Patent: *Nov. 25, 2025

(54) POLYMERIZABLE LIQUID CRYSTAL COMPOUND, POLYMERIZABLE COMPOSITION, POLYMER, RETARDATION FILM, METHOD FOR PRODUCING RETARDATION FILM, TRANSFER LAMINATE, OPTICAL MEMBER, METHOD FOR PRODUCING OPTICAL MEMBER, AND DISPLAY DEVICE

(71) Applicant: DAI NIPPON PRINTING CO., LTD., Tokyo-to (JP)

(72) Inventors: Mami Motooka, Tokyo-to (JP); Ken-ichi Okuyama, Tokyo-to (JP); Kazuyuki Okada, Tokyo-to (JP); Terutaka Takahashi, Tokyo-to (JP); Mitsuru Endo, Tokyo-to (JP); Shunsuke Irie, Tokyo-to (JP); Tsuyoshi Sakaguchi, Tokyo-to (JP); Kei Akiyama, Tokyo-to (JP); Kohei Ishikawa, Tokyo-to (JP)

(73) Assignee: DAI NIPPON PRINTING CO., LTD., Tokyo (JP)

( * ) Notice: Subject to any disclaimer, the term of this patent is extended or adjusted under 35 U.S.C. 154(b) by 449 days.

This patent is subject to a terminal disclaimer.

(21) Appl. No.: 18/080,812

(22) Filed: Dec. 14, 2022

(65) Prior Publication Data

US 2023/0137250 A1 May 4, 2023

Related U.S. Application Data

(63) Continuation of application No. 16/754,870, filed as application No. PCT/JP2018/037765 on Oct. 10, 2018, now Pat. No. 11,560,518.

(30) Foreign Application Priority Data

Oct. 13, 2017 (JP) ................................ 2017-199651
Jun. 15, 2018 (JP) ................................ 2018-114613

(51) Int. Cl.

| | |
|---|---|
| ***C09K 19/38*** | (2006.01) |
| ***C07D 263/58*** | (2006.01) |
| ***C07D 277/82*** | (2006.01) |
| ***C07D 417/14*** | (2006.01) |
| ***C07D 519/00*** | (2006.01) |
| ***C08F 22/24*** | (2006.01) |
| ***G02B 5/30*** | (2006.01) |

(52) U.S. Cl.

CPC ........ *C09K 19/3861* (2013.01); *C07D 263/58* (2013.01); *C07D 277/82* (2013.01); *C07D 417/14* (2013.01); *C07D 519/00* (2013.01); *C08F 22/24* (2013.01); *G02B 5/3016* (2013.01); *G02B 5/3083* (2013.01)

(58) Field of Classification Search

CPC .. C07D 263/58; C07D 277/68; C07D 277/82; C07D 417/14; C07D 513/04; C07D 519/00; C09K 2019/0448; C08F 2/48; G02F 1/13; G02F 1/13363; G02B 5/3083; G02B 5/3016

See application file for complete search history.

(56) References Cited

U.S. PATENT DOCUMENTS

| | | | | |
|---|---|---|---|---|
| 11,560,518 | B2 * | 1/2023 | Motooka | C07D 263/58 |
| 2015/0175564 | A1 | 6/2015 | Sakamoto et al. | |
| 2015/0274647 | A1 | 10/2015 | Sakamoto et al. | |
| 2017/0369783 | A1 | 12/2017 | Horiguchi et al. | |
| 2018/0022716 | A1 | 1/2018 | Horiguchi et al. | |
| 2019/0322936 | A1 | 10/2019 | Sakamoto et al. | |

FOREIGN PATENT DOCUMENTS

| | | | |
|---|---|---|---|
| JP | H10-068816 | A | 3/1998 |
| JP | 2001-004837 | A | 1/2001 |
| JP | 4186981 | B2 | 11/2008 |
| JP | 2010-522893 | A | 7/2010 |
| JP | 5463666 | B2 | 4/2014 |
| JP | 5826759 | B2 | 12/2015 |
| JP | 2016/136533 | A | 7/2016 |
| JP | 5962760 | B2 | 8/2016 |
| WO | 2008/119427 | A1 | 10/2008 |
| WO | 2011/050896 | A1 | 5/2011 |
| WO | 2014/061709 | A1 | 4/2014 |
| WO | 2016/104317 | A1 | 6/2016 |
| WO | 2016/136533 | A | 9/2016 |

OTHER PUBLICATIONS

Lub et al.; The synthesis of liquid-crystalline diacrylates derived from cyclohexane units; Recueil des Travaux Chimiques des Pays-Bas; 1996; pp. 321-328; vol. 115, No. 6.
May 2, 2022 Office Action issued in U.S. Appl. No. 16/754,870.
Sep. 19, 2022 Notice of Allowance issued in U.S. Appl. No. 16/754,870.

* cited by examiner

*Primary Examiner* — Valerie Rodriguez-Garcia
(74) *Attorney, Agent, or Firm* — Oliff PLC

(57) ABSTRACT

A polymerizable liquid crystal compound represented by the following general formula (1):

General Formula (1)

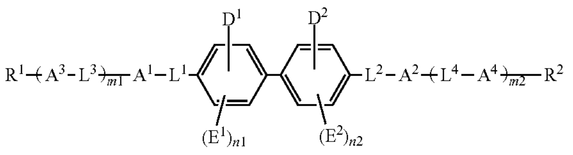

(the symbols in the general formula (1) are as described in the DESCRIPTION.)

13 Claims, 2 Drawing Sheets

POLYMERIZABLE LIQUID CRYSTAL COMPOUND, POLYMERIZABLE COMPOSITION, POLYMER, RETARDATION FILM, METHOD FOR PRODUCING RETARDATION FILM, TRANSFER LAMINATE, OPTICAL MEMBER, METHOD FOR PRODUCING OPTICAL MEMBER, AND DISPLAY DEVICE

CROSS-REFERENCE TO RELATED APPLICATIONS

This is a Continuation of application Ser. No. 16/754,870 filed Apr. 9, 2020, which in turn is a national stage entry of PCT/JP2018/037765 filed Oct. 10, 2018, which claims priority to JP 2018-114613 filed Jun. 15, 2018, and JP 2017-199651 filed Oct. 13, 2017. The disclosure of the prior applications is hereby incorporated by reference herein in its entirety.

TECHNICAL FIELD

The present disclosure relates to a polymerizable liquid crystal compound, a polymerizable composition, a polymer, a retardation film, a method for producing the retardation film, a transfer laminate, an optical member, a method for producing the optical member, and a display device.

BACKGROUND ART

Hitherto, about display devices such as a liquid crystal display device and a light emitting display device, a structure has been suggested in which optical members such as a retardation film and a polarizing plate are arranged onto their panel plane.

For example, in a light emitting display device such as an organic light emitting display device, a metallic electrode excellent in reflectivity is fitted thereto in order to use light from its light emitting layer effectively. In the meantime, the use of the metallic electrode makes the reflection of external light large. Thus, to restrain the external light reflection, the light emitting display device is known to use a circularly polarizing plate on its viewing side, the plate containing a quarter wavelength plate serving to convert linearly polarized light into circularly polarized light, and a polarizer.

In addition to the quarter wavelength plate, examples of retardation films include a half-wavelength plate that converts the polarization vibration plane of a linearly polarized light by 90° and the like. These retardation films can correctly convert a specific monochromatic light into a retardation of ¼λ or ½λ of the light wavelength. However, retardation films in the prior have a problem in that a polarized light emitted therethrough is converted into a colored polarized light. This is because materials constituting the retardation films have wavelength dispersion property with respect to retardation and a distribution occurs in the polarized state of each wavelength for white light in which light in the visible region is mixed. To prevent this problem, it is needed to control wavelength dispersion property to give a retardation designed for each wavelength, and there is a demand for a wide-bandwidth retardation film that can give a uniform retardation for light in a wide wavelength range, that is, a retardation film with reverse wavelength dispersion property.

A retardation film is produced by stretching a film or by applying a polymerizable composition containing a liquid crystal compound onto a support subjected to an alignment treatment, drying the solvent to align the liquid crystal compound, and then polymerizing the compound by ultraviolet rays or heat.

To produce the retardation film with reverse wavelength dispersion property, for example, a method for producing the retardation film by laminating two retardation layers at different angles in the alignment axis direction, were proposed (Patent Literatures 1 and 2). However, such a laminate has a problem in that it needs two retardation layers and the production is complicated when laminating the two retardation layers, and the thickness of the retardation film is large.

With the advancement and spread of mobile information terminals, there is an increasing demand for a thin display device. As a result, there is also a demand for a thin retardation film, which is a component of the display device.

Accordingly, the development of a liquid crystal compound with reverse wavelength dispersion property is underway, which has a property that enables the wavelength dispersion property of a birefringence index (Δn) to be small or reverse, such that a retardation layer with reverse wavelength dispersion property can be composed of one layer (for example, Patent Literatures 3 and 4). When the slope of a graph having the wavelength λ of incident light on the retardation film on the horizontal axis and its birefringence index (Δn=refractive index $n_e$ for extraordinary light-refractive index $n_0$ for ordinary light) on the vertical axis, is positive (upward-sloping), it is generally said that the wavelength dispersion of its birefringence index is reverse, or the liquid crystal compound serving as a material constituting the retardation film has reverse wavelength dispersion property.

However, for example, liquid crystal compounds with reverse wavelength dispersion property in the prior art, such as the compounds disclosed in Patent Literatures 3 and 4, have a small birefringence index (Δn) and a large film thickness is needed to obtain a desired retardation (Re (λ)=birefringence index Δn (λ)×film thickness d).

Also, for example, in a quarter wavelength plate, if ideal reverse wavelength dispersion property is obtained, light of all wavelengths in the visible region can be converted into circularly polarized light, and perfect antireflection of outside light is possible. However, since the reverse wavelength dispersion property of liquid crystal compounds with reverse wavelength dispersion property in the prior art is insufficient, it is needed to get closer to ideal reverse wavelength dispersion property.

As a polymerizable compound that has a practical low melting point, exhibits excellent solubility in a general-purpose solvent, and can produce an optical film that achieves uniform conversion of polarized light over a wide wavelength range, Patent Literature 5 discloses a structure in which one tetravalent benzene ring group in the main chain of a compound has two side chains. The polymerizable compound itself of Patent Literature 5 is shown to have no liquid crystallinity (Table 1 in Patent Literature 5). It is shown that an optical film with reverse wavelength dispersion property is obtained by mixing the polymerizable compound of Patent Literature 5 with a liquid crystal compound with reverse wavelength dispersion property in the prior art; however, the reverse wavelength dispersion property of the optical film is far from ideal reverse wavelength dispersion property.

As a polymerizable compound having high storage stability without crystal precipitation when added to a polymerizable composition, Patent Literature 6 discloses a polymerizable compound in which one trivalent benzene ring group M of the main chain of the compound has one side chain, and of two substituent groups in the main chain direction of the trivalent benzene ring group M, one substituent group has one ring structure, and the other substituent group has two ring structures.

As the polymerizable compound having high storage stability without crystal precipitation when added to a polymerizable composition, Patent Literature 7 discloses the same compound as Patent Literature 6 and the same structure as Patent Literature 5 in which one tetravalent benzene ring group in the main chain of the compound has two side chains.

Patent Literatures 6 and 7 merely show that no crystal precipitation occurs and high storage stability is obtained when the polymerizable compound is added to the polymerizable composition, and that discoloration and removal from a substrate are less likely to occur when an optical film is produced by adding the polymerizable compound to a base liquid crystal.

CITATION LIST

Patent Literature 1: Japanese Patent Application Laid-Open (JP-A) No. H10-68816

Patent Literature 2: JP-A No. 2001-4837

Patent Literature 3: Japanese translation of PCT International Application No. 2010-522893

Patent Literature 4: Patent No. JP5962760

Patent Literature 5: International Publication No. WO2014/061709

Patent Literature 6: International Publication No. WO2016/136533

Patent Literature 7: International Publication No. WO2016/104317

SUMMARY OF INVENTION

Technical Problem

In light of the above circumstances, an object of embodiments in the present disclosure is to provide a polymerizable liquid crystal compound with a large birefringence index ($\Delta n$) and reverse wavelength dispersion property; a polymerizable composition containing the polymerizable liquid crystal compound; a polymer obtained by polymerizing the polymerizable liquid crystal compound or the polymerizable composition; a retardation film containing a retardation layer that contains a cured product of the polymerizable composition; a method for producing the retardation film; a transfer laminate configured to transfer the retardation layer; an optical member containing the retardation film; a method for producing the optical member; and a display device.

Solution to Problem

One embodiment in the present disclosure provides a polymerizable liquid crystal compound represented by the following general formula (1):

General Formula (1)

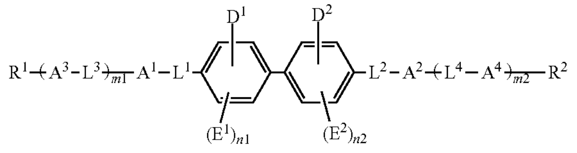

where $L^1$, $L^2$, $L^3$ and $L^4$ each independently represent —O—, —S—, —$OCH_2$—, —$CH_2O$—, —$CH_2CH_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —$SCH_2$—, —$CH_2S$—, —$CF_2O$—, —$OCF_2$—, —$CF_2S$—, —$SCF_2$—, —CH═CH—COO—, —CH═CH—OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH═CH—, —N═N—, —CH═N—, —N═CH—, —CH═N—N═CH—, —CF═CF—, —C≡C— or a single bond;

$A^1$ and $A^2$ each independently represent a divalent alicyclic hydrocarbon group containing 3 to 20 carbon atoms and optionally being unsubstituted or substituted by at least one substituent group E, and any carbon atom of the alicyclic hydrocarbon group is optionally substituted by a heteroatom;

$A^3$ and $A^4$ each independently represent a divalent alicyclic or aromatic hydrocarbon group containing 3 to 20 carbon atoms and optionally being unsubstituted or substituted by at least one substituent group E, and any carbon atom of the alicyclic or aromatic hydrocarbon group is optionally substituted by a heteroatom;

$R^1$ and $R^2$ each independently represent a group selected from the following general formula (R-1):

$-L^5-R^{sp1}—Z^1$ General formula (R-1):

where $L^5$ represents —O—, —S—, —$OCH_2$—, —$CH_2O$—, —$CH_2CH_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —$SCH_2$—, —$CH_2S$—, —$CF_2O$—, —$OCF_2$—, —$CF_2S$—, —$SCF_2$—, —CH═CH—COO—, —CH═CH—OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH═CH—, —N═N—, —CH═N—, —N═CH—, —CH═N—N═CH—, —CF═CF—, —C≡C— or a single bond; $R^{sp1}$ represents a single bond or an alkylene group containing 1 to 20 carbon atoms, in which one —$CH_2$— or two or more non-adjacent —$CH_2$— are each independently optionally substituted by —O—, —COO—, —OCO—, —OCO—O—, —CO—NH—, —NH—CO—, —CH═CH— or —C≡C—; and $Z^1$ represents a polymerizable functional group;

$D^1$ and $D^2$ each independently represent a group selected from the following general formula (D-1);

the substituent groups E, $E^1$ and $E^2$ each independently represent a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group containing 1 to 20 carbon atoms, in which one —$CH_2$— or two or more non-adjacent —$CH_2$— are each independently optionally substituted by —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF— or —C≡C—, and any hydrogen atom in the alkyl group is optionally substituted by a fluorine atom, or the substituent groups E, $E^1$ and $E^2$ each independently represent a group represented by $-L^E-R^{spE}—Z^E$ where $L^E$, $R^{spE}$ and $Z^E$ represent the same as those defined above as $L^5$, $R^{sp1}$ and $Z^1$, respectively, and $L^E$, $R^{spE}$ and $Z^E$ are optionally the same as or different from $L^5$, $R^{sp1}$ and $Z^1$, respectively; and when plural substituent groups Es, as well as plural substituent groups $E^1$s and plural substituent groups $E^2$s, are present in the compound, they are optionally the same or different from each other;

when plural $L^3$s, as well as plural $L^4$s, plural $A^3$s and plural $A^4$s, are present, they are optionally the same or different from each other;

m1 and m2 each independently represent an integer of 1 to 4; and n1 and n2 each independently represent an integer of from 0 to 3, General Formula (D-1)

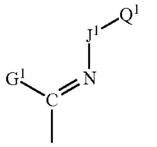

where $G^1$ represents a hydrogen atom or an alkyl group containing 1 to 6 carbon atoms, and the alkyl group is optionally unsubstituted or substituted by at least one substituent group E;

$Q^1$ represents an organic group containing 2 to 30 carbon atoms and an aromatic hydrocarbon group; any carbon atom of the aromatic hydrocarbon group is optionally substituted by a heteroatom; and the aromatic hydrocarbon group is optionally unsubstituted or substituted by at least one substituent group E;

$J^1$ represents —O—, —S—, —COO—, —OCO—, —OCO—O—, $—NQ^2-$, $—N═CQ^2-$, $—CO—NQ^2-$, $—OCO—NQ^2-$ or $—O—NQ^2-$; $Q^2$ represents a hydrogen atom, an alkyl group containing 1 to 20 carbon atoms, a cycloalkyl group containing 3 to 12 carbon atoms, a cycloalkenyl group containing 3 to 12 carbon atoms, an organic group containing 2 to 30 carbon atoms and an aromatic hydrocarbon group (any carbon atom of the aromatic hydrocarbon group is optionally substituted by a heteroatom) or $-(L^6-A^5)_q-L^7-R^{sp2}—Z^2$; the alkyl group, the cycloalkyl group, the cycloalkenyl group and the aromatic hydrocarbon group are each optionally unsubstituted or substituted by at least one substituent group E; the alkyl group is optionally substituted by the cycloalkyl group or the cycloalkenyl group; one $—CH_2—$ or two or more non-adjacent $—CH_2—$ in the alkyl group are each independently optionally substituted by —O—, —S—, —CO—, —COO—, —OCO—, —CO—S—, —S—CO—, $—SO_2—$, —O—CO—O—, —CO—NH—, —NH—CO—, —CH═CH—COO—, —CH═CH—OCO—, —COO—CH═CH—, —OCO—CH═CH—, —CH═CH—, —CF═CF— or —C≡C—; one $—CH_2—$ or two or more non-adjacent $—CH_2—$ in the cycloalkyl or cycloalkenyl group are each independently optionally substituted by —O—, —CO—, —COO—, —OCO— or —O—CO—O—; $L^6$, $A^5$, $L^7$, $R^{sp2}$ and $Z^2$ represent the same as those defined above as $L^1$ to $L^4$, $A^1$ to $A^4$, $L^5$, $R^{sp1}$ and $Z^1$, respectively, and $L^6$, $A^5$, $L^7$, $R^{sp2}$ and $Z^2$ are optionally the same as or different from $L^1$ to $L^4$, $A^l$ to $A^4$, $L^5$, $R^{sp1}$ and $Z^1$, respectively; q is an integer of 0 to 4; when plural $L^6$s, as well as plural $A^5$s, are present, they are optionally the same or different from each other; and $Q^1$ and $Q^2$ are optionally bound to each other to form a ring.

One embodiment in the present disclosure provides a polymerizable composition containing the polymerizable liquid crystal compound in one embodiment in the present disclosure.

One embodiment in the present disclosure provides a polymerizable composition containing the polymerizable liquid crystal compound in one embodiment in the present disclosure and, in addition, a polymerizable liquid crystal compound which is different from the polymerizable liquid crystal compound.

One embodiment in the present disclosure provides a polymer obtained by polymerizing the polymerizable liquid crystal compound in one embodiment in the present disclosure or the polymerizable composition in one embodiment in the present disclosure.

One embodiment in the present disclosure provides a retardation film containing a retardation layer, wherein the retardation layer contains a cured product of the polymerizable composition in one embodiment in the present disclosure.

One embodiment in the present disclosure provides a method for producing a retardation film, including a step of forming a retardation layer by:

a step of forming, into a film, the polymerizable composition in one embodiment in the present disclosure, a step of aligning at least the polymerizable compound in the polymerizable composition formed into the film, and a step of polymerizing at least the polymerizable compound after the aligning step.

One embodiment in the present disclosure provides a transfer laminate configured to transfer a retardation layer, wherein the transfer laminate contains a retardation layer and a support supporting the retardation layer in a removable manner, and wherein the retardation layer contains a cured product of the polymerizable composition in one embodiment in the present disclosure.

One embodiment in the present disclosure provides an optical member containing the retardation film in one embodiment in the present disclosure and a polarizing plate disposed thereon.

One embodiment in the present disclosure provides a method for producing an optical member, the method including:

a step of preparing a transfer laminate configured to transfer a retardation layer, wherein the transfer laminate contains a retardation layer and a support supporting the retardation layer in a removable manner, and wherein the retardation layer contains a cured product of the polymerizable composition in one embodiment in the present disclosure, a transfer step in which a transfer receiving object containing at least a polarizing plate, is faced to the retardation layer of the transfer laminate, and the transfer laminate is transferred onto the transfer receiving object, and a removal step in which the support is removed from the transfer laminate transferred onto the transfer receiving object.

One embodiment in the present disclosure provides a display device including the retardation film or optical member according to any one of the embodiments concerned in the present disclosure.

Advantageous Effects of Invention

The embodiments in the disclosure can provide a polymerizable liquid crystal compound with a large birefringence index (Δn) and reverse wavelength dispersion property; a polymerizable composition containing the polymerizable liquid crystal compound; a polymer obtained by polymerizing the polymerizable liquid crystal compound or the polymerizable composition; a retardation film containing a retardation layer that contains a cured product of the polymerizable composition; a method for producing the retardation film; a transfer laminate configured to transfer the retardation layer; an optical member containing the retardation film; a method for producing the optical member; and a display device.

DESCRIPTION OF EMBODIMENTS

Figure 1:
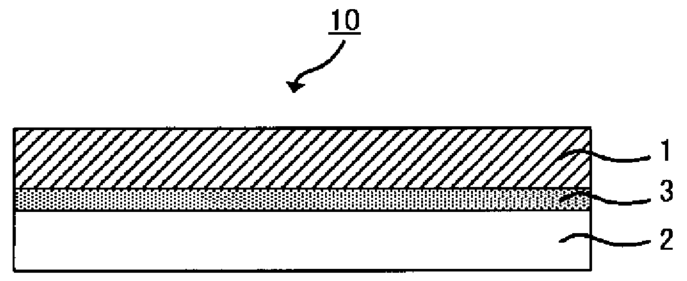
FIG. 1 is a schematic sectional view showing an embodiment of a retardation film.

Hereinafter, descriptions will be made about embodiments, examples and others in the present disclosure with reference to the drawings and so on. However, about the present disclosure, many different embodiments can be carried out. Thus, the present invention should not be interpreted with any limitation to described contents of the present embodiments, the examples, and the others, which will be given as examples. In order to make a description about each of the drawings clearer, the width, the thickness, the shape and any other factors of each part or portion therein may be schematically illustrated, differently from that of a part or portion in an actual form. However, the illustrated factors are each a mere example not to limit the interpretation of the present disclosure. In the document DESCRIPTION, and each of the drawings, to the same element as in any one of the drawings referred to already is attached the same reference number; thus, a detailed description thereabout is appropriately omitted. For the convenience of the descriptions, any word such as a word "upward" or "downward" may be used. However, the direction represented by the word may be flipped upside down.

In the DESCRIPTION, in a case where, for example, any member or a constituent of any region is "on (or beneath) of a different member or a constituent of a different region, examples of this case include not only a case where the member is just on (or just beneath) of the different constituent, but also a case where the member or the constituent is over or above (or under or below) of the different constituent, that is, a case where an additional member is included between the two to be over or above (or under or below) the constituent unless otherwise specified.

The alignment-regulating force in the present disclosure means an action that causes a liquid crystal compound in a retardation layer to be arranged in a specific direction.

In the present disclosure, the wording "(meth)acryl" denotes the word "acryl" or "methacryl". The wording "(meth)acrylate" denotes the word "acrylate" or "methacrylate".

In the present DESCRIPTION, the terms "plate", "sheet" and "film" should not be distinguished from each other based on a difference between their designations. The wording "film plane (plate plane or sheet plane)" denotes the following when a film-form (plate-form or sheet-form) member which is a target is viewed wholly and macroscopically: a plane of the film-form member (plate-form member or sheet-form member), which is the target, the direction of this plane being consistent with the flat plane direction of the member.

A. Polymerizable Liquid Crystal Compound

The polymerizable liquid crystal compound in the present disclosure is a compound represented by the following general formula (1):

General Formula (1)

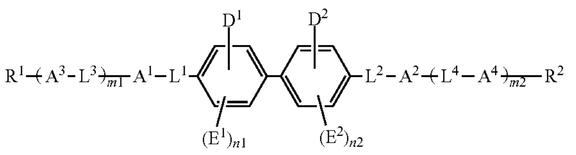

where $L^1$, $L^2$, $L^3$ and $L^4$ each independently represent —O—, —S—, —$OCH_2$—, —$CH_2O$—, —$CH_2CH_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —$SCH_2$—, —$CH_2S$—, —$CF_2O$—, —$OCF_2$—, —$CF_2S$—, —$SCF_2$—, —CH═CH—COO—, —CH═CH—OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH═CH—, —N═N—, —CH═N—, —N═CH—, —CH═N—N═CH—, —CF═CF—, —C≡C— or a single bond;

$A^1$ and $A^2$ each independently represent a divalent alicyclic hydrocarbon group containing 3 to 20 carbon atoms and optionally being unsubstituted or substituted by at least one substituent group E, and any carbon atom of the alicyclic hydrocarbon group is optionally substituted by a heteroatom;

$A^3$ and $A^4$ each independently represent a divalent alicyclic or aromatic hydrocarbon group containing 3 to 20 carbon atoms and optionally being unsubstituted or substituted by at least one substituent group E, and any carbon atom of the alicyclic or aromatic hydrocarbon group is optionally substituted by a heteroatom;

$R^1$ and $R^2$ each independently represent a group selected from the following general formula (R-1):

$$-L^5-R^{sp1}—Z^1$$ General formula (R-1):

where $L^5$ represents —O—, —S—, —$OCH_2$—, —$CH_2O$—, —$CH_2CH_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —$SCH_2$—, —$CH_2S$—, —$CF_2O$—, —$OCF_2$—, —$CF_2S$—, —$SCF_2$—, —CH═CH—COO—, —CH═CH—OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH═CH—, —N═N—, —CH═N—, —N═CH—, —CH═N—N═CH—, —CF═CF—, —C≡C— or a single bond; $R^{sp1}$ represents a single bond or an alkylene group containing 1 to 20 carbon atoms, in which one —$CH_2$— or two or more non-adjacent —$CH_2$— are each independently optionally substituted by —O—, —COO—, —OCO—, —OCO—O—, —CO—NH—, —NH—CO—, —CH═CH— or —C≡C—; and $Z^1$ represents a polymerizable functional group;

$D^1$ and $D^2$ each independently represent a group selected from the following general formula (D-1);

the substituent groups E, $E^1$ and $E^2$ each independently represent a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group containing 1 to 20 carbon atoms, in which one —$CH_2$— or two or more non-adjacent —$CH_2$— are each independently optionally substituted by —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF— or —C≡C—, and any hydrogen atom in the alkyl group is optionally substituted by a fluorine atom, or the substituent groups E, $E^1$ and $E^2$ each independently represent a group represented by -$L^E$-$R^{spE}$—$Z^E$ where $L^E$, $R^{spE}$ and $Z^E$ represent the same as those defined above as $L^5$, $R^{sp1}$ and $Z^1$, respectively, and $L^E$, $R^{spE}$ and $Z^E$ are optionally the same as or different from $L^5$, $R^{sp1}$ and $Z^1$, respectively; and when plural substituent groups Es, as well as plural substituent groups $E^1$s and plural substituent groups $E^2$s, are present in the compound, they are optionally the same or different from each other;

when plural $L^3$s, as well as plural $L^4$s, plural $A^3$s and plural $A^4$s, are present, they are optionally the same or different from each other;

m1 and m2 each independently represent an integer of 1 to 4; and n1 and n2 each independently represent an integer of from 0 to 3, General Formula (D-1)

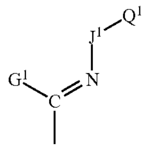

where $G^1$ represents a hydrogen atom or an alkyl group containing 1 to 6 carbon atoms, and the alkyl group is optionally unsubstituted or substituted by at least one substituent group E;

$Q^1$ represents an organic group containing 2 to 30 carbon atoms and an aromatic hydrocarbon group; any carbon atom of the aromatic hydrocarbon group is optionally substituted by a heteroatom; and the aromatic hydrocarbon group is optionally unsubstituted or substituted by at least one substituent group E;

$J^1$ represents —O—, —S—, —COO—, —OCO—, —OCO—O—, —$NQ^2$-, —N═$CQ^2$-, —CO—$NQ^2$-, —OCO—$NQ^2$- or —O—$NQ^2$; $Q^2$ represents a hydrogen atom, an alkyl group containing 1 to 20 carbon atoms, a cycloalkyl group containing 3 to 12 carbon atoms, a cycloalkenyl group containing 3 to 12 carbon atoms, an organic group containing 2 to 30 carbon atoms and an aromatic hydrocarbon group (any carbon atom of the aromatic hydrocarbon group is optionally substituted by a heteroatom) or -$(L^6$-$A^5)_q$-$L^7$-$R^{sp2}$—$Z^2$; the alkyl group, the cycloalkyl group, the cycloalkenyl group and the aromatic hydrocarbon group are each optionally unsubstituted or substituted by at least one substituent group E; the alkyl group is optionally substituted by the cycloalkyl group or the cycloalkenyl group; one —$CH_2$— or two or more non-adjacent —$CH_2$— in the alkyl group are each independently optionally substituted by —O—, —S—, —CO—, —COO—, —OCO—, —CO—S—, —S—CO—, —$SO_2$—, —O—CO—O—, —CO—NH—, —NH—CO—, —CH═CH—COO—, —CH═CH—OCO—, —COO—CH═CH—, —OCO—CH═CH—, —CH═CH—, —CF═CF— or —C≡C—; one —$CH_2$— or two or more non-adjacent —$CH_2$— in the cycloalkyl or cycloalkenyl group are each independently optionally substituted by —O—, —CO—, —COO—, —OCO— or —O—CO—O—; $L^6$, $A^5$, $L^7$, $R^{sp2}$ and $Z^2$ represent the same as those defined above as $L^1$ to $L^4$, $A^l$ to $A^4$, $L^5$, $R^{sp1}$ and $Z^1$, respectively, and $L^6$, $A^5$, $L^7$, $R^{sp2}$ and $Z^2$ are optionally the same as or different from $L^1$ to $L^4$, $A^1$ to $A^4$, $L^5$, $R^{sp1}$ and $Z^1$, respectively; q is an integer of 0 to 4; when plural $L^6$s, as well as plural $A^5$s, are present, they are optionally the same or different from each other; and $Q^1$ and $Q^2$ are optionally bound to each other to form a ring.

For the compound represented by the general formula (1) in the present disclosure, the above-specified main chain structure stating from $R^1$ to $R^2$ contains the specified structure. Accordingly, it is a compound which is improved in intermolecular alignment property and which shows liquid crystallinity by itself. Also, since the compound represented by the general formula (1) in the present disclosure contains the polymerizable functional groups in its terminals, it is a polymerizable liquid crystal compound.

The compound represented by the general formula (1) in the present disclosure has high alignment property between molecules, due to the biphenylene group contained its main chain moiety. Moreover, since the two benzene rings of the biphenylene group contain one side chain each, that is, a total of two side chains, the compound becomes a compound with a large birefringence index (Δn) while having reverse wavelength dispersion property.

In general, a compound with reverse wavelength dispersion property is poor in solubility. However, in the compound represented by the general formula (1) in the present disclosure, decreased solubility can be improved by the alicyclic hydrocarbon groups introduced to $A^1$ and $A^2$ adjacent to the biphenylene group.

The polymerizable liquid crystal compound represented by the general formula (1) in the present disclosure has a large birefringence index (Δn) and reverse wavelength dispersion property. Accordingly, a retardation layer with desired reverse wavelength dispersion property can be obtained by using a small amount of the polymerizable liquid crystal compound, and a thinner retardation layer can be obtained.

Also, the polymerizable liquid crystal compound represented by the general formula (1) in the present disclosure has a large birefringence index (Δn) and reverse wavelength dispersion property. Accordingly, the retardation of a material with desired reverse wavelength dispersion property can be controlled by adding a small amount of the polymerizable liquid crystal compound to a different liquid crystal compound.

In the general formula (1), $L^1$, $L^2$, $L^3$ and $L^4$ each independently represent —O—, —S—, —$OCH_2$—, —$CH_2O$—, —$CH_2CH_2$—, —CO—, —COO—, —CO—S—, —S—CO—, —O—CO—O—, —CO—NH—, —NH—CO—, —OCO—NH—, —NH—COO—, —NH—CO—NH—, —NH—O—, —O—NH—, —$SCH_2$—, —$CH_2S$—, —$CF_2O$—, —$OCF_2$—, —$CF_2S$—, —$SCF_2$—, —CH═CH—COO—, —CH═CH—OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH═CH—, —N═N—, —CH═N—, —N═CH—, —CH═N—N═CH—, —CF═CF—, —C≡C— or a single bond. $L^1$, $L^2$, $L^3$ and $L^4$ each independently represent a divalent linking group or a single bond. When plural $L^3$s, as well as plural $L^4$s, each independently appear, they are optionally the same or different from each other.

In particular, from the viewpoint of liquid crystallinity, availability of raw materials and easy synthesis, $L^1$ and $L^2$ each independently represent preferably —COO—, —OCO—, —$OCH_2$—, —$CH_2O$—, —$CF_2O$—, —$OCF_2$—, —$CH_2CH_2$—, —$CF_2CF_2$—, —CH═CH—COO—, —CH═CH—OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO—, —CH═CH—, —CF═CF—, —C≡C— or a single bond, more preferably —COO—, —OCO—, —$OCH_2$—, —$CH_2O$—, —$CF_2O$—, —$OCF_2$—, —$CH_2CH_2$—, —COO—$CH_2CH_2$—, —OCO—$CH_2CH_2$—, —$CH_2CH_2$—COO—, —$CH_2CH_2$—OCO—, —CH═CH—, —C≡C— or a single bond, still more preferably —COO—, —OCO—, —$OCH_2$—, —$CH_2O$—, —$CF_2O$—, —$OCF_2$— or a single bond, even more preferably —COO—, —OCO—, —$OCH_2$—, —$CH_2O$— or a single bond, and particularly preferably —COO—, —OCO—, —$OCH_2$— or —$CH_2O$—.

In particular, from the viewpoint of availability of raw materials and easy synthesis, $L^3$ and $L^4$ each independently represent preferably —O—, —S—, —$OCH_2$—, —$CH_2O$—, —COO—, —OCO—, —CO—S—, —S—CO—, —O—CO—O—, —CO—NH—, —NH—CO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO— or a single bond (when plural $L^3$s, as well as plural $L^4$s, are present, they may be the same or different from each other), more preferably —$OCH_2$—, —$CH_2O$—, —COO—, —OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO— or a single bond (when plural $L^3$s, as well as plural $L^4$s, are present, they may be the same or different from each other), and particularly preferably —O—, —COO—, —OCO—, —COO—CH═CH—, —OCO—CH═CH—, —COO—$CH_2CH_2$—, —OCO—$CH_2CH_2$— or a single bond.

In the general formula (1), $A^1$ and $A^2$ each independently represent a divalent alicyclic hydrocarbon group containing 3 to 20 carbon atoms and optionally being unsubstituted or substituted by at least one substituent group E, and any carbon atom of the alicyclic hydrocarbon group is optionally substituted by a heteroatom. More specifically, any carbon atom of the alicyclic hydrocarbon group is optionally substituted by an oxygen atom, a sulfur atom or a nitrogen atom.

As the divalent alicyclic hydrocarbon group containing 3 to 20 carbon atoms, examples include a divalent cycloalkanediyl group containing 3 to 20 carbon atoms, and a divalent alicyclic condensed ring group containing 10 to 20 carbon atoms.

As the divalent cycloalkanediyl group containing 3 to 20 carbon atoms, examples include a cyclopropanediyl group; a cyclobutanediyl group such as a cyclobutane-1,2-diyl group and a cyclobutane-1,3-diyl group; a cyclopentanediyl group such as a cyclopentane-1,2-diyl group and a cyclopentane-1,3-diyl group; a cyclohexanediyl group such as a cyclohexane-1,2-diyl group, a cyclohexane-1,3-diyl group and a cyclohexane-1,4-diyl group; a cycloheptanediyl group such as a cycloheptane-1,2-diyl group, a cycloheptane-1,3-diyl group and a cycloheptane-1,4-diyl group; a cyclooctanediyl group such as a cyclooctane-1,2-diyl group, a cyclooctane-1,3-diyl group, a cyclooctane-1,4-diyl group and a cyclooctane-1,5-diyl group; a cyclodecanediyl group such as a cyclodecane-1,2-diyl group, a cyclodecane-1,3-diyl group, a cyclodecane-1,4-diyl group and a cyclodecane-1,5-diyl group; a cyclododecanediyl group such as a cyclododecane-1,2-diyl group, a cyclododecane-1,3-diyl group, a cyclododecane-1,4-diyl group and a cyclododecane-1,5-diyl group; a cyclotetradecanediyl group such as a cyclotetradecane-1,2-diyl group, a cyclotetradecane-1,3-diyl group, a cyclotetradecane-1,4-diyl group, a cyclotetradecane-1,5-diyl group and a cyclotetradecane-1,7-diyl group; and a cycloeicosanediyl group such as a cycloeicosane-1,2-diyl group and a cycloeicosane-1,10-diyl group. The cycloalkanediyl group is optionally unsubstituted or substituted by at least one substituent group E.

Any carbon atom of the cycloalkanediyl group is optionally substituted by an oxygen atom, a sulfur atom or a nitrogen atom. Examples of such a cycloalkanediyl group include a tetrahydropyran-2,5-diyl group, a 1,3-dioxane-2,5-diyl group and a tetrahydrothiopyran-2,5-diyl group.

As the divalent alicyclic condensed ring group containing 10 to 20 carbon atoms, examples include a decalindiyl group such as a decahydronaphthalene-2,5-diyl group, a decahydronaphthalene-2,6-diyl group and a decahydronaphthalene-2,7-diyl group; an adamantanediyl group such as an adamantane-1,2-diyl group and an adamantane-1,3-diyl group; and a bicyclo[2.2.1]heptanediyl group such as a bicyclo[2.2.1]heptane-2,3-diyl group, a bicyclo[2.2.1]heptane-2,5-diyl group and a bicyclo[2.2.1]heptane-2,6-diyl group. The alicyclic condensed ring group is optionally unsubstituted or substituted by at least one substituent group E. Also, any carbon atom of the alicyclic condensed ring group is optionally substituted by an oxygen atom, a sulfur atom or a nitrogen atom.

Among them, $A^1$ and $A^2$ each independently represent preferably an alicyclic hydrocarbon group containing 3 to 12 carbon atoms and optionally being unsubstituted or substituted by at least one substituent group E, more preferably a cycloalkanediyl group containing 3 to 12 carbon atoms, even more preferably a cyclopentane-1,3-diyl group, a cyclohexane-1,4-diyl group, a cycloheptane-1,4-diyl group or a cyclododecane-1,5-diyl group, each of which is optionally unsubstituted or substituted by at least one substituent group E, and particularly preferably a cyclohexane-1,4-diyl group optionally being unsubstituted or substituted by at least one substituent group E, from the viewpoint of the ease of improving particularly liquid crystallinity and improving the alignment property of the polymer.

In the divalent alicyclic hydrocarbon group containing 3 to 20 carbon atoms, a cis- or trans-stereoisomer based on a difference in the steric configuration of carbon atoms bound to $L^2$ and $L^3$ (or $L^2$ and $L^4$) is optionally present. The divalent alicyclic hydrocarbon group containing 3 to 20 carbon atoms may be cis, trans, or a mixture of a cis-isomer and a trans-isomer. From the viewpoint of excellent alignment property, the divalent alicyclic hydrocarbon group containing 3 to 20 carbon atoms is preferably trans or cis, and more preferably trans.

In the general formula (1), $A^3$ and $A^4$ each independently represent a divalent alicyclic or aromatic hydrocarbon group containing 3 to 20 carbon atoms and optionally being unsubstituted or substituted by at least one substituent group E, and any carbon atom of the alicyclic or aromatic hydrocarbon group is optionally substituted by a heteroatom. More specifically, any carbon atom of the alicyclic hydrocarbon group and the aromatic hydrocarbon group is optionally substituted by an oxygen atom, a sulfur atom or a nitrogen atom. The aromatic hydrocarbon group is optionally an aromatic heterocyclic group, optionally contains a condensed ring structure, or is optionally a structure in which an alicyclic hydrocarbon group and an aromatic hydrocarbon group are condensed. When plural $A^3$s, as well as plural $A^4$s, are each independently present, they may be the same or different from each other.

As the divalent aromatic hydrocarbon group optionally being substituted by a heteroatom as $A^3$ and $A^4$, examples include a divalent aromatic hydrocarbon group containing 6 to 20 carbon atoms and optionally being substituted by a heteroatom. As an aromatic hydrocarbon ring constituting the aromatic hydrocarbon group optionally being substituted by a heteroatom, examples include a benzene ring, a naphthalene ring, an anthracene ring and a phenanthrene ring. As an aromatic heterocycle, examples include a furan ring, a pyridine ring, a pyrimidine ring and a pyrazine ring.

As the divalent alicyclic hydrocarbon group containing 3 to 20 carbon atoms as $A^3$ and $A^4$, examples include those exemplified above as the divalent alicyclic hydrocarbon group containing 3 to 20 carbon atoms as $A^1$ and $A^2$.

As the divalent alicyclic hydrocarbon group or aromatic hydrocarbon group containing 3 to 20 carbon atoms and optionally being substituted by a heteroatom as $A^3$ and $A^4$, examples include a benzene-1,4-diyl group (a 1,4-phenylene group), a cyclohexane-1,4-diyl group, a cyclohexene-1,4-diyl group, a tetrahydropyran-2,5-diyl group, a 1,3-dioxane-2,5-diyl group, a tetrahydrothiopyran-2,5-diyl group, a 1,4-bicyclo(2,2,2)octylene group, a decahydronaphthalene-2,6-diyl group, a pyridine-2,5-diyl group, a pyrimidine-2,5-diyl group, a pyrazine-2,5-diyl group, a 1,2,3,4-tetrahydronaphthalene-2,6-diyl group, a naphthalene-2,6-diyl group, a naphthalene-1,4-diyl group, a phenanthrene-2,7-diyl group, a 9,10-dihydrophenanthrene-2,7-diyl group, a 1,2,3,4,4a,9,10a-octahydrophenanthrene 2,7-diyl group or a fluorene 2,7-diyl group. The alicyclic hydrocarbon group and the aromatic hydrocarbon group is optionally unsubstituted or substituted by at least one substituent group E.

From the viewpoint of improving particularly liquid crystallinity and improving the alignment property of the polymer, $A^3$ and $A^4$ in the general formula (1) each independently represent preferably a benzene-1,4-diyl group, a cyclohexane-1,4-diyl group, a pyridine-2,5-diyl group, a pyrimidine-2,5-diyl group, a naphthalene-2,6-diyl group, a naphthalene-1,4-diyl group, a 1,2,3,4-tetrahydronaphthalene-2,6-diyl group, a decahydronaphthalene-2,6-diyl group, or a 1,3-dioxane-2,5-diyl group.

$A^3$ and $A^4$ in the general formula (1) are each independently preferably a benzene-1,4-diyl group, a naphthalene-2,6-diyl group, or a cyclohexane-1,4-diyl group, more preferably a benzene-1,4-diyl group or a cyclohexane-1,4-diyl group, and particularly preferably a benzene-1,4-diyl group, each of which is optionally unsubstituted or substituted by at least one substituent group E. When $A^3$ and $A^4$ are each independently these groups, the liquid crystallinity of the polymerizable liquid crystal compound in the present embodiment is easily improved, and the alignment property of the polymer is easily improved.

The substituent group E each independently represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group containing 1 to 20 carbon atoms, in which one $—CH_2—$ or two or more non-adjacent $—CH_2—$ are each independently optionally substituted by —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF— or —C≡C—, and any hydrogen atom in the alkyl group is optionally substituted by a fluorine atom, or the substituent group E each independently represents a group represented by $-L^E-R^{spE}—Z^E$ where $L^E$, $R^{spE}$ and $Z^E$ represent the same as those defined below as $L^5$, $R^{sp1}$ and $Z^1$, respectively, and $L^E$, $R^{spE}$ and $Z^E$ are optionally the same as or different from $L^3$, $R^{sp1}$ and $Z^1$, respectively; and when plural substituent group Es are present in the compound, they are optionally the same or different from each other.

From the viewpoint of liquid crystallinity and easy synthesis, the substituent group E represents preferably a fluorine atom, a chlorine atom, a pentafluorosulfuranyl group, a nitro group, a methylamino group, a dimethylamino group, a diethylamino group, a diisopropylamino group, or a linear or branched alkyl group containing 1 to 20 carbon atoms, in which any hydrogen atom is optionally substituted by a fluorine atom, and one $—CH_2—$ or two or more non-adjacent $—CH_2—$ are each independently optionally substituted by a group selected from —O—, —S—, —CO—, —COO—, —OCO—, —O—CO—O—, —CH═CH—, —CF═CF— and —C≡C—, more preferably a fluorine atom, a chlorine atom, or a linear or branched alkyl group containing 1 to 12 carbon atoms, in which any hydrogen atom is optionally substituted by a fluorine atom, and one $—CH_2—$ or two or more non-adjacent $—CH_2—$ are each independently optionally substituted by a group selected from —O—, —COO— and —OCO—, still more preferably a fluorine atom, a chlorine atom, or a linear or branched alkyl or alkoxy group containing 1 to 12 carbon atoms, in which any hydrogen atom is optionally substituted by a fluorine atom, and particularly preferably a fluorine atom, a chlorine atom, or a linear alkyl or alkoxy group containing 1 to 8 carbon atoms.

As the substituent group E optionally being substituted on $A^3$ and $A^4$, especially, as the substituent group E optionally being substituted on $A^3$ and $A^4$ to which $R^1$ and $R^2$ are respectively bound, a group represented by $-L^E-R^{spE}—Z^E$ is also preferable.

In the general formula (1), m1 and m2 each independently represent an integer of from 1 to 4.

When the liquid crystallinity and alignment property of the polymerizable compound in the present embodiment are important, it is preferable that any one of m1 and m2 is an integer of from 1 to 3 or both m1 and m2 are each an integer of from 1 to 3; it is more preferable that both m1 and m2 are each an integer of from 1 to 3; and it is even more preferable that both m1 and m2 are 1 or 2 each.

$R^1$ and $R^2$ each independently represent a group selected from the following general formula (R-1):

$$-L^3-R^{sp1}—Z^1 \qquad \text{General formula (R-1):}$$

where $L^5$ represents —O—, —S—, —$OCH_2$—, —$CH_2O$—, —$CH_2CH_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —$SCH_2$—, —$CH_2S$—, —$CF_2O$—, —$OCF_2$—, —$CF_2S$—, —$SCF_2$—, —CH═CH—COO—, —CH═CH—OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH═CH—, —N═N—, —CH═N—, —N═CH—, —CH═N—N═CH—, —CF═CF—, —C≡C— or a single bond.

More specifically, from the viewpoint of availability of raw materials and easy synthesis, $L^5$ in the general formula (R-1) each independently represents preferably —O—, —S—, —COO—, —OCO—, —CO—S—, —S—CO—, —O—CO—O—, —CO—NH—, —NH—CO—, —$CH_2CH_2$—COO—, —$CH_2CH_2$—OCO— or a single bond, and more preferably —O—, —COO—, —OCO—, —O—CO—O— or a single bond. When plural $L^3$s are present, they may be the same or different from each other.

In the general formula (R-1), $R^{sp1}$ represents a single bond or an alkylene group containing 1 to 20 carbon atoms, in which one —$CH_2$— or two or more non-adjacent —$CH_2$— are each independently optionally substituted by —O—, —COO—, —OCO—, —OCO—O—, —CO—NH—, —NH—CO—, —CH═CH— or —C≡C—.

More specifically, from the viewpoint of availability of raw materials and easy synthesis, $R^{sp1}$ in the general formula (R-1) each independently represents preferably a single bond or an alkylene group containing 1 to 12 carbon atoms, in which one —$CH_2$— or two or more non-adjacent —$CH_2$— are each independently optionally substituted by —O—, —COO— or —OCO—, more preferably a single bond or an alkylene group containing 1 to 12 carbon atoms, and even more preferably an alkylene group containing 2 to 10 carbon atoms. When plural $Rsp^1$s are present, they may be the same or different from each other.

In the general formula (R-1), $Z^1$ represents a polymerizable functional group. As the polymerizable functional group, any group that is applicable to polymerizable liquid crystal compounds in the prior art, can be used with no limitation.

The polymerizable functional group each independently represents preferably a group selected from the following formulae (Z-1) to (Z-8). In the following formulae (Z-1) to (Z-8), "*" (an asterisk) indicates the binding position to $R^{sp1}$:

(Z-1)

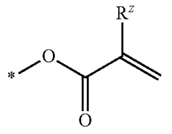

(Z-2)

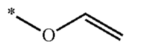

(Z-3)

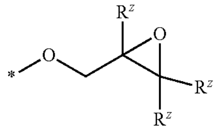

(Z-4)

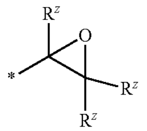

(Z-5)

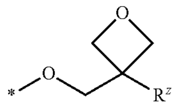

(Z-6)

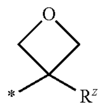

(Z-7)

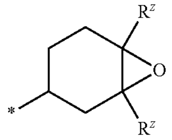

(Z-8)

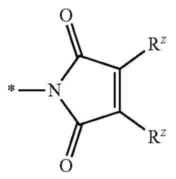

Where $R^z$ is each independently a hydrogen atom, a fluorine atom, a chlorine atom, a bromine atom, an iodine atom, a methyl group, an ethyl group or a trifluoromethyl group.

When UV polymerization is carried out as the polymerization method, $Z^1$ is preferably the formula (Z-1), (Z-2), (Z-3), (Z-5) or (Z-7), more preferably the formula (Z-1), (Z-3) or (Z-7), even more preferably the formula (Z-1), and particularly preferably the formula (Z-1) in which $R^z$ is a hydrogen atom, a methyl group or a trifluoromethyl group.

In the general formula (1), specific examples of "Lc1: $-L^1-A^1-(L^3-A^3)_{m1}-L^5-R^{sp1}—Z^1$" and "Lc2: $-L^2-A^2-(L^4-A^4)_{m2}-L^5-R^{sp1}—Z^1$" include, but are not limited to, groups represented by the following Lc-1 to Lc-244. In the polymerizable liquid crystal compound represented by the general formula (1), Lc1 and Lc2 may be the same or different from each other.

TABLE 1
| | | | m1/m2 = 1 | | | | |
|---|---|---|---|---|---|---|---|
| Lc1/Lc2 | $L^1/L^2$ | $A^1/A^2$ | $L^3/L^4$ | $A^3/A^4$ | $L^5$ | $R^{sp1}$ | $Z^1$ |
| Lc-1 | —OCO— | 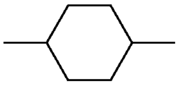 | —COO— | 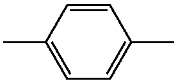 | —O— | $-(CH_2)_n-$ | Formula (Z-1) |
| Lc-2 | | | | | Single bond | | |
| Lc-3 | | | | | —OCO— | | |
| Lc-4 | | | | | —OCOO— | | |
| Lc-5 | | | | 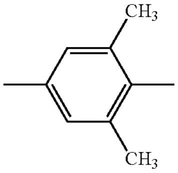 | —O— | | |
| Lc-6 | | | | | Single bond | | |
| Lc-7 | | | | | —OCO— | | |
| Lc-8 | | | | | —OCOO— | | |
| Lc-9 | | | | 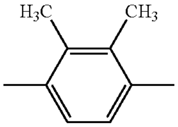 | —O— | | |
| Lc-10 | | | | | Single bond | | |
| Lc-11 | | | | | —OCO— | | |
| Lc-12 | | | | | —OCOO— | | |
| Lc-13 | | | | 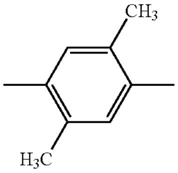 | —O— | | |
| Lc-14 | | | | | Single bond | | |
| Lc-15 | | | | | —OCO— | | |
| Lc-16 | | | | | —OCOO— | | |
| Lc-17 | | | | 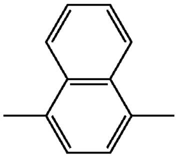 | —O— | | |
| Lc-18 | | | | | Single bond | | |
| Lc-19 | | | | | —OCO— | | |
| Lc-20 | | | | | —OCOO— | | |
| Lc-21 | | | | 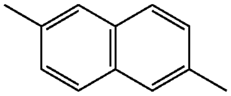 | —O— | | |
| Lc-22 | | | | | Single bond | | |
| Lc-23 | | | | | —OCO— | | |
| Lc-24 | | | | | —OCOO— | | |
| Lc-25 | —OCO— | 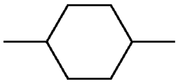 | —OCO— | 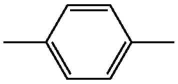 | —O— | $-(CH_2)_n-$ | Formula (Z-1) |
| Lc-26 | | | | | Single bond | | |
| Lc-27 | | | | | —OCO— | | |
| Lc-28 | | | | | —OCOO— | | |

TABLE 1-continued
| | | | m1/m2 = 1 | | | | |
|---|---|---|---|---|---|---|---|
| Lc1/Lc2 | $L^1/L^2$ | $A^1/A^2$ | $L^3/L^4$ | $A^3/A^4$ | $L^5$ | $R^{sp1}$ | $Z^1$ |
| Lc-29 | | | | 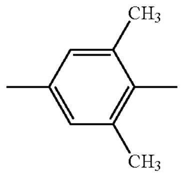 | —O— | | |
| Lc-30 | | | | | Single bond | | |
| Lc-31 | | | | | —OCO— | | |
| Lc-32 | | | | | —OCOO— | | |
| Lc-33 | | | | 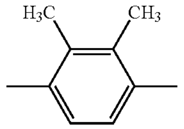 | —O— | | |
| Lc-34 | | | | | Single bond | | |
| Lc-35 | | | | | —OCO— | | |
| Lc-36 | | | | | —OCOO— | | |
| Lc-37 | | | | 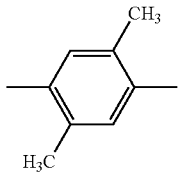 | —O— | | |
| Lc-38 | | | | | Single bond | | |
| Lc-39 | | | | | —OCO— | | |
| Lc-40 | | | | | —OCOO— | | |
| Lc-41 | | | | 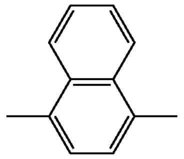 | —O— | | |
| Lc-42 | | | | | Single bond | | |
| Lc-43 | | | | | —OCO— | | |
| Lc-44 | | | | | —OCOO— | | |
| Lc-45 | | | | 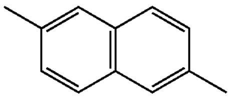 | —O— | | |
| Lc-46 | | | | | Single bond | | |
| Lc-47 | | | | | —OCO— | | |
| Lc-48 | | | | | —OCOO— | | |
TABLE 2
| | | | m1/m2 = 1 | | | | |
|---|---|---|---|---|---|---|---|
| Lc1/Lc2 | $L^1/L^2$ | $A^1/A^2$ | $L^3/L^4$ | $A^3/A^4$ | $L^5$ | $R^{sp1}$ | $Z^1$ |
| Lc-49 | —OCO— | 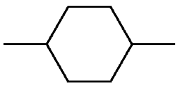 | Single bond | 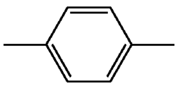 | —O— | $—(CH_2)_n—$ | Formula (Z-1) |
| Lc-50 | | | | | —OCO— | | |
| Lc-51 | | | | | —OCOO— | | |
| Lc-52 | | | —COO— | | —COO— | | |

TABLE 2-continued
| | | | m1/m2 = 1 | | | | |
|---|---|---|---|---|---|---|---|
| Lc1/Lc2 | $L^1/L^2$ | $A^1/A^2$ | $L^3/L^4$ | $A^3/A^4$ | $L^5$ | $R^{sp1}$ | $Z^1$ |
| Lc-53 | | | —OCO— | | —COO— | | |
| Lc-54 | | | | | —CONH— | | |
| Lc-55 | | | —COO— | 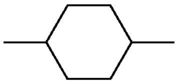 | —O— | | |
| Lc-56 | | | | | —OCO— | | |
| Lc-57 | | | | | —OCOO— | | |
| Lc-58 | | | —OCO— | | —O— | | |
| Lc-59 | | | | | —OCO— | | |
| Lc-60 | | | | | —OCOO— | | |
| Lc-61 | —COO— | 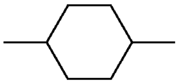 | —COO— | 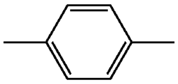 | —O— | $-(CH_2)_n-$ | Formula (Z-1) |
| Lc-62 | | | | | Single bond | | |
| Lc-63 | | | | | —OCO— | | |
| Lc-64 | | | | | —OCOO— | | |
| Lc-65 | | | | 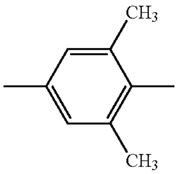 | —O— | | |
| Lc-66 | | | | | Single bond | | |
| Lc-67 | | | | | —OCO— | | |
| Lc-68 | | | | | —OCOO— | | |
| Lc-69 | | | | 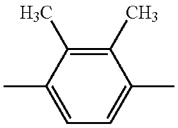 | —O— | | |
| Lc-70 | | | | | Single bond | | |
| Lc-71 | | | | | —OCO— | | |
| Lc-72 | | | | | —OCOO— | | |
| Lc-73 | | | | 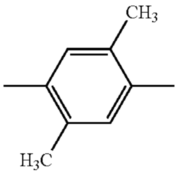 | —O— | | |
| Lc-74 | | | | | Single bond | | |
| Lc-75 | | | | | —OCO— | | |
| Lc-76 | | | | | —OCOO— | | |
| Lc-77 | | | | 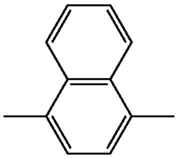 | —O— | | |
| Lc-78 | | | | | Single bond | | |
| Lc-79 | | | | | —OCO— | | |
| Lc-80 | | | | | —OCOO— | | |

TABLE 2-continued

| | | | m1/m2 = 1 | | | | |
|---|---|---|---|---|---|---|---|
| Lc1/Lc2 | $L^1/L^2$ | $A^1/A^2$ | $L^3/L^4$ | $A^3/A^4$ | $L^5$ | $R^{sp1}$ | $Z^1$ |
| Lc-81 | | | | 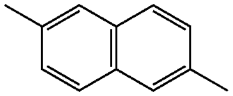 | —O— | | |
| Lc-82 | | | | | Single bond | | |
| Lc-83 | | | | | —OCO— | | |
| Lc-84 | | | | | —OCOO— | | |

TABLE 3

| | | | m1/m2 = 1 | | | | |
|---|---|---|---|---|---|---|---|
| Lc1/Lc2 | $L^1/L^2$ | $A^1/A^2$ | $L^3/L^4$ | $A^3/A^4$ | $L^5$ | $R^{sp1}$ | $Z^1$ |
| Lc-85 | —OCO— | 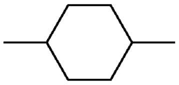 | $-COO(CH_2)_m-$ | 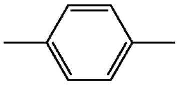 | —O— | $-(CH_2)_n-$ | Formula (Z-1) |
| Lc-86 | | | | | Single bond | | |
| Lc-87 | | | | | —OCO— | | |
| Lc-88 | | | | | —OCOO— | | |
| Lc-89 | | | | 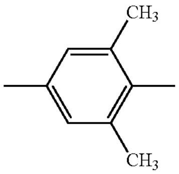 | —O— | | |
| Lc-90 | | | | | Single bond | | |
| Lc-91 | | | | | —OCO— | | |
| Lc-92 | | | | | —OCOO— | | |
| Lc-93 | | | | 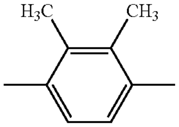 | —O— | | |
| Lc-94 | | | | | Single bond | | |
| Lc-95 | | | | | —OCO— | | |
| Lc-96 | | | | | —OCOO— | | |
| Lc-97 | | | | 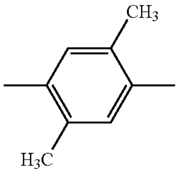 | —O— | | |
| Lc-98 | | | | | Single bond | | |
| Lc-99 | | | | | —OCO— | | |
| Lc-100 | | | | | —OCOO— | | |
| Lc-101 | | | | 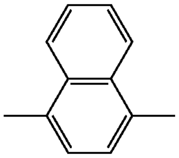 | —O— | | |
| Lc-102 | | | | | Single bond | | |
| Lc-103 | | | | | —OCO— | | |
| Lc-104 | | | | | —OCOO— | | |

TABLE 3-continued
| | | | m1/m2 = 1 | | | | |
|---|---|---|---|---|---|---|---|
| Lc1/Lc2 | $L^1/L^2$ | $A^1/A^2$ | $L^3/L^4$ | $A^3/A^4$ | $L^5$ | $R^{sp1}$ | $Z^1$ |
| Lc-105 | | | | 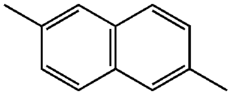 | —O— | | |
| Lc-106 | | | | | Single bond | | |
| Lc-107 | | | | | —OCO— | | |
| Lc-108 | | | | | —OCOO— | | |
| Lc-109 | —OCO— | 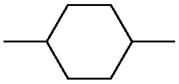 | $—OCO(CH_2)_m—$ | 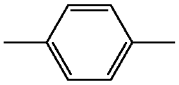 | —O— | $—(CH_2)_n—$ | Formula (Z-1) |
| Lc-110 | | | | | Single bond | | |
| Lc-111 | | | | | —OCO— | | |
| Lc-112 | | | | | —OCOO— | | |
| Lc-113 | | | | 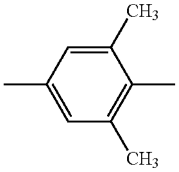 | —O— | | |
| Lc-114 | | | | | Single bond | | |
| Lc-115 | | | | | —OCO— | | |
| Lc-116 | | | | | —OCOO— | | |
| Lc-117 | | | | 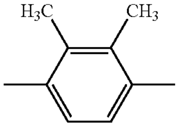 | —O— | | |
| Lc-118 | | | | | Single bond | | |
| Lc-119 | | | | | —OCO— | | |
| Lc-120 | | | | | —OCOO— | | |
| Lc-121 | | | | 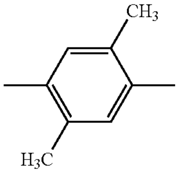 | —O— | | |
| Lc-122 | | | | | Single bond | | |
| Lc-123 | | | | | —OCO— | | |
| Lc-124 | | | | | —OCOO— | | |
| Lc-125 | | | | 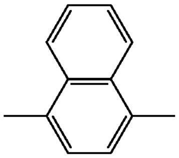 | —O— | | |
| Lc-126 | | | | | Single bond | | |
| Lc-127 | | | | | —OCO— | | |
| Lc-128 | | | | | —OCOO— | | |
| Lc-129 | | | | 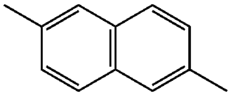 | —O— | | |

TABLE 3-continued

| | | | m1/m2 = 1 | | | | |
|---|---|---|---|---|---|---|---|
| Lc1/Lc2 | $L^1/L^2$ | $A^1/A^2$ | $L^3/L^4$ | $A^3/A^4$ | $L^5$ | $R^{sp1}$ | $Z^1$ |
| Lc-130 | | | | | Single bond | | |
| Lc-131 | | | | | —OCO— | | |
| Lc-132 | | | | | —OCOO— | | |

TABLE 4

| | | | m1/m2 = 1 | | | | |
|---|---|---|---|---|---|---|---|
| Lc1/Lc2 | $L^1/L^2$ | $A^1/A^2$ | $L^3/L^4$ | $A^3/A^4$ | $L^5$ | $R^{sp1}$ | $Z^1$ |
| Lc-133 | —COO— | 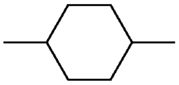 | $—COO(CH_2)_m—$ | 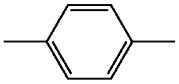 | —O— | $—(CH_2)_n—$ | Formula (Z-1) |
| Lc-134 | | | | | Single bond | | |
| Lc-135 | | | | | —OCO— | | |
| Lc-136 | | | | | —OCOO— | | |
| Lc-137 | | | | 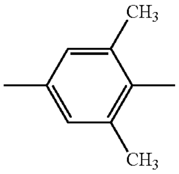 | —O— | | |
| Lc-138 | | | | | Single bond | | |
| Lc-139 | | | | | —OCO— | | |
| Lc-140 | | | | | —OCOO— | | |
| Lc-141 | | | | 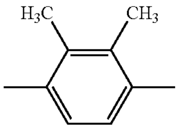 | —O— | | |
| Lc-142 | | | | | Single bond | | |
| Lc-143 | | | | | —OCO— | | |
| Lc-144 | | | | | —OCOO— | | |
| Lc-145 | | | | 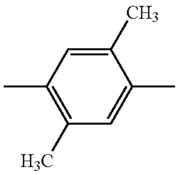 | —O— | | |
| Lc-146 | | | | | Single bond | | |
| Lc-147 | | | | | —OCO— | | |
| Lc-148 | | | | | —OCOO— | | |
| Lc-149 | | | | 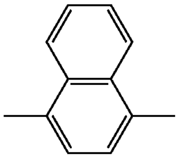 | —O— | | |
| Lc-150 | | | | | Single bond | | |
| Lc-151 | | | | | —OCO— | | |
| Lc-152 | | | | | —OCOO— | | |
| Lc-153 | | | | 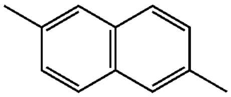 | —O— | | |

TABLE 4-continued
| | | | m1/m2 = 1 | | | | |
|---|---|---|---|---|---|---|---|
| Lc1/Lc2 | $L^1/L^2$ | $A^1/A^2$ | $L^3/L^4$ | $A^3/A^4$ | $L^5$ | $R^{sp1}$ | $Z^1$ |
| Lc-154 | | | | | Single bond | | |
| Lc-155 | | | | | —OCO— | | |
| Lc-156 | | | | | —OCOO— | | |
| Lc-157 | —COO— | 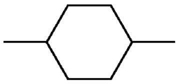 | $—OCO(CH_2)_m—$ | 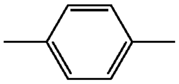 | —O— | $—(CH_2)_n—$ | Formula (Z-1) |
| Lc-158 | | | | | Single bond | | |
| Lc-159 | | | | | —OCO— | | |
| Lc-160 | | | | | —OCOO— | | |
| Lc-161 | | | | 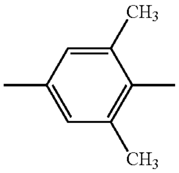 | —O— | | |
| Lc-162 | | | | | Single bond | | |
| Lc-163 | | | | | —OCO— | | |
| Lc-164 | | | | | —OCOO— | | |
| Lc-165 | | | | 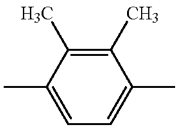 | —O— | | |
| Lc-166 | | | | | Single bond | | |
| Lc-167 | | | | | —OCO— | | |
| Lc-168 | | | | | —OCOO— | | |
| Lc-169 | | | | 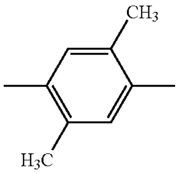 | —O— | | |
| Lc-170 | | | | | Single bond | | |
| Lc-171 | | | | | —OCO— | | |
| Lc-172 | | | | | —OCOO— | | |
| Lc-173 | | | | 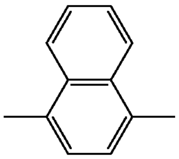 | —O— | | |
| Lc-174 | | | | | Single bond | | |
| Lc-175 | | | | | —OCO— | | |
| Lc-176 | | | | | —OCOO— | | |
| Lc-177 | | | | 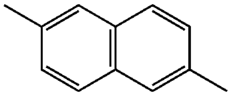 | —O— | | |
| Lc-178 | | | | | Single bond | | |
| Lc-179 | | | | | —OCO— | | |
| Lc-180 | | | | | —OCOO— | | |

TABLE 5

| Lc1/ Lc2 | $L^1/L^2$ | $A^1/A^2$ | m1/m2 = 2 $L^3/L^4$ | $A^3/A^4$ | $L^3/L^4$ | $A^3/A^4$ | $L^5$ | $R^{sp1}$ | $Z^1$ |
|---|---|---|---|---|---|---|---|---|---|
| Lc-181 | —OCO— | 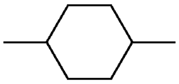 | —COO— | 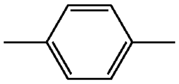 | —COO— | 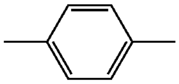 | —O— | —$(CH_2)_n$— | Formula (Z-1) |
| Lc-182 | | | | | —OCO— | | —O— | | |
| Lc-183 | | | | | —COO— | | —OCO— | | |
| Lc-184 | | | | | —OCO— | | —OCO— | | |
| Lc-185 | | | | | —COO— | | —OCOO— | | |
| Lc-186 | | | | | —OCO— | | —OCOO— | | |
| Lc-187 | | | | | —COO— | | —COO— | | |
| Lc-188 | | | | | —OCO— | | —COO— | | |
| Lc-189 | | | —OCO— | | —COO— | | —O— | | |
| Lc-190 | | | | | —OCO— | | —O— | | |
| Lc-191 | | | | | —COO— | | —OCO— | | |
| Lc-192 | | | | | —OCO— | | —OCO— | | |
| Lc-193 | —OCO— | 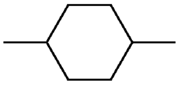 | —OCO— | 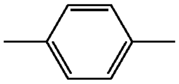 | —COO— | 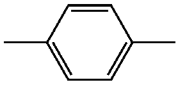 | —OCOO— | —$(CH_2)_n$— | Formula (Z-1) |
| Lc-194 | | | | | —OCO— | | —OCOO— | | |
| Lc-195 | | | | | —COO— | | —COO— | | |
| Lc-196 | | | | | —OCO— | | —COO— | | |
| Lc-197 | | | —COO— | 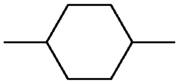 | —COO— | | —O— | | |
| Lc-198 | | | | | —OCO— | | —O— | | |
| Lc-199 | | | | | —COO— | | —OCO— | | |
| Lc-200 | | | | | —OCO— | | —OCO— | | |
| Lc-201 | | | | | —COO— | | —OCOO— | | |
| Lc-202 | | | | | —OCO— | | —OCOO— | | |
| Lc-203 | | | | | —COO— | | —COO— | | |
| Lc-204 | | | | | —OCO— | | —COO— | | |
| Lc-205 | —OCO— | 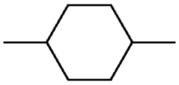 | —OCO— | 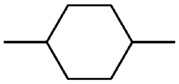 | —COO— | 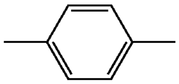 | —O— | —$(CH_2)_n$— | Formula (Z-1) |
| Lc-206 | | | | | —OCO— | | —O— | | |
| Lc-207 | | | | | —COO— | | —OCO— | | |
| Lc-208 | | | | | —OCO— | | —OCO— | | |
| Lc-209 | | | | | —COO— | | —OCOO— | | |
| Lc-210 | | | | | —OCO— | | —OCOO— | | |

TABLE 5-continued

| Lc1/ | | | m1/m2 = 2 | | | | | | |
|---|---|---|---|---|---|---|---|---|---|
| Lc2 | $L^1/L^2$ | $A^1/A^2$ | $L^3/L^4$ | $A^3/A^4$ | $L^3/L^4$ | $A^3/A^4$ | $L^5$ | $R^{sp1}$ | $Z^1$ |
| Lc-211 | | | | | —COO— | | —COO— | | |
| Lc-212 | | | | | —OCO— | | —COO— | | |
| Lc-213 | | | —COO— | 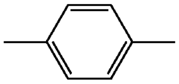 | —COO— | 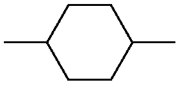 | —O— | | |
| Lc-214 | | | | | —OCO— | | —O— | | |
| Lc-215 | | | | | —COO— | | —OCO— | | |
| Lc-216 | | | | | —OCO— | | —OCO— | | |
| Lc-217 | —OCO— | 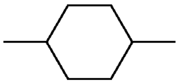 | —COO— | 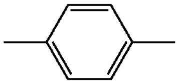 | —COO— | 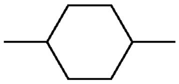 | —OCOO— | $—(CH_2)_n—$ | Formula (Z-1) |
| Lc-218 | | | | | —OCO— | | —OCOO— | | |
| Lc-219 | | | | | —COO— | | —COO— | | |
| Lc-220 | | | | | —OCO— | | —COO— | | |
| Lc-221 | | | —OCO— | | —COO— | | —O— | | |
| Lc-222 | | | | | —OCO— | | —O— | | |
| Lc-223 | | | | | —COO— | | —OCO— | | |
| Lc-224 | | | | | —OCO— | | —OCO— | | |
| Lc-225 | | | | | —COO— | | —OCOO— | | |
| Lc-226 | | | | | —OCO— | | —OCOO— | | |
| Lc-227 | | | | | —COO— | | —COO— | | |
| Lc-228 | | | | | —OCO— | | —COO— | | |

TABLE 6

| Lc1/ | | | m1/m2 = 2 | | | | | | |
|---|---|---|---|---|---|---|---|---|---|
| Lc2 | $L^1/L^2$ | $A^1/A^2$ | $L^3/L^4$ | $A^3/A^4$ | $L^3/L^4$ | $A^3/A^4$ | $L^5$ | $R^{sp1}$ | $Z^1$ |
| Lc-229 | —OCO— | 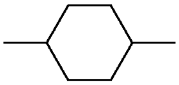 | —COO— | 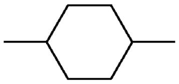 | —COO— | 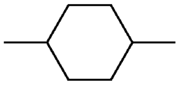 | —O— | $—(CH_2)_n—$ | Formula (Z-1) |
| Lc-230 | | | | | —OCO— | | —O— | | |
| Lc-231 | | | | | —COO— | | —OCO— | | |
| Lc-232 | | | | | —OCO— | | —OCO— | | |
| Lc-233 | | | | | —COO— | | —OCOO— | | |
| Lc-234 | | | | | —OCO— | | —OCOO— | | |
| Lc-235 | | | | | —COO— | | —COO— | | |
| Lc-236 | | | | | —OCO— | | —COO— | | |
| Lc-237 | | | —OCO— | | —COO— | | —O— | | |

TABLE 6-continued

| Lc1/ | | | | m1/m2 = 2 | | | | | |
|---|---|---|---|---|---|---|---|---|---|
| Lc2 | $L^1/L^2$ | $A^1/A^2$ | $L^3/L^4$ | $A^3/A^4$ | $L^3/L^4$ | $A^3/A^4$ | $L^5$ | $R^{sp1}$ | $Z^1$ |
| Lc-238 | | | | | —OCO— | | —O— | | |
| Lc-239 | | | | | —COO— | | —OCO— | | |
| Lc-240 | | | | | —OCO— | | —OCO— | | |
| Lc-241 | | | | | —COO— | | —OCOO— | | |
| Lc-242 | | | | | —OCO— | | —OCOO— | | |
| Lc-243 | | | | | —COO— | | —COO— | | |
| Lc-244 | | | | | —OCO— | | —COO— | | |

For the groups represented by the above-listed Lc-1 to Lc-244, m1 and m2 in $L^3$ and $L^4$ represent 1 or 2 and are preferably 2. Also, n in $R^{sp1}$ represents 1 to 20. In particular, n in $R^{sp1}$ preferably 2 or more, and more preferably 4 or more. On the other hand, n in $R^{sp1}$ is preferably 12 or less, and more preferably 10 or less.

For $Z^1$, $R^z$ in the formula (Z-1) is each independently preferably a hydrogen atom or a methyl group, and more preferably a hydrogen atom.

In the general formula (D-1), $G^1$ represents a hydrogen atom or an alkyl group containing 1 to 6 carbon atoms, and the alkyl group is optionally unsubstituted or substituted by at least one substituent group E. In particular, the substituent group E is preferably F, Cl, $CF_3$, $OCF_3$ or a cyano group. $G^1$ is preferably a hydrogen atom or an alkyl group containing 1 to 6 carbon atoms and being unsubstituted or substituted by at least one F. $G^1$ is more preferably a hydrogen atom.

$Q^1$ represents an organic group containing 2 to 30 carbon atoms and an aromatic hydrocarbon group in which any carbon atom of the aromatic hydrocarbon group is optionally substituted by a heteroatom. $Q^1$ represents an organic group containing 2 to 30 carbon atoms and at least one aromatic ring selected from the group consisting of an aromatic hydrocarbon ring and an aromatic heterocycle. The aromatic ring is preferably a group selected from the following formulae (Q-1) to (Q-22).

From the viewpoint of excellent wavelength dispersion property, $Q^1$ is preferably an organic group containing an aromatic heterocycle in which at least one carbon atom is substituted by a heteroatom. From the viewpoint of excellent wavelength dispersion property and high birefringence, $Q^1$ is more preferably an organic group having an aromatic heterocycle that is a condensed ring of a 5-membered ring and a 6-membered ring.

For example, the aromatic heterocycle that is a condensed ring of a 5-membered ring and a 6-membered ring, is preferably an aromatic heterocycle in which at least one carbon atom of a group selected from the following formulae (Q-10), (Q-11), (Q-21) and (Q-22) is substituted by a heteroatom.

(Q-1)

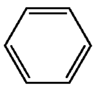

-continued (Q-2)

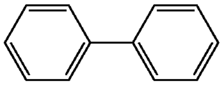

(Q-3)

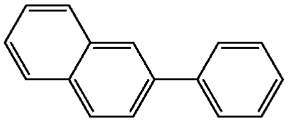

(Q-4)

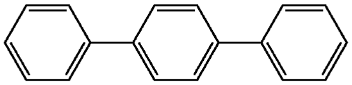

(Q-5)

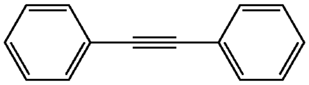

(Q-6)

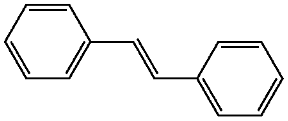

(Q-7)

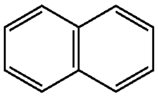

(Q-8)

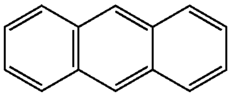

(Q-9)

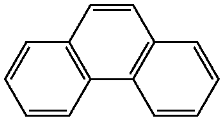

(Q-10)

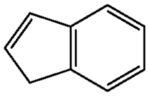

(Q-11)

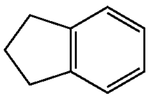

-continued (Q-12)

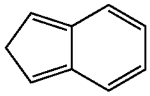

(Q-13)

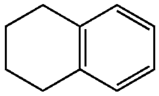

(Q-14)

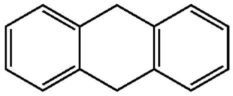

(Q-15)

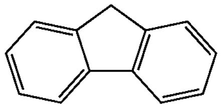

(Q-16)

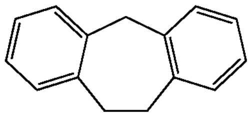

(Q-17)

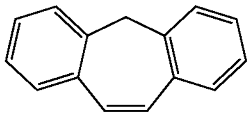

(Q-18)

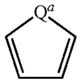

(Q-19)

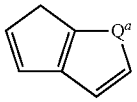

(Q-20)

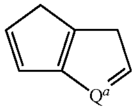

(Q-21)

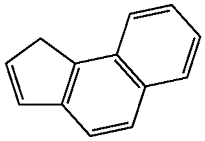

(Q-22)

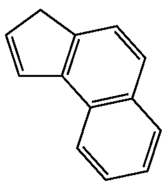

These groups contain a bond at any position thereof. $Q^a$ represents —O—, —S—, —$NR^{Qa}$— (where $R^{Qa}$ represents a hydrogen atom or an alkyl group containing 1 to 8 carbon atoms) or —CO—. Also, —CH═ in these groups is each independently optionally substituted by —N═, and —$CH_2$— is each independently optionally substituted by —O—, —S—, —$NR^{Qa}$— (where $R^{Qa}$ represents a hydrogen atom or an alkyl group containing 1 to 8 carbon atoms), —SO—, —$SO_2$— or —CO— (except in cases where oxygen atoms are directly bound to each other). At least one hydrogen atom bound to these rings is optionally substituted by the substituent group E. Examples of an alkyl group constituting the alkyl group include a methyl group, an ethyl group, a propyl group, an isopropyl group, a butyl group, an isobutyl group, a sec-butyl group, a tert-butyl group, a pentyl group and a hexyl group. The number of carbon atoms of the alkyl group is preferably from 1 to 4, more preferably 1 or 2, and even more preferably 1.

The group represented by the formula (Q-1) preferably represents a group which is selected from the following formulae (Q-1-1) to (Q-1-8) and which is optionally unsubstituted or substituted by at least one substituent group E. These groups contain a bond at any position thereof.

(Q-1-1)

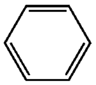

(Q-1-2)

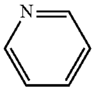

(Q-1-3)

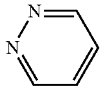

(Q-1-4)

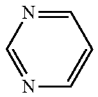

(Q-1-5)

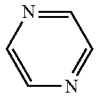

(Q-1-6)

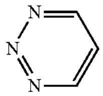

(Q-1-7)

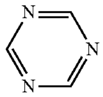

(Q-1-8)

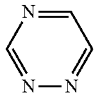

The group represented by the formula (Q-7) preferably represents a group which is selected from the following formulae (Q-7-1) to (Q-7-7) and which is optionally unsubstituted or substituted by at least one substituent group E. These groups contain a bond at any position thereof.

(Q-7-1)

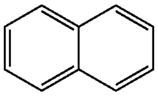

-continued (Q-7-2)

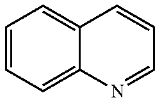

(Q-7-3)

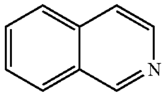

(Q-7-4)

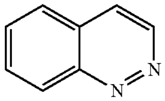

(Q-7-5)

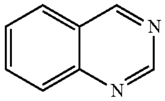

(Q-7-6)

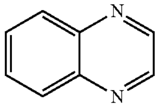

(Q-7-7)

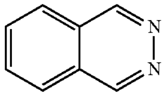

The group represented by the formula (Q-10) preferably represents a group which is selected from the following formulae (Q-10-1) to (Q-10-9) and which is optionally unsubstituted or substituted by at least one substituent group E.

(Q-10-1)

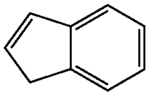

(Q-10-2)

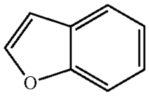

(Q-10-3)

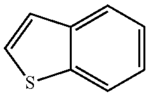

(Q-10-4)

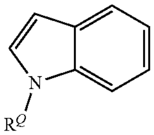

(Q-10-5)

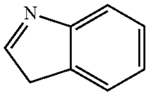

(Q-10-6)

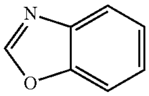

-continued (Q-10-7)

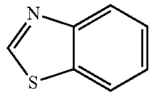

(Q-10-8)

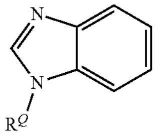

(Q-10-9)

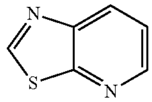

In the above formulae, $R^Q$ represents a hydrogen atom or an alkyl group containing 1 to 6 carbon atoms. These groups contain a bond at any position thereof.

The group represented by the formula (Q-11) preferably represents a group which is selected from the following formulae (Q-11-1) to (Q-11-12) and which is optionally unsubstituted or substituted by at least one substituent group E.

(Q-11-1)

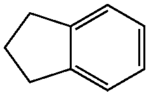

(Q-11-2)

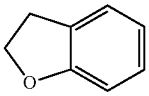

(Q-11-3)

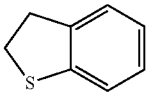

(Q-11-4)

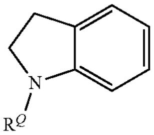

(Q-11-5)

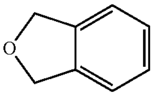

(Q-11-6)

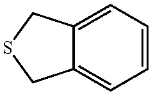

(Q-11-7)

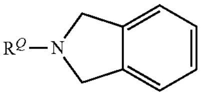

(Q-11-8)

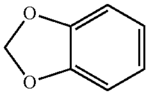

-continued (Q-11-9)

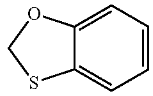

(Q-11-10)

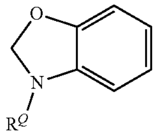

(Q-11-11)

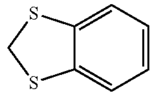

(Q-11-12)

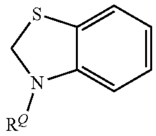

In the above formulae, $R^Q$ represents a hydrogen atom or an alkyl group containing 1 to 6 carbon atoms. These groups contain a bond at any position thereof.

The group represented by the formula (Q-13) preferably represents a group which is selected from the following formulae (Q-13-1) to (Q-13-19) and which is optionally unsubstituted or substituted by at least one substituent group E.

(Q-13-1)

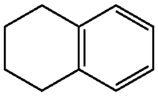

(Q-13-2)

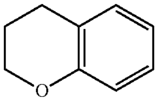

(Q-13-3)

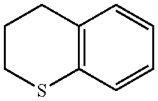

(Q-13-4)

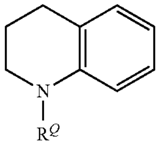

(Q-13-5)

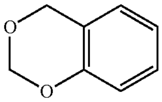

(Q-13-6)

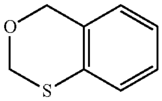

-continued (Q-13-7)

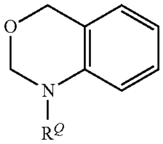

(Q-13-8)

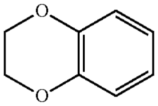

(Q-13-9)

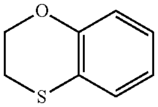

(Q-13-10)

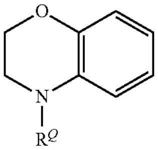

(Q-13-11)

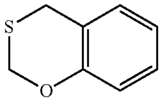

(Q-13-12)

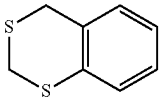

(Q-13-13)

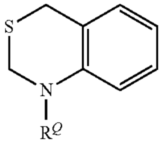

(Q-13-14)

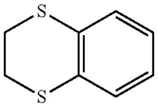

(Q-13-15)

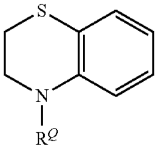

(Q-13-16)

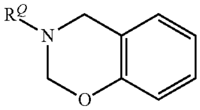

(Q-13-17)

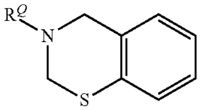

-continued (Q-13-18)

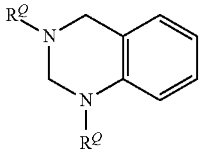

(Q-13-19)

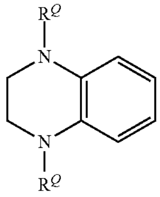

In the above formulae, $R^Q$ represents a hydrogen atom or an alkyl group containing 1 to 6 carbon atoms. These groups contain a bond at any position thereof.

The group represented by the formula (Q-14) preferably represents a group which is selected from the following formulae (Q-14-1) to (Q-14-10) and which is optionally unsubstituted or substituted by at least one substituent group E.

(Q-14-1)

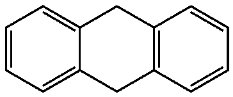

(Q-14-2)

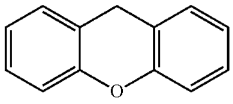

(Q-14-3)

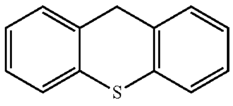

(Q-14-4)

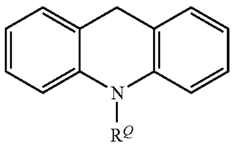

(Q-14-5)

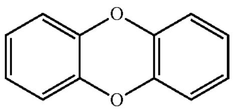

(Q-14-6)

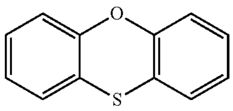

(Q-14-7)

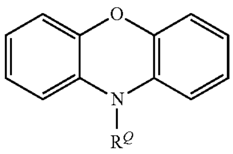

-continued (Q-14-8)

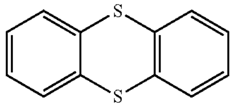

(Q-14-9)

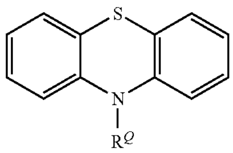

(Q-14-10)

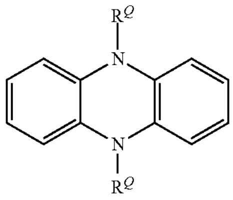

In the above formulae, $R^Q$ represents a hydrogen atom or an alkyl group containing 1 to 6 carbon atoms. These groups contain a bond at any position thereof.

The group represented by the formula (Q-15) preferably represents a group which is selected from the following formulae (Q-15-1) to (Q-15-4) and which is optionally unsubstituted or substituted by at least one substituent group E.

(Q-15-1)

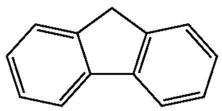

(Q-15-2)

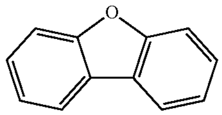

(Q-15-3)

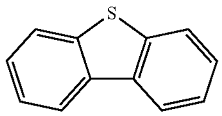

(Q-15-4)

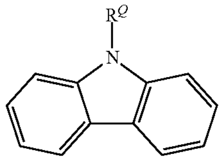

In the above formulae, $R^Q$ represents a hydrogen atom or an alkyl group containing 1 to 6 carbon atoms. These groups contain a bond at any position thereof.

The group represented by the formula (Q-16) preferably represents a group which is selected from the following formulae (Q-16-1) to (Q-16-16) and which is optionally unsubstituted or substituted by at least one substituent group E.

(Q-16-1)

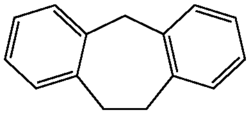

(Q-16-2)

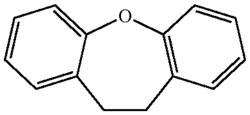

(Q-16-3)

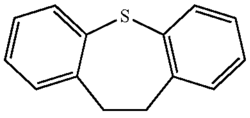

(Q-16-4)

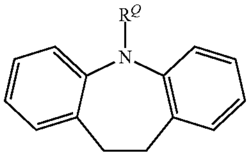

(Q-16-5)

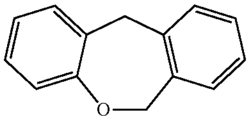

(Q-16-6)

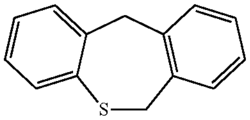

(Q-16-7)

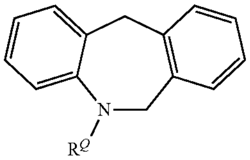

(Q-16-8)

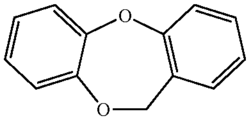

(Q-16-9)

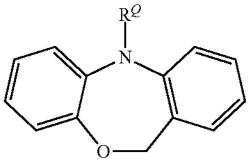

(Q-16-10)

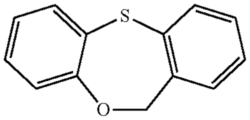

(Q-16-11)

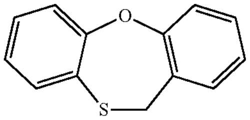

-continued (Q-16-12)

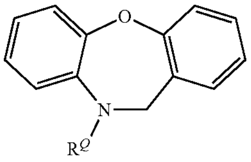

(Q-16-13)

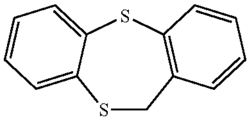

(Q-16-14)

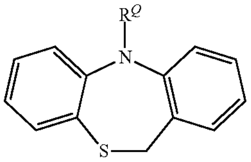

(Q-16-15)

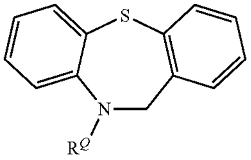

(Q-16-16)

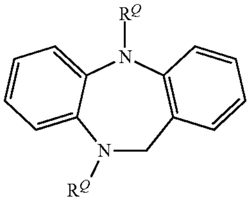

In the above formulae, $R^Q$ represents a hydrogen atom or an alkyl group containing 1 to 6 carbon atoms. These groups contain a bond at any position thereof.

The group represented by the formula (Q-17) preferably represents a group which is selected from the following formulae (Q-17-1) to (Q-17-4) and which is optionally unsubstituted or substituted by at least one substituent group E.

(Q-17-1)

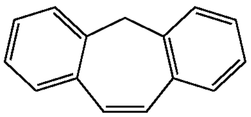

(Q-17-2)

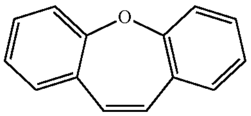

(Q-17-3)

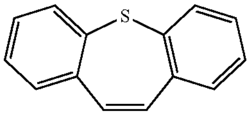

-continued (Q-17-4)

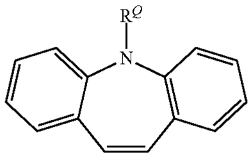

In the above formulae, $R^Q$ represents a hydrogen atom or an alkyl group containing 1 to 6 carbon atoms. These groups contain a bond at any position thereof.

The group represented by the formula (Q-18) preferably represents a group which is selected from the following formulae (Q-18-1) to (Q-18-6) and which is optionally unsubstituted or substituted by at least one substituent group E.

(Q-18-1)

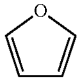

(Q-18-2)

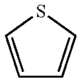

(Q-18-3)

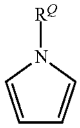

(Q-18-4)

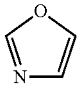

(Q-18-5)

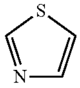

(Q-18-6)

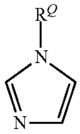

In the above formulae, $R^Q$ represents a hydrogen atom or an alkyl group containing 1 to 6 carbon atoms. These groups contain a bond at any position thereof.

The group represented by the formula (Q-19) preferably represents a group which is selected from the following formulae (Q-19-1) to (Q-19-6) and which is optionally unsubstituted or substituted by at least one substituent group E.

(Q-19-1)

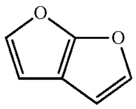

-continued (Q-19-2)

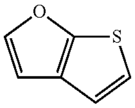

(Q-19-3)

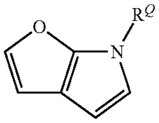

(Q-19-4)

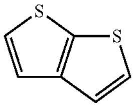

(Q-19-5)

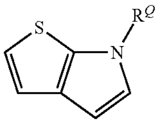

(Q-19-6)

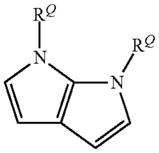

In the above formulae, $R^Q$ represents a hydrogen atom or an alkyl group containing 1 to 6 carbon atoms. These groups contain a bond at any position thereof.

The group represented by the formula (Q-20) preferably represents a group which is selected from the following formulae (Q-20-1) to (Q-20-9) and which is optionally unsubstituted or substituted by at least one substituent group E.

(Q-20-1)

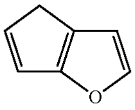

(Q-20-2)

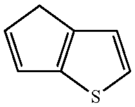

(Q-20-3)

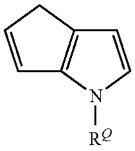

(Q-20-4)

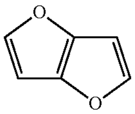

(Q-20-5)

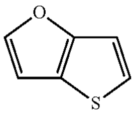

-continued (Q-20-6)

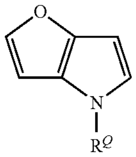

(Q-20-7)

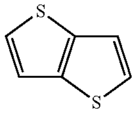

(Q-20-8)

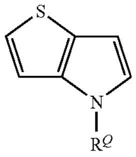

(Q-20-9)

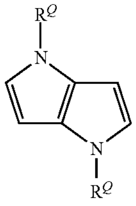

In the above formulae, $R^Q$ represents a hydrogen atom or an alkyl group containing 1 to 6 carbon atoms. These groups contain a bond at any position thereof.

The group represented by the formula (Q-21) preferably represents a group which is selected from the following formulae (Q-21-1) to (Q-21-3) and which is optionally unsubstituted or substituted by at least one substituent group E.

The group represented by the formula (Q-22) preferably represents a group which is selected from the following formulae (Q-22-1) to (Q-22-3) and which is optionally unsubstituted or substituted by at least one substituent group E.

(Q-21-1)

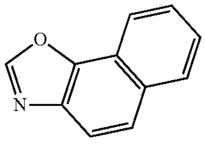

(Q-21-2)

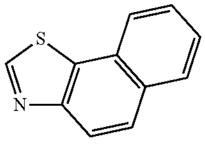

(Q-21-3)

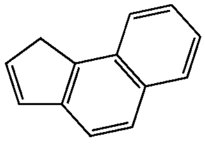

-continued (Q-22-1)

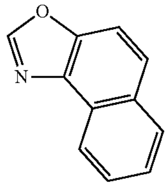

(Q-22-2)

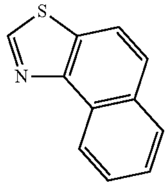

(Q-22-3)

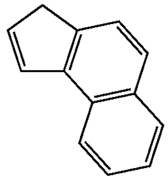

The aromatic group contained in $Q^1$ more preferably represents a group which is selected from the formulae (Q-1-1), (Q-7-1), (Q-7-2), (Q-7-7), (Q-8), (Q-10-2), (Q-10-3), (Q-10-4), (Q-10-5), (Q-10-6), (Q-10-7), (Q-10-8), (Q-10-9), (Q-11-2), (Q-11-3), (Q-11-4), (Q-11-5), (Q-11-6), (Q-11-7), (Q-11-8), (Q-11-9), (Q-11-10), (Q-11-11), (Q-11-12), (Q-21-1), (Q-21-2), (Q-22-1) and (Q-22-2) and which is optionally unsubstituted or substituted by at least one substituent group E. The aromatic group contained in $Q^1$ particularly preferably represents a group which is selected from the formulae (Q-10-2), (Q-10-3), (Q-10-4), (Q-10-5), (Q-10-6), (Q-10-7), (Q-10-8), (Q-10-9), (Q-21-1), (Q-21-2), (Q-22-1) and (Q-22-2) and which is optionally unsubstituted or substituted by at least one substituent group E.

In particular, the substituent group $E^Q$ in the case where the aromatic group contained in $Q^1$ is substituted, is preferably a fluorine atom, a chlorine atom, a bromine atom, an iodine atom, a nitro group, a cyano group, an isocyano group, an amino group, a hydroxyl group, a mercapto group, a methylamino group, a dimethylamino group, a diethylamino group, a diisopropylamino group, a thioisocyano group, or a linear or branched alkyl group containing 1 to 20 carbon atoms, in which one $—CH_2—$ or two or more non-adjacent $—CH_2—$ are each independently optionally substituted by —O—, —S—, —CO—, —COO—, —OCO—, —CO—S—, —S—CO—, —O—CO—O—, —CO—NH— or —NH—CO—, and in which any hydrogen atom in the alkyl group is optionally substituted by a fluorine atom. The substituent group $E^Q$ is more preferably a fluorine atom, a chlorine atom, a bromine atom, or a linear or branched alkyl group containing 1 to 20 carbon atoms, in which one $—CH_2—$ or two or more non-adjacent $—CH_2—$ are each independently optionally substituted by —O—, —S—, —CO—, —COO—, —OCO—, —CO—S—, —S—CO—, —O—CO—O—, —CO—NH— or —NH—CO—, and in which any hydrogen atom in the alkyl group is optionally substituted by a fluorine atom.

Also, $Q^1$ particularly preferably represents a group selected from the following formulae (Q-10-2), (Q-10-2a), (Q-10-3), (Q-10-3a), (Q-10-3b), (Q-10-6), (Q-10-6a), (Q-10-6b), (Q-10-6c), (Q-10-6d), (Q-10-7), (Q-10-7a), (Q-10-7b), (Q-10-7c), (Q-10-7d), (Q-10-7e), (Q-10-7f), (Q-10-9), (Q-10-9a), (Q-10-9b), (Q-21-1), (Q-21-2), (Q-22-1) and (Q-22-2).
(Q-10-2)
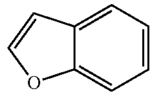
(Q-10-2-a)
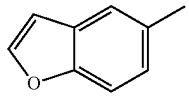
(Q-10-3)
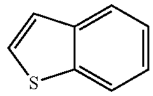
(Q-10-3-a)
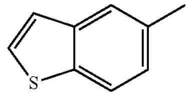
(Q-10-3-b)
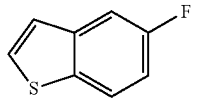
(Q-10-6)
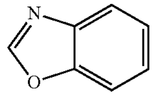
(Q-10-6-a)
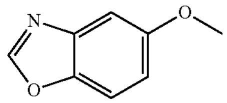
(Q-10-6-b)
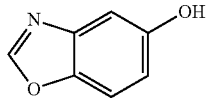
(Q-10-6-c)
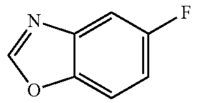
(Q-10-6-d)
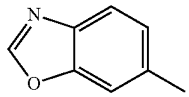
(Q-10-7)
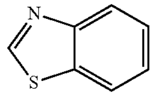
(Q-10-7-a)
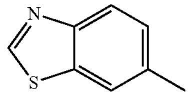
(Q-10-7-b)
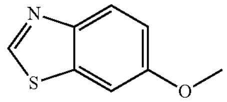
-continued
(Q-10-7-c)
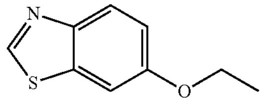
(Q-10-7-d)
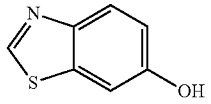
(Q-10-7-e)
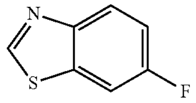
(Q-10-7-f)
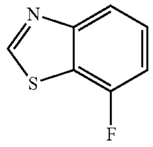
(Q-10-9)
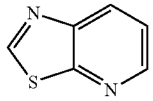
(Q-10-9-a)
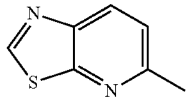
(Q-10-9-b)
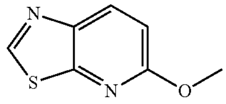
(Q-21-1)
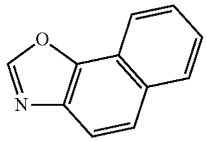
(Q-21-2)
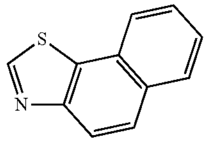
(Q-22-1)
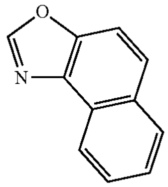
(Q-22-2)
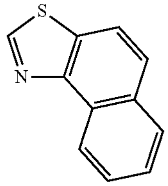
$J^1$ represents —O—, —S—, —COO—, —OCO—, —OCO—O—, —$NQ^2$-, —N═$CQ^2$-, —CO—$NQ^2$-, —OCO—$NQ^2$- or —O—$NQ^2$-; $Q^2$ represents a hydrogen atom, an alkyl group containing 1 to 20 carbon atoms, a cycloalkyl group containing 3 to 12 carbon atoms, a cycloalkenyl group containing 3 to 12 carbon atoms, an organic group containing 2 to 30 carbon atoms and an aromatic hydrocarbon group (any carbon atom of the aromatic hydrocarbon group is optionally substituted by a heteroatom) or $-(L^6-A^5)_q-L^7-R^{sp2}—Z^2$; the alkyl group, the cycloalkyl group, the cycloalkenyl group and the aromatic hydrocarbon group are each optionally unsubstituted or substituted by at least one substituent group E; the alkyl group is optionally substituted by the cycloalkyl group or the cycloalkenyl group; one $—CH_2—$ or two or more non-adjacent $—CH_2—$ in the alkyl group are each independently optionally substituted by —O—, —S—, —CO—, —COO—, —OCO—, —CO—S—, —S—CO—, $—SO_2—$, —O—CO—O—, —CO—NH—, —NH—CO—, —CH═CH—COO—, —CH═CH—OCO—, —COO—CH═CH—, —OCO—CH═CH—, —CH═CH—, —CF═CF— or —C≡C—; one $—CH_2—$ or two or more non-adjacent $—CH_2—$ in the cycloalkyl or cycloalkenyl group are each independently optionally substituted by —O—, —CO—, —COO—, —OCO— or —O—CO—O—; $L^6$, $A^5$, $L^7$, $R^{sp2}$ and $Z^2$ represent the same as those defined above as $L^1$ to $L^4$, $A^1$ to $A^4$, $L^5$, $R^{sp1}$ and $Z^1$, respectively, and $L^6$, $A^5$, $L^7$, $R^{sp2}$ and $Z^2$ are optionally the same as or different from $L^1$ to $L^4$, $A^1$ to $A^4$, $L^5$, $R^{sp1}$ and $Z^1$, respectively; q is an integer of 0 to 4; when plural $L^b$s, as well as plural $A^5$s, are present, they are optionally the same or different from each other.

From the viewpoint of excellent birefringence and easy synthesis, in particular, $J^1$ is preferably —O—, —S—, $—N═CQ^2-$ or $—NQ^2-$. From the viewpoint of excellent wavelength dispersion property and birefringence, $J^1$ is more preferably —O—, —S— or $—NQ^2-$.

As used herein, $Q^2$ preferably represents any one of the following: an alkyl or alkenyl group containing 1 to 20 carbon atoms, which is optionally substituted by at least one substituent group E, and in which one $—CH_2—$ or two or more non-adjacent $—CH_2—$ are each independently optionally substituted by —O—, —CO—, —COO—, —OCO— or —O—CO—O—; a cycloalkyl group containing 3 to 12 carbon atoms, which is optionally substituted by at least one substituent group E, and in which one $—CH_2—$ or two or more non-adjacent $—CH_2—$ are each independently optionally substituted by —O—, —CO—, —COO—, —OCO— or —O—CO—O—; a cycloalkenyl group containing 3 to 12 carbon atoms, which is optionally substituted by at least one substituent group E, and in which one $—CH_2—$ or two or more non-adjacent $—CH_2—$ are each independently optionally substituted by —O—, —CO—, —COO—, —OCO— or —O—CO—O—; the alkyl or alkenyl group which is optionally substituted by the cycloalkyl, cycloalkenyl or aryl group; and $-(L^6-A^5)$ $q-L^7-R^{sp2}—Z^2$.

$Q^2$ may be appropriately selected depending on the intended purpose of use. For example, $Q^2$ is preferably a structure not containing a heteroatom, from the viewpoint of birefringence. $Q^2$ is preferably a structure containing more heteroatoms, and $Q^2$ particularly preferably contains a structure in which one $—CH_2—$ or two or more non-adjacent $—CH_2—$ are each independently substituted by —O—, —CO—, —COO—, —OCO— or —O—CO—O—, from the point of view that the solvent solubility of the compound is improved, and the substrate to be used in combination can be selected from a wide selection. Also, $Q^2$ is preferably $-(L^6-A^5)$ $q-L^7-R^{sp2}—Z^2$, from the point of view that the hardness of the film is improved to improve the durability.

As the unsubstituted alkyl or alkenyl group containing 1 to 20 carbon atoms, the cycloalkyl group containing 3 to 12 carbon atoms, the cycloalkenyl group containing 3 to 12 carbon atoms, and the alkyl or alkenyl group which is optionally substituted by the cycloalkyl, cycloalkenyl or aryl group, examples include a methyl group, an ethyl group, an n-propyl group, an isopropyl group, an n-butyl group, a sec-butyl group, a t-butyl group, an n-pentyl group, an n-hexyl group, a 1-methylpentyl group, an n-heptyl group, a 1-ethylpentyl group, an n-octyl group, a 2-ethylhexyl group, an n-nonyl group, an n-decyl group, a 3,7-dimethyloctyl group, an n-undecyl group, an n-dodecyl group, a vinyl group, an allyl group, an isopropenyl group, a butynyl group, a cyclopentyl group, a cyclohexyl group, a cyclopentenyl group, a cyclohexenyl group, a cyclooctenyl group, a cyclopentylmethyl group, a cyclohexylmethyl group and a benzyl group.

In particular, the substituent group in $Q^2$ is preferably a fluorine atom, a chlorine atom, a bromine atom, a cyano group, a hydroxyl group, a mercapto group, a methylamino group, a dimethylamino group, a diethylamino group, a diisopropylamino group, or a linear or branched alkyl group containing 1 to 20 carbon atoms, in which one $—CH_2—$ or two or more non-adjacent $—CH_2—$ are each independently optionally substituted by —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF— or —C≡C—. The substituent group in $Q^2$ is more preferably a fluorine atom, a chlorine atom, a cyano group, a hydroxyl group, or a linear or branched alkyl group containing 1 to 20 carbon atoms, in which one $—CH_2—$ or two or more non-adjacent $—CH_2—$ are each independently optionally substituted by —O—, —CO—, —COO—, —OCO— or —O—CO—O—.

From the viewpoint of birefringence, solvent solubility or durability, $Q^2$ preferably represents any one of the following: an alkyl or alkenyl group containing 1 to 20 carbon atoms, which is optionally substituted by at least one substituent group E, and in which one $—CH_2—$ or two or more non-adjacent $—CH_2—$ are each independently optionally substituted by —O—, —CO—, —COO—, —OCO— or —O—CO—O—; a cycloalkyl group containing 3 to 12 carbon atoms, which is optionally substituted by at least one substituent group E, and in which one $—CH_2—$ or two or more non-adjacent $—CH_2—$ are each independently optionally substituted by —O—, —CO—, —COO—, —OCO— or —O—CO—O—; a cycloalkenyl group containing 3 to 12 carbon atoms, which is optionally substituted by at least one substituent group E, and in which one $—CH_2—$ or two or more non-adjacent $—CH_2—$ are each independently optionally substituted by —O—, —CO—, —COO—, or —O—CO—O—; the alkyl or alkenyl group which is optionally substituted by the cycloalkyl or cycloalkenyl group; and $-(L^6-A^5)q-L^7-R^{sp2}—Z^2$. $Q^2$ more preferably represents any one of the following: a linear or branched alkyl group containing 1 to 20 carbon atoms, in which any hydrogen atom is optionally substituted by a fluorine atom, and in which one $—CH_2—$ or two or more non-adjacent $—CH_2—$ are each independently optionally substituted by —O—, —CO—, —COO— or —OCO—; a cycloalkyl group containing 3 to 12 carbon atoms, in which any hydrogen atom is optionally substituted by a fluorine atom, and in which one $—CH_2—$ or two or more non-adjacent $—CH_2—$ are each independently optionally substituted by —O—, —CO—, —OCO— or —OCO—, or the alkyl group which is optionally substituted by the cycloalkyl group; and $-(L^6-A^5)q-L^7-R^{sp2}—Z^2$. $Q^2$ even more preferably represents any one of the following: a linear or branched alkyl group containing 1 to 12 carbon atoms, in which one $—CH_2—$ or two or more non-adjacent $—CH_2—$ are each independently optionally substituted by —O—; a cycloalkyl group containing 3 to 12 carbon atoms, in which one $—CH_2—$ or two or more non-adjacent $—CH_2—$ are each independently optionally substituted by —O—; the alkyl group which is optionally substituted by the cycloalkyl group; or $-(L^6-A^5)$ $q-L^7-R^{sp2}—Z^2$.

The preferred structure of $-(L^6-A^5)q-L^7-R^{sp2}—Z^2$ is favorably the same as the preferred structures defined above in relation to $L^1$ to $L^4$, $A^1$ to $A^4$, $L^5$, $R^{sp1}$ and $Z^1$. In this structure, q represents an integer of from 0 to 4, preferably an integer of from 0 to 2, more preferably an integer of 0 or 1, and particularly preferably 0.

From the viewpoint of birefringence and solvent solubility, in particular, $Q^2$ is preferably a linear or branched alkyl group containing 2 to 20 carbon atoms, in which a hydrogen atom is optionally substituted by a fluorine atom, and in which one $—CH_2—$ or two or more non-adjacent $—CH_2—$ are each independently optionally substituted by —O—, —CO—, —COO— or —OCO—, a cycloalkyl group containing 3 to 12 carbon atoms, in which a hydrogen atom is optionally substituted by a fluorine atom, and in which one $—CH_2—$ or two or more non-adjacent $—CH_2—$ are each independently optionally substituted by —O—, —CO—, —COO— or —OCO—, or the alkyl group which is optionally substituted by the cycloalkyl group, more preferably a linear or branched alkyl group containing 2 to 20 carbon atoms, in which a hydrogen atom is optionally substituted by a fluorine atom, and in which one $—CH_2—$ or two or more non-adjacent $—CH_2—$ are each independently substituted by —O—, —CO—, —COO— or —OCO—, and even more preferably a linear alkyl group containing 2 to 20 carbon atoms, in which a hydrogen atom is optionally substituted by a fluorine atom, and in which one $—CH_2—$ or two or more non-adjacent $—CH_2—$ are each independently optionally substituted by —O—, —CO—, —COO— or —OCO—.

The number of carbon atoms of $Q^2$ is preferably 4 or more, and more preferably 12 or less.

$Q^1$ and $Q^2$ are optionally bound to form a ring. In this case, examples include a cyclic group represented by $—NQ^1Q^2$ or $—N{=}CQ^1Q^2$. As the ring formed by $Q^1$, $Q^2$ and the nitrogen or carbon atom to which $Q^1$ and $Q^2$ are bound, examples include a ring which contains an aromatic ring and which contains 2 to 30 carbon atoms, preferably from 2 to 18, and more preferably from 2 to 14. In particular, the cyclic group represented by $—NQ^1Q^2$ preferably represents a group which is selected from the following formulae (QQ-1) to (QQ-22) and which is optionally unsubstituted or substituted by at least one substituent group E. The cyclic group represented by $—N{=}CQ^1Q^2$ preferably represents the following formula (QQ-23) or (QQ-24).

(QQ-1)

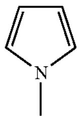

(QQ-2)

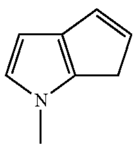

-continued (QQ-3)

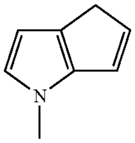

(QQ-4)

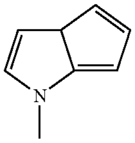

(QQ-5)

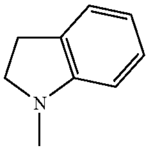

(QQ-6)

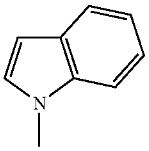

(QQ-7)

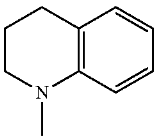

(QQ-8)

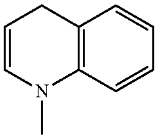

(QQ-9)

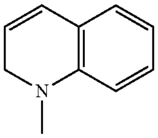

(QQ-10)

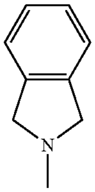

(QQ-11)

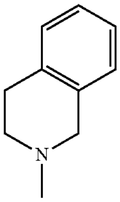

-continued (QQ-12)

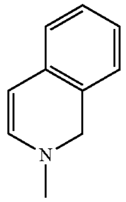

(QQ-13)

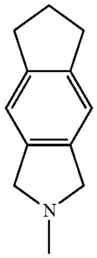

(QQ-14)

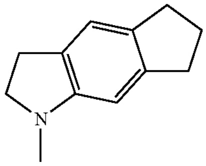

(QQ-15)

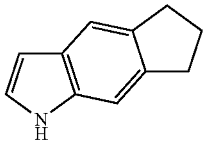

(QQ-16)

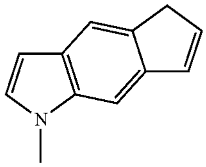

(QQ-17)

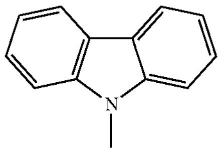

(QQ-18)

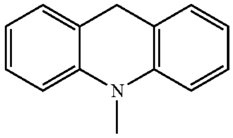

(QQ-19)

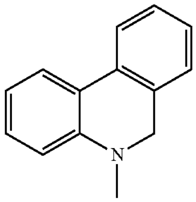

-continued (QQ-20)

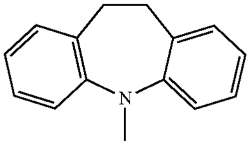

(QQ-21)

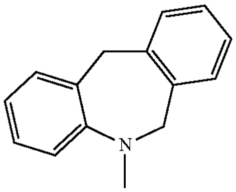

(QQ-22)

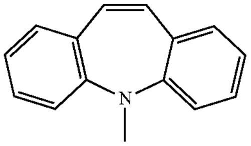

(QQ-23)

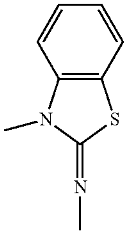

(QQ-24)

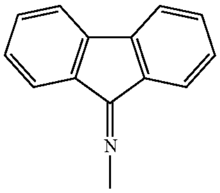

Also, —CH= in the group selected from the formulae (QQ-1) to (QQ-22) is each independently optionally substituted by —N=, and —$CH_2$— is each independently optionally substituted by —O—, —S—, —$NR^{Q2}$— (where $R^{Q2}$ represents a hydrogen atom or an alkyl group containing 1 to 8 carbon atoms), —SO—, —$SO_2$— or —CO— (except in cases where oxygen atoms are directly bound to each other). At least one hydrogen atom bound to these rings is optionally substituted by the substituent group E. Examples of an alkyl group constituting the alkyl group include a methyl group, an ethyl group, a propyl group, an isopropyl group, a butyl group, an isobutyl group, a sec-butyl group, a tert-butyl group, a pentyl group and a hexyl group. The number of carbon atoms of the alkyl group is preferably from 1 to 4, more preferably 1 or 2, and even more preferably 1.

From the viewpoint of wavelength dispersion property, liquid crystallinity and easy synthesis, the total number of π electrons contained in $J^1$ and $Q^1$ is preferably from 4 to 24, and more preferably from 4 to 20.

From the viewpoint of availability of raw materials, excellent solubility and high birefringence index, $D^2$ and $D^2$ each represent particularly preferably a group selected from the following formulae (D-1) to (D-47).

(D-1)
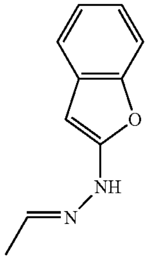
(D-2)
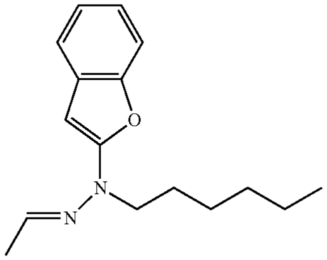
(D-3)
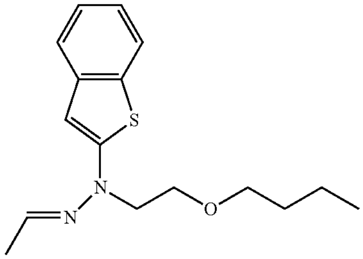
(D-4)
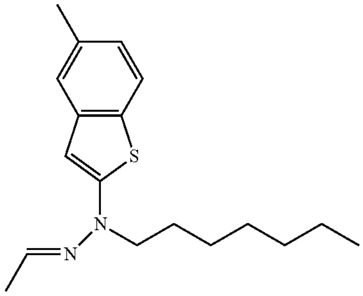
(D-5)
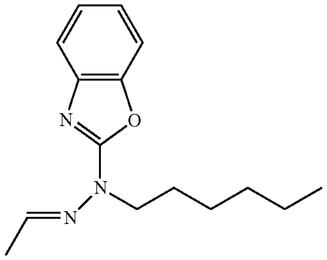
(D-6)
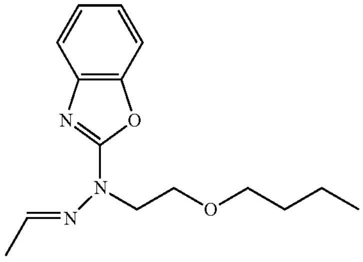
-continued
(D-7)
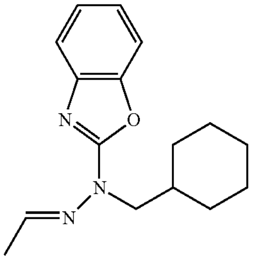
(D-8)
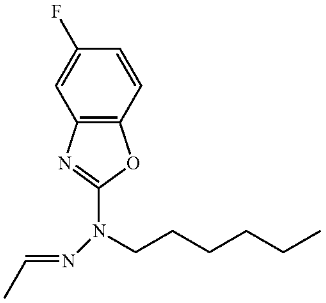
(D-9)
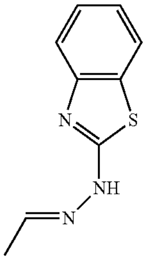
(D-10)
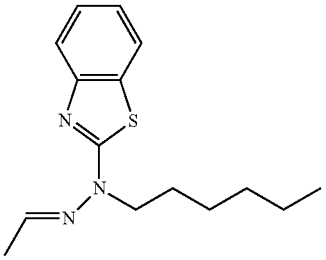
(D-11)
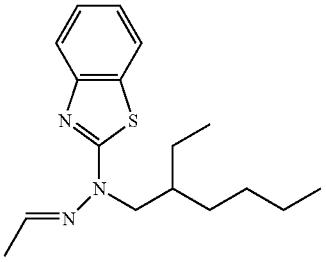
(D-12)
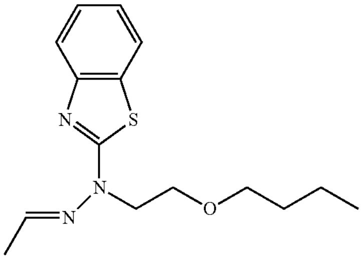

-continued
(D-13)
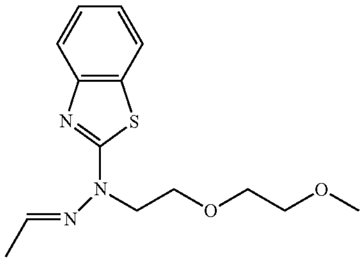
(D-14)
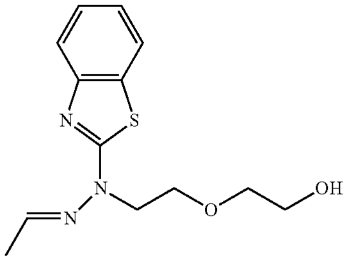
(D-15)
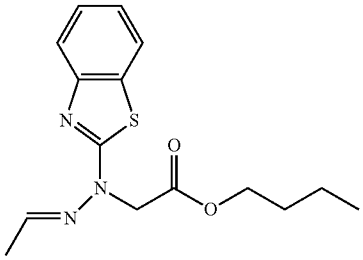
(D-16)
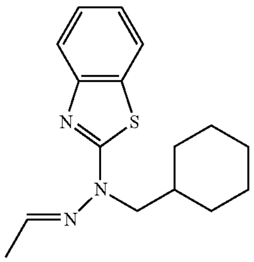
(D-17)
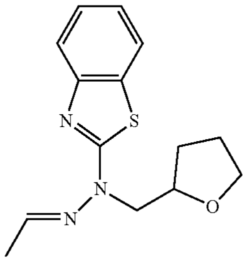
(D-18)
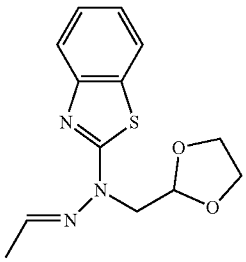
-continued
(D-19)
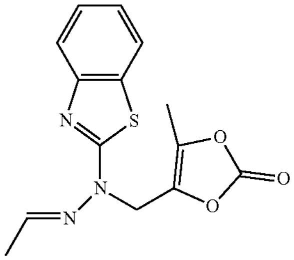
(D-20)
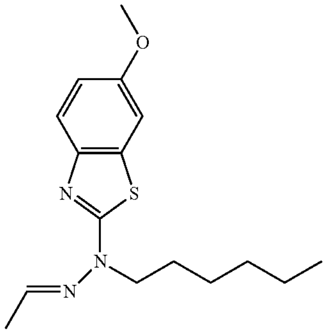
(D-21)
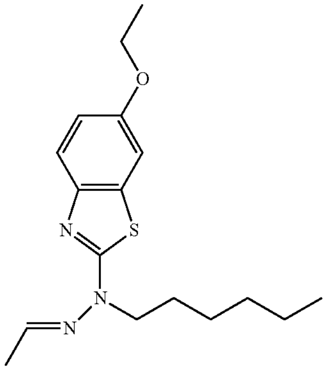
(D-22)
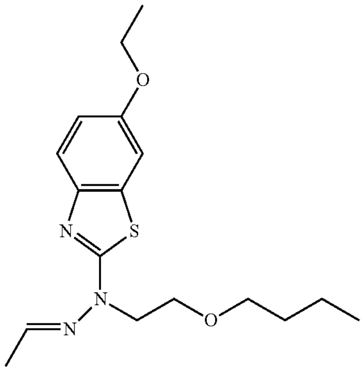

-continued
(D-23)
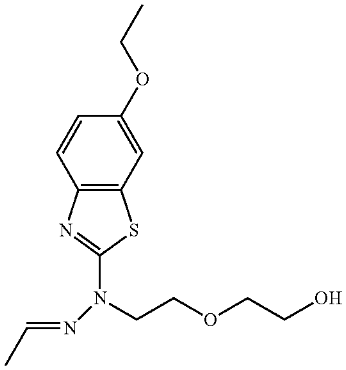
(D-24)
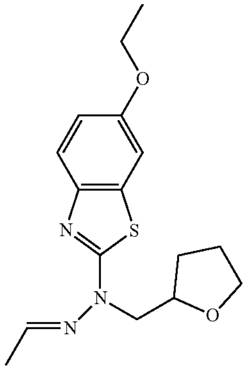
(D-25)
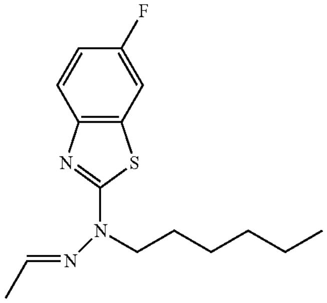
(D-26)
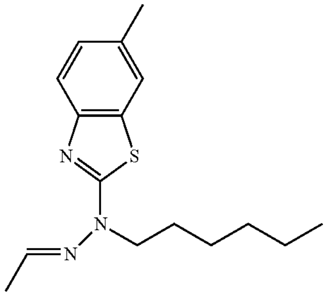
-continued
(D-27)
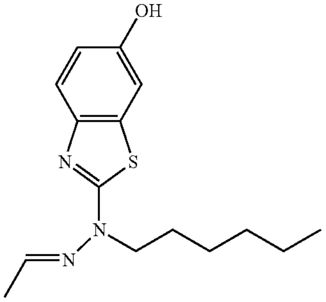
(D-28)
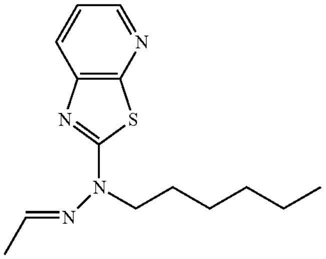
(D-29)
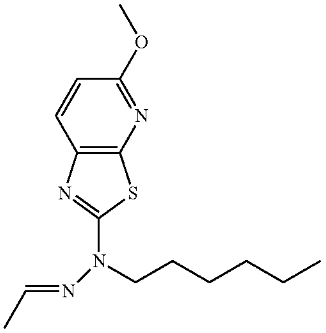
(D-30)
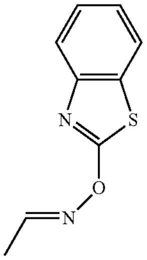
(D-31)
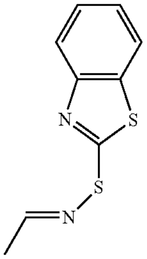

-continued
(D-32)
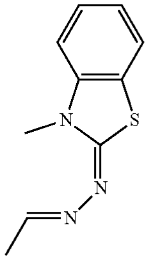
(D-33)
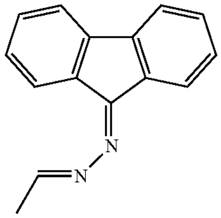
(D-34)
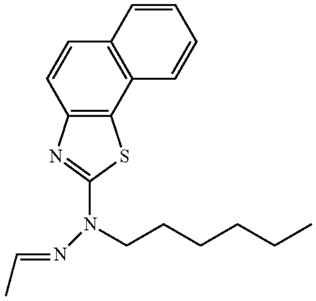
(D-35)
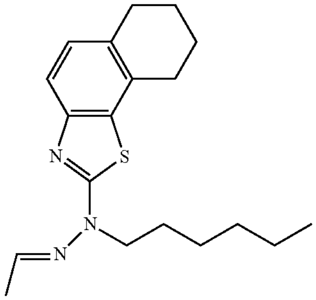
(D-36)
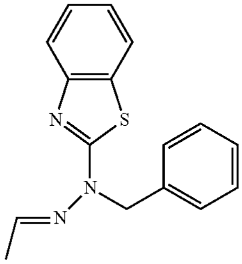
-continued
(D-37)
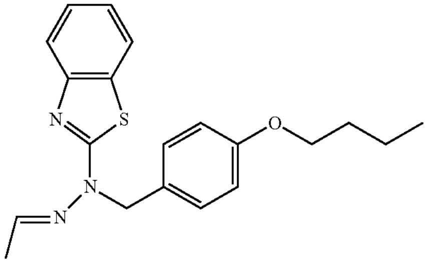
(D-38)
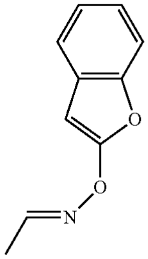
(D-39)
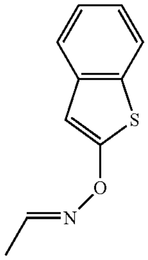
(D-40)
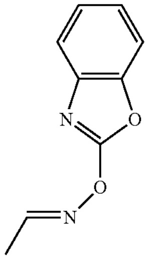
(D-41)
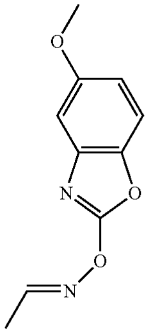

-continued (D-42)

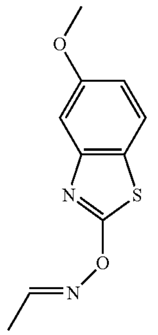

(D-43)

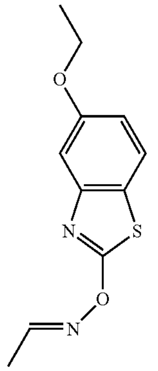

(D-44)

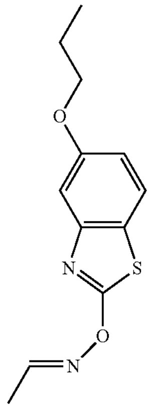

(D-45)

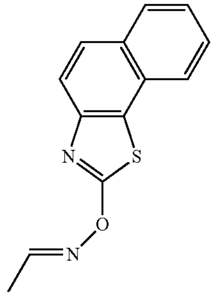

-continued (D-46)

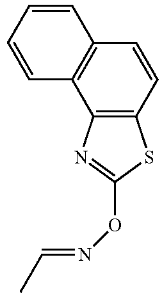

(D-47)

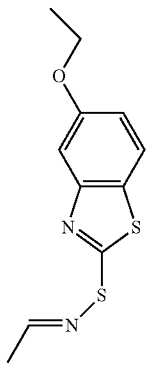

$E^1$ and $E^2$ which are optionally substituted on the benzene ring of the biphenylene group, are each independently optionally the same as the substituent group E.

From the viewpoint of excellent birefringence and easy synthesis, in particular, $E^1$ and $E^2$ which are optionally substituted on the benzene ring of the biphenylene group, are preferably a fluorine atom, a chlorine atom, a hydroxyl group, a mercapto group, a methylamino group, a dimethylamino group, or a linear or branched alkyl group containing 1 to 6 carbon atoms, in which one —$CH_2$— or two or more non-adjacent —$CH_2$— are each independently optionally substituted by —O—, —S—, —CO—, —COO—, —OCO—, —CO—S—, —S—CO—, —O—CO—O—, —CO—NH— or —NH—CO—.

Also, n1 and n2 each independently represent an integer of from 0 to 3, preferably from 0 to 2, and more preferably 0 or 1.

When $E^1$ and $E^2$ are each independently substituted by the biphenylene group, from the viewpoint of excellent birefringence, the substation position is preferably the 6- or 6'-position of the biphenylene group. In this case, the torsion angle of two benzene rings in the biphenylene group is large, and the π-conjugated structure can be cut easily.

The structure of the biphenylene group contained in the main chain moiety preferably represents a group selected from the following formulae (Co-1) to (Co-8).

(Co-1)

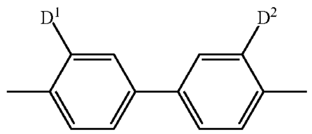

-continued (Co-2)

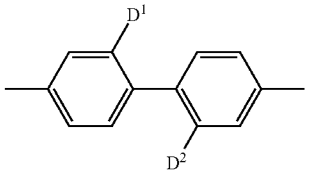

(Co-3)

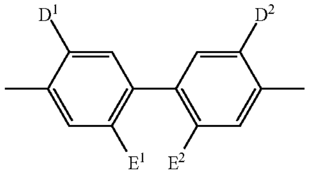

(Co-4)

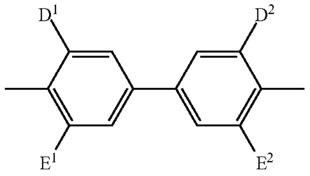

(Co-5)

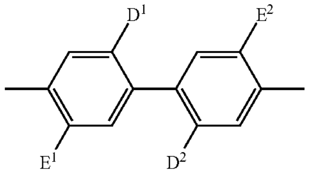

(Co-6)

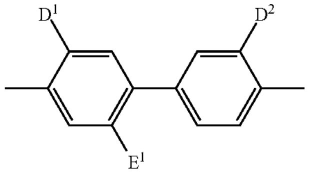

(Co-7)

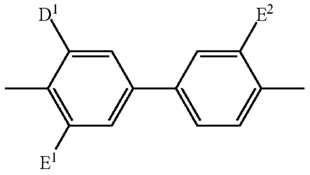

(Co-8)

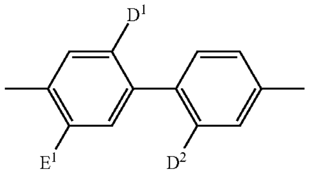

As the compound represented by the general formula (1), examples include the following compounds (i) to (xci). In the following tables, the term "Core" represents the structure of the biphenylene group; Lc1 represents $-L^1-A^1-(L^3-A^3)_{m1}-L^5-R^{sp1}-Z^1$; and Lc2 represents $-L^2-A^2-(L^4-A^4)_{m2}-L^5-R^{sp1}-Z^1$.

TABLE 7

| Compound | Core | D1 | D2 | E1 | E2 | Lc1 | Lc2 |
|---|---|---|---|---|---|---|---|
| (i) | Co-1 | D-1 | D-1 | H | H | Any one | Any one |
| (ii) | Co-1 | D-2 | D-2 | H | H | of Lc-1 | of Lc-1 |
| (iii) | Co-1 | D-3 | D-3 | H | H | to Lc-244 | to Lc-244 |
| (iv) | Co-1 | D-4 | D-4 | H | H | | |
| (v) | Co-1 | D-5 | D-5 | H | H | | |
| (vi) | Co-1 | D-6 | D-6 | H | H | | |
| (vii) | Co-1 | D-7 | D-7 | H | H | | |
| (viii) | Co-1 | D-8 | D-8 | H | H | | |
| (ix) | Co-1 | D-9 | D-9 | H | H | | |
| (x) | Co-1 | D-10 | D-10 | H | H | | |
| (xi) | Co-1 | D-11 | D-11 | H | H | | |
| (xii) | Co-1 | D-12 | D-12 | H | H | | |
| (xiii) | Co-1 | D-13 | D-13 | H | H | | |
| (xiv) | Co-1 | D-14 | D-14 | H | H | | |
| (xv) | Co-1 | D-15 | D-15 | H | H | | |
| (xvi) | Co-1 | D-16 | D-16 | H | H | | |
| (xvii) | Co-1 | D-17 | D-17 | H | H | | |
| (xviii) | Co-1 | D-18 | D-18 | H | H | | |
| (xix) | Co-1 | D-19 | D-18 | H | H | | |
| (xx) | Co-1 | D-20 | D-20 | H | H | | |
| (xxi) | Co-1 | D-21 | D-21 | H | H | | |
| (xxii) | Co-1 | D-22 | D-22 | H | H | | |
| (xxiii) | Co-1 | D-23 | D-23 | H | H | | |
| (xxiv) | Co-1 | D-24 | D-24 | H | H | | |
| (xxv) | Co-1 | D-25 | D-25 | H | H | | |
| (xxvi) | Co-1 | D-26 | D-26 | H | H | | |
| (xxvii) | Co-1 | D-27 | D-27 | H | H | | |
| (xxviii) | Co-1 | D-28 | D-28 | H | H | | |
| (xxix) | Co-1 | D-29 | D-29 | H | H | | |
| (xxx) | Co-1 | D-30 | D-30 | H | H | | |
| (xxxi) | Co-1 | D-31 | D-31 | H | H | | |
| (xxxii) | Co-1 | D-32 | D-32 | H | H | | |
| (xxxiii) | Co-1 | D-33 | D-33 | H | H | | |
| (xxxiv) | Co-2 | D-1 | D-1 | H | H | | |
| (xxxv) | Co-2 | D-2 | D-2 | H | H | | |
| (xxxvi) | Co-2 | D-3 | D-3 | H | H | | |
| (xxxvii) | Co-2 | D-4 | D-4 | H | H | | |
| (xxviii) | Co-2 | D-5 | D-5 | H | H | | |
| (xxxix) | Co-2 | D-6 | D-6 | H | H | | |
| (xl) | Co-2 | D-7 | D-7 | H | H | | |
| (xli) | Co-2 | D-8 | D-8 | H | H | | |
| (xlii) | Co-2 | D-9 | D-9 | H | H | | |
| (xliii) | Co-2 | D-10 | D-10 | H | H | | |
| (xlix) | Co-2 | D-11 | D-11 | H | H | | |
| (xlv) | Co-2 | D-12 | D-12 | H | H | | |
| (xlvi) | Co-2 | D-13 | D-13 | H | H | | |
| (xlvii) | Co-2 | D-14 | D-14 | H | H | | |
| (xlviii) | Co-2 | D-15 | D-15 | H | H | | |
| (xlix) | Co-2 | D-16 | D-16 | H | H | | |
| (l) | Co-2 | D-17 | D-17 | H | H | | |

TABLE 8

| Compound | Core | D1 | D2 | E1 | E2 | Lc1 | Lc2 |
|---|---|---|---|---|---|---|---|
| (li) | Co-2 | D-18 | D-18 | H | H | Any one | Any one |
| (lii) | Co-2 | D-19 | D-19 | H | H | of Lc-1 | of Lc-1 |
| (liii) | Co-2 | D-20 | D-20 | H | H | to Lc-244 | to Lc-244 |
| (liv) | Co-2 | D-21 | D-21 | H | H | | |
| (lv) | Co-2 | D-22 | D-22 | H | H | | |
| (lvi) | Co-2 | D-23 | D-23 | H | H | | |
| (lvii) | Co-2 | D-24 | D-24 | H | H | | |
| (lviii) | Co-2 | D-25 | D-25 | H | H | | |
| (lix) | Co-2 | D-26 | D-26 | H | H | | |
| (lx) | Co-2 | D-27 | D-27 | H | H | | |
| (lxi) | Co-2 | D-28 | D-28 | H | H | | |
| (lxii) | Co-2 | D-29 | D-29 | H | H | | |
| (lxiii) | Co-2 | D-30 | D-30 | H | H | | |
| (lxiv) | Co-2 | D-31 | D-31 | H | H | | |
| (lxv) | Co-2 | D-32 | D-32 | H | H | | |
| (lxvi) | Co-2 | D-33 | D-33 | H | H | | |
| (lxvii) | Co-3 | D-10 | D-10 | CH3 | CH3 | | |
| (lxviii) | Co-4 | D-10 | D-10 | CH3 | CH3 | | |
| (lxix) | Co-5 | D-10 | D-10 | CH3 | CH3 | | |
| (lxx) | Co-6 | D-10 | D-10 | CH3 | H | | |
| (lxxi) | Co-7 | D-10 | D-10 | CH3 | H | | |
| (lxxii) | Co-8 | D-10 | D-10 | CH3 | H | | |

TABLE 8-continued

| Compound | Core | D1 | D2 | E1 | E2 | Lc1 | Lc2 |
|---|---|---|---|---|---|---|---|
| (lxxiii) | Co-6 | D-10 | D-10 | CF3 | H | | |
| (lxxiv) | Co-7 | D-10 | D-10 | CF3 | H | | |
| (lxxv) | Co-8 | D-10 | D-10 | CF3 | H | | |
| (lxxvi) | Co-1 | D-1 | D-3 | H | H | | |
| (lxxvii) | Co-1 | D-10 | D-8 | H | H | | |
| (lxxviii) | Co-1 | D-34 | D-34 | H | H | | |
| (lxxix) | Co-1 | D-35 | D-36 | H | H | | |
| (lxxx) | Co-1 | D-36 | D-36 | H | H | | |
| (lxxxi) | Co-1 | D-37 | D-37 | H | H | | |
| (lxxxii) | Co-1 | D-38 | D-38 | H | H | | |
| (lxxxiii) | Co-1 | D-39 | D-39 | H | H | | |
| (lxxxiv) | Co-1 | D-40 | D-40 | H | H | | |

TABLE 8-continued

| Compound | Core | D1 | D2 | E1 | E2 | Lc1 | Lc2 |
|---|---|---|---|---|---|---|---|
| (lxxxv) | Co-1 | D-41 | D-41 | H | H | | |
| (lxxxvi) | Co-1 | D-42 | D-42 | H | H | | |
| (lxxxvii) | Co-1 | D-43 | D-43 | H | H | | |
| (lxxxviii) | Co-1 | D-44 | D-44 | H | H | | |
| (lxxxix) | Co-1 | D-45 | D-45 | H | H | | |
| (xc) | Co-1 | D-46 | D-46 | H | H | | |
| (xci) | Co-1 | D-47 | D-47 | H | H | | |

Typical structural formulae of the compounds (i) to (xci) in Tables 7 and 8 are exemplified below. The structural formulae of the compounds (i) to (xci) are not limited to the following examples.

(v)-1

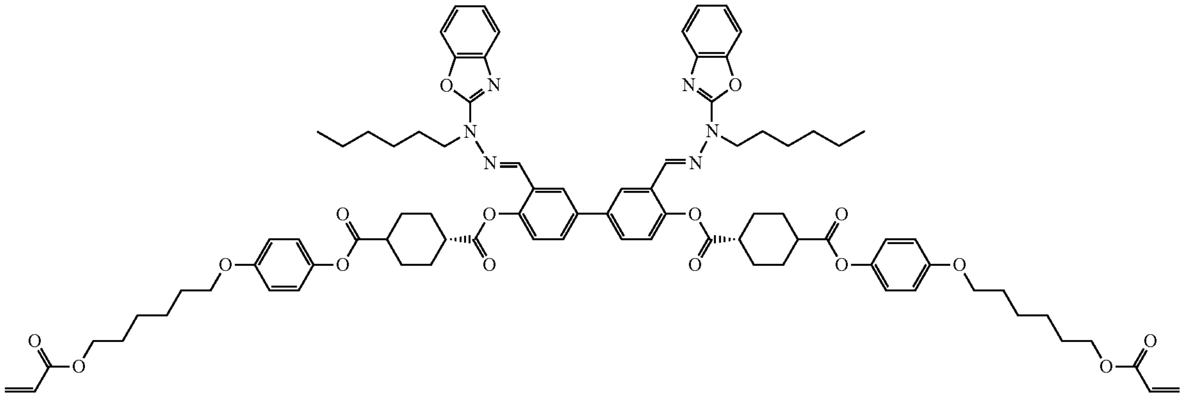

(vi)-1

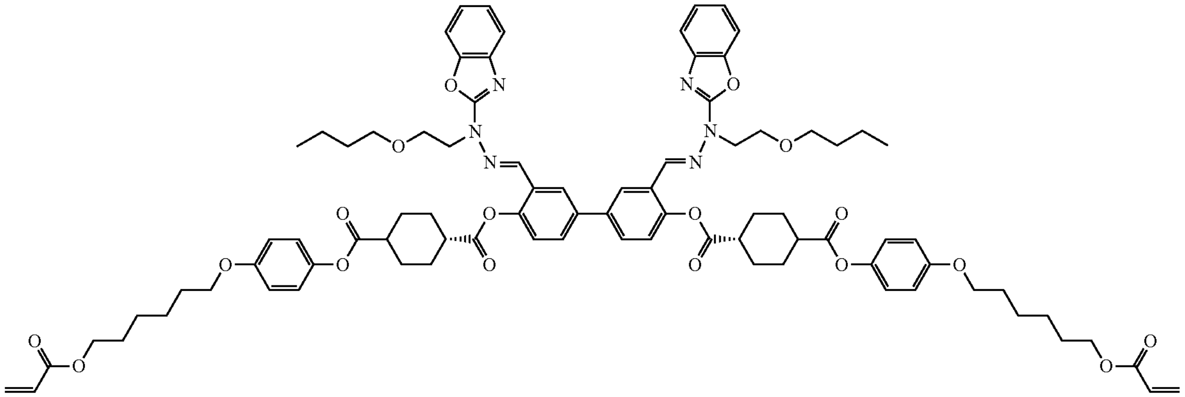

(x)-1

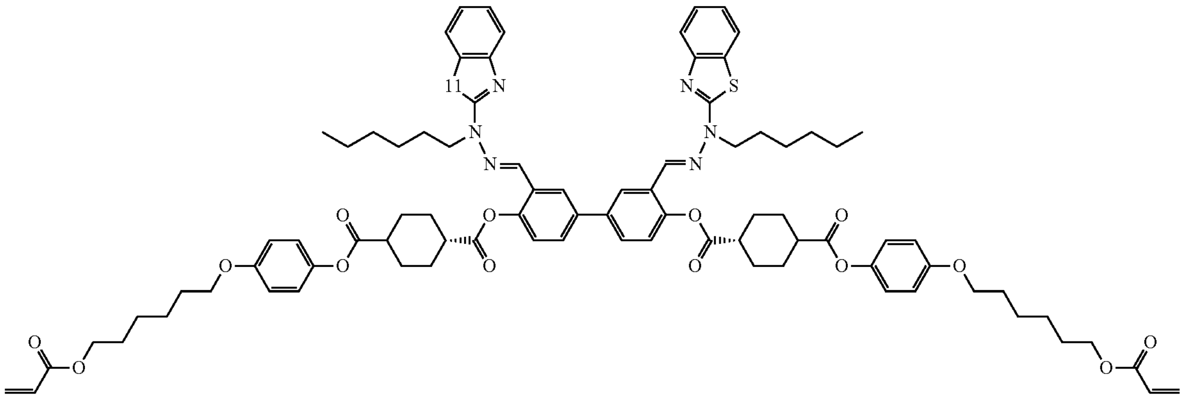

-continued
(xii)-1
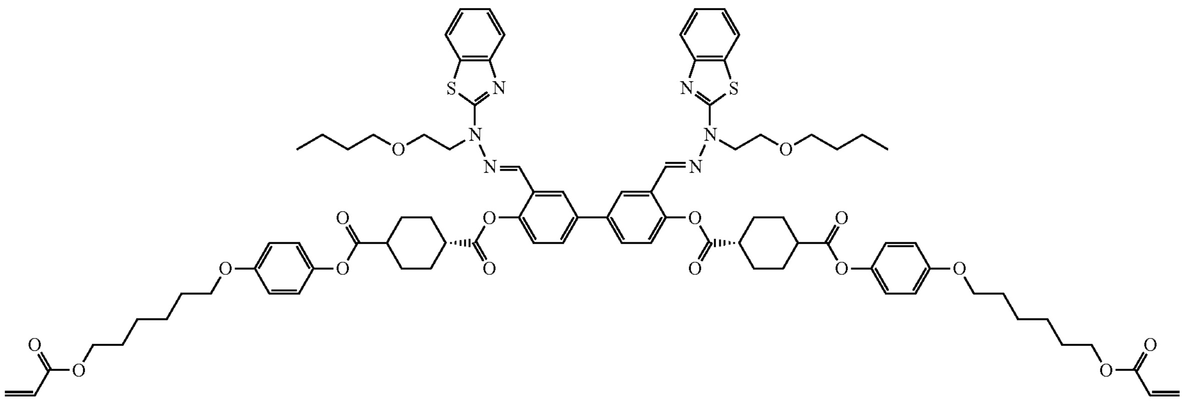
(xiii)-1
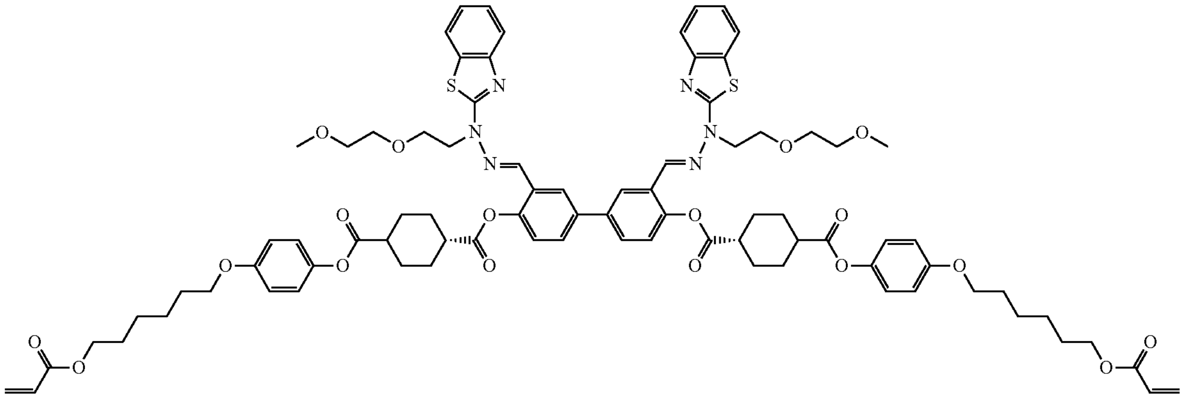
(xiv)-1
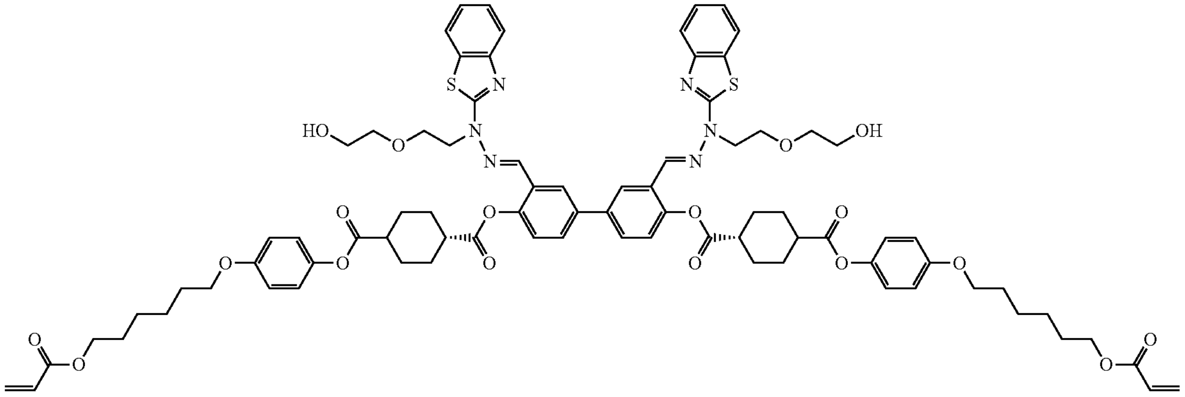

-continued
(xv)-1
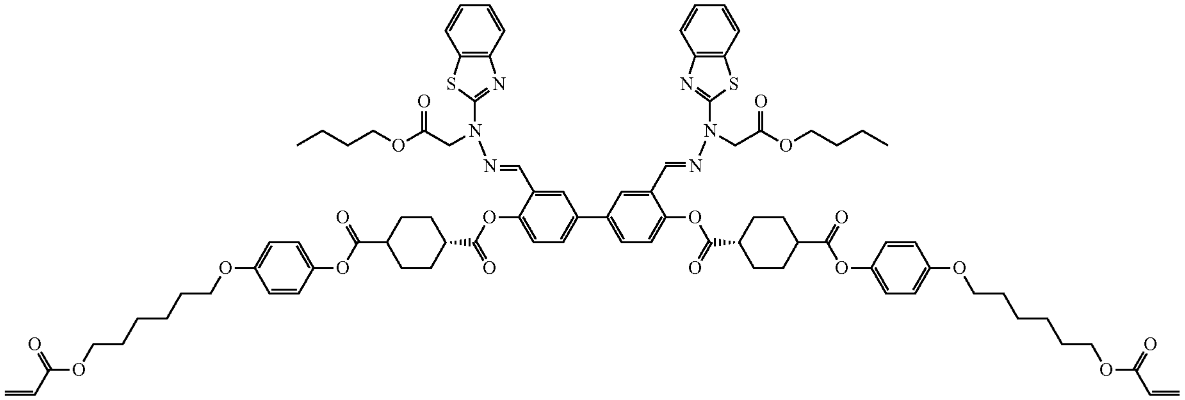
(xvi)-1
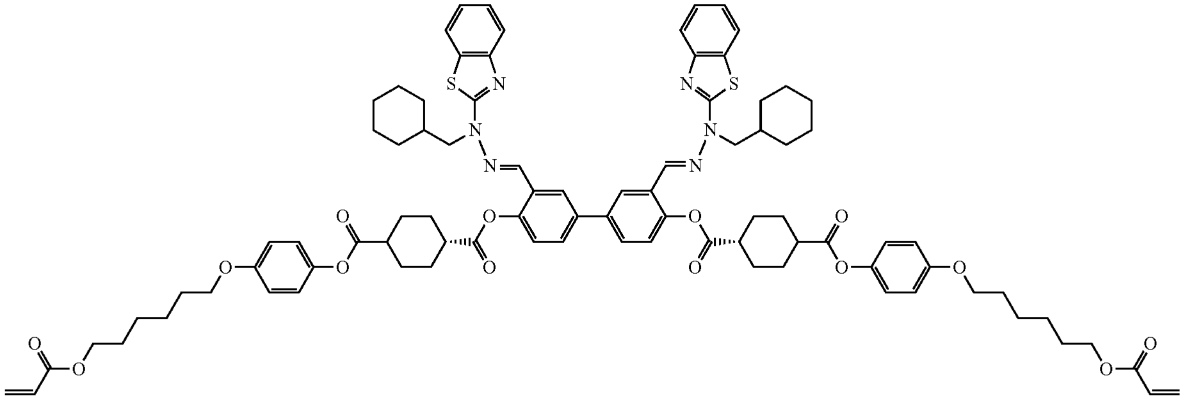
(xvii)-1
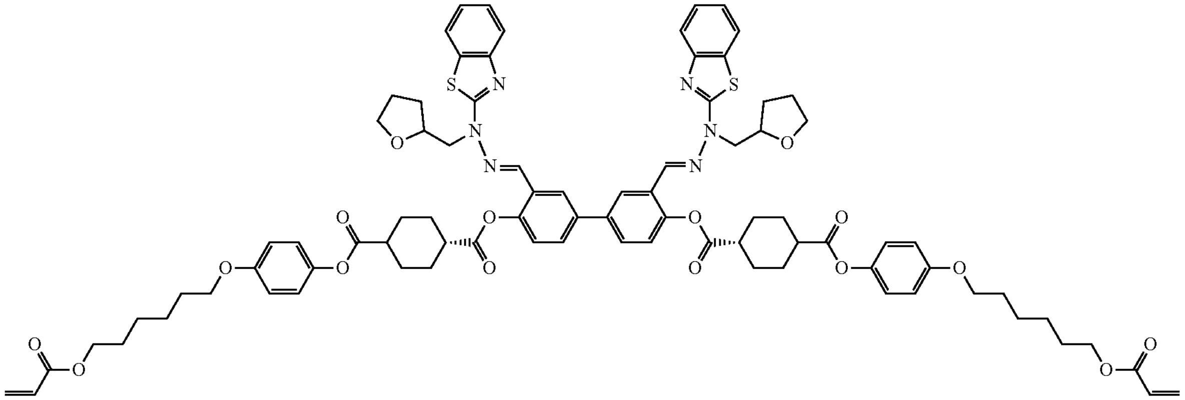

-continued
(xx)-1
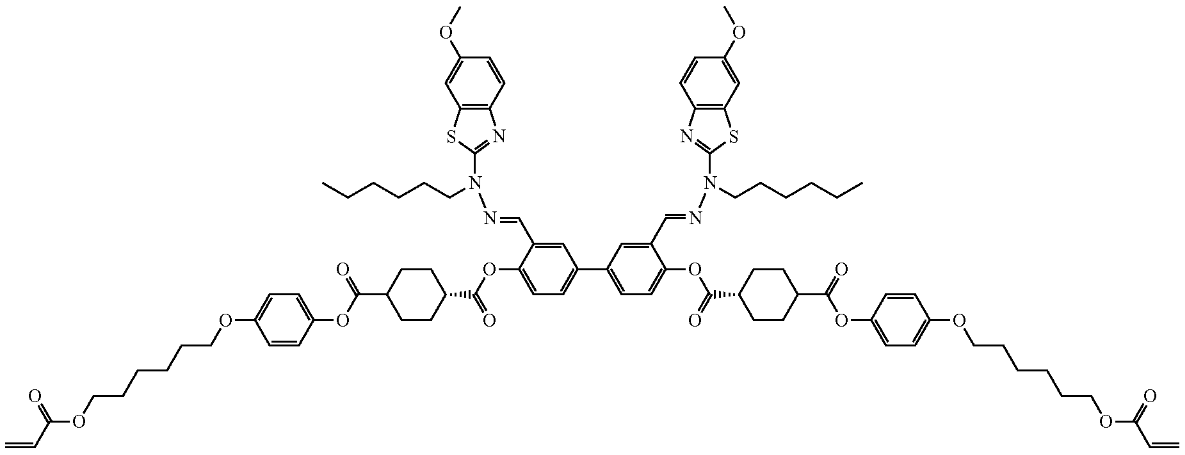
(xxi)-1
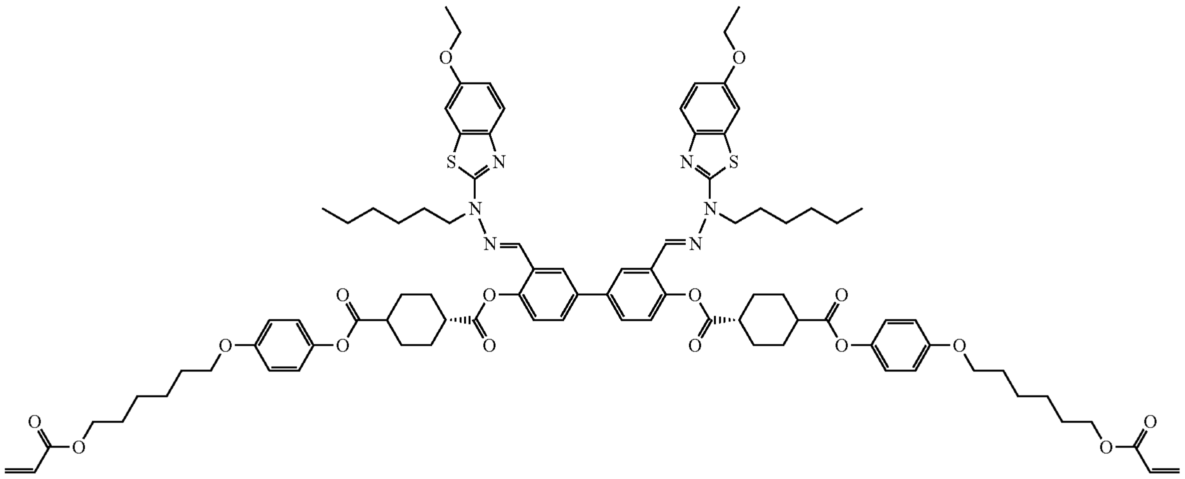
(xxii)-1
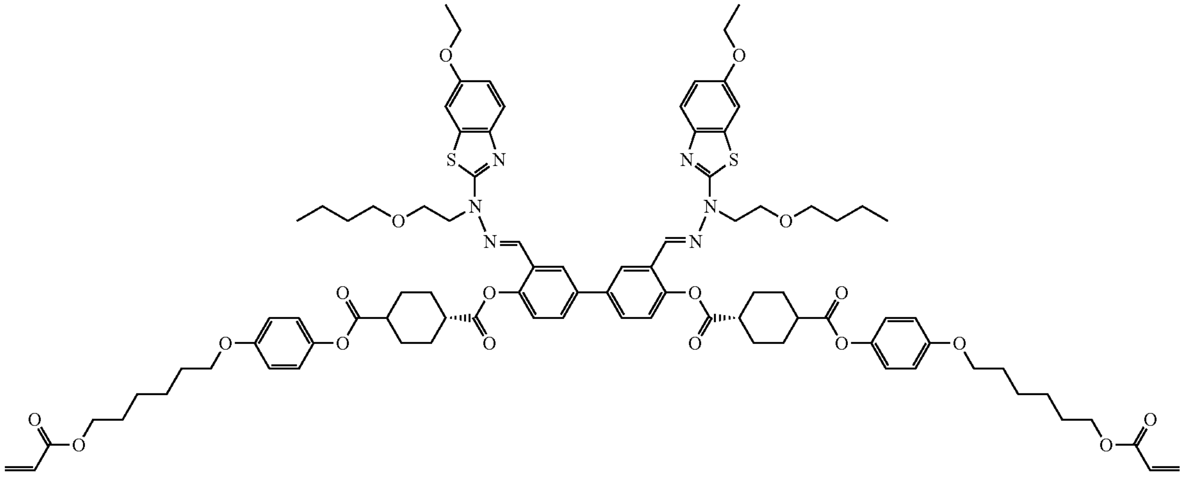

-continued
(xxv)-1
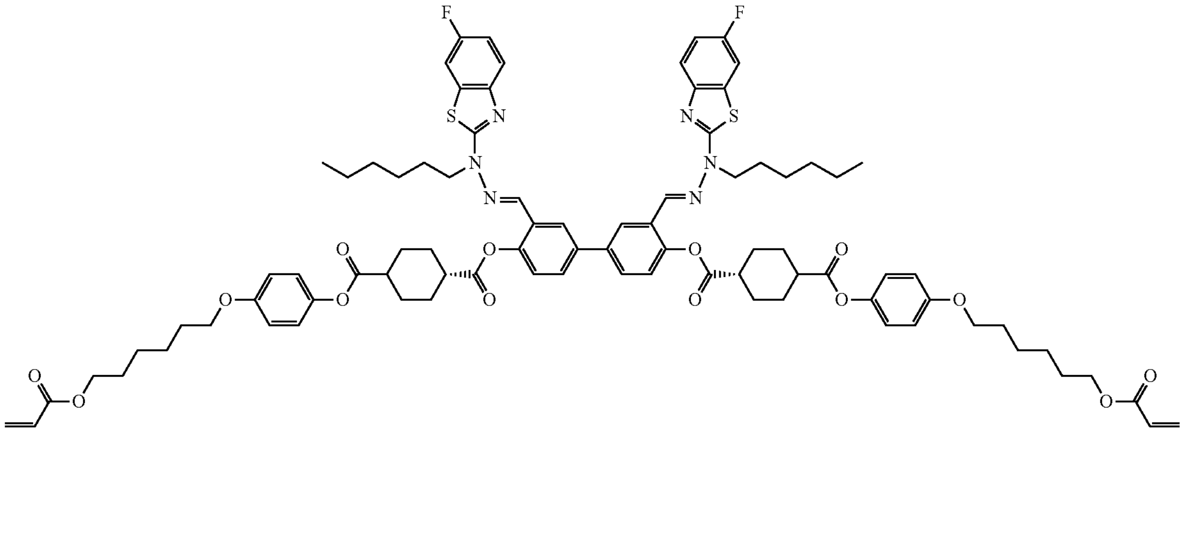
(xxvi)-1
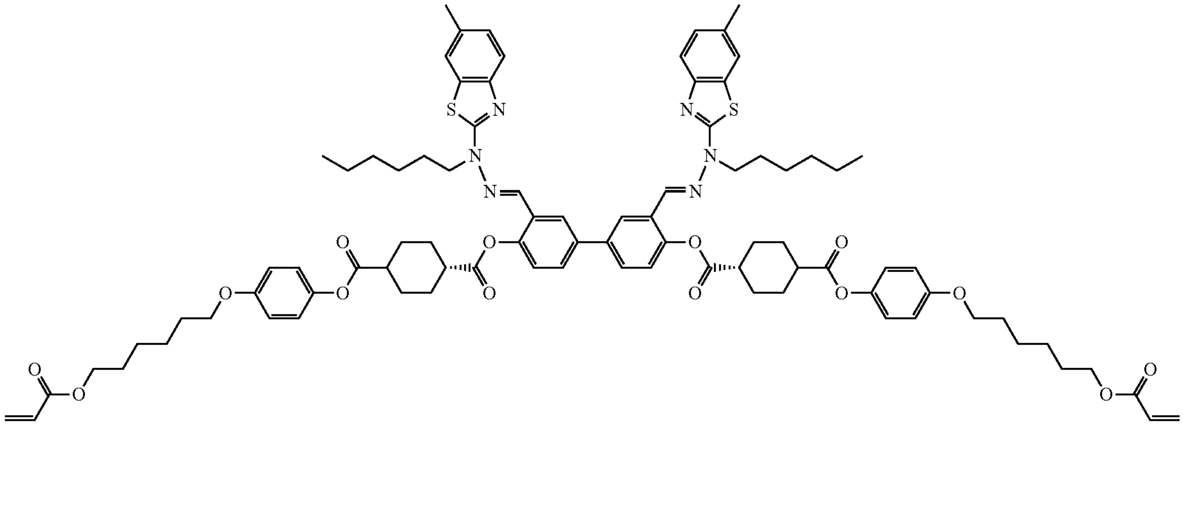
(x)-2
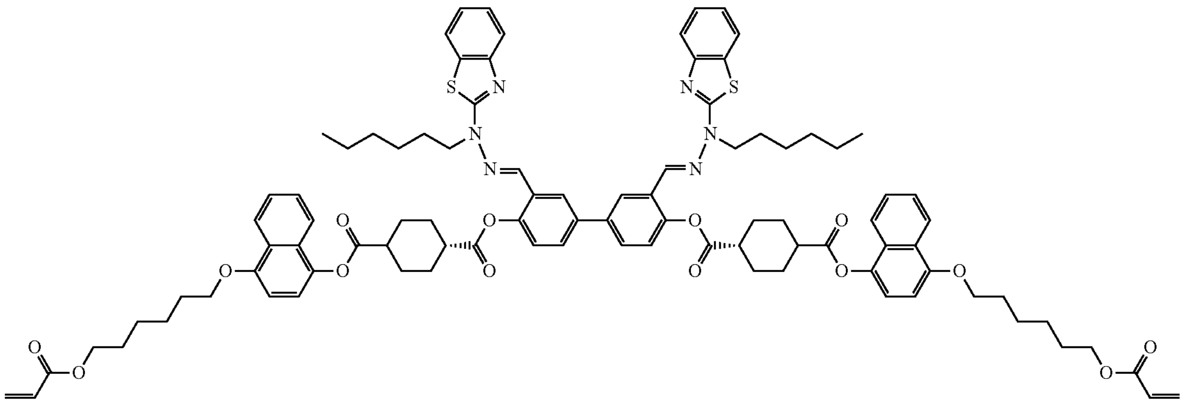

-continued
(x)-3
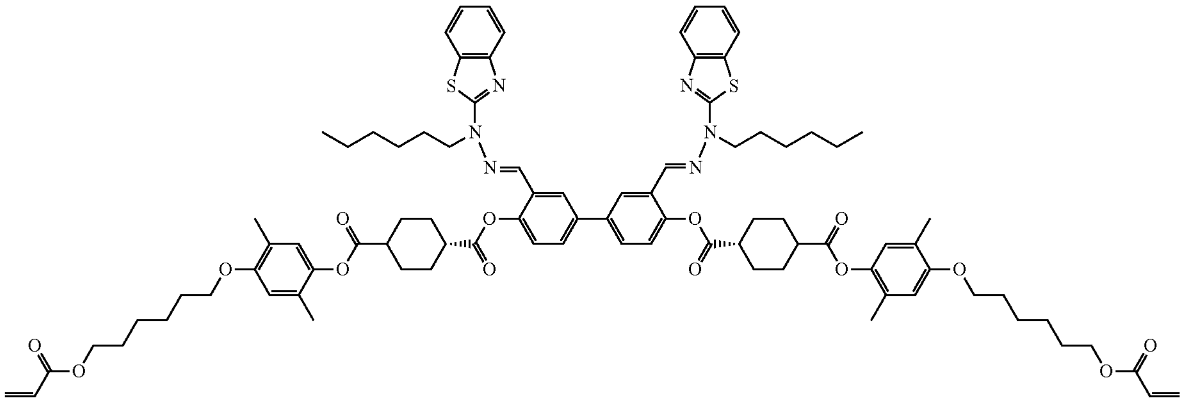
(x)-4
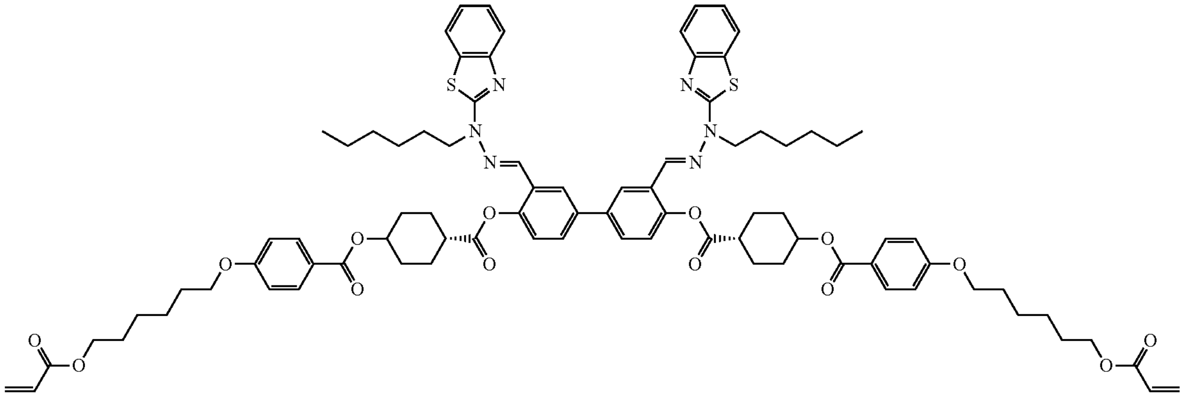
(xxviii)-1
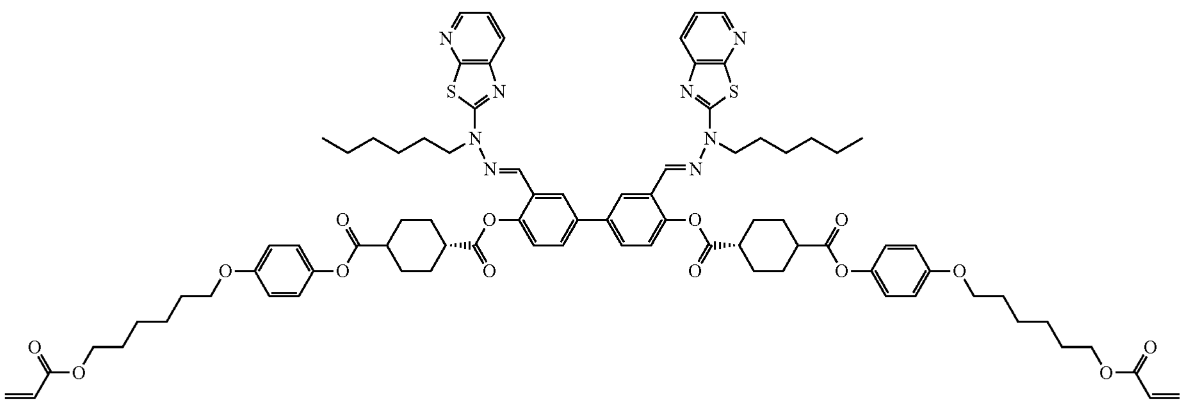

-continued
(lxx)-1
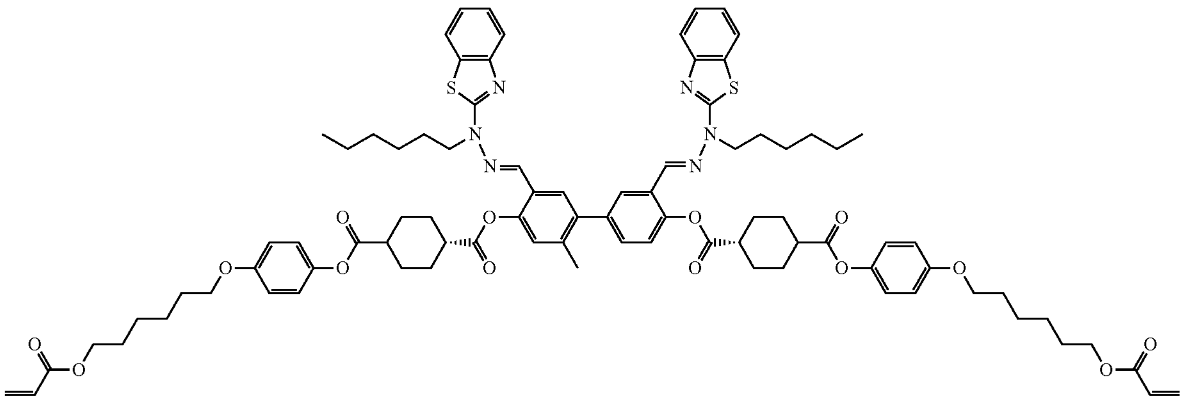
(lxxi)-1
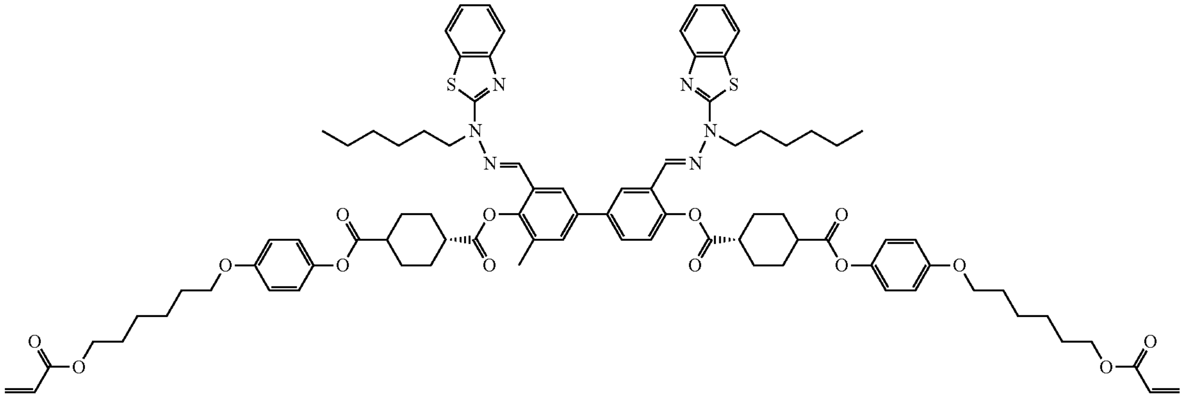
(lxvii)-1
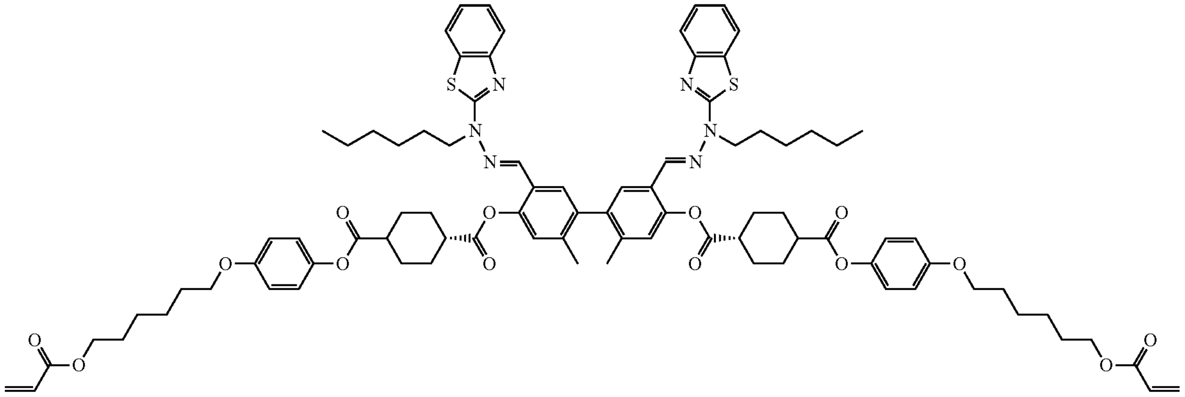

-continued
(lxxiii)-1
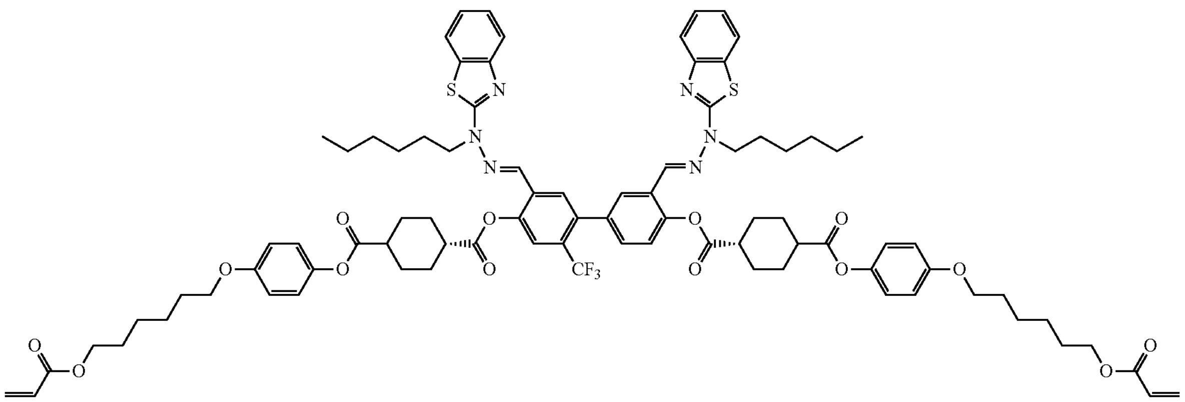
(xliii)-1
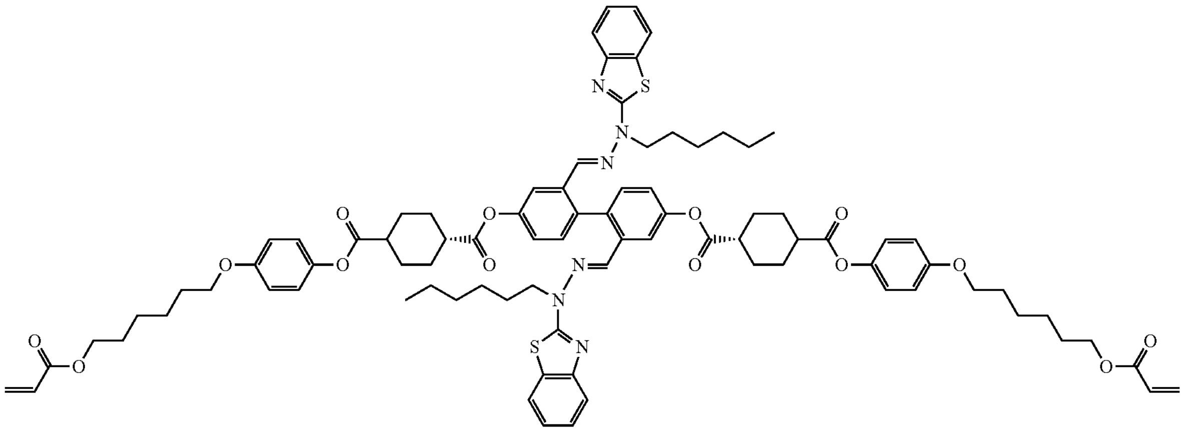
(xxxii)-1
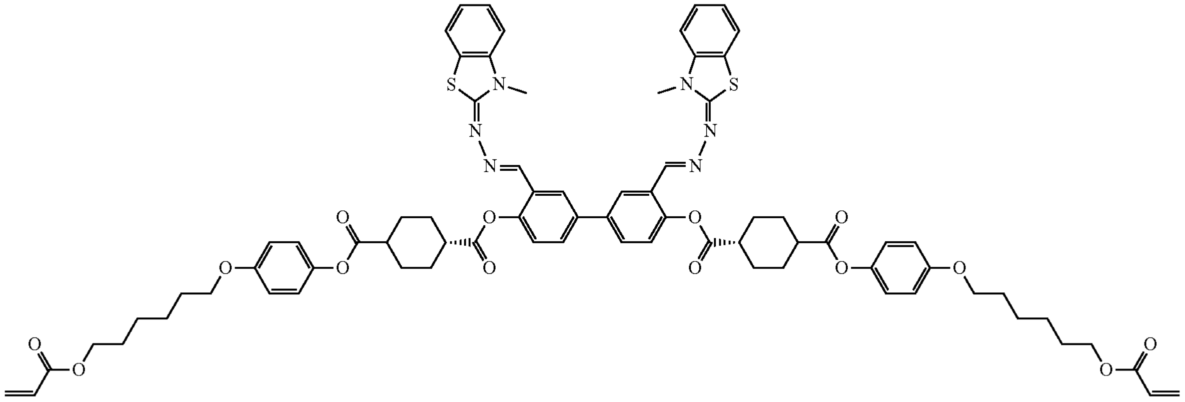

-continued
(xxx)-1
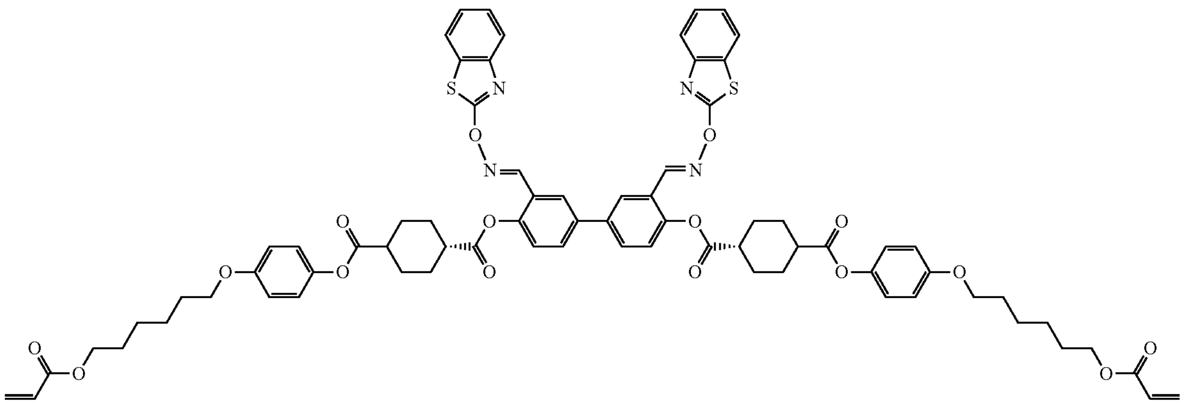
(lxxxvii)-1
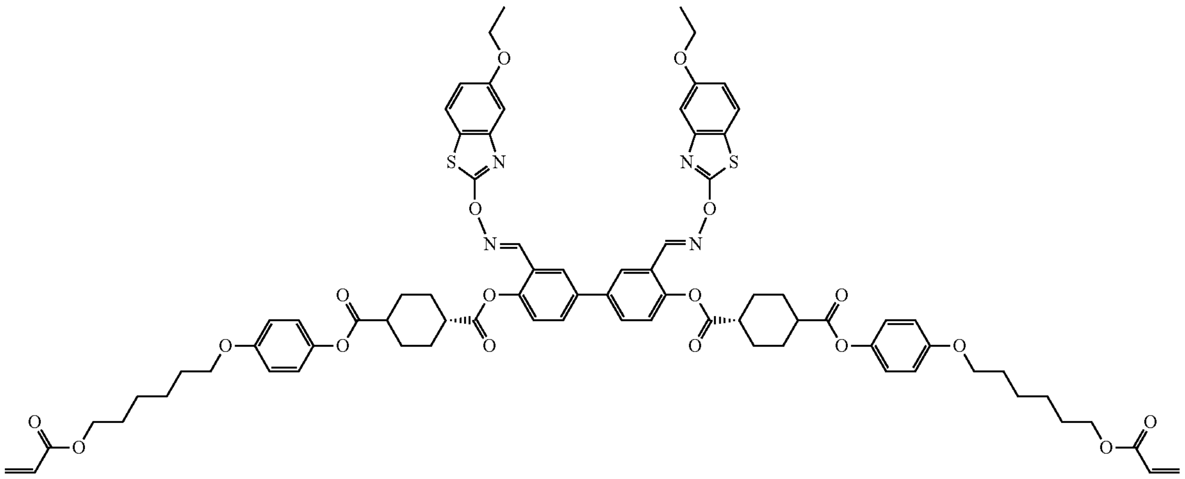
(xxxi)-1
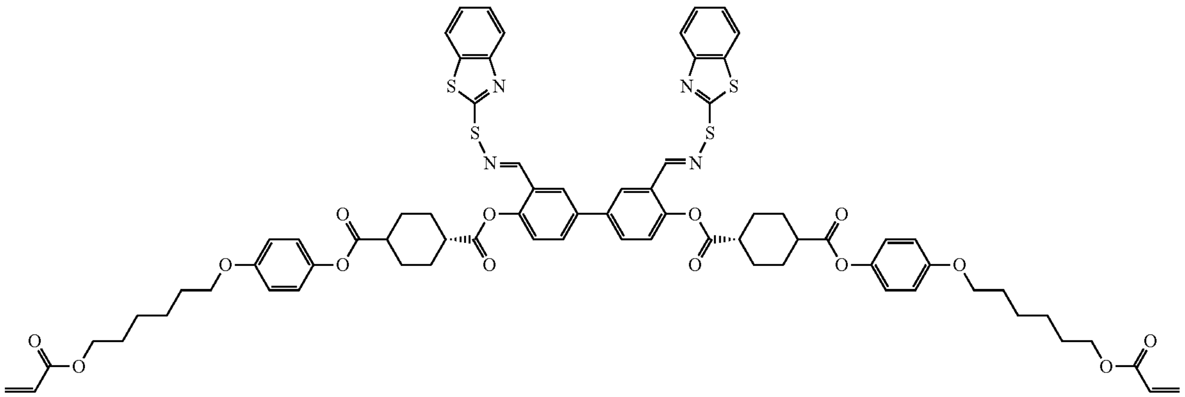

-continued (xci)-1

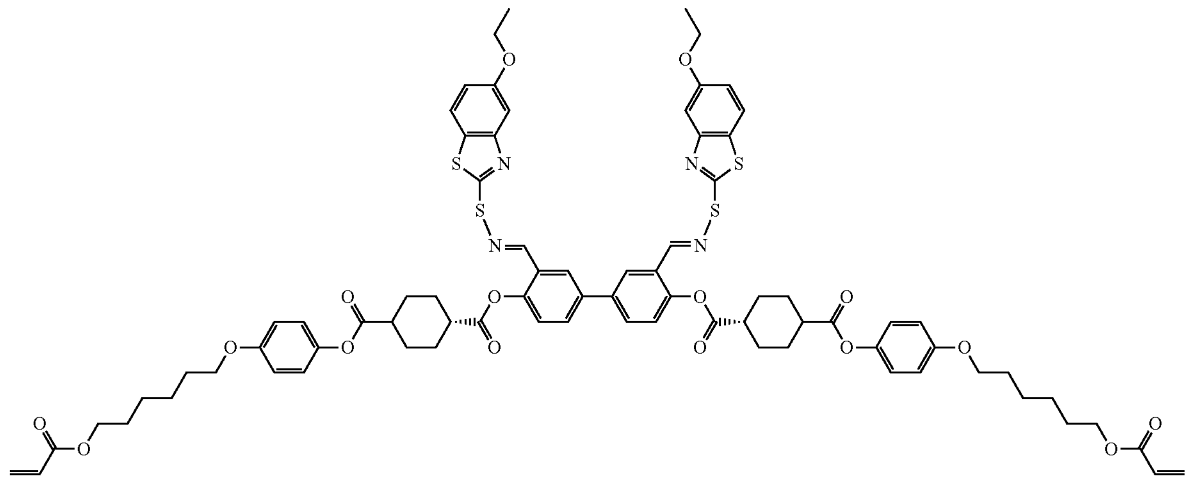

The compound represented by the general formula (1) can be produced by the following method. For example, the compound can be produced by appropriately combining known organic synthesis reaction reactions described in Methoden der Organischen Chemie, Organic Reactions, Organic Syntheses, Comprehensive Organic Synthesis, Shin Jikken Kagaku Kouza, etc. (e.g., condensation reaction, esterification reaction, Williamson reaction, Ullmann reaction, Wittig Reaction, Schiff's base formation reaction, benzylation reaction, Sonogashira reaction, Suzuki-Miyaura reaction, Negishi reaction, Kumada reaction, Hiyama reaction, Buchwald-Hartwig reaction, Friedel-Crafts reaction, Heck reaction, aldol reaction and Duff reaction) depending on the structure of the compound. Hereinafter, a production method example will be described. The present disclosure is not limited to these structures and production method.

For example, in the case of a compound in which $L^4$ and $L^2$ are each *—OCO— ("*" indicates the binding position to the biphenylene group) and $G^4$ is a hydrogen atom, the compound can be produced as follows.

First, 4,4'-dihydroxybiphenyl or a compound represented by the following formula (ip-1), which is 4,4'-dihydroxybiphenyl further introduced with the substituent group E, is prepared. Aldehyde groups are introduced in desired positions thereof by Duff reaction or the like to produce an intermediate A represented by the following formula (ip-2).

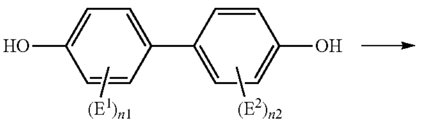

(ip-1)

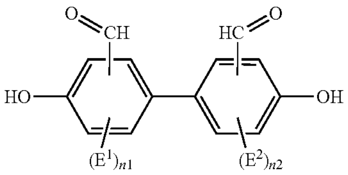

(ip-2)

Next, the intermediate A represented by the formula (ip-2) is reacted with an intermediate B represented by HOOC-$A^4$-($L^3$-$A^3$)$_{m1}$-$R^1$ (where $A^1$, $L^3$, $A^3$, $R^4$ and m1 mean the same as described above) by condensation reaction or the like to obtain an intermediate C represented by the following formula (ip-3). Also, the intermediate C represented by the formula (ip-3) is reacted with an intermediate D represented by HOOC-$A^2$-($L^4$-$A^4$)-$R^2$ (where $A^2$, $L^4$, A4, $R^2$ and m2 means the same as described above) to obtain an intermediate E represented by the following formula (ip-4). When the structure of the intermediate B is the same as that of the intermediate D, the intermediate E can be obtained by reacting the intermediate A with the intermediate B.

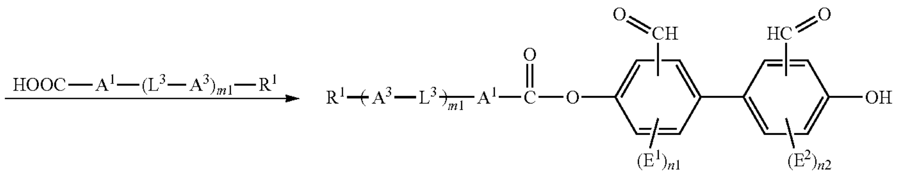

(ip-3)

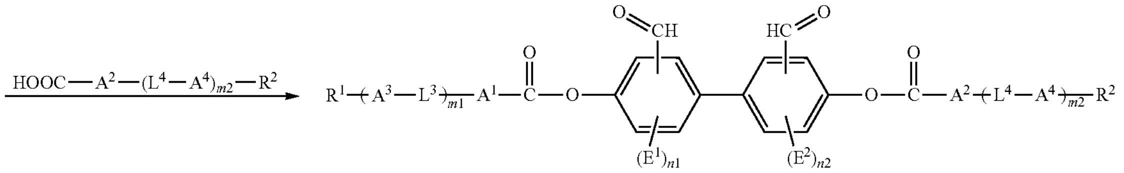

(ip-4)

Next, the intermediate E represented by the formula (ip-4) is reacted with, for example, an intermediate F represented by $Q^1$-$J^1$-$NH_2$ to produce a compound represented by the following formula (1-ex1).

(1-exl)

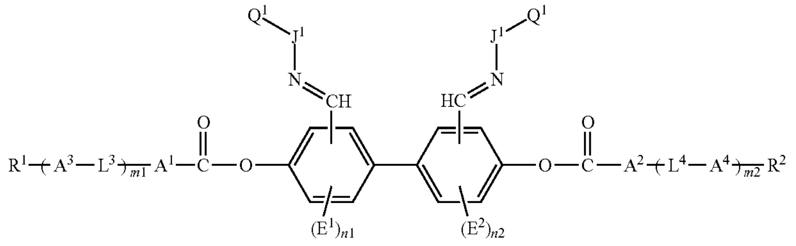

The intermediate A represented by the formula (ip-2) may be obtained as follows, depending on the type or substitution position of $E^1$ and $E^2$, the substitution position of $D^1$ and $D^2$, etc. For example, aldehyde groups are introduced in 3,4-methylenedioxyphenol (manufactured by Tokyo Chemical Industry Co., Ltd.) or a derivative thereof by Duff reaction, and Suzuki-Miyaura coupling reaction is carried out thereon to produce the intermediate A.

Also, the compound represented by the formula (1-ex1) may be obtained as follows, for example. $D^1$ and $D^2$, each of which serves as a side chain moiety, are introduced in the intermediate A represented by the formula (ip-2) in advance to obtain an intermediate G. Then, the intermediate G is reacted with the intermediate B represented by HOOC-$A^2$-($L^3$-$A^3$)$_{m1}$-$R^1$ (where $A^1$, $L^3$, $A^3$, $R^1$ and m1 mean the same as described above) or the intermediate D represented by HOOC-$A^2$-($L^4$-$A^4$)$_{m2}$ $L^4$ (where $A^2$, $A^4$, $R^2$ and m2 mean the same as described above) to obtain the compound represented by the formula (1-ex1).

The intermediates used in the production may be appropriately selected from commercially-available products or can be appropriately synthesized by conventionally-known methods.

In the present disclosure, the structure of the polymerizable liquid crystal compound can be analyzed by appropriately combining nuclear magnetic resonance spectrometry (NMR), pyrolysis gas chromatography mass spectroscopy (Py-GC-MS), matrix assisted laser desorption/ionization time-of-flight mass spectrometry (MALDI-TOFMS), etc.

The polymerizable liquid crystal compound in the present disclosure is a polymerizable liquid crystal compound with excellent alignment property, a large birefringence index ($\Delta n$) and reverse wavelength dispersion property. For example, when a polymerizable composition only containing the polymerizable liquid crystal compound in the present disclosure and a photopolymerization initiator, is prepared to form a cured film (retardation layer) thereof and the cured film is measured for its birefringence index ($\Delta n$), all by the method described below in Example 1, the birefringence index ($\Delta n$) is preferably 0.075 or more, and more preferably 0.08 or more.

When the polymerizable composition only containing the polymerizable liquid crystal compound in the present disclosure and the photopolymerization initiator, is prepared to form the cured film (retardation layer) thereof and the cured film is measured for its retardation value, Re (450)/Re (550) is preferably in a range of 0.50 or more and less than 0.95, more preferably in a range of 0.55 or more and less than 0.93, even more preferably in a range of 0.60 or more and less than 0.90, and particularly preferably in a range of 0.60 or more and 0.83 or less, or may be in a range of 0.60 or more and less than 0.80, in order to obtain excellent reverse wavelength dispersion property and get closer to ideal reverse wavelength dispersion property. Also, Re (650)/Re (550) is preferably more than 1, and more preferably in a range of 1.02 or more and 1.1 or less.

The method for testing the retardation value may be the following method, for example.

[Testing Method]

A rubbing-treated, polyimide alignment film-attached glass piece (an alignment-treated glass substrate manufactured by EHC Co., Ltd.) is prepared, which is an alignment-treated glass substrate to which POLYIMIDE LX-1400 (product name, manufactured by: Hitachi Chemical Co., Ltd.) is applied and subjected to rubbing treatment in the following condition:

Roller Rotational Speed: 600 rpm

Transfer Rate: 30 mm/sec

Reciprocating number of times: 3

The polymerizable liquid crystal compound in the present disclosure (100 parts by mass) and 2-methyl-1-(4-methylthiophenyl)-2-morpholinopropane-1-on (4 parts by mass) are dissolved in cyclopentanone (900 parts by mass) to obtain a polymerizable composition. The polymerizable composition is formed into a film by applying, on the alignment film of the substrate, the polymerizable composition to give a 1 μm-thick film when cured. The film is dried for 120 seconds at a temperature calculated by adding 10° C. to the solid-liquid crystal phase transition temperature (° C.) of the polymerizable liquid crystal compound contained in the polymerizable composition. Thereafter, the dried film is irradiated with ultraviolet rays at an irradiation dose of 400 $mJ/cm^2$ to form a retardation layer. For the retardation layer, its in-plane retardation Re (450) for a wavelength of 450 nm and its in-plane retardation Re (550) for a wavelength of 550 nm are measured by a retardation measuring device (e.g., production name: KOBRA-WR, manufactured by: Oji Scientific Instruments).

The same results can be obtained by forming the retardation layer by the method described below in Example 1 and measuring its retardation values.

For the polymerizable liquid crystal compound in the present disclosure, from the viewpoint of wider selection of applicable substrates, the solid-liquid crystal phase transition temperature is preferably 25° C. or more and 200° C. or less, more preferably 30° C. or more and 180° C. or less, and even more preferably 30° C. or more and 150° C. or less. When the solid-liquid crystal phase transition temperature is low, load applied in the process of liquid crystal alignment is reduced, and the polymerizable composition can be applied to a substrate sensitive to high temperature.

The solid-liquid crystal phase transition temperature means a temperature at which the liquid crystal compound is turned from a solid into a liquid crystal. In the present disclosure, the solid-liquid crystal phase transition temperature is checked by texture observation using a polarizing microscope equipped with a temperature control stage, during the temperature is raised. That is, the point when a solid melts into a liquid during the temperature is raised in the polarizing microscopy, and a bright field is observed in crossed Nicol observation using a polarizing microscope (the polarizing plate is in a crossed state) is defined as the solid-liquid crystal phase transition temperature.

From the viewpoint of wider selection of applicable substrates, the polymerizable liquid crystal compound in the present disclosure is soluble in an amount of preferably 10% by mass or more, and more preferably 20% by mass or more, in at least one solvent selected from the group consisting of methyl ethyl ketone, methyl isobutyl ketone, cyclopentanone and cyclohexanone.

B. Polymerizable Composition

The polymerizable composition in the present disclosure is a composition containing at least the polymerizable liquid crystal compound in the present disclosure.

Since the polymerizable composition in the present disclosure contains the polymerizable liquid crystal compound in the present disclosure, as described above, it can be a polymerizable composition with a large birefringence index (Δn) and reverse wavelength dispersion property.

The polymerizable composition in the present disclosure contains at least the polymerizable liquid crystal compound in the present disclosure. In addition to the polymerizable liquid crystal compound, the polymerizable composition preferably contains a photopolymerization initiator.

From the viewpoint of controlling the retardation and reverse wavelength dispersion property and controlling the alignment property, solubility and phase transition temperature, the polymerizable composition may further include a polymerizable liquid crystal compound which is different from the polymerizable liquid crystal compound in the present disclosure, and the polymerizable composition may further include a different component as far as the advantageous effects thereof are not impaired. Hereinafter, the individual components included in the polymerizable composition in the present disclosure will be described in turn.

1. Polymerizable Liquid Crystal Compound in the Present Disclosure

In the polymerizable composition in the present disclosure, the polymerizable liquid crystal compound in the present disclosure may be the same as described in item "A. Polymerizable Liquid Crystal Compound". Thus, a description thereon is omitted herein.

In the polymerizable composition in the present disclosure, one kind of the polymerizable liquid crystal compound in the present disclosure may be singly used, or two or more kinds of such compounds may be used in combination. In the present embodiment, the content rate of the polymerizable liquid crystal compound in the present disclosure is preferably 50 parts by mass or more and 99.9 parts by mass or less, more preferably 54 parts by mass or more and 99 parts by mass or less, and even more preferably 57 parts by mass or more and 98 parts by mass or less, for 100 parts by mass of solid components in the polymerizable composition, since a polymerizable composition with a large birefringence index (Δn) and reverse wavelength dispersion property can be obtained.

In the present disclosure, solid components denote all components from which any solvent is removed. Examples thereof include the polymerizable liquid crystal compound different from the polymerizable liquid crystal compound in the present disclosure, which will be detailed below, even when this compound is in a liquid form.

2. Photopolymerization Initiator

In the present embodiment, the photopolymerization initiator may be appropriately selected from photopolymerization initiators known in the prior art. Specific and preferred examples of the photopolymerization initiator include aromatic ketones including thioxanthone, α-aminoalkylphenones, α-hydroxyketones, acylphosphine oxides, oxime esters, aromatic onium salts, organic peroxides, thio compounds, hexaaryl biimidazole compounds, ketoxime ester compounds, borate compounds, azinium compounds, metallocene compounds, active ester compounds, compounds each containing a carbon-halogen bond, and alkylamine compounds. Out of these examples, at least one initiator selected from the group consisting of an acylphosphine oxide-based polymerization initiator, an α-aminoalkylphenone-based polymerization initiator, an α-hydroxyketone-based polymerization initiator, and an oxime ester-based polymerization initiator is preferred, since even the inside of the coating film is cured, and the durability of the coating film is improved.

Examples of the acylphosphine oxide-based polymerization initiator include bis(2,4,6-trimethylbenzoyl)-phenyl-phosphine oxide (for example, trade name: IRGACURE 819, manufactured by BASF Corp.), bis(2,6-dimethoxybenzoyl)-2,4,4-trimethyl-pentylphenylphosphin e oxide, and 2,4,6-trimethylbenzoyl-diphenyl-phosphine oxide (trade name: LUCIRIN TPO, manufactured by BASF Corp., and others).

Examples of the α-aminoalkylphenone-based polymerization initiator include 2-methyl-1-(4-methylthiophenyl)-2-morpholinopropane-1-one (for example, IRGACURE 907, manufactured by BASF Corp.), 2-benzyl-2-(dimethylamino)-1-(4-morpholinophenyl)-1-butanone (for example, IRGACURE 369, manufactured by BASF Corp.), and 2-(dimethylamino)-2-[(4-methylphenyl)methyl]-1-[4-(4-morpholin yl)phenyl]-1-butanone (IRGACURE 379EG, manufactured by BASF Corp.)

Examples of the α-hydroxyketone-based polymerization initiator include 2-hydroxy-1-{4-[4-(2-hydroxy-2-methylpropionyl)-benzyl]-pheny 1}-2-methyl-propane-1-one (for example, trade name: IRGACURE 127, manufactured by BASF Corp., and others), 2-hydroxy-4'-hydroxyethoxy-2-methyl propiophenone (for example, trade name: IRGACURE 2959, manufactured by BASF Corp., and others), 1-hydroxy-cyclohexyl-phenyl-ketone (for example, trade name: IRGACURE 184, manufactured by BASF Corp., and others), and oligo{2-hydroxy-2-methyl-1-[4-(1-methylvinyl)phenyl]propanone} (for example, trade name: ESACURE ONE, manufactured by Lamberti Inc., and others).

Examples of the oxime ester-based polymerization initiator include 1,2-octanedione,1-[4-(phenylthio)-,2-(O-benzoyloxime)] (trade name: IRGACURE OXE-01, manufactured by BASF Corp.), ethanone,1-[9-ethyl-6-(2-methylbenzoyl)-9H-carbazol-3-yl]-,1-(o-acetyloxime) (trade name: IRGACURE OXE-02, manufactured by BASF Corp.), methanone, ethanone, 1-[9-ethyl-6-(1,3-dioxolane, 4-(2-methoxyphenoxy)-9H-carbazol-3-yl]-,1-(o-acetyloxime) (trade name: ADEKA OPT-N-1919, manufactured by Adeka Corp.)

In the present embodiment, one kind of the photopolymerization initiator may be singly used, or two or more kinds of such initiators may be used in combination.

In the present embodiment, to promote the curing of the polymerizable composition, the content rate of the photopolymerization initiator is preferably 0.1 parts by mass or more and 10 parts by mass or less, and more preferably 1 part by mass or more and 8 parts by mass or less, for 100 parts by mass of solid components in the polymerizable composition.

3. Polymerizable Liquid Crystal Compound Different from the Polymerizable Liquid Crystal Compound in the Present Disclosure In the polymerizable composition in the present disclosure, the polymerizable liquid crystal compound different from the polymerizable liquid crystal compound in the present disclosure, can be appropriately selected from conventionally-known polymerizable liquid crystal compounds. The polymerizable liquid crystal compound different from the polymerizable liquid crystal compound in the present disclosure, may be a polymerizable liquid crystal compound with normal dispersion, for which the slope of a graph having the wavelength λ of incident light on the retardation film on the horizontal axis and its birefringence index on the vertical axis, is negative (downward-sloping), a polymerizable liquid crystal compound with reverse wavelength dispersion property, or a polymerizable liquid crystal compound showing substantially no wavelength dispersion property (flat dispersion or low wavelength dispersion). As the polymerizable liquid crystal compound different from the polymerizable liquid crystal compound in the present disclosure, examples include compounds with reverse wavelength dispersion property, such as the polymerizable liquid crystal compounds disclosed in Patent Nos. JP5463666, JP4186981, JP5962760 and JP5826759, and compounds with flat dispersion property such as the compound described in Recueil des Travaux Chimiques des Pays-Bas (1996), 115(6), 321-328.

In the present embodiment, the different polymerizable liquid crystal compound is preferably a polymerizable liquid crystal compound containing a polymerizable functional group at least in one terminal of its rodlike mesogen, and is more preferably a polymerizable liquid crystal compound containing polymerizable functional groups in both terminals of its rodlike mesogen respectively, from the viewpoint of the ease of alignment in a combination of the different polymerizable liquid crystal compound with the polymerizable liquid crystal compound. The polymerizable liquid crystal compound containing two or more polymerizable functional groups per molecule, can improve the hardness and durability of the coating film.

As the polymerizable liquid crystal compound used in the present disclosure, examples include polymerizable liquid crystal compounds represented by the following general formulae (II-1) and (II-2) which have the same structure as the main chain moiety of the above-described polymerizable compound.

General Formula (II-1)

$$Z^{10}—R^{sp10}—L^{30}—\!\!\left[A^{20}—L^{10}\right]_{s1}—A^{10}—L^{20}—R^{sp20}—Z^{20}$$

General Formula (II-2)

$$Z^{10}—R^{sp10}—L^{30}—\!\!\left[A^{20}—L^{10}\right]_{s2}—A^{10}—R$$

where $Z^{10}$ and $Z^{20}$ each independently represent a polymerizable functional group; $R^{sp10}$ and $R^{sp20}$ each independently represent a single bond or an alkylene group containing 1 to 20 carbon atoms, in which one —$CH_2$— or two or more non-adjacent —$CH_2$— are substituted by —O—, —COO—, —OCO— or —OCOO—; $L^{10}$, $L^{20}$ and $L^{30}$ each independently represent —O—, —S—, —$OCH_2$—, —$CH_2O$—, —CO—, —OCOO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH═CH—OCO—, —CH═CH—OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—OCO—, —$CH_2$—OCO—, —CH═CH—, —CF═CF—, —C≡C— or a single bond; $A^{10}$ and $A^{20}$ each independently represent a benzene-1,4-diyl group, a cyclohexane-1,4-diyl group, a pyridine-2,5-diyl group, a pyrimidine-2,5-diyl group, a naphthalene-2,6-diyl group, a naphthalene-1,4-diyl group, a tetrahydronaphthalene-2,6-diyl group or a 1,3-dioxane-2,5-diyl group; $A^1$ and $A^{20}$ are each independently optionally unsubstituted or substituted by an alkyl group, an alkyl halide group, an alkoxy group, an alkoxy halide group, a halogen atom, a cyano group or a nitro group; R represents a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group containing 1 to 20 carbon atoms, in which one —$CH_2$— or two or more non-adjacent —$CH_2$— are each independently optionally unsubstituted or substituted by —O—, —S—, —CO—, —OCO—, —OCO—, —CO—S—, —S—CO—, —O—CO—O—, —CO—NH—, —NH—CO—, —CH=CH—CO—, —CH=CH—OCO—, —COO—CH=CH—, —OCO—CH=CH—, —CH=CH—, —CF=CF— or —C≡C—; s1 and s2 represent 0, 1, 2, 3 or 4 and when s1 and s2 each independently represent 2, 3 or 4, two, three or four $A^{20}$s may be the same or different from each other, and two, three or four $L^{10}$s may be the same or different from each other.

As the polymerizable functional group which the polymerizable liquid crystal compound contains, examples include those exemplified above as $Z^1$ and so on in the above-described polymerizable compound. As the polymerizable functional group which the polymerizable liquid crystal compound contains, examples include cyclic-ether-containing groups, such as an oxirane ring and an oxetane ring, and ethylenic-double-bond-containing groups. Out of these examples, ethylenic-double-bond-containing groups are preferred since the liquid crystal compound shows light curability and are excellent in handleability. Examples of the cyclic-ether-containing groups include a glycidyl group. Examples of the ethylenic-double-bond-containing groups include vinyl, allyl and (meth)acryloyl groups. Out of these examples, a (meth)acryloyl group is preferred.

In the present embodiment, the polymerizable liquid crystal compound is preferably one or more compounds selected from compounds each represented by the following general formula (III) and compounds each represented by the following general formula (IV) from the viewpoint of the alignment property:

General Formula (III)

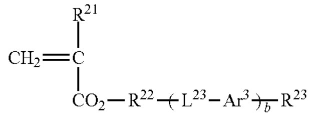

where $R^{21}$ represents a hydrogen atom or a methyl group; $R^{22}$ represents a group represented by $—(CH_2)_p—$ or $—(C_2H_4O)—$; $L^{23}$ represents a direct bond or a linking group represented by —O—, —O—C(=O)— or —C(=O)—O—; $Ar^3$ represents a benzene-1,4-diyl group, a cyclohexane-1,4-diyl group, a pyridine-2,5-diyl group, a pyrimidine-2,5-diyl group, a naphthalene-2,6-diyl group, a naphthalene-1,4-diyl group, a tetrahydronaphthalene-2,6-diyl group or a 1,3-dioxane-2,5-diyl group, and $Ar^3$ is optionally unsubstituted or substituted by an alkyl group, an alkyl halide group, an alkoxy group, an alkoxy halide group, a halogen atom, a cyano group or a nitro group; plural $L^{23}$s, as well as plural $Ar^3$s, may be the same or different from each other; $R^{23}$ represents —F, —Cl, —CN, $—OCF_3$, $—OCF_2H$, —NCO, —NCS, $—NO_2$, $—NHC(=O)—R^{24}$, $—C(=O)—OR^{24}$, —OH, —SH, —CHO, $—SO_3H$, $—NR^{24}_2$, $—R^{25}$ or $—OR^{25}$; $R^{24}$ represents a hydrogen atom, or an alkyl group containing 1 or more and 6 or less carbon atoms; $R^{25}$ represents an alkyl group containing 1 or more and 6 or less carbon atoms; b is an integer of 2 or more and 5 or less; and p and p' are each independently an integer of 2 or more and 10 or less, General Formula (IV)

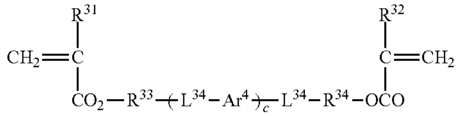

where $R^{31}$ and $R^{32}$ each independently represent a hydrogen atom or a methyl group; $R^{33}$ represents a group represented by $—(CH_2)_q—$ or $—(C_2H_4O)_{q'}—$; $R^{34}$ represents a group represented by $—(CH_2)_r—$ or $—(OC_2H_4)_{r'}—$; $L^{34}$ represents a direct bond or a linking group represented by —O—, —O—C(=O)— or —C(=O)—O—; $Ar^4$ represents a benzene-1,4-diyl group, a cyclohexane-1,4-diyl group, a pyridine-2,5-diyl group, a pyrimidine-2,5-diyl group, a naphthalene-2,6-diyl group, a naphthalene-1,4-diyl group, a tetrahydronaphthalene-2,6-diyl group or a 1,3-dioxane-2,5-diyl group, and $Ar^4$ is optionally unsubstituted or substituted by an alkyl group, an alkyl halide group, an alkoxy group, an alkoxy halide group, a halogen atom, a cyano group or a nitro group; plural $L^{34}$s, as well as plural $Ar^4$s, may be the same or different from each other; c is an integer of 2 or more and 5 or less; and q, q', r and r' are each independently an integer of 2 or more and 10 or less.

Also, p and p' in the general formula (III) and q, q', r and r' in the general formula (IV) are each preferably 2 or more and 8 or less, more preferably 2 or more and 6 or less, and even more preferably 2 or more and 5 or less from the viewpoint of the alignment property.

$Ar^3$ and $Ar^4$ each represent a benzene-1,4-diyl group, a cyclohexane-1,4-diyl group, a pyridine-2,5-diyl group, a pyrimidine-2,5-diyl group, a naphthalene-2,6-diyl group, a naphthalene-1,4-diyl group, a tetrahydronaphthalene-2,6-diyl group or a 1,3-dioxane-2,5-diyl group. Among them, $Ar^3$ and $Ar^4$ are more preferably a benzene-1,4-diyl group, a naphthalene-2,6-diyl group, or a cyclohexane-1,4-diyl group each. $Ar^3$ and $Ar^4$ may have the substituent group each, and examples of the substituent group include an alkyl group, an alkyl halide group, an alkoxy group, an alkoxy halide group, a halogen atom, a cyano group and a nitro group. More preferred examples thereof include an alkyl group containing 1 or more and 5 or less carbon atoms, and a halogen atom.

The alkyl group containing 1 or more and 6 or less carbon atoms as $R^{24}$ and $R^{25}$ in the general formula (III) may be linear, branched or cyclic. Examples of such an alkyl group include linear alkyl groups such as a methyl group, an ethyl group, an n-propyl group, an n-butyl group, an n-pentyl group and an n-hexyl group; branched alkyl groups such as an i-propyl group, an i-butyl group, a t-butyl group and a 2-methylbutyl group; and cycloalkyl groups such as a cyclopropyl group, a cyclobutyl group, a cyclopentyl group and a cyclohexyl group. Among them, $R^{24}$ is preferably a hydrogen atom or an alkyl group containing 1 or more and 5 or less carbon atoms, and more preferably a hydrogen atom or an alkyl group containing 1 or more and 3 or less carbon atoms. $R^{25}$ is preferably an alkyl group containing 1 or more and 5 or less carbon atoms, and more preferably an alkyl group containing 1 or more and 3 or less carbon atoms.

Among them, from the viewpoint of alignment property, $R^{23}$ is preferably —Cl, —CN, $—OCF_3$, $—OCF_2H$, —NCO, —NCS, $—NO_2$, $—NHC(=O)—R^{25}$, $—C(=O)—OR^{24}$, —OH, —SH, —CHO, $—SO_3H$, $—NR^{24}_2$, $—R^{25}$ or $—OR^{23}$, and more preferably —Cl, —CN, $—OCF_3$, $—C(=O)—OR^{24}$, $—R^{25}$ or $—OR^{23}$.

The mesogen structure contained in the polymerizable liquid crystal compound is preferably a partial structure represented by each of chemical formulae (V-1) to (V-6) illustrated below, and in particular, the mesogen structure is preferably a partial structure represented by at least one selected from the group consisting of the chemical formulae (V-1), (V-2), (V-4), (V-5) and (V-6) each containing three or more cyclic structures. Any hydrogen atom in a phenylene group or naphthylene group in the partial structure represented by each of the chemical formulae (V-1) to (V-6) may be substituted by an alkyl group containing 1 or more and 3 or less carbon atoms, or a halogen atom.

(V-1)

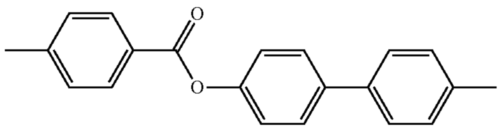

(V-2)

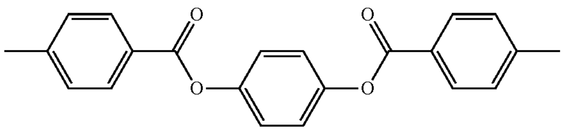

(V-3)

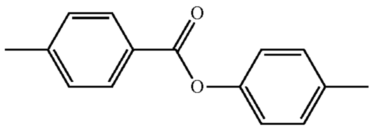

-continued (V-4)

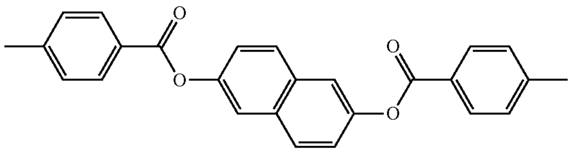

(V-5)

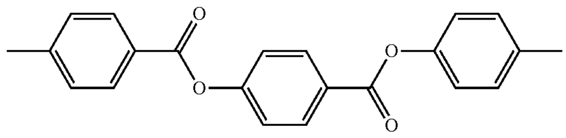

(V-6)

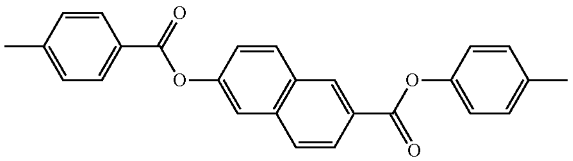

Preferred and specific examples of the compounds represented by the general formulae (III) and (IV) include, but are not limited to, compounds represented by the following chemical formulae (1) to (22).

(1)

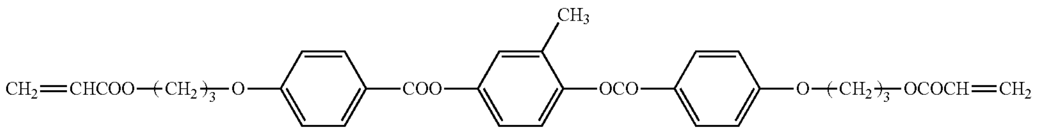

(2)

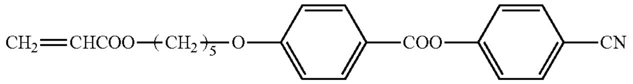

(3)

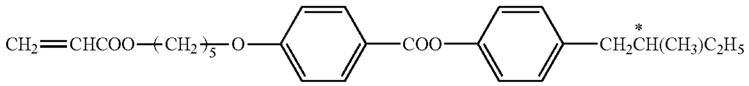

(4)

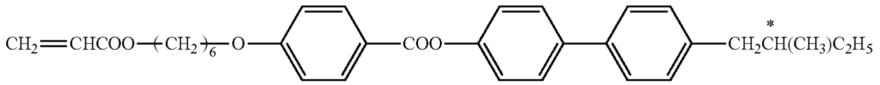

(5)

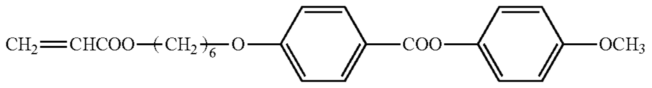

(6)

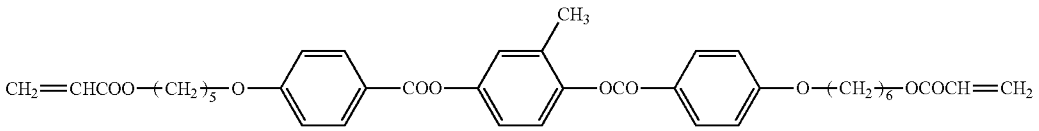

-continued
(7)
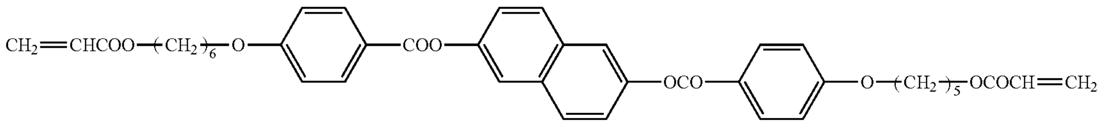
(8)
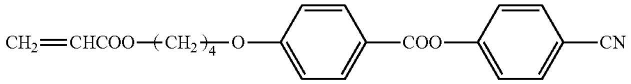
(9)
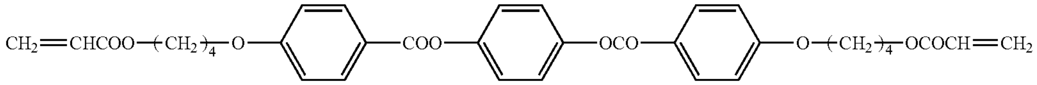
(10)
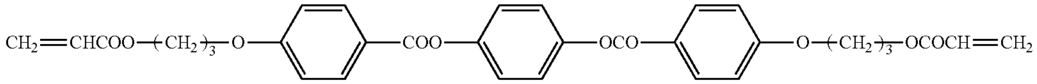
(11)
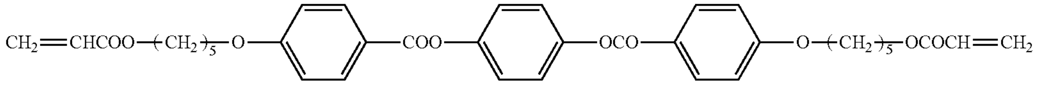
(12)
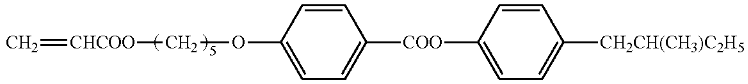
(13)
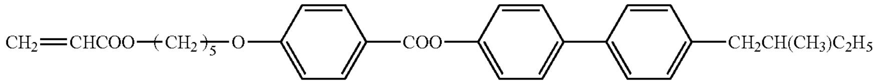
(14)
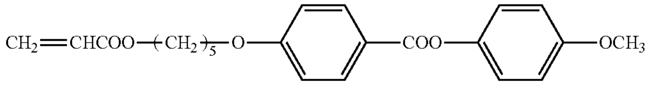
(15)
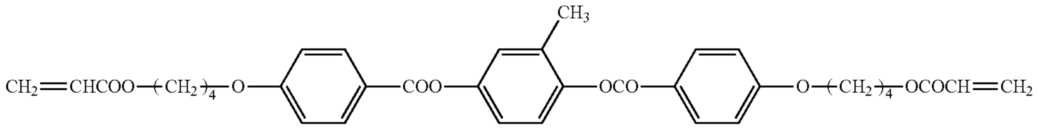
(16)
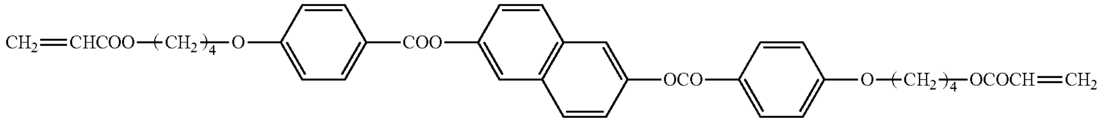
(17)
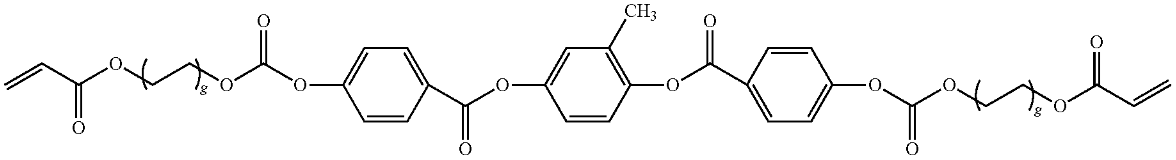
In the above formula, g is an integer of from 2 to 5.
(18)
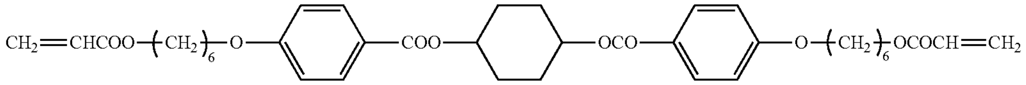
(19)
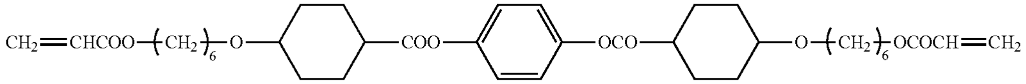

-continued (20)

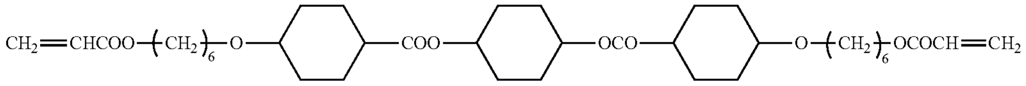

(21)

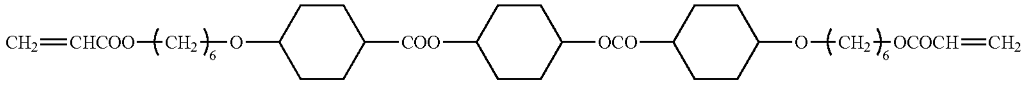

(22)

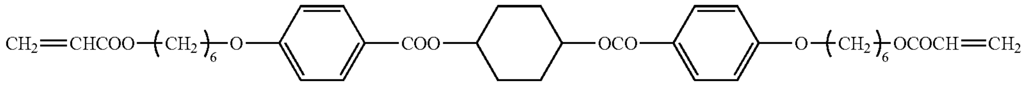

As described above, since the reverse wavelength dispersion property of the polymerizable liquid crystal compound in the present disclosure is excellent, even if a compound with a wide range of wavelength dispersion property is added, the retardation value of a cured product of the composition is likely to show reverse wavelength dispersion property. For the polymerizable liquid crystal compound in the present disclosure, when the retardation value is measured as described above, Re (450)/Re (550) has a tendency to be relatively small.

Accordingly, from the viewpoint of controlling the wavelength dispersion property to ideal wavelength dispersion property, the polymerizable liquid crystal compound different from the polymerizable liquid crystal compound in the present disclosure, preferably further contains a polymerizable liquid crystal compound for which the value of the ratio of the in-plane retardation for a wavelength of 450 nm (Re (450)) and the in-plane retardation for a wavelength of 550 nm (Re (550)) measured in the following testing method (that is, Re (450)/Re (550)) is larger than Re (450)/Re (550) of the contained polymerizable liquid crystal compound in the disclosed embodiments. The polymerizable liquid crystal compound different from the polymerizable liquid crystal compound in the present disclosure, can be selected from those for which Re (450)/Re (550) is 0.6 or more and less than 1.2. The polymerizable liquid crystal compound different from the polymerizable liquid crystal compound in the present disclosure, is preferably selected from those for which Re (450)/Re (550) is 0.8 or more and less than 1.2, and more preferably from those for which Re (450)/Re (550) is 0.9 or more and less than 1.2.

[Testing Method]

A rubbing-treated, polyimide alignment film-attached glass piece (an alignment-treated glass substrate manufactured by EHC Co., Ltd.) is prepared. The polymerizable liquid crystal compound (100 parts by mass) and 2-methyl-1-(4-methylthiophenyl)-2-morpholinopropane-1-on (4 parts by mass) are dissolved in cyclopentanone (900 parts by mass) to obtain a polymerizable composition. The polymerizable composition is formed into a film by applying, on the alignment film of the substrate, the polymerizable composition to give a 1 μm-thick film when cured. The film is dried for 120 seconds at a temperature calculated by adding 10° C. to the solid-liquid crystal phase transition temperature (° C.) of the polymerizable liquid crystal compound. Thereafter, the dried film is irradiated with ultraviolet rays at an irradiation dose of 400 $mJ/cm^2$ to form a retardation layer. For the retardation layer, its in-plane retardation Re (450) for a wavelength of 450 nm and its in-plane retardation Re (550) for a wavelength of 550 nm are measured by a retardation measuring device (e.g., production name: KOBRA-WR, manufactured by: Oji Scientific Instruments).

In the present embodiment, from the viewpoint of improving the solvent solubility of the polymerizable composition, the polymerizable liquid crystal compound different from the polymerizable liquid crystal compound in the present disclosure, is preferably soluble in an amount of 20% by mass or more in at least one solvent selected from the group consisting of methyl ethyl ketone, methyl isobutyl ketone, cyclopentanone and cyclohexanone. This is because, once the solubility of the polymerizable composition is improved, a uniform coating film can be easily formed when the polymerizable composition is formed into a film; load applied to the production process and device for drying the solvent is reduced; wider selection of appliable substrates is provided; and since the liquid crystal phase transition temperature range of the composition is widened, the process margin at the time of alignment is widened, and the alignment property gets more uniform and better.

In the present embodiment, one kind of the polymerizable liquid crystal compound different from the polymerizable liquid crystal compound in the present disclosure may be singly used, or two or more kinds of such compounds may be used in combination.

In the present embodiment, the content of the polymerizable liquid crystal compound different from the polymerizable liquid crystal compound in the present disclosure, may be appropriately controlled to control the desired retardation, etc., and is not particularly limited. The content of the polymerizable liquid crystal compound different from the polymerizable liquid crystal compound in the present disclosure, is preferably 7 parts by mass or more and 49.9 parts by mass or less, more preferably 10 parts by mass or more and 45 parts by mass or less, and even more preferably 10 parts by mass or more and 42 parts by mass or less, with respect to 100 parts by mass of the solid content of the polymerizable composition.

The content of the polymerizable liquid crystal compound different from the polymerizable liquid crystal compound in the present disclosure, may be appropriately controlled to control the desired retardation, etc. The content of the polymerizable liquid crystal compound different from the polymerizable liquid crystal compound in the present disclosure, is preferably 50 parts by mass or less, and more preferably 45 parts by mass or less, with respect to the total amount (100 parts by mass) of the polymerizable liquid crystal compound in the present disclosure and the polymerizable liquid crystal compound different from the polymerizable liquid crystal compound in the present disclosure.

4. Other Components

The polymerizable composition of the present embodiment may include any other component as far as the advantageous effects thereof are not impaired. Specifically, the composition may include, as the other component, for example, a leveling agent, an antioxidant or a light stabilizer, or a solvent from the viewpoint of the coatability of the composition. Also, the polymerizable composition of the present embodiment may contain a polymerizable compound which does not show liquid crystallinity when used alone but which allows control of retardation, reverse wavelength dispersion property, phase transition temperature, hardness and durability when used in combination with the polymerizable liquid crystal compound in the present disclosure. These components may each be any one selected appropriately from materials known in the prior art.

To improve the hardness and durability of the coating film, the polymerizable composition preferably further contains a polymerizable compound containing two or more polymerizable functional groups per molecule. As the polymerizable compound containing two or more polymerizable functional groups per molecule, the polymerizable liquid crystal compound as described above or a polymerizable compound having no liquid crystallinity can be used.

As the polymerizable compound containing two or more polymerizable functional groups per molecule, a so-called polyfunctional monomer can be used, such as trimethylolpropane tri(meth)acrylate, tripropylene glycol di(meth)acrylate, diethylene glycol di(meth)acrylate, dipropylene glycol di(meth)acrylate, pentaerythritol tri(meth)acrylate, pentaerythritol tetra(meth)acrylate, dipentaerythritol hexa(meth)acrylate, 1,6-hexanediol di(meth)acrylate, neopentyl glycol di(meth)acrylate, trimethylolpropane tri(meth)acrylate, ditrimethylolpropane tetra(meth)acrylate, dipentaerythritol penta(meth)acrylate, tripentaerythritol octa(meth)acrylate, tetrapentaerythritol deca(meth)acrylate, isocyanuric acid tri(meth)acrylate, isocyanuric acid di(meth)acrylate, polyester tri(meth)acrylate, polyester di(meth)acrylate, bisphenol di(meth)acrylate, diglycerin tetra(meth)acrylate, adamantyl di(meth)acrylate, isobornyl di(meth)acrylate, dicyclopentane di(meth)acrylate, tricyclodecane di(meth) acrylate, ditrimethylolpropane tetra(meth)acrylate, and these (meth)acrylates modified with PO, EO or the like. Since a crosslinking reaction is promoted to improve the durability of the coating film, a polymerizable compound containing three or more polymerizable functional groups per molecule is preferred, such as pentaerythritol triacrylate (PETA), dipentaerythritol hexaacrylate (DPHA), pentaerythritol tetraacrylate (PETTA), dipentaerythritol pentaacrylate (DPPA) and trimethylolpropane triacrylate (TMPTA).

When the polymerizable compound having no liquid crystallinity is used in the present embodiment, the content is preferably 40 parts by mass or less, more preferably 30 parts by mass or less, and even more preferably 20 parts by mass or less, with respect to 100 parts by mass of the solid content of the polymerizable composition.

In the present embodiment, the polymerizable compound different from the polymerizable liquid crystal compound in the present disclosure, is preferably soluble in an amount of 20% by mass or more in at least one solvent selected from the group consisting of methyl ethyl ketone, methyl isobutyl ketone, cyclopentanone and cyclohexanone. This is because, since the solvent solubility of the polymerizable composition is improved, a uniform coating film can be easily formed when the polymerizable composition is formed into a coating film; load applied to the production process and device for drying the solvent is reduced; and wide selection of applicable substrates is provided.

The leveling agent is preferably a fluorine type or a silicone type leveling agent. Specific examples of the leveling agent include MEGAFACE series manufactured by DIC Corp. and described in JP 2010-122325A, TSF series manufactured by Momentive Performance Materials Japan Inc., and FTERGENT series manufactured by Neos Co., Ltd. When the leveling agent is used in the present embodiment, the content rate thereof is preferably set to an amount of 0.001 parts by mass or more and 5 parts by mass or less for 100 parts by mass of solid components in the polymerizable composition.

The polymerizable composition of the present embodiment optionally includes a solvent from the viewpoint of the coatability thereof. The solvent is sufficient to be selected appropriately from solvents known in the prior art in each of which the individual components included in the polymerizable composition can be dissolved or dispersed. Specific examples thereof include hydrocarbon solvents such as hexane, cyclohexane and toluene; ketone solvents such as methyl ethyl ketone, methyl isobutyl ketone, cyclopentanone and cyclohexanone; ether solvents such as tetrahydrofuran, 1,3-dioxolan and propylene glycol monoethyl ether (PGME); halogenated alkyl solvents such as chloroform and dichloromethane; ester solvents such as ethyl acetate and propylene glycol monomethyl ether acetate; amide solvents such as N,N-dimethylformamide and N-methylpyrrolidone; sulfoxide solvents such as dimethylsulfoxide; and alcohol solvents such as methanol, ethanol and propanol. In the present embodiment, one kind of the solvent may be singly used, or two or more kinds of such solvents may be used in combination.

The polymerizable composition in the present embodiment is favorably applicable to various applications, due to its excellent alignment property. For example, the polymerizable composition in the present embodiment is favorably used as a liquid crystal composition in applications such as the below-described retardation film or various kinds of optical member applications.

C. Polymer

The polymer in the present disclosure is obtained by polymerizing the polymerizable liquid crystal compound in the present disclosure or by polymerizing the polymerizable composition in the present disclosure. The polymerizing method can be appropriately selected depending on the polymerizable functional group contained in the polymerizable liquid crystal compound in the present disclosure.

The polymer obtained by polymerizing the polymerizable liquid crystal compound or polymerizable composition in the present disclosure without aligning the compound or composition, is applicable as a light scattering plate, a polarized light eliminating plate, and a moire fringe preventing plate, for example.

The polymer obtained by aligning the polymerizable liquid crystal compound or polymerizable composition in the present disclosure and polymerizing the compound or composition, has optical anisotropy and is favorably used as the below-described retardation film or various kinds of optical member applications.

D. Retardation Film

The retardation film in the present disclosure is a retardation film containing a retardation layer, wherein the retardation layer contains a cured product of the polymerizable composition in the present disclosure.

Since the retardation layer is composed of the cured product of the polymerizable composition, as described above, the retardation film in the present embodiment is a retardation film with excellent alignment property, a large birefringence index (Δn) and reverse wavelength dispersion property.

Figure 2:
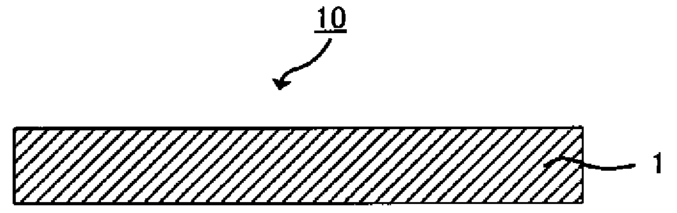
FIG. 2 is a schematic sectional view showing an embodiment of a retardation film.
Figure 3:
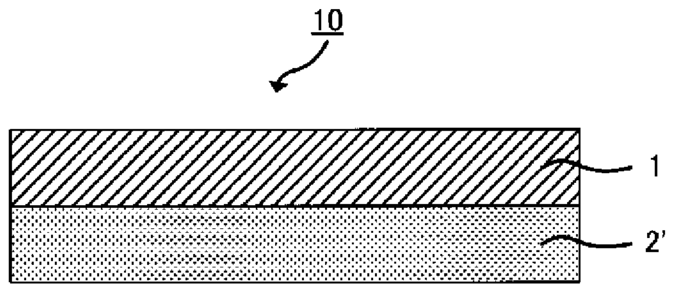
FIG. 3 is a schematic sectional view showing an embodiment of a retardation film.

With reference to the drawings, the layer structure of the retardation film will be described. FIGS. 1 to 3 each show one embodiment of the retardation film in the present disclosure. The one embodiment illustrated in FIG. 1, which is a retardation film 10, is a retardation film in which an alignment film 3 and a retardation layer 1 are laminated in this order on a substrate 2. The one embodiment illustrated in FIG. 2, which is a retardation film 10, is a retardation film made only of a retardation layer 1. In the one embodiment illustrated in FIG. 3, which is a retardation film 10, a retardation layer 1 is directly formed on a substrate 2'. In the retardation film illustrated in FIG. 3, a means for expressing alignment-regulating force may be given to the surface of the substrate 2' on the retardation-layer-1-side surface of the substrate 2'. The alignment-regulating force in the present disclosure means an action that causes an alignment component in a retardation layer to be arranged in a specific direction.

1. Retardation Layer

The retardation layer 1 of an embodiment in the present disclosure is made of the cured product of the polymerizable composition in the present disclosure, which contains the polymerizable liquid crystal compound in the present disclosure.

The polymerizable liquid crystal compound in the present disclosure, and the polymerizable composition in the present disclosure may each be the same as described about the polymerizable liquid crystal compound and polymerizable composition of the embodiment in the present disclosure. Thus, any description thereabout is omitted herein.

The retardation layer is preferably a retardation layer in which the main chain moiety with the alignment property of the polymerizable liquid crystal compound in the present disclosure, and the optionally contained polymerizable liquid crystal compound are cured in the state of being substantially horizontally aligned with respect to the film surface. The cured product of the polymerizable composition of the embodiment in the present disclosure contains a structure obtained by polymerizing the polymerizable functional groups of the polymerizable compound at least partially. Since the cured product contains this structure, which is obtained by polymerizing the polymerizable functional groups of the polymerizable compound at least partially, the retardation layer of the present embodiment is a retardation layer improved in durability.

The retardation can be measured, using an automatically birefringence measuring instrument (for example, trade name: KOBRA-WR, manufactured by Oji Scientific Instruments Co., Ltd.) Measuring-light is radiated into the retardation layer perpendicularly or obliquely to a surface of this layer. From a chart of the optical retardation of the retardation layer and the incident angle of the measuring-light, verification can be attained about the anisotropy of increasing or decreasing the retardation of the retardation layer and the degree of the vertical (thickness) direction alignment of liquid crystal.

By collecting a material from the retardation layer, and then analyzing the material, it can be verified that the retardation layer includes the structure obtained by polymerizing at least a part of the polymerizable functional groups of the polymerizable liquid crystal compound in the present disclosure contained in the polymerizable composition in the present disclosure, and the optionally contained polymerizable liquid crystal compound. A method for the analysis can make use of NMR, IR, GC-MS, XPS and TOF-SIMS, and a combination of two or more of these methods.

The retardation layer may include a photopolymerization initiator, a leveling agent, an antioxidant, a light stabilizer, and other components. The retardation layer may not include a photopolymerization initiator or some other component that may be wholly decomposed when light radiation is performed to cause a reaction of the polymerizable functional groups of the polymerizable liquid crystal compound.

The thickness of the retardation layer may be appropriately set in accordance with the use purpose thereof.

For example, to use the retardation film in the present disclosure as a broadband quarter wavelength plate, the film thickness may be controlled, such that Re (550) of the obtained retardation film is 113 nm or more and 163 nm or less, preferably 135 nm or more and 140 nm or less, and particularly preferably about 137.5 nm. To use the retardation film as a half-wavelength plate, the film thickness may be controlled, such that Re (550) of the obtained optical film is 250 nm or more and 300 nm or less, preferably 273 nm or more and 277 nm or less, and particularly preferably about 275 nm.

By appropriately controlling the amount of the applied polymerizable composition or the concentration of the polymerizable liquid crystal compound, the film thickness can be controlled to give a desired retardation. Since the retardation value (Re (λ)) of the obtained retardation layer is determined by the following formula, the film thickness d may be controlled to obtain the desired Re (λ).

$$Re(\lambda)=d\times\Delta n(\lambda)$$

where Re (λ) represents the retardation value at a wavelength of λ nm; d represents the film thickness; and Δn (λ) represents the birefringence index at a wavelength of λ nm.

In particular, the thickness is preferably in a range of 0.1 μm or more and 5 μm or less, and more preferably in a range of 0.5 μm or more and 3 μm or less.

Since the birefringence index (Δn) of the polymerizable liquid crystal compound in the present disclosure is large, the desired retardation can be realized by the film with a smaller thickness than ever before.

The wavelength dispersion property of the retardation film of the present disclosure can be determined as desired, depending on the content of the polymerizable liquid crystal compound in the present disclosure contained in the retardation layer and the content of the different polymerizable liquid crystal compound that is optionally contained therein. If, in the retardation layer, the content of the polymerizable liquid crystal compound in the present disclosure is increased, the reverse wavelength dispersion property demonstrates a tendency to increase.

When, to get closer to ideal reverse wavelength dispersion property, the polymerizable composition containing the polymerizable liquid crystal compound in the present disclosure and the photopolymerization initiator only is prepared by the method described below in Example 1 and formed into the cured film (the retardation layer), Re (450)/Re (550) is preferably in a range of 0.75 or more and less than 0.95, more preferably in a range of 0.78 or more and less than 0.93, and even more preferably in a range of from 0.80 or more and less than 0.90. Also, Re (650)/Re (550) is preferably more than 1, and more preferably in a range of 1.02 or more and 1.1 or less.

2. Alignment Film

In the present document DESCRIPTION, an alignment film is a layer for arranging a liquid crystal component included in a retardation layer into a predetermined direction.

The alignment film used in the embodiment in the present disclosure is preferably a horizontal alignment film since the polymerizable composition of the embodiment in the present disclosure is horizontally aligned with ease.

The horizontal alignment film may be a film having a function of aligning the long axis of a mesogen of the liquid crystal component included in the retardation layer substantially horizontally with respect to the horizontal alignment film surface (the film surface) by being provided as a coating film.

The horizontal alignment film can be appropriately selected from conventionally-known horizontal alignment films such as alignment films provided with alignment-regulating force by a rubbing method, a photo-alignment method, a molding method, etc. Among them, the horizontal alignment film is preferably a horizontal alignment film provided with alignment-regulating force by a rubbing method, a photo-alignment method or a molding method.

In the case of providing alignment-regulating force by the rubbing method, a polymer that expresses alignment-regulating force by rubbing, is used in the horizontal alignment film. Examples of the polymer include polyvinyl alcohol, polyimide, polyamide and derivatives thereof. Among them, the polymer is preferably polyvinyl alcohol.

The method for forming the horizontal alignment film by the rubbing method, may be appropriately selected from conventionally-known methods. For example, the horizontal alignment film can be obtained by forming a coating film containing the polymer on the transparent substrate and then rubbing the coating film with a known rubbing roller or the like.

In the case of forming the horizontal alignment film by the photo-alignment method, a photo-alignment composition containing a photo-alignment material that expresses alignment-regulating force by applying polarized light, is used as the composition for alignment film. The photo-alignment material may be a photodimerizable or photoisomerizable material. Specific examples thereof include a polymer containing cinnamate, coumarin, benzylidenephthalimidine, benzylideneacetophenone, diphenylacetylene, stilbazole, uracil, quinoline, maleinimide or a cinnamylideneacetic acid derivative. Preferred examples include a polymer containing at least one of cinnamate and coumarin, and derivatives thereof. Specific examples of such a photodimerizable material include compounds disclosed in Japanese Patent Application Laid-Open (JP-A) No. H9-118717, Japanese translation of PCT International Application No. H10-506420, Japanese translation of PCT International Application No. 2003-505561, WO2010/150748 and JP-A No. 2015-151548.

The method for forming the photo-alignment film by the photo-alignment method may be appropriately selected from conventionally-known methods. For example, the photo-alignment film can be obtained by uniformly applying the photo-alignment composition on the transparent substrate, irradiating them with polarized light, and then irradiating the whole surface of the coating film with light.

In the case of forming the horizontal alignment film by the molding method, the composition for alignment film may be appropriately selected from compositions that can be molded into a desired fine convexo-concave shape. For example, a molding composition containing an ultraviolet curable resin, thermosetting resin, electron beam-curable resin or the like, can be used. Among them, an ultraviolet curable resin is preferably used from the viewpoint of the ease of forming the alignment film. Specific examples of the ultraviolet curable resin include, in addition to the above-defined polymerizable monomer and oligomer, urethane acrylate, epoxy acrylate, polyester acrylate, polyether acrylate and melamine acrylate. One kind of the ultraviolet curable resin may be singly used, or two or more kinds of such ultraviolet curable resins may be used in combination.

The method for forming the horizontal alignment film by the molding method may be appropriately selected from conventionally-known methods. For example, the alignment film provided with the desired fine convexo-concave shape can be obtained by uniformly applying the molding composition on the transparent substrate, placing the coating film on a mold in the desired fine convexo-concave shape, pressing them and then irradiating them with ultraviolet rays.

The horizontal alignment film may be a horizontal alignment film subjected to a patterning treatment to dispose, in a pattern, a moiety with alignment performance. As the horizontal alignment film subjected to the patterning treatment, a known horizontal alignment film can be used and is not particularly limited. Examples thereof include a rubbing alignment film subjected to a patterning treatment by mask rubbing, a photo-alignment film subjected to a patterning treatment by mask exposure, and an alignment film subjected to a patterning treatment by printing or the like.

The thickness of the horizontal alignment film is not particularly limited, as long as the horizontal alignment film makes it possible to arrange the polymerizable rodlike liquid crystal compound in the horizontal direction, and can be appropriately set. The thickness of the horizontal alignment film is usually 1 nm or more, and preferably 60 nm or more. On the other hand, from the viewpoint of producing a thin film, the thickness of the horizontal alignment film may be 15 μm or less, preferably 10 μm or less, more preferably 1 μm or less, and even more preferably 0.3 μm or less.

3. Substrate

In the present embodiment, examples of the substrate include a glass substrate, a metallic substrate, and a resin substrate. In particular, the substrate preferably has transparency, and is appropriately selectable from transparent substrates known in the prior art. The transparent substrate may be, besides the glass substrate, a transparent resin substrate formed, using a resin such as an acetylcellulose resin such as triacetylcellulose, a polyester resin such as polyethylene terephthalate, polyethylene naphthalate, polybutylene terephthalate or polylactic acid, an olefin based resin such as polypropylene, polyethylene or polymethylpentene, acrylic resin, polyurethane resin, polyethersulfone, polycarbonate, polysulfone, polyether, polyetherketone, acrylonitrile, methacrylonitrile, cycloolefin polymer, or cycloolefin copolymer.

The transmittance of the transparent substrate is preferably 80% or more, and more preferably 90% or more in a visible ray band. The transmittance of the transparent substrate is measurable in accordance with JIS K7361-1 (Test Method for Total Light Transmittance of Plastic-Transparent Material).

When the retardation layer is formed in a roll-to-roll manner, the transparent substrate is preferably made of a flexible material having a flexibility permitting the substrate to be wound into a roll form.

Examples of the flexible material include cellulose derivatives, norbornene-based polymers, cycloolefin polymers, polymethyl methacrylate, polyvinyl alcohol, polyimide, polyarylate, polyethylene terephthalate, polysulfone, polyethersulfone, amorphous polyolefin, modified acrylic polymers, polystyrene, epoxy resins, polycarbonate, and polyesters. It is in particular preferred in the present embodiment to use a cellulose derivative or polyethylene terephthalate. This is because cellulose derivatives are especially excellent in optical isotropy, so that the substrate can be made excellent in optical properties. Moreover, polyethylene terephthalate is high in transparency and excellent in mechanical properties to be preferred.

The thickness of the substrate used in the present embodiment is not particularly limited, as far as the thickness is in a range making it possible to give a required self-supporting performance to the substrate in accordance with the use purpose of the retardation film, and other factors. The thickness is usually in a range of about 10 μm or more and 1000 μm or less.

In particular, the thickness of the substrate is preferably in a range of 25 μm or more and 125 μm or less, and especially preferably in a range of 30 μm or more and 100 μm or less. If the thickness is larger than in the former range, the following may be caused, for example, at the time of forming a long retardation film and subsequently cutting the film to be made into retardation film pieces: erosion products are increased or the cutting edge is worn away earlier than usual.

The structure of the substrate used in the present embodiment is not limited to a structure made of a single layer. Thus, the structure may be a structure composed of layers laminated onto each other. When the substrate has the structure composed of layers laminated onto each other, the layers which are layers having the same composition, or layers having compositions different from each other may be laminated.

When the alignment film used in the present embodiment is a film containing an ultraviolet curable resin, a primer layer may be formed on the substrate to improve adhesion between the transparent substrate and the ultraviolet curable resin. This primer layer may be any as long as it has adhesion to both the substrate and the ultraviolet curable resin, and is visible-ray-optically transparent to transmit ultraviolet rays. This layer can make use of, for example, a material selected appropriately from vinyl-chloride/vinyl-acetate copolymer based and urethane-based materials, and others.

An anchor coat layer may be laminated onto the substrate. The anchor coat layer can improve the substrate in strength. The material of the anchor coat layer may be a metal alkoxide, in particular, a metal silicon alkoxide sol. The metal alkoxide is usually used in the form of a solution in an alcohol. The anchor coat layer needs to be an even and flexible film. Thus, the thickness of the anchor coat layer is preferably about 0.04 μm more and 2 μm or less, and more preferably about 0.05 μm or more and 0.2 μm or less.

When the substrate contains the anchor coat layer, the substrate and the anchor coat layer may be improved in close adhesion between the two by laminating a binder layer into between the substrate and the anchor coat layer, or by incorporating, into the anchor coat layer, a material for enhancement of close adhesion with the substrate. A binder material used to form the binder layer is usable without any especial restriction as far as the material is a material that can improve the close adhesion between the substrate and the anchor coat layer. Examples of the binder material include silane coupling agents, titanium coupling agents, and zirconium coupling agents.

4. Method for Producing Retardation Film

A method of an embodiment in the present disclosure for producing a retardation film, is a method for producing a retardation film, including a step of forming a retardation layer by:

- a step of forming, into a film, the polymerizable composition in the embodiment in the present disclosure (a film forming step),
- a step of aligning at least the polymerizable compound in the polymerizable composition formed into the film (an aligning step), and
- a step of polymerizing at least the polymerizable compound after the aligning step (a polymerizing step).

The polymerizable composition may be the same as described in the item "B. Polymerizable Composition". Thus, any description thereabout is omitted herein.

(1) Step of Forming Polymerizable Composition into Film

The polymerizable composition is applied uniformly onto a support to form a film.

The film thickness is controlled to give a desired retardation by, as described above, appropriately controlling the amount of the applied polymerizable composition and the concentration of the polymerizable liquid crystal compound.

"Onto a support" may be "on the above-defined substrate", or may be, when the substrate contains the alignment film, "on the alignment film of the substrate".

The method for coating is not particularly limited as long as it is a method capable of forming a film having a desired thickness with a good precision, and may be appropriately selected. Examples thereof include gravure coating, reverse coating, knife coating, dip coating, spray coating, air knife coating, spin coating, roll coating, printing, dip pulling-up, curtain coating, die coating, casting, bar coating, extrusion coating, and E type coating methods.

(2) Aligning Step

Next, at least the polymerizable liquid crystal compound in the polymerizable composition formed into the film, is aligned. The polymerizable liquid crystal compound in the polymerizable composition made into the film is adjusted into a temperature at which it can be aligned, so as to be heated. This heating treatment makes it possible to align and dry the main chain moiety with the alignment property of the polymerizable liquid crystal compound in the present disclosure, as well as the optionally contained polymerizable liquid crystal compound different from the polymerizable compound in the present disclosure, and to fix them while keeping the alignment state.

The temperature at which the alignment can be carried out, is varied in accordance with individual substances in the polymerizable composition; thus, a temperature therefor needs to be appropriately adjusted. The heating treatment is conducted, for example, preferably at 60° C. or more and 200° C. or less, and more preferably at 60° C. or more and 100° C. or less.

The heating means is appropriately selectable from known heating and drying means to be usable.

Moreover, the heating period may be appropriately selected, for example, from periods in a range of 10 seconds or more and 2 hours or less, and preferably in a range of 20 seconds or more and 30 minutes or less.

(3) Polymerizing Step

After the aligning step, at least the polymerizable compound is polymerized. The polymerizable compound can be polymerized by, for example, light irradiation to the coating film fixed in the state that the alignment state of the polymerizable compound and the optionally contained polymerizable liquid crystal compound is maintained in the aligning step. Thus, a retardation layer made of the cured product of the polymerizable composition can be gained.

The light irradiation is preferably ultraviolet-ray irradiation. For the ultraviolet-ray irradiation, ultraviolet rays are used which are emitted from light rays of, for example, an ultra-high-pressure mercury lamp, a high-pressure mercury lamp, a low-pressure mercury lamp, a carbon arc, a xenon arc, or a metal halide lamp. The irradiance level of the energy beam source may be appropriately selected. Preferably, the accumulated irradiation dose thereof at an ultraviolet wavelength of 365 nm is, for example, in a range of 10 $mJ/cm^2$ or more and 10000 $mJ/cm^2$ or less.

5. Usage

The retardation film in the present disclosure is favorably used as, for example, an antireflection quarter wavelength plate, and is favorably used for an optical member for various display devices that will be detailed later.

E. Transfer Laminate

A transfer laminate in the present disclosure is a transfer laminate configured to transfer a retardation layer, wherein the transfer laminate contains a retardation layer and a support supporting the retardation layer in a removable manner, and wherein the retardation layer is made of a cured product of the polymerizable composition in the present disclosure.

The transfer laminate of the present embodiment is a laminate containing a retardation layer made of a cured product of the above-mentioned polymerizable composition; thus, the transfer laminate is a laminate restraining the precipitation of the polymerizable compound and having excellent optical properties. The transfer laminate of the present embodiment makes it possible to transfer, onto, for example, any other optical member, the retardation layer in the present disclosure which is, for example, a thin film including no substrate.

Figure 5:
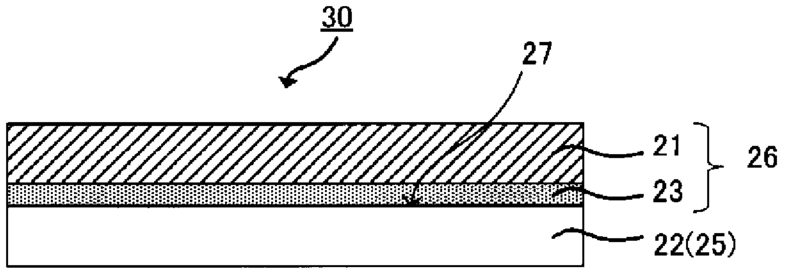
FIG. 5 is a schematic sectional view showing an embodiment of a transfer laminate.

The transfer laminate of the present embodiment makes it possible to provide, for example, the retardation film 10 which has been illustrated in FIG. 2, which is made only of the retardation layer 1, or a retardation film illustrated in FIG. 5, which includes no substrate and is made only of a laminate 26 in which an alignment film 23 and a retardation layer 21 are laminated onto each other. In other words, as far as the retardation layer is at least peelable and removable, an alignment film and others may be laminated on the retardation layer, which is supplied to be transferred from the transfer laminate.

Hereinafter, a description will be made about the structure of such a transfer laminate. However, the polymerizable composition of the embodiment in the present disclosure has been described above; thus, any description thereabout is omitted herein.

Figure 4:
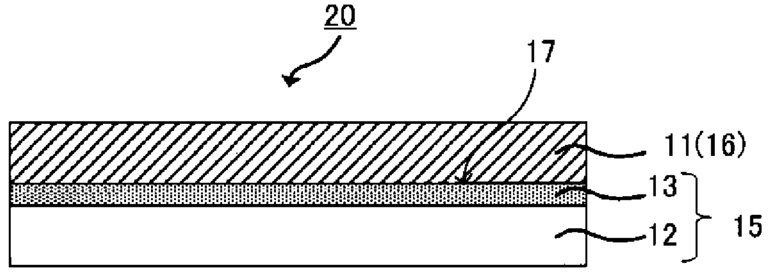
FIG. 4 is a schematic sectional view showing an embodiment of a transfer laminate.

The layer structure of the transfer laminate will be described with reference to the drawings. FIGS. 4 and 5 each show one embodiment of the transfer laminate in the present disclosure.

The one embodiment illustrated in FIG. 4, which is a transfer laminate 20, is a transfer laminate in which as a retardation layer 16 supplied to be transferred, and a support 15 supporting the retardation layer in a removable manner, an alignment film 13 and a retardation layer 11 are laminated in this order onto a second substrate 12. In the transfer laminate illustrated in FIG. 4, the peel strength between the second substrate 12 and the alignment film 13 is larger than the peel strength between the alignment film 13 and the retardation layer 11. In this way, the transfer laminate illustrated in FIG. 4 is an example in which a peel is attained at an interface 17 between the alignment film and the retardation layer so that the retardation layer 11 (16) can be transferred.

The one embodiment shown in FIG. 5, which is a transfer laminate 30, is a transfer laminate in which as a retardation layer 26 supplied to be transferred, and a support 25 supporting the retardation layer in a removable manner, an alignment film 23 and a retardation layer 21 are laminated in this order onto a second substrate 22. In the transfer laminate illustrated in FIG. 5, the peel strength between the second substrate 22 and the alignment film 23 is smaller than the peel strength between the alignment film 23 and the retardation layer 21. In this way, the transfer laminate illustrated in FIG. 5 is an example in which a peel is attained at an interface 27 between the second substrate 22 and the alignment film 23 so that, as the retardation layer 26 supplied to be transferred, the retardation layer 21 and the alignment film 23 can be transferred.

For example, whether the peel strength between the second substrate and the alignment film is larger or smaller than the peel strength between the alignment film and the retardation layer can be checked by peeling the retardation layer and then checking at which of the two interfaces the peel is made. The checking at which of the two interfaces the peel is made can be analyzed by, for example, IR.

Figure 6:
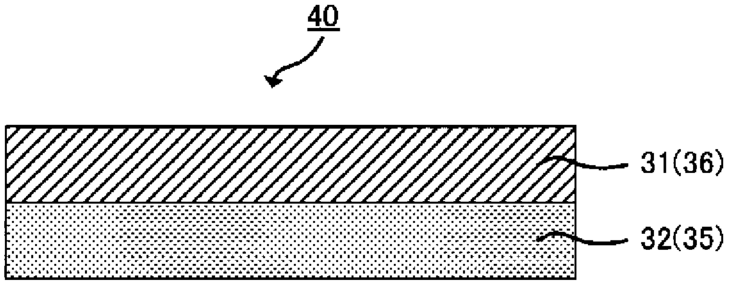
FIG. 6 is a schematic sectional view showing an embodiment of a transfer laminate.

The one embodiment shown in FIG. 6, which is a transfer laminate 40, is a transfer laminate in which as a retardation layer 36 supplied to be transferred, and a support 35 supporting the retardation layer in a removable manner, a retardation layer 31 is laminated in this order onto a second substrate 32.

Hereinafter, each of the present embodiments will be described. Its retardation layer may be the same retardation layer as described in the item "D. Retardation Film". Thus, any description thereabout is omitted herein.

Moreover, its alignment film and its substrate may be the same alignment film and substrate as described in the item "D. Retardation Film". Examples of the method for adjusting any one of the peel strengths in the present embodiment include methods described below.

In order to make the peel strength between the second substrate 12 and the alignment film 13 larger than the peel strength between the alignment film 13 and the retardation layer 11 to gain the transfer laminate 20 illustrated in FIG. 4, for example, a method is usable in which a solvent contained in a composition for forming the alignment film is rendered a solvent in which the second substrate can be dissolved. The second substrate is preferably a resin substrate. Surface treatment may be applied to surfaces of the substrate to improve the substrate in adhesion. In such a case, close adhesion between the resin substrate and the alignment film can be improved.

Moreover, in order to make the peel strength between the alignment film and the retardation layer small to make the peel strength between the substrate and the alignment film larger than the peel strength between the alignment film and the retardation layer, the solvent resistance of the alignment film is preferably made relatively high. In a case where the alignment film is relatively high in solvent resistance, the alignment film is not easily dissolved in the solvent in the polymerizable composition when the polymerizable composition is applied onto the alignment film to form the retardation layer. Consequently, the close adhesion between the alignment film and the retardation layer can be lowered.

In order to make the peel strength between the second substrate 22 and the alignment film 23 smaller than the peel strength between the alignment film 23 and the retardation layer 21 to gain the transfer laminate 30 illustrated in FIG. 5, for example, a release treatment may be applied onto a surface of the substrate, or a release layer may be formed thereonto. This way makes it possible to heighten the substrate in peelability, and make the peel strength between the substrate and the alignment layer smaller than the peel strength between the alignment layer and the retardation layer.

Examples of the release treatment include fluorine treatment, silicone treatment, and other surface treatments.

Examples of the material of the release layer include fluorine-containing release agents, silicone type release agents, and wax type release agents. The method for forming the release layer is, for example, a method of coating a release agent by dip coating, spray coating, roll coating, or some other coating method.

Also, in order to gain the transfer laminate 40 illustrated in FIG. 6, a release treatment may be applied onto a surface of the substrate, or a release layer may be formed thereonto, as required.

The substrate used in the transfer laminate may have flexibility or may not have flexibility. Preferably, the substrate has flexibility since the substrate is easily peeled to be removed.

When the substrate used in the transfer laminate is a sheet of anyone of the above-mentioned materials, usually, the thickness of the substrate is preferably in a range of 20 μm or more and 200 μm or less from the viewpoint of the balance between a sufficient self-supporting performance of the substrate, and the flexibility thereof that permits the substrate to be adapted to the production of the transfer laminate in the present embodiment and the transfer step thereof.

A retardation layer that can be supplied from the transfer laminate in the present disclosure is favorably used for the same use purposes as that of the retardation film, and favorably used as an antireflection quarter wavelength plate, for example. The retardation layer that can be supplied from the transfer laminate in the present disclosure can be transferred to an optical member for various display devices and is favorably used to supply a thin optical member.

F. Optical Member

An optical member in the present disclosure is an optical member containing the retardation film in the present disclosure and a polarizing plate disposed thereon.

Figure 7:
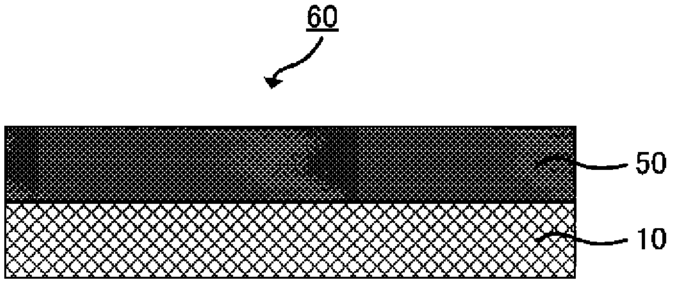
FIG. 7 is a schematic sectional view showing an embodiment of an optical member.

The optical member of the present embodiment will be described with reference to the drawings. FIG. 7 is a schematic sectional view showing an embodiment of the optical member.

In an example of an optical member 60 in FIG. 7, a polarizing plate 50 is located on a retardation film 10, which is the retardation film in the present disclosure. The optical member optionally contains a pressure-sensitive-adhesive layer (adhesive layer) (not illustrated) between the retardation film 10 and the polarizing plate 50.

In the present embodiment, the polarizing plate is a plate-form member through which only a light ray vibrating in a specific direction is transmitted, and may be appropriately selected from polarizing plates known in the prior art. The polarizing plate is, for example, a polyvinyl alcohol film, a polyvinyl formal film, a polyvinyl acetal film, or an ethylene/vinyl-acetate copolymer saponified film, all of which have been dyed with iodine or a dye, and then stretched.

In the present embodiment, a pressure-sensitive-adhesive or adhesive for the pressure-sensitive-adhesive layer (adhesive layer) may be appropriately selected from such adhesives known in the prior art. Thus, a pressure-sensitive-adhesive or adhesive in any adhering form is usable, examples thereof including pressure-sensitive-adhesives, two-part curable adhesives, ultraviolet curable adhesives, thermally curable adhesives, and holt-melt adhesives.

The optical member of the present embodiment may further contain, besides the polarizing plate, a different layer which a known optical member contains. Examples of the different layer include retardation layers different from the retardation layer of the present embodiment, an antireflective layer, a diffusion layer, an antiglare layer, an antistatic layer, and a protective film. However, the different layer is not limited to these layers.

The optical member of the present embodiment is favorably usable as, for example, an optical member for restraining the reflection of external light or a wide-viewing-angle polarizing plate for various display devices.

A method in the present disclosure for producing an optical member is not particularly limited, and may be appropriately selected from methods of laminating a polarizing plate onto the retardation film in the present disclosure. The method is, for example, a producing method of laminating a polarizing plate onto the retardation film in the present disclosure via a pressure-sensitive-adhesive layer or adhesive layer.

A method of an embodiment in the present disclosure for producing an optical member is an optical member producing method including:

- a transfer laminate preparing step of preparing the transfer laminate in the present disclosure,
- a transfer step in which a transfer receiving object containing at least a polarizing plate, is faced to the retardation layer of the transfer laminate, and the transfer laminate is transferred onto the transfer receiving object, and
- a removal step in which the support is removed from the transfer laminate transferred onto the transfer receiving object.

The optical member producing method of the embodiment in the present disclosure, using the above-defined transfer laminate, makes it possible to obtain an optical member containing the polarizing plate, and only the retardation layer out of the retardation film in the present disclosure.

The transfer laminate used in the optical member producing method of the embodiment in the present disclosure may be the same as described in the item "E. Transfer laminate". Thus, any description thereabout is omitted herein.

The transfer receiving object used in the optical member producing method of the embodiment in the present disclosure is typically a transfer receiving object containing an adhesive layer and a polarizing plate. However, the transfer receiving object is not limited thereto. The transfer receiving object may further contain one or more of the same different layers as the optical member of the embodiment in the present disclosure may contain.

G. Display Device

A display device in the present disclosure contains the retardation film in the present embodiment, or the optical member in the present embodiment.

Examples of the display device include light emitting display devices and liquid crystal display devices. However, the display device is not limited to these examples.

The display device contains, particularly, the retardation film in the present embodiment or the optical member in the present embodiment; thus, in particular, the display device which is, for example, an organic light emitting display device containing a transparent electrode layer, a light emitting layer and an electrode layer in this order has an advantageous effect of improving the viewing angle while external light reflection is restrained.

Figure 8:
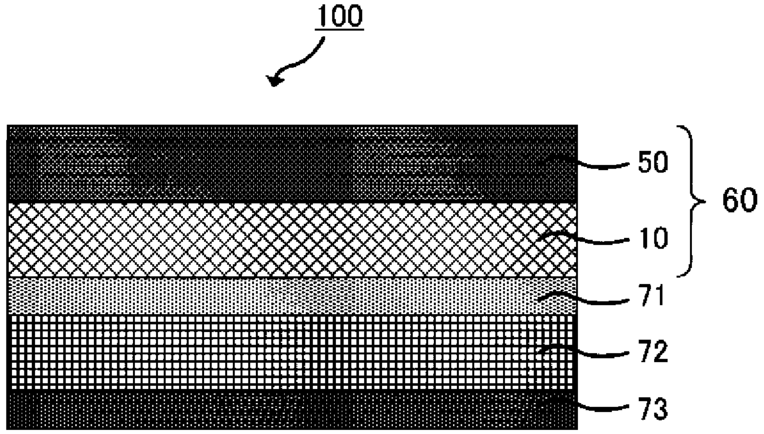
FIG. 8 is a schematic sectional view showing an embodiment of a display device.

The following will describe an example of a light emitting display device that is one embodiment, referring to a figure. FIG. 8 is a schematic sectional view showing one embodiment of the optical member.

In the example in FIG. 8, which is an organic light emitting display device 100, a polarizing plate 50 is located on a light-emitting-out surface side of the same retardation film 10 as described above, and further this display device contains, on the surface of the retardation film that is opposite to the former surface, a transparent electrode layer 71, a light emitting layer 72, and an electrode layer 73 in this order.

The light emitting layer 72 contains, for example, a structure in which from the transparent electrode layer 71 side of the device, the following layers are laminated in turn: a hole injecting layer; a hole transporting layer; a light emitting layer; and an electron injecting layer. In the present embodiment, known layers and other constituents are appropriately used for the transparent electrode layer, the hole injecting layer, the hole transporting layer, the light emitting layer, the electron injecting layer, the electrode layer, and other constituents. The light emitting display device produced in this manner is applicable to, for example, an organic EL display in a passive driving manner, and an organic EL display in an active driving manner.

The display device in the present embodiment is not limited to the above-mentioned structure, and is applicable into an appropriately-selective known structure.

EXAMPLES

For each compound produced below, the chemical structure was confirmed by $^{1}H$ NMR measurement using a product JEOL JNM-LA400WB manufactured by JEOL Ltd.

Also for each compound produced below, the phase transition temperature was checked by texture observation using a polarizing microscope ("BX51" manufactured by Olympus Corporation) equipped with a temperature control stage, during the temperature was raised. C denotes crystal. N denotes nematic phase. I denotes isotropic liquid. For example, "C 130 N 180 I" denotes transition from crystal to nematic phase at 130° C. and transition from nematic phase to isotropic liquid at 180° C.

Production Example 1: Production of Compound 1 Represented by Formula (1-1)

First, in a 500 mL recovery flask, 4,4'-dihydroxybiphenyl represented by the formula (1-1-1) (27 g, 150 mmol) and hexamethylenetetramine (46 g, 330 mmol) were dissolved in trifluoroacetic acid (320 ml). The reaction system was reacted at 110° C. for 3 hours. After the end of the reaction, 4 N hydrochloric acid (3 L) was added thereto in an ice bath, and the reaction system was stirred overnight. After the end of the stirring, the precipitation was filtrated to be collected. To the resultant crude product was added water (1 L), and the resultant was stirred for 1 hour to be suspended and purified. The precipitation was filtrated, and the resultant crystal was dried to yield an intermediate 1 represented by the formula (1-1-2) (7.5 g, 21 mmol, yield 21%).

To a suspension of cyclohexanedicarboxylic acid (172 g, 1.0 mol), 6-(4-hydroxyphenyl) hexyl acrylate (manufactured by DKSH) (53 g, 200 mmol) and N,N-dimethylaminopyridine (DMAP) (0.98 g, 8.0 mmol) in dichloromethane (1 L) was dropwise added a solution of N,N-dicyclohexylcarbodiimide (DCC) (43 g, 210 mmol) in dichloromethane (50 mL). After the end of the addition, the reaction system was stirred for 12 hours, and the precipitation was filtrated to be collected, and then washed with a sodium hydrogen carbonate aqueous solution and 1N hydrochloric acid. Thereafter, the solvent was distilled off. The resultant crude product was purified by open column chromatography to synthesize a carboxylic acid derivative 1 represented by the formula (1-1-3).

Next, to a suspension of the intermediate 1 represented by the formula (1-1-2) (7.0 g, 29 mmol), the carboxylic acid derivative 1 represented by the formula (1-1-3) (32 g, 76 mmol) and N,N-dimethylaminopyridine (DMAP) (0.14 g, 1.2 mmol) in dichloromethane (70 mL) was dropwise added a solution of N,N-dicyclohexylcarbodiimide (DCC) (19 g, 90 mmol) in dichloromethane (14 mL). After the end of the addition, the reaction system was stirred for 12 hours, and the precipitation was filtrated to be collected. Thereafter, the solvent was distilled off. To the resultant crude product was added chloroform (70 mL), and the resultant was stirred for 1 hour to be suspended and purified. The precipitation was filtrated, and the resultant crystal was dried to yield an intermediate 2 represented by the formula (1-1-4) (23 g, 22 mmol, yield 75%).

Next, 2-hydrazinobenzothiazole (5.0 g, 30 mmol) and potassium hydroxide (2.5 g, 45 mmol) were added to N,N-dimethylformamide (90 mL). The reaction system was heated at 80° C. After a predetermined temperature was reached, hexyl p-toluenesulfonate (9.2 g, 36 mmol) was dropwise added thereto. After the end of the addition, the reaction system was stirred for 4 hours. After the end of the reaction, water (10 ml) was added thereto to perform extraction. The solvent was distilled off. The residue was purified by silica gel chromatography, and the solvent was distilled off to yield an intermediate 3 represented by the formula (1-1-5) (3.0 g, 12 mmol, yield 400).

The intermediate 2 represented by the formula (1-1-4) (2.0 g, 1.9 mmol) and 12 N hydrochloric acid (15 mg) were dissolved in tetrahydrofuran (10 mL). Thereto was dropwise added a solution of the intermediate 3 represented by the formula (1-1-5) (1.2 g, 5.0 mmol) in tetrahydrofuran (3 mL). After the end of the addition, the reaction system was stirred for 12 hours, and then the resultant was dropwise added to methanol (50 ml). The resultant precipitation was filtrated. Thereafter, the solvent was distilled off. To the resultant crude product was added methanol (20 mL), and the resultant was stirred for 1 hour to be suspended and purified. The precipitation was filtrated, and the resultant crystal was dried to yield a compound 1 represented by the formula (1-1) (1.4 g, 0.94 mmol, yield 490).

Phase transition temperature (during the temperature rise): C 130 N 180 I $^{1}H$ NMR ($CDCl_3$; δppm): 8.39 (s, 2H), 7.80 (s, 2H), 7.70-7.60 (m, 4H), 7.35-7.20 (m, 6H), 7.05-6.85 (m, 10H), 6.41 (dd, 2H), 6.25-6.10 (m, 2H), 5.83 (dd, 2H), 4.34 (t, 4H), 4.17 (t, 4H), 3.97 (t, 4H), 2.70-2.55 (m, 4H), 2.45-2.35 (m, 8H), 1.95-1.65 (m, 20H), 1.55-1.30 (m, 20H), 0.88 (t, 6H).

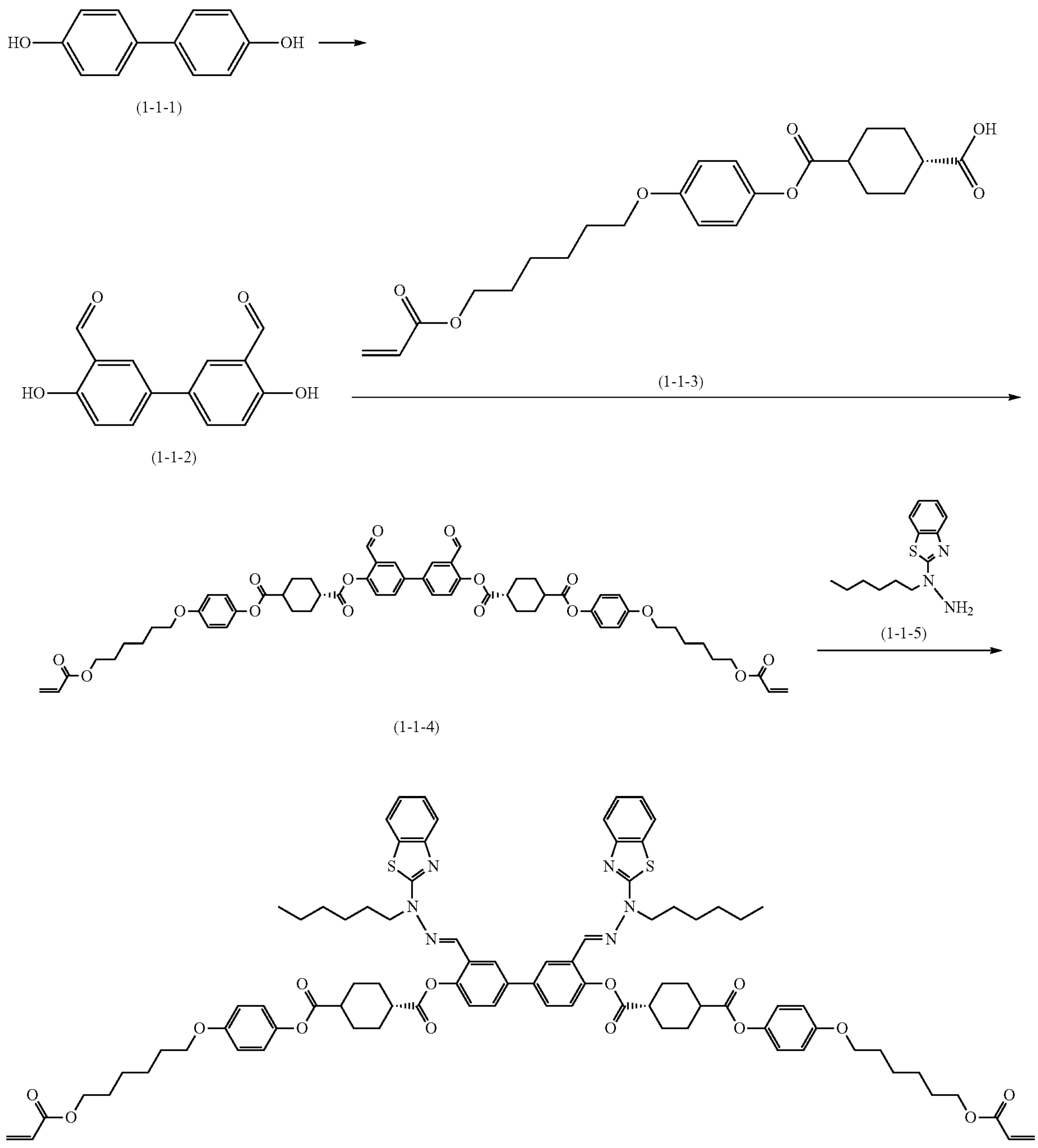

(1-1-1)

(1-1-2)

(1-1-3)

(1-1-4)

(1-1-5)

(1-1)

Production Example 2: Production of Compound 2 Represented by Formula (1-2)

To ethylene glycol (20 ml) was added 2-amino-6-fluorobenzothiazole (4.0 g, 24 mmol). In an ice bath, hydrazine monohydrate (3.6 g, 71 mmol) and 12 N hydrochloric acid (1.9 g, 55 mmol) were dropwise added thereto. The reaction system was stirred at 130° C. for 5 hours. After the end of the reaction, the reaction liquid was cooled to room temperature. Thereafter, water (300 ml) was added thereto. The precipitation was filtrated, and the resultant crystal was dried to yield an intermediate 4 (3.5 g, 19 mmol, yield 80%).

Next, a compound 2 represented by the formula (1-2) (1.2 g, 0.78 mmol, yield 41%) was yielded in the same way as in Production Example 1, except that in the process of yielding the intermediate 3, an equimolar amount of the intermediate 4 was used instead of 2-hydrazinobenzothiazole to yield an intermediate 5 represented by the formula (1-2-5).

Phase transition temperature (during the temperature rise): C 141 N 208 I $^1$H NMR ($CDCl_3$; δppm): 8.39 (s, 2H), 7.80 (s, 2H), 7.52 (d, 2H), 7.21 (d, 2H), 7.05-6.75 (m, 12H), 6.41 (dd, 2H), 6.25-6.10 (m, 2H), 5.83 (dd, 2H), 4.34 (t, 4H), 4.17 (t, 4H), 3.97 (t, 4H), 2.70-2.55 (m, 4H), 2.45-2.35 (m, 8H), 1.95-1.65 (m, 20H), 1.55-1.30 (m, 20H), 0.88 (t, 6H).

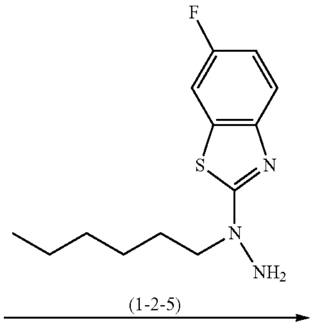

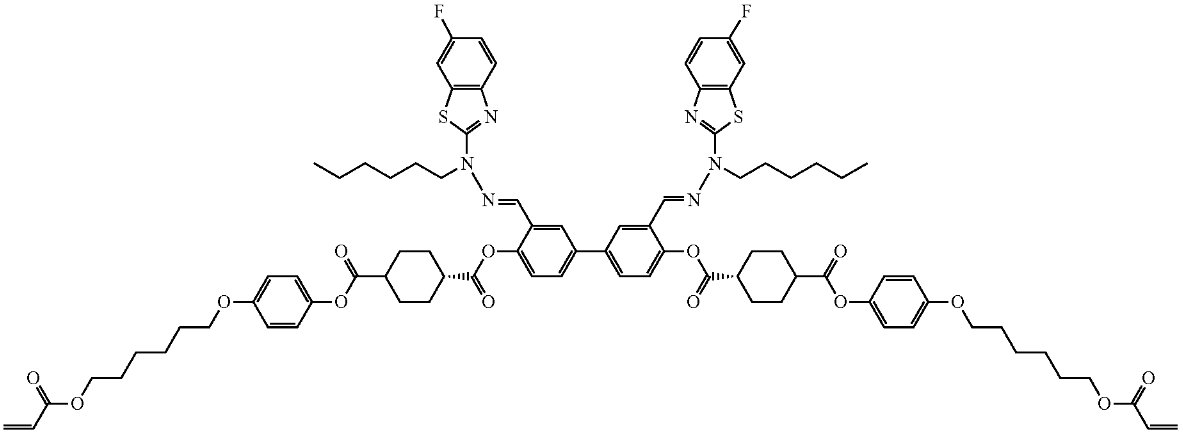

(1-2)

Production Example 3: Production of Compound 3 Represented by Formula (1-3)

An intermediate 6 (3.1 g, 16 mmol, yield 68%) was yielded in the same way as in Production Example 2, except that in the process of producing the intermediate 4, an equimolar amount of 2-amino-6-ethoxybenzothiazole was used instead of 2-amino-6-fluorobenzothiazole.

Next, a compound 3 represented by the formula (1-3) (1.3 g, 0.83 mmol, yield 43%) was yielded in the same way as in Production Example 1, except that in the process of yielding the intermediate 3, the intermediate 6 was used instead of 2-hydrazinobenzothiazole to yield an intermediate 7 represented by the formula (1-3-5).

Phase transition temperature (during the temperature rise): C 147 N 241 I $^1$H NMR ($CDCl_3$; δppm): 8.39 (s, 2H), 7.80 (s, 2H), 7.52 (d, 2H), 7.21 (d, 2H), 7.05-6.75 (m, 12H), 6.41 (dd, 2H), 6.25-6.10 (m, 2H), 5.83 (dd, 2H), 4.34 (t, 4H), 4.17 (t, 4H), 3.97 (t, 4H), 3.65 (t, 4H), 2.70-2.55 (m, 4H), 2.45-2.35 (m, 8H), 1.95-1.65 (m, 20H), 1.55-1.30 (m, 26H), 0.88 (t, 6H).

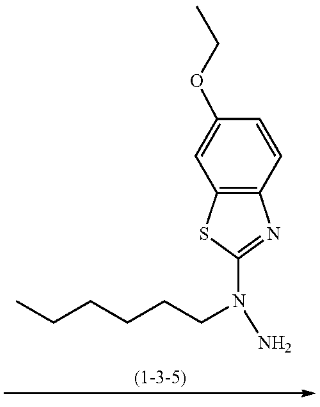

-continued

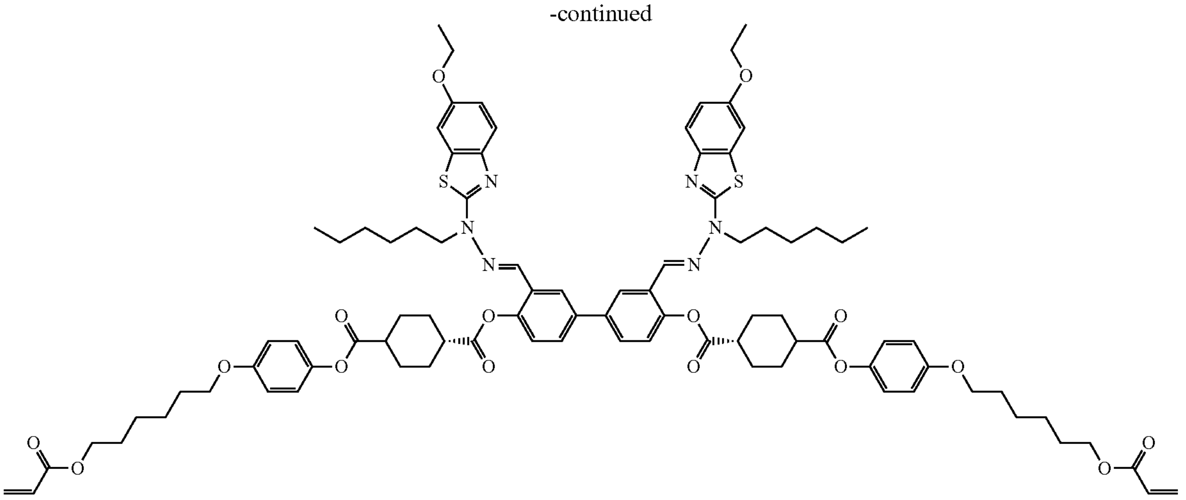

(1-3)

Production Example 4: Production of Compound 4 Represented by Formula (1-4)

A compound 4 represented by the formula (1-4) (1.2 g, 0.77 mmol, yield 40%) was yielded in the same way as in Production Example 1, except that in the process of yielding the intermediate 3, an equimolar amount of 1-bromo-2-(2-methoxyethoxy)ethane was used instead of hexyl p-toluene-sulfonate to yield an intermediate 8 represented by the formula (1-4-5).

Phase transition temperature (during the temperature rise): C 116 N 205 I $^1$H NMR ($CDCl_3$; δppm): 8.39 (s, 2H), 8.13 (s, 2H), 7.70-7.60 (m, 4H), 7.35-7.20 (m, 6H), 7.05-6.85 (m, 10H), 6.41 (dd, 2H), 6.25-6.10 (m, 2H), 5.83 (dd, 2H), 4.53 (t, 4H), 4.18 (t, 4H), 4.02-3.85 (m, 8H), 3.65 (t, 4H), 3.51 (t, 4H), 3.32 (s, 4H), 2.70-2.55 (m, 4H), 2.45-2.35 (m, 8H), 1.95-1.30 (m, 20H).

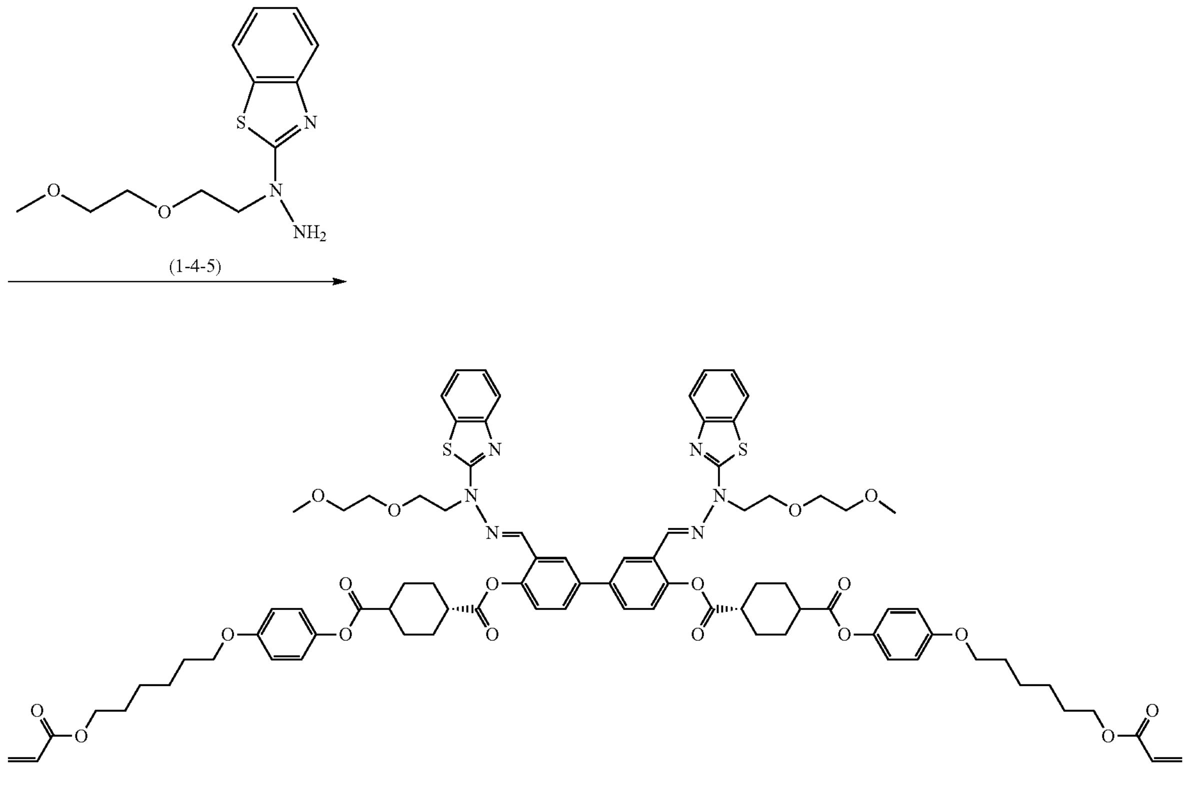

(1-4)

Production Example 5: Production of Compound 5 Represented by Formula (1-5)

An intermediate 9 (2.4 g, 12 mmol, yield 52%) was yielded in the same way as in Production Example 2, except that in the process of producing the intermediate 4, an equimolar amount of 5-methoxy[1,3]thiazolo[5,4-b]pyridine-2-amne was used instead of 2-amino-6-fluorobenzothiazole.

Next, a compound 5 represented by the formula (1-5) (1.1 g, 0.69 mmol, yield 36%) was yielded in the same way as in Production Example 1, except that in the process of yielding the intermediate 3, the intermediate 9 was used instead of 2-hydrazinobenzothiazole to yield an intermediate 10 represented by the formula (1-5-5).

Phase transition temperature (during the temperature rise): C 134 N 176 I $^1$H NMR ($CDCl_3$; δppm): 8.39 (s, 2H), 7.80 (s, 2H), 7.52 (d, 2H), 7.21 (d, 2H), 7.05-6.75 (m, 10H), 6.41 (dd, 2H), 6.25-6.10 (m, 2H), 5.83 (dd, 2H), 4.34 (t, 4H), 4.17 (t, 4H), 3.97 (t, 4H), 2.70-2.55 (m, 4H), 2.45-2.35 (m, 8H), 1.95-1.65 (m, 20H), 1.55-1.30 (m, 26H), 0.88 (t, 6H).

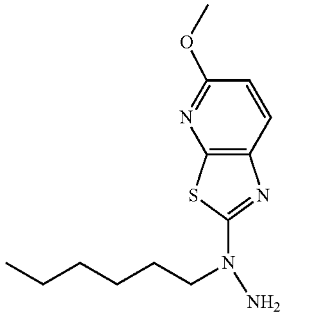

(1-5-5)

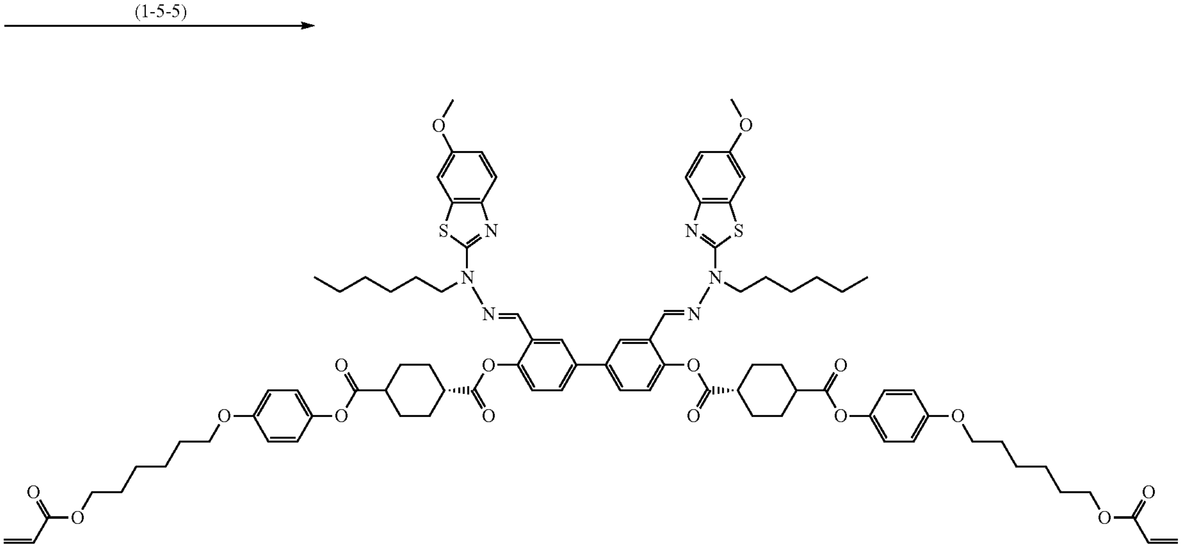

(1-5)

Production Example 6: Production of Compound 6 Represented by Formula (1-6)

2-Bromo-5-hydroxybenzaldehyde (21 g, 110 mmol) and 2-formyl-4-methoxyphenylboronic acid (20 g, 110 mmol) were dissolved in toluene: ethanol at 3:1 (400 mL). A 2 M sodium carbonate aqueous solution (100 ml) was added thereto. The reaction system was heated at 60° C. After a predetermined temperature was reached, tetrakis(triphenylphosphine)palladium(0) (2.4 g, 2.1 mmol) was added thereto. The reaction system was heated at 80° C. After a predetermined temperature was reached, the reaction system was stirred for 10 hours. After the end of the reaction, the resultant was cooled to room temperature. After insoluble matters were filtered, the organic layer was extracted and concentrated. The residue was purified by silica gel chromatography, and the solvent was distilled off to yield an intermediate 11 (11 g, 44 mmol, yield 42%). The structure of the target product was identified by 1H-NMR.

A compound 6 represented by the formula (1-6) (1.1 g, 0.74 mmol, yield 39%) was yielded in the same way as in Production Example 1, except that the carboxylic acid derivative 1 represented by the formula (1-1-3) and the intermediate 11 instead of the intermediate 1 represented by the formula (1-1-2) were used to yield an intermediate 12, and the intermediate 12 was used instead of the intermediate 2 represented by the formula (1-1-4).

Phase transition temperature (during the temperature rise): C 165 N 180 I $^1$H NMR ($CDCl_3$; δppm): 8.39 (s, 2H), 7.92 (s, 2H), 7.70-7.60 (m, 4H), 7.35-7.20 (m, 6H), 7.05-6.85 (m, 10H), 6.41 (dd, 2H), 6.25-6.10 (m, 2H), 5.83 (dd, 2H), 4.34 (t, 4H), 4.17 (t, 4H), 3.97 (t, 4H), 2.70-2.55 (m, 4H), 2.45-2.35 (m, 8H), 1.95-1.65 (m, 20H), 1.55-1.30 (m, 20H), 0.88 (t, 6H).

(1-6)

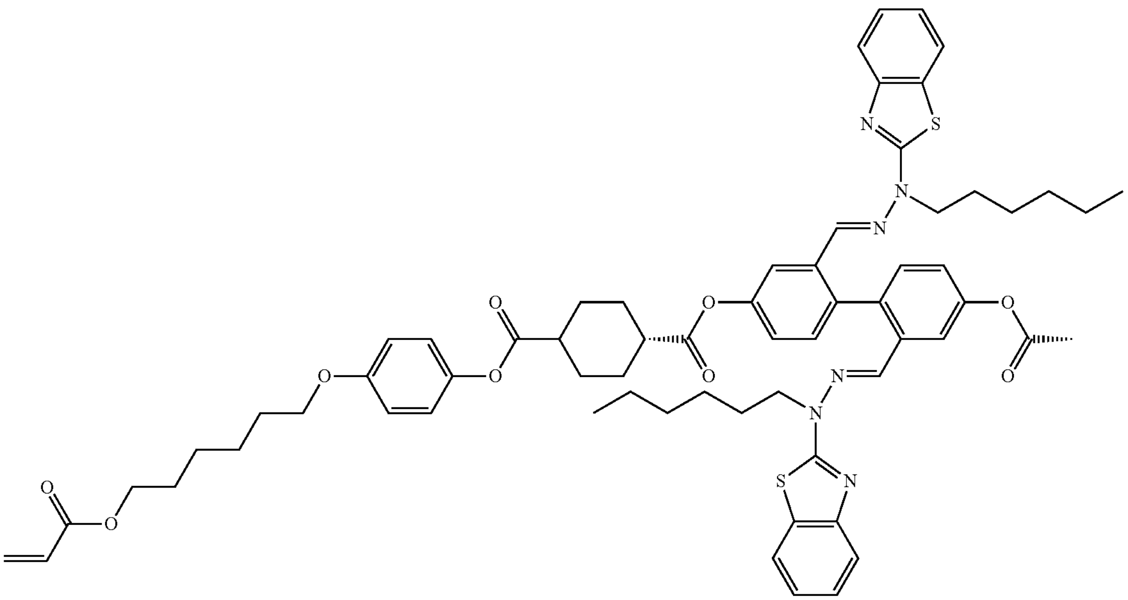

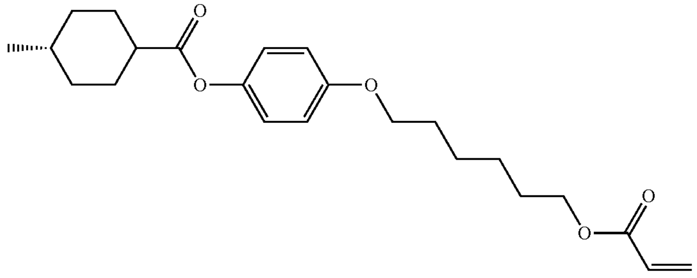

Production Example 7: Production of Compound 7 Represented by Formula (1-7)

An intermediate 13 was yielded in the same way as in Production Example 6, except that in the production of the intermediate 11, an equimolar amount of 5-bromo-2-hydroxy-4-methylbenzaldehyde was used instead of 2-bromo-5-hydroxybenzaldehyde, and an equimolar amount of 3-formyl-4-methoxyphenylboronic acid was used instead of 2-formyl-4-methoxyphenylboronic acid.

Next, a compound 7 represented by the formula (1-7) (0.81 g, 0.53 mmol, yield 24%) was yielded in the same way as in Production Example 1, except that the carboxylic acid derivative 1 represented by the formula (1-1-3) and the intermediate 13 instead of the intermediate 1 represented by the formula (1-1-2) were used to yield an intermediate 14, and the intermediate 14 was used instead of the intermediate 2 represented by the formula (1-1-4).

Phase transition temperature (during the temperature rise): C 152 N 171 I $^{1}$H NMR ($CDCl_3$; δppm): 8.39 (s, 2H), 7.80 (s, 2H), 7.70-7.60 (m, 4H), 7.35-7.20 (m, 6H), 7.05-6.85 (m, 9H), 6.41 (dd, 2H), 6.25-6.10 (m, 2H), 5.83 (dd, 2H), 4.34 (t, 4H), 4.17 (t, 4H), 3.97 (t, 4H), 2.70-2.55 (m, 7H), 2.45-2.35 (m, 8H), 1.95-1.65 (m, 20H), 1.55-1.30 (m, 20H), 0.88 (t, 6H).

(1-7)

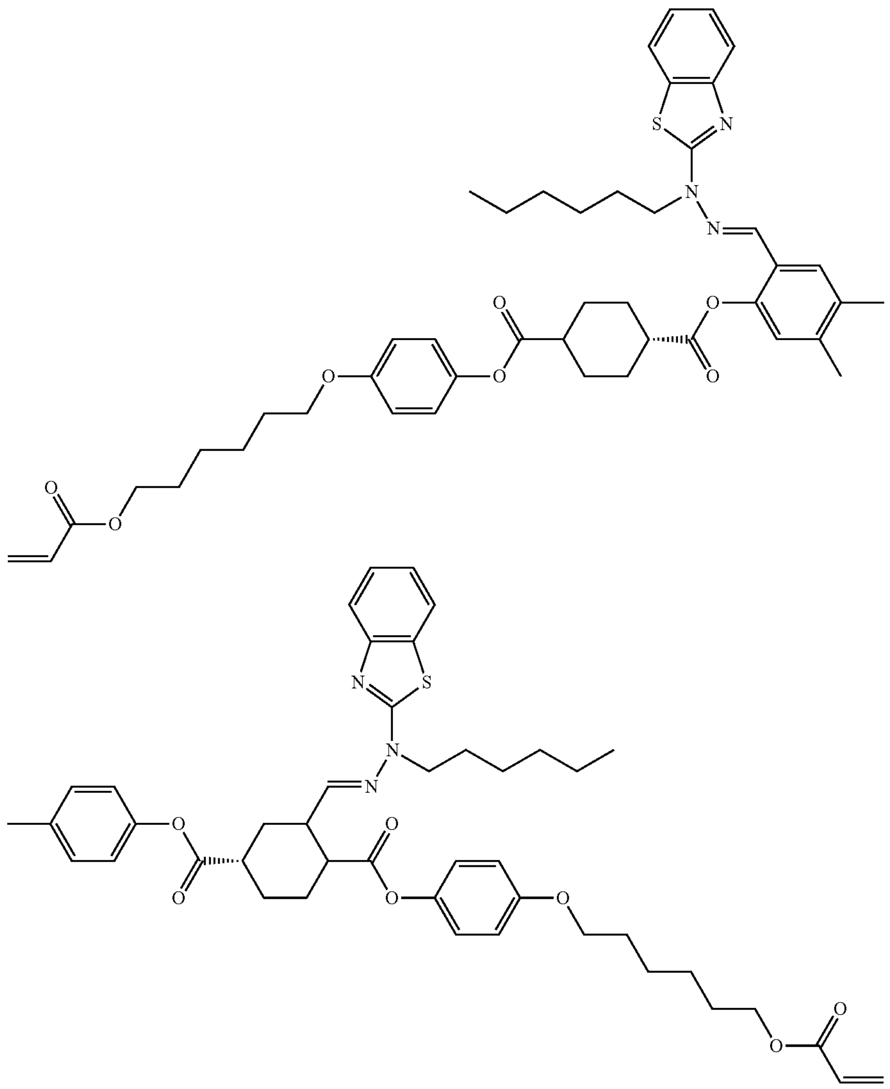

Production Example 8: Production of Compound 8 Represented by Formula (1-8)

First, 6-bromohexanol (7.3 g, 41 mmol) was added to a suspension of ethyl 4-hydroxybenzoate (7.0 g, 44 mmol) and potassium carbonate (6.5 g, 47 mmol) in DMF (250 ml). The reaction system was stirred at 80° C. for 8 hours. After the end of the reaction, the reaction liquid was diluted with water, and then ethyl acetate was added thereto to perform extraction. The solvent was distilled off. To the resultant crude product was added an aqueous solution of potassium hydroxide (2.8 g, 47 mmol). The reaction system was reacted at 100° C. for 4 hours for hydrolysis. After the end of the reaction, a hydrochloric acid aqueous solution was added thereto, and then ethyl acetate was added thereto to perform extraction. The solvent was distilled off. The residue was purified by silica gel chromatography, and the solvent was distilled off to yield p-(6-hydroxyhexyloxy) benzoic acid with a yield of 83% (8.7 g, 37 mmol).

Next, a suspension of p-(6-hydroxyethoxy)benzoic acid (7.1 g, 30 mmol), acryloyl chloride (2.5 g, 27 mmol) and dimethylaniline (DMA) (3.3 g, 27 mmol) in tetrahydrofuran (150 mL) was stirred for 12 hours. After the end of the reaction, water and ethyl acetate were added thereto. The resultant was separated into two liquid phases. The solvent was then distilled off. The residue was purified by silica gel chromatography, and the solvent was distilled off to yield 4-[6-(acryloyloxy)hexyloxy]benzoic acid with a yield of 85% (7.4 g, 26 mmol).

Next, trans-4-hydroxycyclohexanecarboxylic acid (5.0 g, 32 mmol) and triethylamine (5.3 g, 52 mmol) were dissolved in tetrahydrofuran (25 ml). The reaction system was stirred in a nitrogen atmosphere at 10° C. or less while cooling. Chloromethyl methyl ether (3.0 g, 37 mmol) was dropwise added thereto, slowly. The reaction system was stirred at room temperature for 8 hours. Ethyl acetate and water were added thereto to extract an organic layer. The organic layer was washed with saturated sodium hydrogen carbonate solution and water and then dried with anhydrous magnesium sulfate to yield trans-4-hydroxycyclohexanecarboxylic acid methoxymethyl (4.8 g, 26 mmol, yield 80%).

To a suspension of 4-[6-(acryloyloxy)hexyloxy]benzoic acid (7.4 g, 26 mmol), trans-4-hydroxycyclohexanecarboxylic acid methoxymethyl (4.7 g, 25 mmol) and N,N-dimethylaminopyridine (DMAP) (0.12 g, 1.0 mmol) in dichloromethane (150 ml) was dropwise added a solution of N,N-dicyclohexylcarbodiimide (DCC) (5.6 g, 27 mmol) in dichloromethane (5 mL). After the end of the addition, the reaction system was stirred for 12 hours, and the precipitation was filtrated to be collected, and then washed with a sodium hydrogen carbonate aqueous solution and 1 N hydrochloric acid. Thereafter, the solvent was distilled off. To a solution of the resultant crude product in tetrahydrofuran (20 ml) was added p-toluenesulfonic acid (pTSA) (0.40 g, 2.1 mmol). The reaction system was heated and stirred at 40° C. 8 hours. Ethyl acetate and water were added thereto to extract an organic layer. The organic layer was washed with saturated sodium hydrogen carbonate solution and water and then dried with anhydrous magnesium sulfate. Thereafter, the solvent was distilled off under reduced pressure. The residue was recrystallized with methanol to yield a carboxylic acid derivative 2 represented by the formula (1-8-3) (5.4 g, 13 mmol, yield 52%).

Next, a compound 8 represented by the formula (1-8) (0.98 g, 0.66 mmol, yield 32%) was yielded in the same way as in Production Example 1, except that the carboxylic acid derivative 2 represented by the formula (1-8-3) was used instead of the carboxylic acid derivative 1 represented by the formula (1-1-3).

Phase transition temperature (during the temperature rise): C 134 N 167 I $^1$H NMR ($CDCl_3$; δppm): 8.39 (s, 2H), 7.80 (s, 2H), 7.70-7.60 (m, 4H), 7.35-7.20 (m, 6H), 7.05-6.85 (m, 10H), 6.41 (dd, 2H), 6.25-6.10 (m, 2H), 5.83 (dd, 2H), 4.52 (t, 4H), 4.20 (t, 4H), 3.95 (t, 4H), 2.70-2.55 (m, 4H), 2.45-2.35 (m, 8H), 1.95-1.65 (m, 20H), 1.55-1.30 (m, 20H), 0.88 (t, 6H).

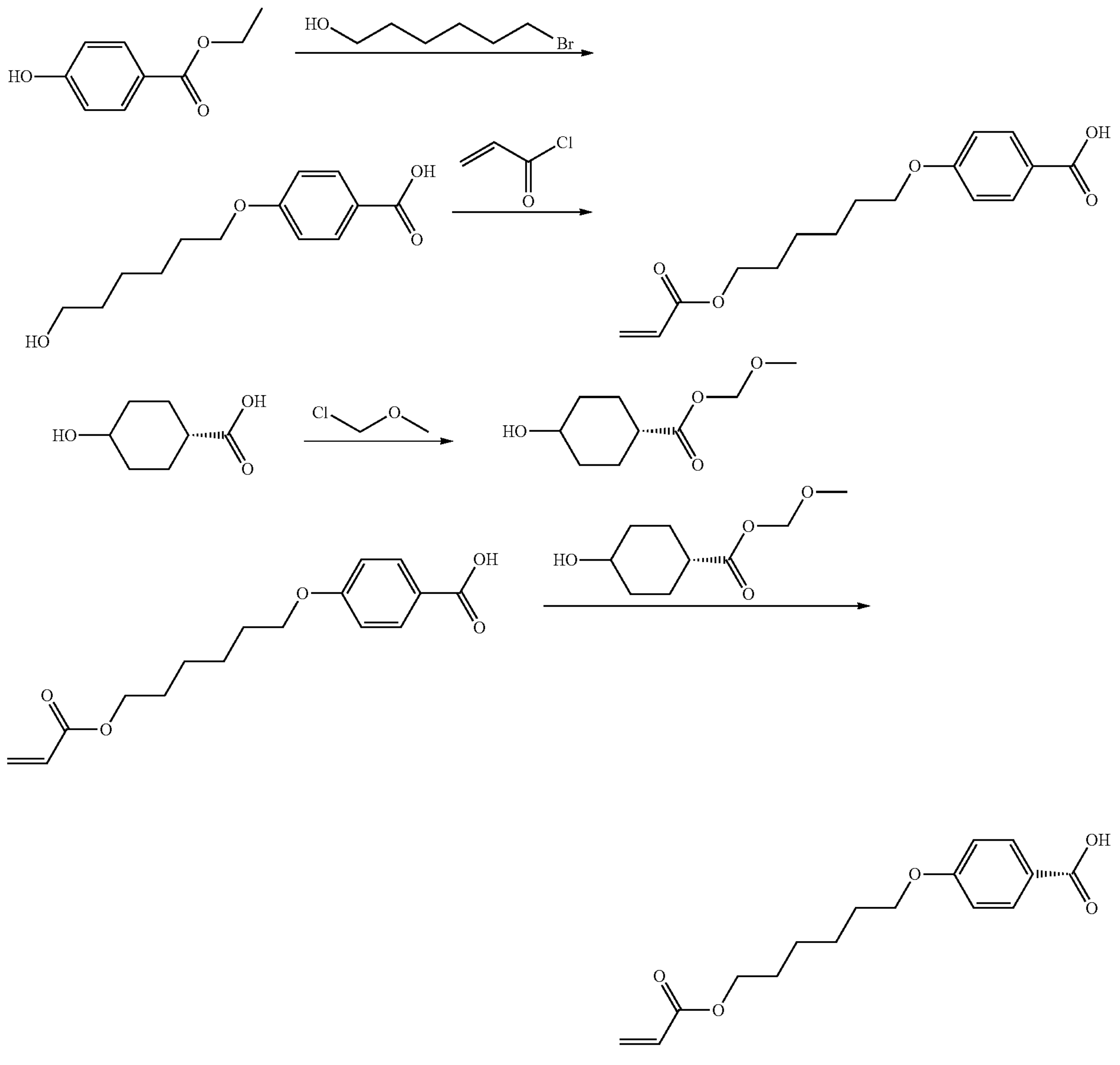

(1-8-3)

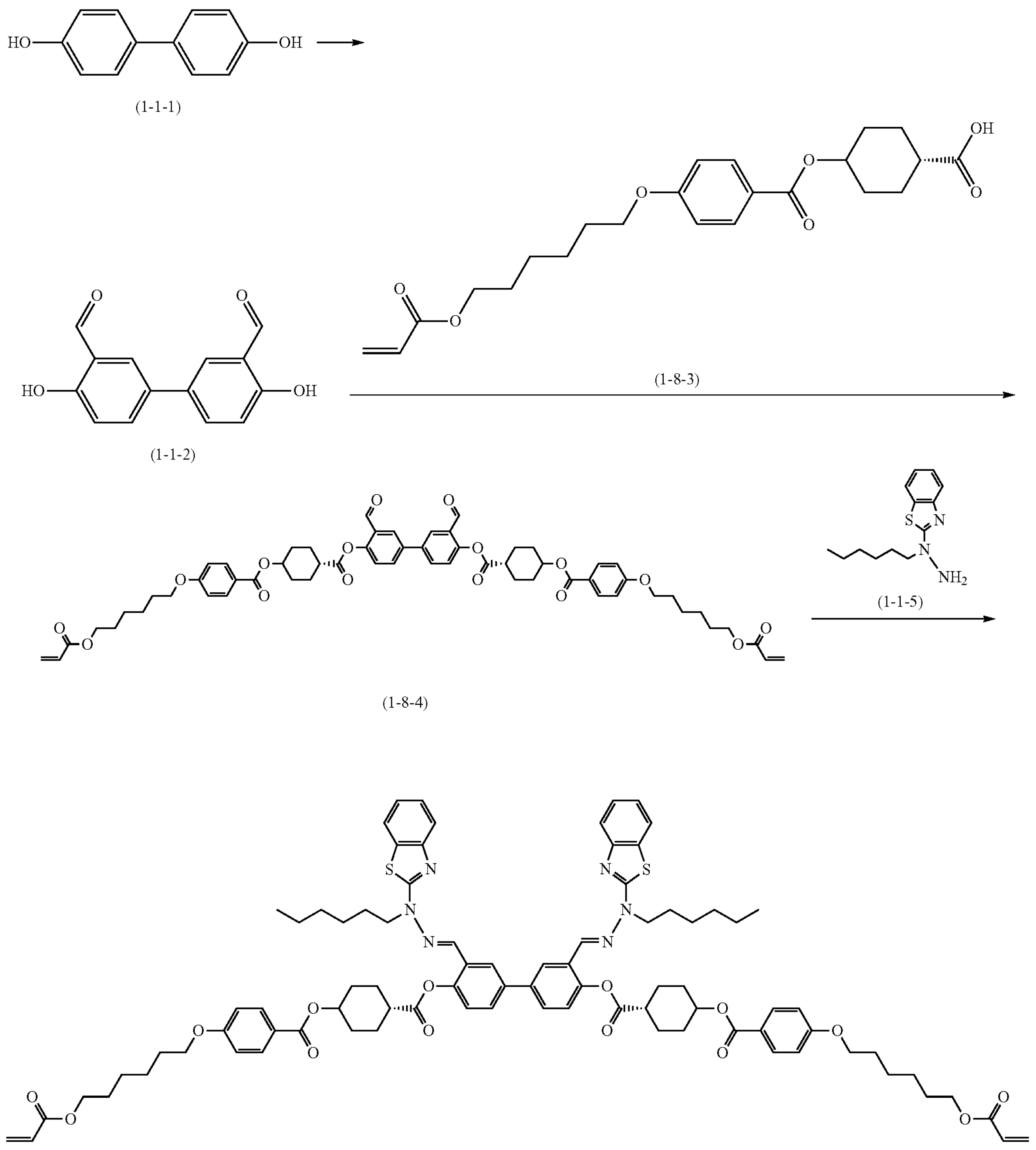

(1-1-1)

(1-1-2)

(1-8-3)

(1-8-4)

(1-1-5)

(1-8)

Production Example 9: Production of Compound 9 Represented by Formula (1-9)

An intermediate 2 represented by the formula (1-1-4) was yielded in the same way as in Production Example 1.

The intermediate 2 (2.0 g, 1.9 mmol) and 3-methyl-2-benzothiazolinonehydrazone hydrochloride (0.82 g, 3.8 mmol) were dissolved in 1-propanol (30 mL). In a reflux condition, the reaction system was stirred for 1 hour. After the end of the reaction, the reaction liquid was cooled to room temperature.

Thereafter, THF (30 ml) was added thereto and dissolved. To the reaction solution was dropwise added a 10% sodium hydrogencarbonate aqueous solution to precipitate a solid. The precipitation was filtrated and washed, and the resultant precipitation was dried to yield a compound 9 represented by the formula (1-9) (0.9 g, 0.66 mmol, yield 33%). The structure of the target product was identified by 1H-NMR.

Phase transition temperature (during the temperature rise): C 140 N 165 I $^1$H NMR (DMSO; δppm): 8.49 (s, 2H), 8.14 (s, 2H), 7.85 (d, 2H), 7.66 (d, 2H), 7.45 (d, 2H), 7.40-7.30 (m, 4H), 7.08 (t, 2H), 6.88 (s, 8H), 6.41 (dd, 2H), 6.25-6.10 (m, 2H), 5.83 (dd, 2H), 4.06 (t, 4H), 3.97 (t, 4H), 3.36 (s, 6H), 2.30-2.20 (m, 4H), 1.90-1.65 (m, 12H), 1.60-1.35 (m, 20H)

(1-9)

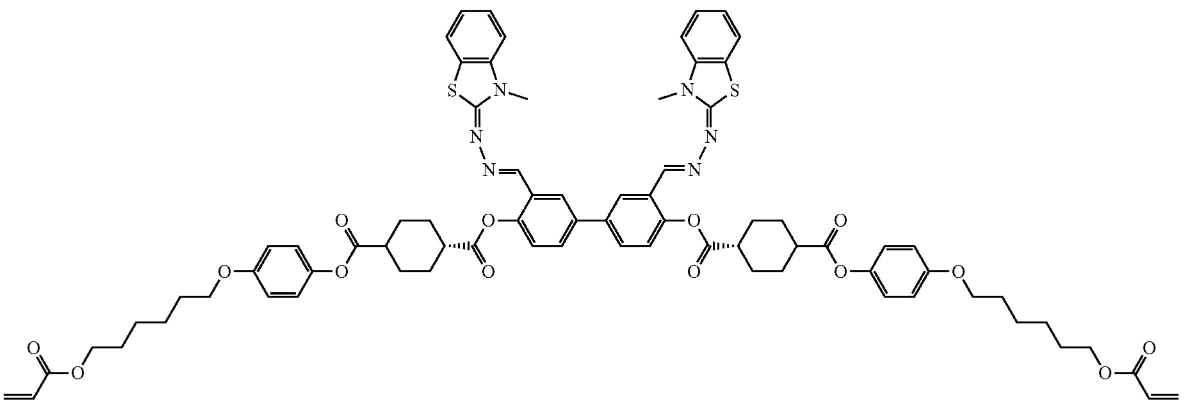

Production Example 10: Production of Compound 10 Represented by Formula (1-10)

A compound 10 represented by the formula (1-10) (1.33 g, 0.87 mmol, yield 43%) was yielded in the same way as in Production Example 1, except that in the process of yielding the intermediate 3, an equimolar amount of 1-(2-bromoethoxy)butane was used instead of hexyl p-toluenesulfonate to yield an intermediate 16 represented by the formula (1-10-5).

Phase transition temperature (during the temperature rise): C 122 N 167 I $^1$H NMR ($CDCl_3$; δppm): 8.39 (s, 2H), 7.80 (s, 2H), 7.70-7.60 (m, 4H), 7.35-7.20 (m, 6H), 7.05-6.85 (m, 10H), 6.41 (dd, 2H), 6.25-6.10 (m, 2H), 5.83 (dd, 2H), 4.34 (t, 4H), 4.17 (t, 4H), 3.97 (t, 4H), 3.65-3.50 (m, 8H), 2.70-2.55 (m, 4H), 2.45-2.35 (m, 8H), 1.95-1.65 (m, 20H), 1.55-1.30 (m, 12H), 0.88 (t, 6H)

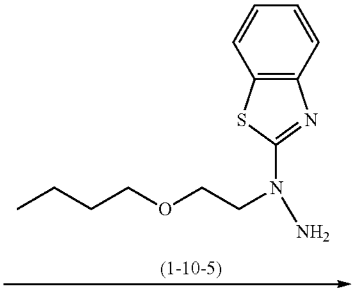

(1-10-5)

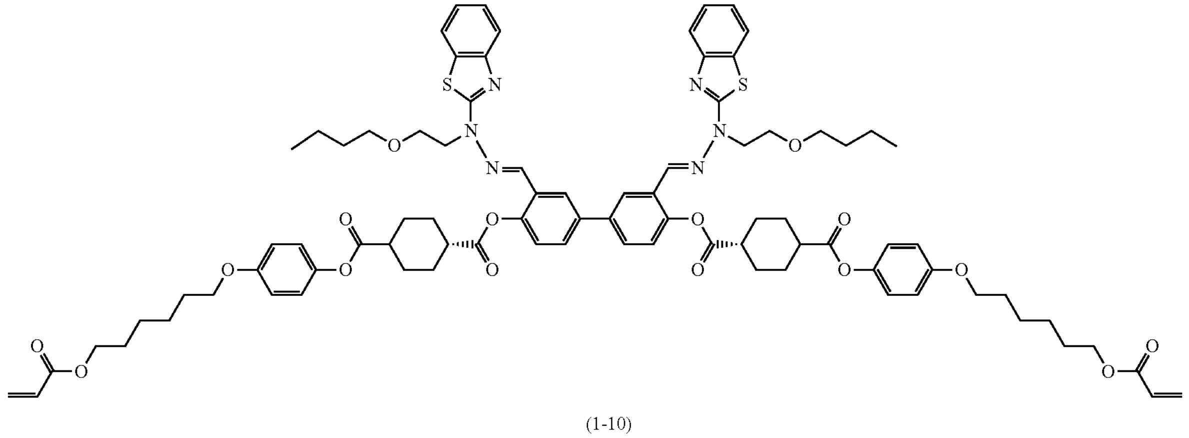

(1-10)

Production Example 11: Production of Compound 11 Represented by Formula (1-11)

To ethylene glycol (20 ml) was added 2-aminobenzoxazole (3.2 g, 24 mmol). In an ice bath, hydrazine monohydrate (3.6 g, 71 mmol) and 12 N hydrochloric acid (1.9 g, 55 mmol) were dropwise added thereto. The reaction system was stirred at 130° C. for 5 hours. After the end of the reaction, the reaction liquid was cooled to room temperature. Thereafter, water (300 ml) was added thereto. The precipitation was filtrated, and the resultant crystal was dried to yield an intermediate 17 (3.5 g, 19 mmol, yield 80%).

Next, a compound 11 represented by the formula (1-11) (1.2 g, 0.78 mmol, yield 41%) was yielded in the same way as in Production Example 1, except that in the process of yielding the intermediate 3, an equimolar amount of the intermediate 17 was used instead of 2-hydrazinobenzothiazole, and an equimolar amount of 1-(2-bromoethoxy)butane was used instead of hexyl p-toluenesulfonate to yield an intermediate 18 represented by the formula (1-11-5).

Phase transition temperature (during the temperature rise): C 119 N 169 I $^1$H NMR ($CDCl_3$; δppm): 8.39 (s, 2H), 7.80 (s, 2H), 7.70-7.55 (m, 2H), 7.41-7.20 (m, 8H), 7.05-6.85 (m, 10H), 6.41 (dd, 2H), 6.25-6.10 (m, 2H), 5.83 (dd, 2H), 4.34 (t, 4H), 4.17 (t, 4H), 3.97 (t, 4H), 2.70-2.55 (m, 4H), 2.45-2.35 (m, 8H), 1.95-1.65 (m, 20H), 1.55-1.30 (m, 20H), 0.88 (t, 6H)

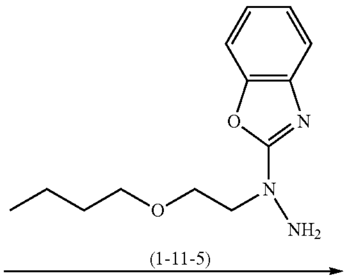
(1-11-5)

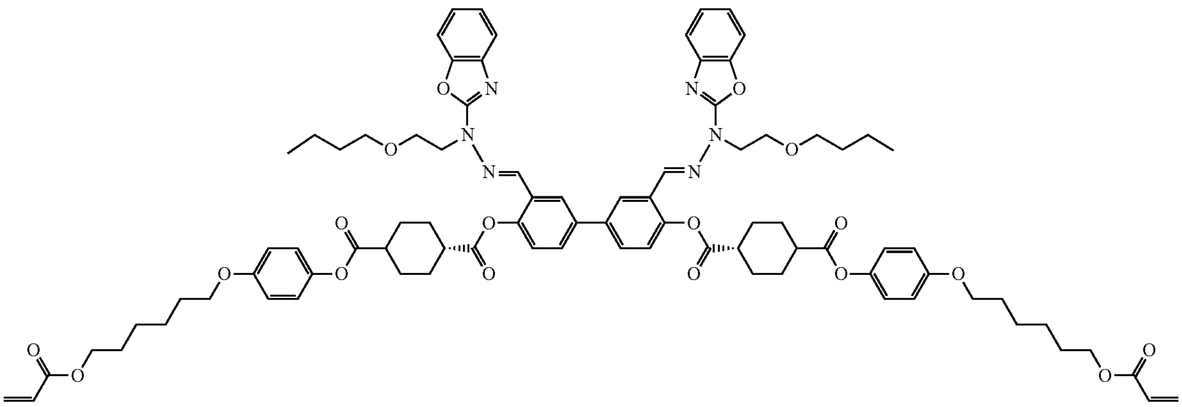

(1-11)

Production Example 12: Production of Compound 12 Represented by Formula (1-12)

A compound 12 represented by the formula (1-12) (1.3 g, 0.84 mmol, yield 44%) was yielded in the same way as in Production Example 1, except that in the process of yielding the intermediate 3, an equimolar amount of 1-bromo-2-ethylhexane was used instead of hexyl p-toluenesulfonate to yield an intermediate 19 represented by the formula (1-12-5).

Phase transition temperature (during the temperature rise): C 125 N 168 I $^1$H NMR ($CDCl_3$; δppm): 8.39 (s, 2H), 7.80 (s, 2H), 7.70-7.60 (m, 4H), 7.35-7.20 (m, 6H), 7.05-6.85 (m, 10H), 6.41 (dd, 2H), 6.25-6.10 (m, 2H), 5.83 (dd, 2H), 4.34 (t, 4H), 4.17 (t, 4H), 3.97 (t, 4H), 2.70-2.55 (m, 4H), 2.45-2.35 (m, 8H), 1.97-1.67 (m, 24H), 1.51-1.32 (m, 18H), 0.99 (t, 6H), 0.88 (t, 6H)

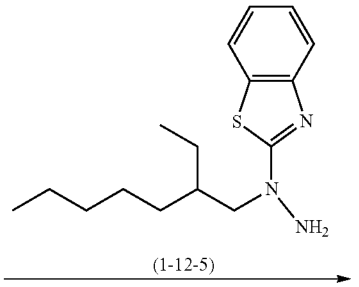

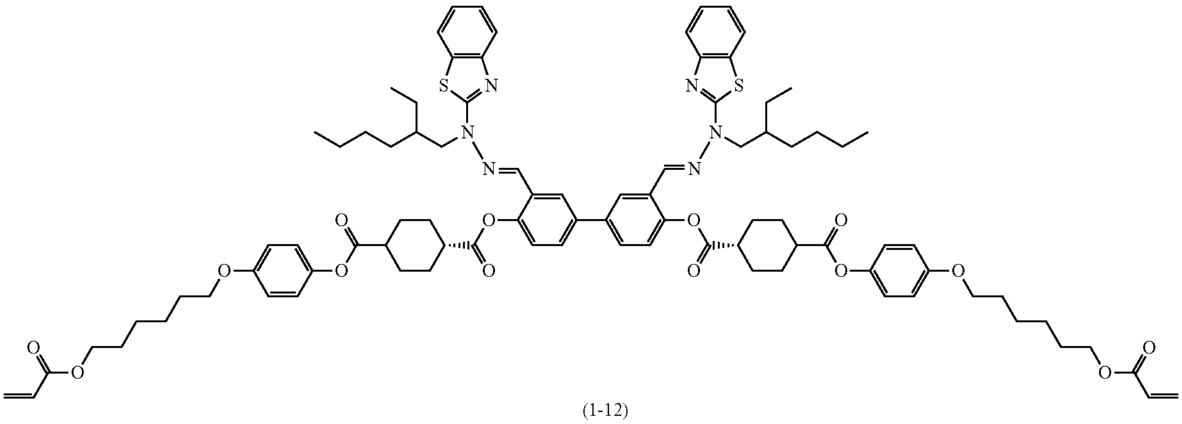

(1-12)

Production Example 13: Production of Compound 13 Represented by Formula (1-13)

A compound 13 represented by the formula (1-13) (1.9 g, 0.79 mmol, yield 41%) was yielded in the same way as in Production Example 1, except that in the process of yielding the intermediate 3, an equimolar amount of tetrahydrofurfuryl bromide was used instead of hexyl p-toluenesulfonate to yield an intermediate 20 represented by the formula (1-13-5).

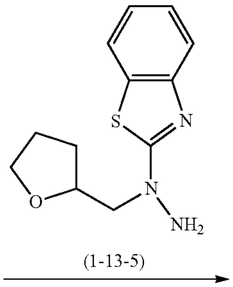

Phase transition temperature (during the temperature rise): C 119 N 171 I $^1$H NMR ($CDCl_3$; δppm): 8.39 (s, 2H), 7.80 (s, 2H), 7.70-7.60 (m, 4H), 7.35-7.20 (m, 6H), 7.05-6.85 (m, 10H), 6.41 (dd, 2H), 6.25-6.10 (m, 2H), 5.83 (dd, 2H), 4.34 (t, 4H), 4.17 (t, 4H), 3.85-3.79 (m, 6H), 2.70-2.55 (m, 4H), 2.45-2.35 (m, 8H), 1.91-1.60 (m, 28H), 1.51-1.32 (m, 4H)

-continued

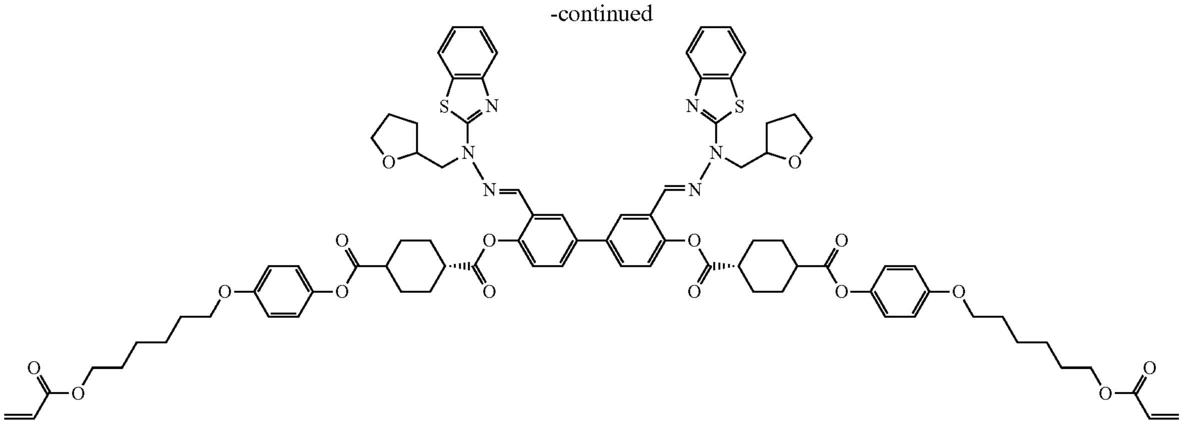

(1-13)

Production Example 14: Production of Compound 14 Represented by Formula (1-14)

In accordance with a literature (Macromolecules (Washington, DC, United States), 40(15), 5337-5343; 2007), 6-chlorohexyl acrylate was synthesized.

To a suspension of the synthesized 6-chlorohexyl acrylate (9.5 g, 50 mmol) and potassium carbonate (14 g, 100 mmol) in dimethylformamide (100 ml) was dropwise added a solution of 2-(4-hydroxyphenyl)ethanol (7.6 g, 55 mmol) in dimethylformamide (30 ml). After the end of the addition, the reaction container was heated to 90° C. for reaction for 5 hours. After the end of the reaction, ethyl acetate (200 ml) was added thereto, and the resultant was washed with pure water and saturated brine. The resultant organic layer was dried with anhydrous sodium sulfate to synthesize 6-(4-(2-hydroxyethyl)phenyl)hexyl acrylate.

Next, a carboxylic acid derivative 3 represented by the formula (1-14-3) (4.2 g, 9.4 mmol) was synthesized in the same way as in Production Example 1, except that in the synthesis of the carboxylic acid derivative 1, 6-(4-(2-hydroxyethyl)phenyl)hexyl acrylate was used instead of 6-(4-hydroxyphenyl)hexyl acrylate.

(1-14-3)

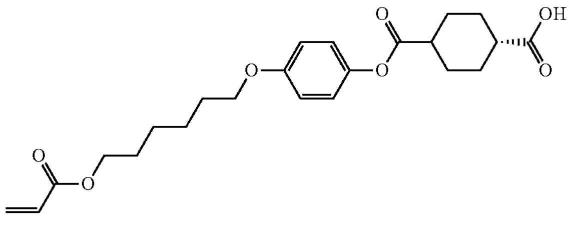

Next, a compound 14 represented by the formula (1-14) (1.2 g, 0.75 mmol, yield 35%) was yielded in the same way as in Production Example 1, except that the carboxylic acid derivative 3 represented by the formula (1-14-3) was used instead of the carboxylic acid derivative 1 represented by the formula (1-1-3).

Phase transition temperature (during the temperature rise): C 118 N 169 I $^1$H NMR ($CDCl_3$; δppm): 8.39 (s, 2H), 7.80 (s, 2H), 7.70-7.60 (m, 4H), 7.35-7.20 (m, 2H), 7.05-6.85 (m, 14H), 6.41 (dd, 2H), 6.25-6.10 (m, 2H), 5.83 (dd, 2H), 4.51 (t, 4H), 4.34 (t, 4H), 4.17 (t, 4H), 3.97 (t, 4H), 3.02 (t, 4H), 2.70-2.55 (m, 4H), 2.45-2.35 (m, 8H), 1.95-1.65 (m, 20H), 1.55-1.30 (m, 20H), 0.88 (t, 6H)

(1-14)

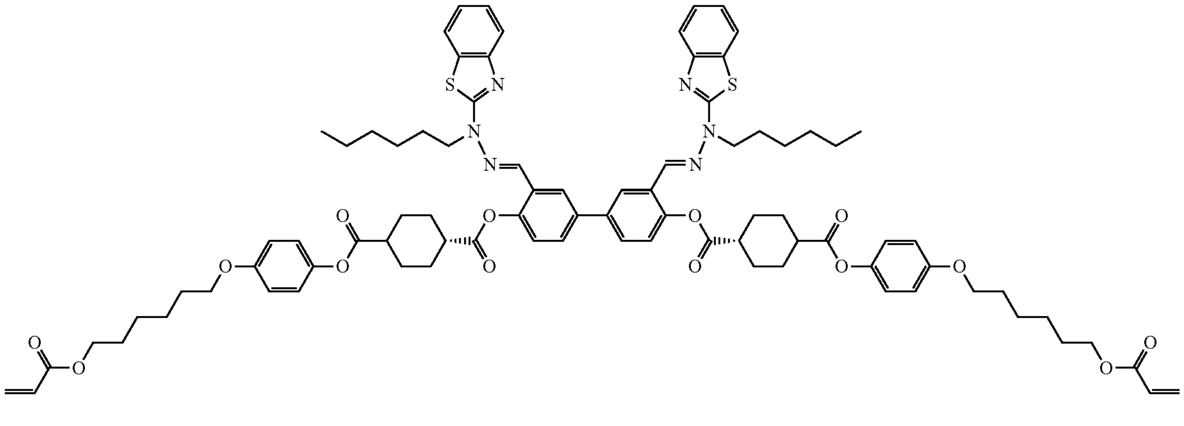

Production Example 15: Production of Compound 15 Represented by Formula (1-15)

A carboxylic acid derivative 4 represented by the formula (1-15-3) (3.9 g, 8.7 mmol) was synthesized in the same way as in Production Example 8, except that in the synthesis of the carboxylic acid derivative 2, an equimolar amount of 3-(4-hydroxyphenyl)methyl propionate was used instead of ethyl 4-hydroxybenzoate.

(1-15-3)

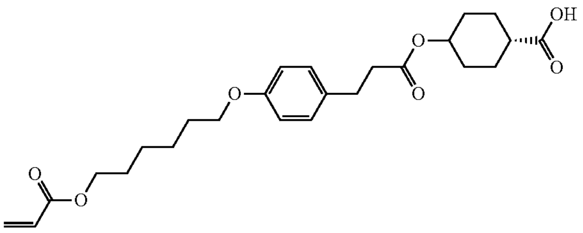

Next, a compound 15 represented by the formula (1-15) (1.3 g, 0.81 mmol, yield 41%) was yielded in the same way as in Production Example 1, except that the carboxylic acid derivative 4 represented by the formula (1-15-3) was used instead of the carboxylic acid derivative 1 represented by the formula (1-1-3).

Phase transition temperature (during the temperature rise): C 105 N 172 I $^{1}$H NMR ($CDCl_3$; δppm): 8.39 (s, 2H), 7.80 (s, 2H), 7.70-7.60 (m, 4H), 7.35-7.20 (m, 6H), 7.05-6.85 (m, 10H), 6.41 (dd, 2H), 6.25-6.10 (m, 2H), 5.83 (dd, 2H), 4.52 (t, 4H), 4.19 (t, 4H), 3.99 (t, 4H), 3.65-3.50 (m, 8H), 2.70-2.55 (m, 12H), 2.45-2.35 (m, 8H), 1.95-1.65 (m, 20H), 1.55-1.30 (m, 12H), 0.88 (t, 6H)

(1-15)

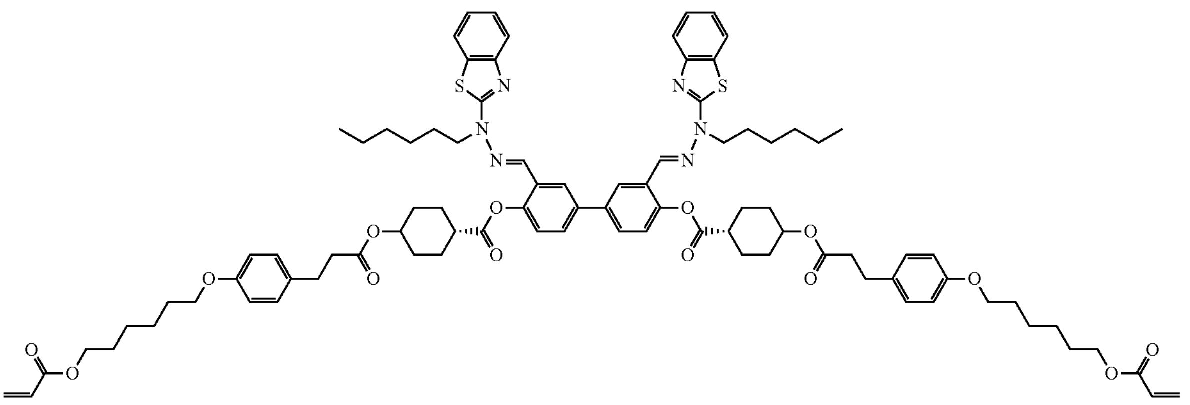

Production Example 16: Production of Compound 16 Represented by Formula (1-16)

In accordance with a literature (Journal of Polymer Science, Part A: Polymer Chemistry, 49 (3), 770-780; 2011), 3-[4-[[6-[(1-oxo-2-propene-1-yl)oxy]hexyl]oxy]phenyl]-2-propen oic acid was synthesized.

Next, a carboxylic acid derivative 5 represented by the formula (1-16-3) (3.8 g, 8.6 mmol) was synthesized in the same way as in Production Example 8, except that in the synthesis of the carboxylic acid derivative 2,3-[4-[[6-[(1-oxo-2-propene-1-yl)oxy]hexyl]oxy]phenyl]-2-propen oic acid was used instead of 4-[6-(acryloyloxy)hexyloxy]benzoic acid.

(1-16-3)

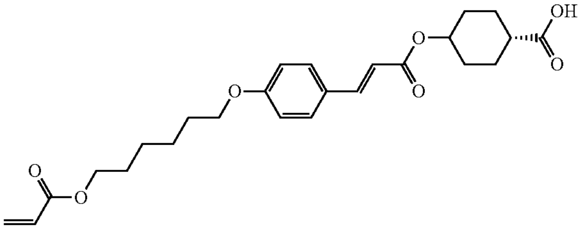

Next, a compound 16 represented by the formula (1-16) (1.0 g, 0.67 mmol, yield 38%) was yielded in the same way as in Production Example 1, except that the carboxylic acid derivative 5 represented by the formula (1-16-3) was used instead of the carboxylic acid derivative 1 represented by the formula (1-1-3).

Phase transition temperature (during the temperature rise): C 141 N 165 I $^1$H NMR ($CDCl_3$; δppm): 8.39 (s, 2H), 7.80 (s, 2H), 7.70-7.55 (m, 6H), 7.35-7.20 (m, 6H), 7.05-6.85 (m, 10H), 6.41 (dd, 2H), 6.35-6.10 (m, 4H), 5.83 (dd, 2H), 4.34 (t, 4H), 4.17 (t, 4H), 3.97 (t, 4H), 2.70-2.55 (m, 4H), 2.45-2.35 (m, 8H), 1.95-1.65 (m, 20H), 1.55-1.30 (m, 20H), 0.88 (t, 6H)

(1-16)

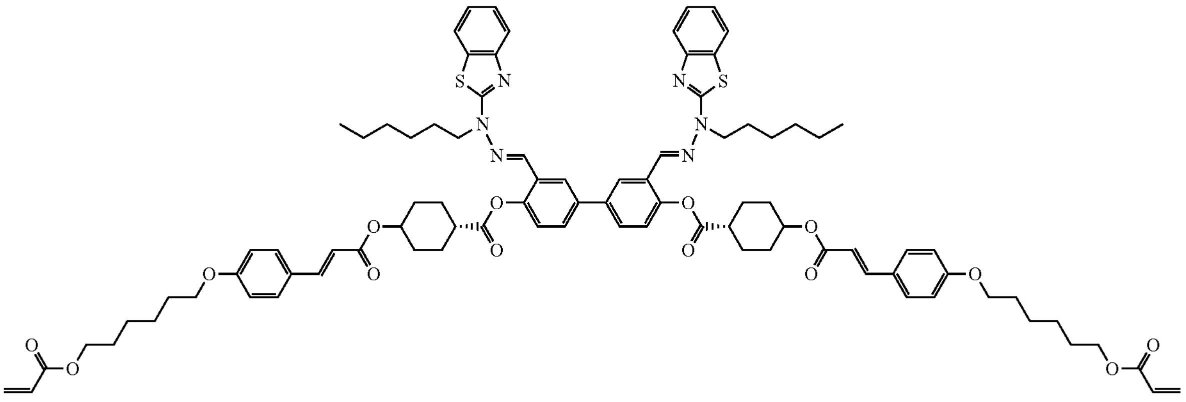

Production Example 17: Production of Compound 17 Represented by Formula (1-17)

An intermediate 2 represented by the formula (1-1-4) was yielded in the same way as in Production Example 1.

The intermediate 2 (2.0 g, 1.9 mmol), hydroxylamine chloride (0.27 g, 3.8 mmol) and sodium acetate trihydrate (0.52 g, 3.8 mmol) were dissolved in tetrahydrofuran (11 mL). The reaction system was stirred for 3 hours at normal temperature. After the end of the reaction, the solvent was distilled off. Ethyl acetate was added thereto to perform extraction, and the resultant was washed with water and then concentrated. Thereafter, to the resultant crude product was added methanol (10 mL), and the resultant was stirred for 1 hour to be suspended and purified. The precipitation was filtrated, and the resultant solid was dried to yield an intermediate 24 represented by the formula (1-17-6) (1.9 g, 1.8 mmol, yield 93%).

The yielded intermediate 24 (1.5 g, 1.4 mmol) and cesium carbonate (0.9 g, 2.8 mmol) were dissolved in toluene (2.8 mL) in a nitrogen atmosphere at 60° C. In the nitrogen atmosphere, 2-iodobenzothiazole (0.95 g, 3.6 mmol), 1,10-phenanthroline (50 mg, 0.3 mmol), potassium sodium tartrate tetrahydrate (0.16 g, 0.6 mmol) and copper(I) iodide (27 mg, 0.14 mmol) were added thereto, and the rection system was stirred at 60° C. for 2 hours. After the end of the reaction, insoluble matters were filtered. Water was added thereto, and then ethyl acetate was added thereto to perform extraction. The solvent was distilled off. The residue was purified by silica gel chromatography, and the solvent was distilled off to yield a compound 17 represented by the formula (1-17) (0.84 g, 0.63 mmol, yield 45%).

Phase transition temperature (during the temperature rise): C 135 N 167 I $^1$H NMR ($CDCl_3$; δppm): 8.39 (s, 2H), 7.80 (s, 2H), 7.70-7.60 (m, 4H), 7.35-7.20 (m, 6H), 7.05-6.85 (m, 10H), 6.41 (dd, 2H), 6.25-6.10 (m, 2H), 5.83 (dd, 2H), 4.34 (t, 4H), 4.17 (t, 4H), 2.70-2.55 (m, 4H), 2.45-2.35 (m, 8H), 1.95-1.65 (m, 20H), 1.55-1.41 (m, 4H)

(1-17-6)

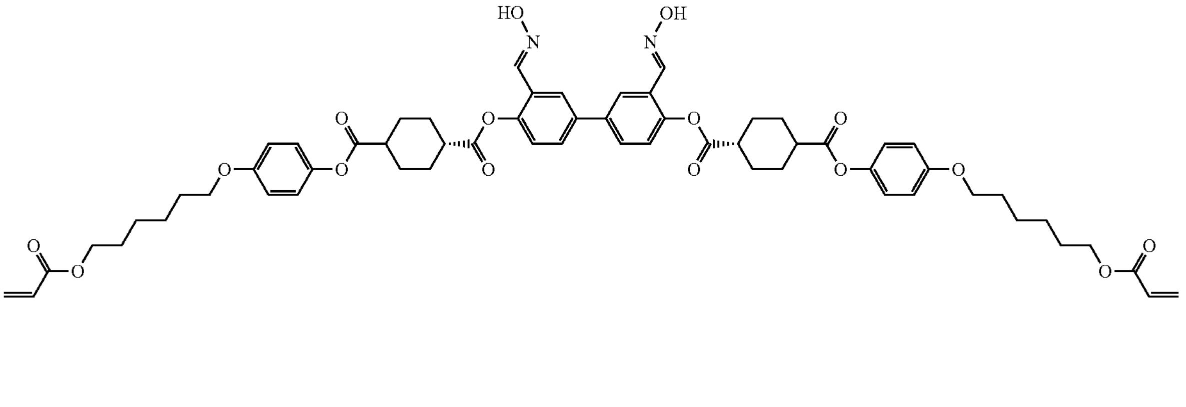

(1-17)
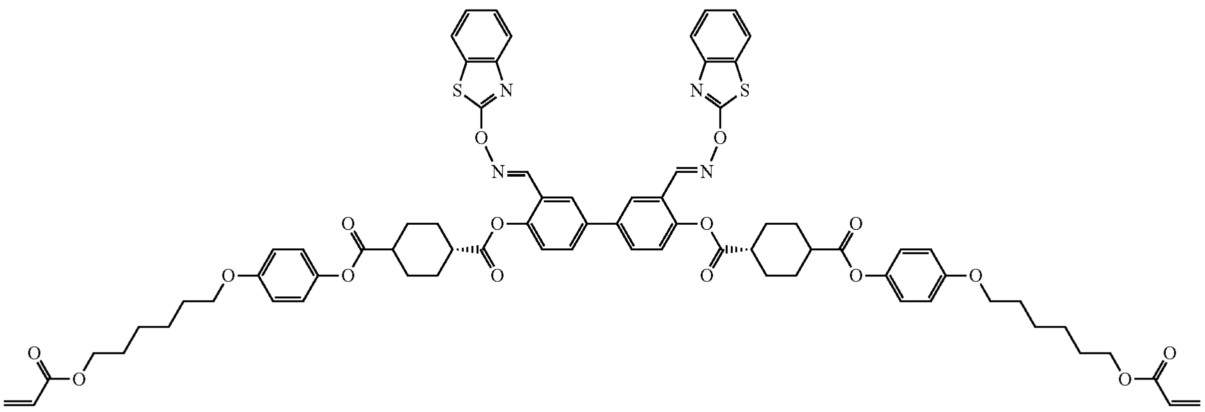
Comparative Production Example 1: Production of Comparative Compound 1 Represented by Formula (C1-1)
A comparative compound 1 represented by the following formula (C1-1) was synthesized by reference to the synthesis of the compound 4 of Example 4 described in Patent No. JP5962760.
Formula (C1-1)
(C1-1)
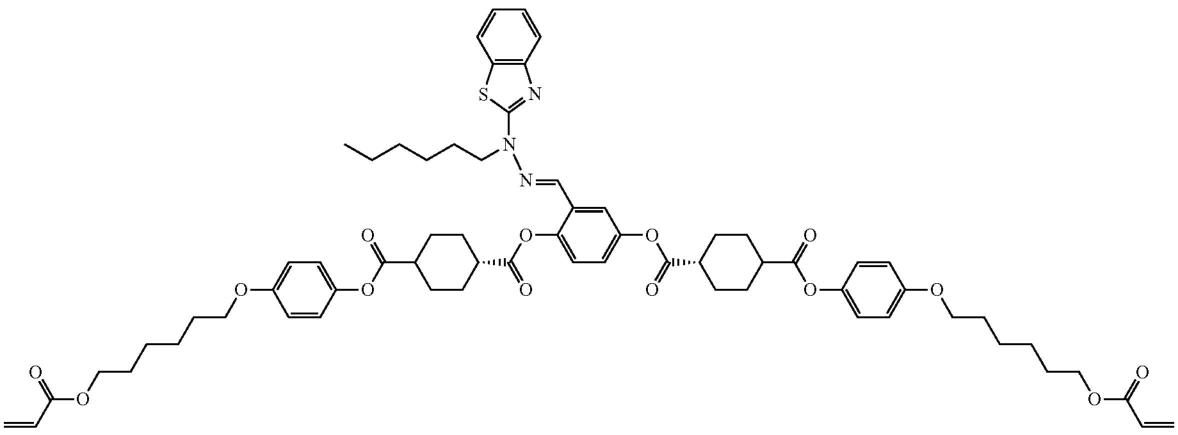

Comparative Production Example 2: Production of Comparative Compound 2 Represented by Formula (C1-2)

A comparative compound 2 represented by the following formula (C1-2) was synthesized by reference to the synthesis of the compound represented by the formula (1-3) of Example 3 described in International Publication No. WO2016/136533.

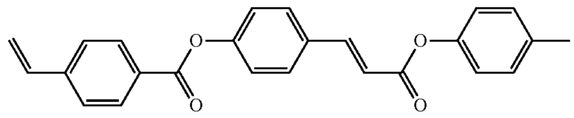

Photo-alignment monomer

Formula (C1-2)

(C1-2)

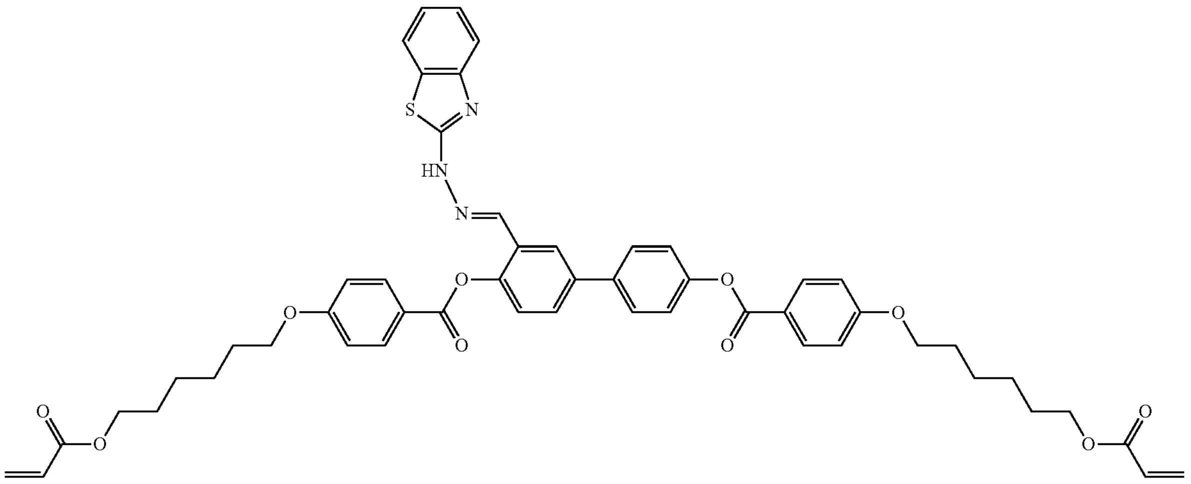

Example 1

(1) Production of Polymerizable Composition

A polymerizable composition 1 was produced by dissolving, into 900 parts by mass of cyclopentanone, 100 parts by mass of a polymerizable liquid crystal compound (the compound 1 represented by the formula (1-1)) and 4 parts by mass of a photopolymerization initiator (2-methyl-1-(4-methylthiophenyl)-2-morpholinopropane-1-on, "IRGACURE 907" manufactured by Ciba Specialty Chemicals Inc.)

(2) Production of Retardation Film or Transfer Laminate (2-1) Preparation of Composition for Photo-Alignment Film In accordance with the description of Production Example 1 in Patent No. JP5626493, hydroxyethyl methacrylate (1.30 g), a photo-alignment monomer represented by the following chemical formula (3.95 g) and, as a polymerization catalyst, α,α'-azobisisobutyronitrile (AIBN) (50 mg) were dissolved in dioxane (25 ml). The reaction system was reacted at 90° C. for 6 hours. After the end of the reaction, the resultant was purified by a reprecipitation method to yield a copolymer 1 in which the photo-alignment monomer represented by the following chemical formula and the hydroxyethyl methacrylate were copolymerized.

A composition for photo-alignment film was prepared, which was the composition of the following composition:

- Copolymer 1 (0.1 parts by mass)
- Hexamethoxymethylmelamine (HMM) (0.01 parts by mass)
- p-Toluenesulfonic acid monohydrate (PTSA) (0.0015 parts by mass)
- Propylene glycol monomethyl ether (PGME) (2.1 parts by mass)

(2-2) Formation of Horizontal Alignment Film

On one surface of a PET substrate ("E5100" manufactured by Toyobo Co., Ltd., thickness 38 μm), the composition for photo-alignment film was applied by bar coating to give a 0.2 μm-thick film when cured. The applied composition was dried and thermally cured by heating the substrate in an oven at 120° C. for 1 minute to form a cured coating film. Thereafter, using a Hg-Xe lamp and a Glan-Taylor prism, the cured coating film surface was irradiated with polarized ultraviolet rays including an emission line of 313 nm in a direction vertical from the substrate normal side at an irradiation dose of 100 $mJ/cm^2$ to form a horizontal alignment film.

(2-3) Production of Retardation Film or Transfer Laminate

The polymerizable composition 1 was formed into a film by applying, on the formed alignment film, the polymerizable composition to give a 1 μm-thick film when cured. Thereafter, the film was dried in an oven for 120 seconds at the corresponding drying temperature shown in Table 9. Using an H-valve (manufactured by Fusion), the dried film was irradiated with ultraviolet rays (UV) at an irradiation dose of 400 $mJ/cm^2$ to form a retardation layer, thereby yielding a retardation film or transfer laminate.

Examples 2 to 17 and Comparative Examples 1 and 2

(1) Production of Polymerizable Composition

Polymerizable compositions 2 to 17 and comparative polymerizable compositions 1 and 2 were yielded in the same way as in Example 1, except that the composition of the components was changed as shown in the following Table 9.

(2) Production of Retardation Film or Transfer Laminate

Retardation films or transfer laminates 2 to 17 and comparative retardation films or transfer laminates 1 and 2 were yielded in the same way as in Example 1, except that the polymerizable compositions 2 to 17 and the comparative polymerizable compositions 1 and 2 were used instead of the polymerizable composition 1.

Evaluation

<Production of Samples>

The PET substrate of the retardation film yielded in each of Examples and Comparative Examples, was removed. The retardation layer and horizontal alignment film thereof were transferred onto a stickiness layer-attached glass piece to yield a sample. The resultant samples were used for evaluation.

<Alignment Property>

The alignment property of the retardation layer was observed with a polarizing microscope and evaluated using the following three-point scale.

(Alignment Property Evaluating Criterion)

A: Uniform alignment was found by visual observation, and the aligned area was found to be 90% or more by the polarizing microscopy.

B: The same level of alignment as A was not found by visual observation, and the aligned area was found to be 50% or more and less than 90% by the polarizing microscopy.

C: No alignment was found by visual observation, and the aligned area was found to be less than 50% by the polarizing microscopy.

<Retardation (Wavelength Dispersion Property)>

In-plane retardations Re at wavelengths 450 nm, 550 nm and 650 nm were measured by a retardation measuring device ("KOBRA-WR" manufactured by Oji Scientific Instruments).

Next, x and y values were calculated as follows using the measured retardations to evaluate wavelength dispersion.

$$x = (\text{In-plane retardation Re at 450 nm})/(\text{In-plane retardation Re at 550 nm})$$

$$y = (\text{In-plane retardation Re at 650 nm})/(\text{In-plane retardation Re at 550 nm})$$

(Wavelength Dispersion Property Evaluating Criterion)

A: $0.6 \leq x < 0.90$ and $1 < y$ (reverse wavelength dispersion property)

B: $0.90 \leq x < 0.95$ and $1 < y$ (reverse wavelength dispersion property)

C: $0.95 \leq x < 1$ and $1 < y$

D: $1 \leq x$ and $1 \geq y$ (normal dispersion)

<Birefringence>

Since there is the following relationship between retardation Re, birefringence index Δn and film thickness d, the birefringence index Δn at 550 nm was evaluated from the in-plane retardation Re at 550 nm and the film thickness d:

$$\text{Retardation Re}(\lambda) = \text{birefringence index } \Delta n(\lambda) \times \text{film thickness } d$$

A: 0.08 or more

B: $0.075 \leq \Delta n < 0.08$

C: Less than 0.075

<Solvent Solubility>

A solubility test was carried out on the compounds yielded in Production Examples and Comparative Production Examples. The solubility of each compound after it was placed in cyclopentanone at 25° C. for 30 minutes, was evaluated by visual observation, provided that the total mass of the compound and the cyclopentanone was defined as 100% by mass, and the compound was 10% by mass.

(Alignment Property Evaluating Criterion)

A: The compound was found to be completely dissolved by visual observation.

C: Insoluble matters were found by visual observation.

TABLE 9

| | Polymerizable liquid crystal compound | Content (% by mass) in polymerizable liquid crystal compound | Alignment property | Wavelength dispersion property | Birefringence | Solvent solubility | Drying temperature (° C.) |
|---|---|---|---|---|---|---|---|
| Example 1 | Compound 1 | 100 | A | A | A | A | 140 |
| Example 2 | Compound 2 | 100 | A | A | A | A | 150 |
| Example 3 | Compound 3 | 100 | A | A | A | A | 150 |
| Example 4 | Compound 4 | 100 | A | A | A | A | 130 |
| Example 5 | Compound 5 | 100 | A | A | A | A | 140 |
| Example 6 | Compound 6 | 100 | A | A | A | A | 170 |
| Example 7 | Compound 7 | 100 | A | A | A | A | 160 |
| Example 8 | Compound 8 | 100 | A | A | A | A | 140 |
| Example 9 | Compound 9 | 100 | B | A | A | A | 150 |
| Example 10 | Compound 10 | 100 | A | A | A | A | 120 |
| Example 11 | Compound 11 | 100 | A | A | A | A | 120 |
| Example 12 | Compound 12 | 100 | A | A | A | A | 120 |
| Example 13 | Compound 13 | 100 | A | A | A | A | 120 |
| Example 14 | Compound 14 | 100 | A | A | A | A | 130 |
| Example 15 | Compound 15 | 100 | A | A | A | A | 120 |
| Example 16 | Compound 16 | 100 | A | A | A | A | 150 |
| Example 17 | Compound 17 | 100 | B | A | A | A | 140 |
| Comparative Example 1 | Comparative compound 1 | 100 | A | A | C | A | 120 |
| Comparative Example 2 | Comparative compound 2 | 100 | B | C | C | A | 120 |

A rubbing-treated, polyimide alignment film-attached glass piece (an alignment-treated glass substrate manufactured by EHC Co., Ltd.) was prepared, which was an alignment-treated glass substrate to which POLYIMIDE LX-1400 (product name, manufactured by: Hitachi Chemical Co., Ltd.) was applied and subjected to rubbing treatment in the following condition:

Roller Rotational Speed: 600 rpm

Transfer Rate: 30 mm/sec

Reciprocating Number of Times: 3

Each of the polymerizable compositions 1 to 17 and the comparative polymerizable compositions 1 and 2 was formed into a film by applying, on the alignment film of the substrate, the polymerizable composition to give a 1 μm-thick film when cured. Thereafter, each film was dried in an oven for 120 seconds at a temperature calculated by adding 10° C. to the solid-liquid crystal phase transition temperature of the polymerizable liquid crystal compound contained in each polymerizable composition. Thereafter, using an H-valve (manufactured by Fusion), the dried film was irradiated with ultraviolet rays (UV) at an irradiation dose of 400 $mJ/cm^2$ to form a retardation layer, thereby yielding a retardation film or transfer laminate.

For the formed retardation layers, their in-plane retardations Re were measured as described above. For the polymerizable compositions 1 to 17 containing the polymerizable liquid crystal compounds 1 to 17 and the comparative polymerizable composition 1 containing the comparative polymerizable liquid crystal compound 1, their evaluation results in accordance with the wavelength dispersion property evaluating criterion were all "A". For the comparative polymerizable composition 2 containing the comparative polymerizable liquid crystal compound 2, its evaluation result in accordance with the wavelength dispersion property evaluating criterion was "C".

Examples 18 to 47

(1) Production of Polymerizable Compositions

Polymerizable compositions 18 to 47 were yielded in the same way as in Example 1, except that the polymerizable liquid crystal compound in the present disclosure and the polymerizable liquid crystal compound different from the polymerizable liquid crystal compound in the present disclosure, were mixed in accordance with the following Table 10, instead of using 100% by mass of the compound 1 (the polymerizable liquid crystal compound in the present disclosure) in the polymerizable liquid crystal compound.

As the polymerizable liquid crystal compound different from the polymerizable liquid crystal compound in the present disclosure, compounds represented by polymerizable liquid crystal compounds B-1 to B-6 represented by the following chemical formulae were prepared.

(2) Production of Retardation Film or Transfer Laminate

Retardation films or transfer laminates 18 to 47 were yielded in the same way as in Example 1, except that the polymerizable compositions 18 to 47 were used instead of the polymerizable composition 1.

Polymerizable liquid crystal compound B-1

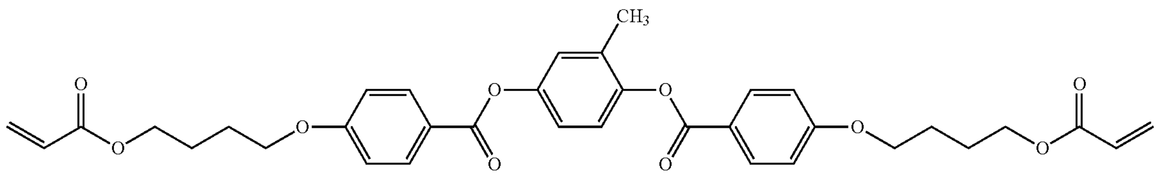

Polymerizable liquid crystal compound B-2

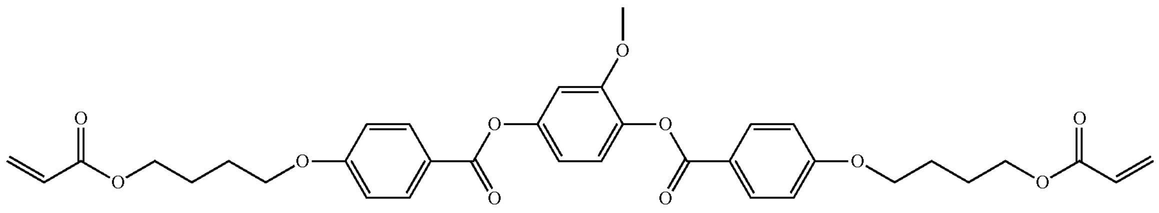

Polymerizable liquid crystal compound B-3

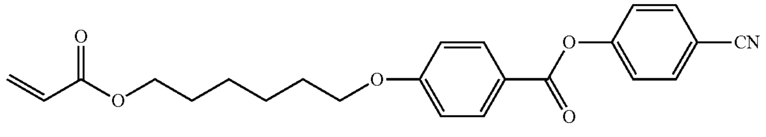

Polymerizable liquid crystal compound B-4

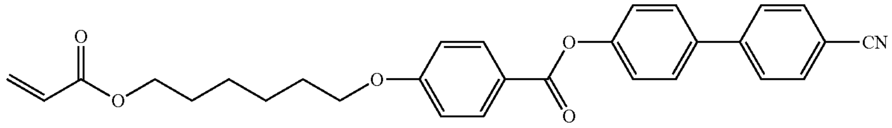

Polymerizable liquid crystal compound B-5

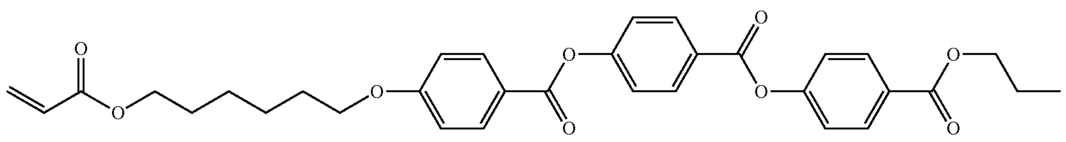

-continued

Polymerizable liquid crystal compound B-6

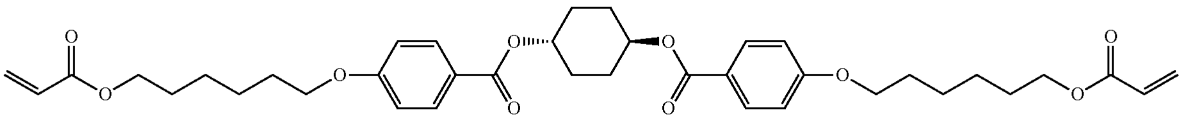

For the compounds represented by the polymerizable liquid crystal compounds B-1 to B-6, their wavelength dispersion properties were evaluated as described below.

A rubbing-treated, polyimide alignment film-attached glass piece (an alignment-treated glass substrate manufactured by EHC Co., Ltd.) was prepared. The polymerizable liquid crystal compound (100 parts by mass) and 2-methyl-1-(4-methylthiophenyl)-2-morpholinopropane-1-on (4 parts by mass) were dissolved in cyclopentanone (900 parts by mass) to yield a polymerizable composition. The polymerizable composition was formed into a film by applying, on the alignment film of the substrate, the polymerizable composition to give a 1 μm-thick film when cured. Thereafter, the film was dried in an oven for 120 seconds at a temperature calculated by adding 10° C. to the solid-liquid crystal phase transition temperature of the contained polymerizable liquid crystal compound. Thereafter, using an H-valve (manufactured by Fusion), the dried film was irradiated with ultraviolet rays (UV) at an irradiation dose of 400 $mJ/cm^2$ to form a retardation layer.

For the formed retardation layers, their in-plane retardations Re were measured as described above. For the polymerizable liquid crystal compounds B-1 to B-5, their evaluation results in accordance with the wavelength dispersion property evaluating criterion were all "D". For the polymerizable liquid crystal compound B-6, its evaluation result in accordance with the wavelength dispersion property evaluating criterion was "C".

Evaluation

<Production of Samples>

The PET substrate of the retardation film yielded in each of Examples was removed. The retardation layer and horizontal alignment film thereof were transferred onto a stickiness layer-attached glass piece to yield a sample. The resultant samples were used for evaluation in the same way as in Example 1.

The evaluation results are shown in Table 10.

TABLE 10

| | Polymerizable liquid crystal compound in present disclosure | Content (% by mass) in polymerizable liquid crystal compound | Different polymerizable liquid crystal compound | Content (% by mass) in polymerizable liquid crystal compound | Different polymerizable liquid crystal compound |
|---|---|---|---|---|---|
| Example 18 | Compound 1 | 90 | B-1 | 10 | |
| Example 19 | Compound 1 | 80 | B-1 | 20 | |
| Example 20 | Compound 1 | 70 | B-1 | 30 | |
| Example 21 | Compound 1 | 60 | B-1 | 40 | |
| Example 22 | Compound 1 | 50 | B-1 | 50 | |
| Example 23 | Compound 1 | 75 | B-2 | 25 | |
| Example 24 | Compound 1 | 75 | B-3 | 25 | |
| Example 25 | Compound 1 | 75 | B-4 | 25 | |
| Example 26 | Compound 1 | 75 | B-5 | 25 | |
| Example 27 | Compound 1 | 85 | B-1 | 10 | B-2 |
| Example 28 | Compound 1 | 80 | B-1 | 10 | B-3 |
| Example 29 | Compound 1 | 80 | B-1 | 10 | B-4 |
| Example 30 | Compound 1 | 80 | B-1 | 10 | B-5 |
| Example 31 | Compound 1 | 80 | B-2 | 10 | B-3 |
| Example 32 | Compound 2 | 80 | B-1 | 20 | |
| Example 33 | Compound 3 | 80 | B-1 | 20 | |
| Example 34 | Compound 4 | 80 | B-1 | 20 | |
| Example 35 | Compound 5 | 80 | B-1 | 20 | |
| Example 36 | Compound 6 | 80 | B-1 | 20 | |
| Example 37 | Compound 7 | 80 | B-1 | 20 | |
| Example 38 | Compound 8 | 80 | B-1 | 20 | |
| Example 39 | Compound 9 | 80 | B-1 | 20 | |
| Example 40 | Compound 10 | 80 | B-1 | 20 | |
| Example 41 | Compound 11 | 80 | B-1 | 20 | |
| Example 42 | Compound 12 | 80 | B-1 | 20 | |
| Example 43 | Compound 13 | 80 | B-1 | 20 | |
| Example 44 | Compound 14 | 80 | B-1 | 20 | |
| Example 45 | Compound 15 | 80 | B-1 | 20 | |
| Example 46 | Compound 16 | 80 | B-1 | 20 | |
| Example 47 | Compound 17 | 80 | B-1 | 20 | |

TABLE 10-continued

| | Content (% by mass) in polymerizable liquid crystal compound | Alignment property | Wavelength dispersion property | Bire-fringence | Drying temperature (° C.) |
|---|---|---|---|---|---|
| Example 18 | | A | A | A | 140 |
| Example 19 | | A | A | A | 140 |
| Example 20 | | A | B | A | 130 |
| Example 21 | | A | B | A | 130 |
| Example 22 | | A | C | A | 120 |
| Example 23 | | A | A | A | 140 |
| Example 24 | | A | A | A | 120 |
| Example 25 | | A | A | A | 140 |
| Example 26 | | A | A | A | 130 |
| Example 27 | 5 | A | A | A | 130 |
| Example 28 | 10 | A | A | A | 120 |
| Example 29 | 10 | A | A | A | 140 |
| Example 30 | 10 | A | A | A | 140 |
| Example 31 | 10 | A | A | A | 140 |
| Example 32 | | A | A | A | 140 |
| Example 33 | | A | A | A | 130 |
| Example 34 | | A | A | A | 120 |
| Example 35 | | A | A | A | 130 |
| Example 36 | | A | A | A | 150 |
| Example 37 | | A | A | A | 150 |
| Example 38 | | A | A | A | 130 |
| Example 39 | | B | A | A | 140 |
| Example 40 | | A | A | A | 100 |
| Example 41 | | A | A | A | 100 |
| Example 42 | | A | A | A | 100 |
| Example 43 | | A | A | A | 100 |
| Example 44 | | A | A | A | 120 |
| Example 45 | | A | A | A | 120 |
| Example 46 | | A | A | A | 130 |
| Example 47 | | B | A | A | 140 |

Examples 48 to 62

(1) Production of Polymerizable Compositions

Polymerizable compositions 48 to 62 were yielded in the same way as in Example 1, except that two or more kinds of the polymerizable liquid crystal compounds in the present disclosure, or the polymerizable liquid crystal compound in the present disclosure and at least one selected from the polymerizable liquid crystal compound different from the polymerizable liquid crystal compound in the present disclosure and the different polymerizable compound were mixed in accordance with the following Table 11, instead of using 100% by mass of the compound 1 (the polymerizable liquid crystal compound in the present disclosure) in the polymerizable liquid crystal compound.

The different polymerizable compound prepared were as follows.

DPHA (M-405): Dipentaerythritol penta and hexaacrylate, product name: ARONIX M-405, manufactured by: Toagosei Co., Ltd.

PETTA (M-450): pentaerythritol tri and tetraacrylate, product name: ARONIX M-450, manufactured by: Toagosei Co., Ltd.

TMPTA (M-309): trimethylolpropane triacrylate, product name: ARONIX M-309, manufactured by: Toagosei Co., Ltd.

(2) Production of Retardation Film or transfer laminate

Retardation films or transfer laminates 48 to 62 were yielded in the same way as in Example 1, except that the polymerizable compositions 48 to 62 were used instead of the polymerizable composition 1.

In Examples 60 to 62, instead of the PET substrate, a TAC substrate ("FUJITAC" manufactured by FUJIFILM Corporation) was used as the substrate.

The substrate of the retardation film yielded in each of Examples was removed. The retardation layer and horizontal alignment film thereof were transferred onto a stickiness layer-attached glass piece to yield a sample. The resultant samples were used for evaluation in the same way as in Example 1.

The evaluation results are shown in Table 11.

TABLE 11

| | Polymerizable liquid crystal compound in present disclosure | Content (% by mass) in plymerizable compound | Polymerizable liquid crystal compound in present disclosure | Content (% by mass) in polymerizable compound | Different polymerizable liquid crystal compound | Content (% by mass) in polymerizable compound | Different polymerizable liquid crystal compound |
|---|---|---|---|---|---|---|---|
| Example 48 | Compound 1 | 90 | | | B-6 | 10 | |
| Example 49 | Compound 1 | 80 | | | B-6 | 20 | |
| Example 50 | Compound 1 | 70 | | | B-6 | 30 | |
| Example 51 | Compound 1 | 60 | | | B-6 | 40 | |
| Example 52 | Compound 1 | 50 | | | B-6 | 50 | |
| Example 53 | Compound 1 | 80 | | | B-1 | 10 | B-6 |

TABLE 11-continued

| | | | | | | | |
|---|---|---|---|---|---|---|---|
| Example 54 | Compound 1 | 70 | | | B-1 | 10 | B-6 |
| Example 55 | Compound 1 | 50 | Compound 3 | 50 | | | |
| Example 56 | Compound 1 | 80 | | | Comparative Compound 2 | 20 | |
| Example 57 | Compound 1 | 80 | | | | | |
| Example 58 | Compound 1 | 80 | | | | | |
| Example 59 | Compound 1 | 80 | | | | | |
| Example 60 | Compound 10 | 80 | | | B-1 | 20 | |
| Example 61 | Compound 10 | 80 | | | B-6 | 20 | |
| Example 62 | Compound 20 | 80 | | | | | |

| | Content (% mass) in polymerizable compound | Different polymerizable compound | Content (% by mass) in polymerizable compound | sub-strate | Alignment property | Wavelength dispersion property | Birefringence | Drying temperature (° C.) |
|---|---|---|---|---|---|---|---|---|
| Example 48 | | | | PET | A | A | A | 130 |
| Example 49 | | | | PET | A | A | A | 130 |
| Example 50 | | | | PET | A | A | A | 120 |
| Example 51 | | | | PET | A | A | A | 120 |
| Example 52 | | | | PET | A | B | A | 120 |
| Example 53 | 10 | | | PET | A | A | A | 130 |
| Example 54 | 20 | | | PET | A | A | A | 120 |
| Example 55 | | | | FET | A | A | A | 140 |
| Example 56 | | | | PET | A | A | A | 130 |
| Example 57 | | DPHA M-405 | 20 | PET | A | A | A | 130 |
| Example 58 | | PETTA M-450 | 20 | PET | A | A | A | 130 |
| Example 59 | | TMPTA M-309 | 20 | PET | A | A | A | 130 |
| Example 60 | | | | TAC | A | A | A | 100 |
| Example 61 | | | | TAC | A | A | A | 100 |
| Example 62 | | DPHA M-405 | 20 | TAC | A | A | A | 100 |

REFERENCE SIGNS LIST

1. Retardation layer
2, 2'. Substrate
3. Alignment film
10. Retardation film
11, 21, 31. Retardation layer
12, 22, 32. Second substrate
13, 23, 33. Alignment film
15, 25, 35. Support peelable to be removed
16, 26, 36. Retardation layer supplied to be transferred
17. Interface between alignment film and retardation layer
27. Interface between second substrate and alignment film
20, 30, 40. Transfer laminate
50. Polarizing plate
60. Optical member
71. Transparent electrode layer
72. Light emitting layer
73. Electrode layer
100. Light emitting display device

The invention claimed is:

1. A polymerizable liquid crystal compound represented by the following General Formula (1):

General Formula (1)

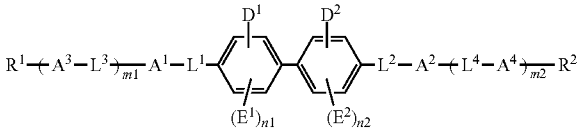

Where:

$L^1$, $L^2$, $L^3$ and $L^4$ each independently represent —O—, —S—, —$OCH_2$—, —$CH_2O$—, —$CH_2CH_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —$SCH_2$—, —$CH_2S$—, —$CF_2O$—, —$OCF_2$—, —$CF_2S$—, —$SCF_2$—, —CH═CH—COO—, —CH═CH—OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH═CH—, —N═N—, —CH═N—, —N═CH—, —CH═N—N═CH—, —CF═CF—, —C≡C— or a single bond;

$A^1$ and $A^2$ each independently represent a divalent alicyclic hydrocarbon group containing 3 to 20 carbon atoms and optionally being unsubstituted or substituted by at least one substituent group E, and any carbon atom of the alicyclic hydrocarbon group is optionally replaced by a heteroatom;

$A^3$ and $A^4$ each independently represent a divalent alicyclic or aromatic hydrocarbon group containing 3 to 20 carbon atoms and optionally being unsubstituted or substituted by at least one substituent group E, and any carbon atom of the alicyclic or aromatic hydrocarbon group is optionally replaced by a heteroatom;

$R^1$ and $R^2$ each independently represent a group selected from the following general formula (R-1):

General formula (R-1): -$L^5$-$R^{sp1}$—$Z^1$ where:

$L^5$ represents —O—, —S—, —$OCH_2$—, —$CH_2O$—, —$CH_2CH_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —$SCH_2$—, —$CH_2S$—, —$CF_2O$—, —$OCF_2$—, —$CF_2S$—, —$SCF_2$—, —CH═CH—COO—, —CH═CH—OCO—, —COO—CH═CH—, —OCO—

CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—, —N=CH—, —CH=N—N=CH—, —CF=CF—, —C≡C— or a single bond;

$R^{sp1}$ represents a single bond or an alkylene group containing 1 to 20 carbon atoms, in which one —$CH_2$— or two or more non-adjacent —$CH_2$— are each independently optionally replaced by —O—, —COO—, —OCO—, —OCO—O—, —CO—NH—, —NH—CO—, —CH=CH— or —C≡C—; and $Z^1$ represents a polymerizable functional group selected from the following formulae (Z-1) to (Z-8):

(Z-1)

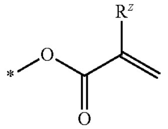

(Z-2)

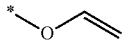

(Z-3)

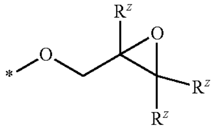

(Z-4)

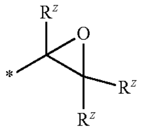

(Z-5)

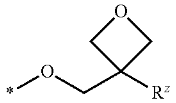

(Z-6)

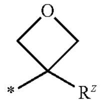

(Z-7)

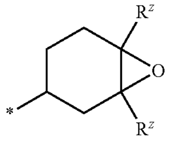

(Z-8)

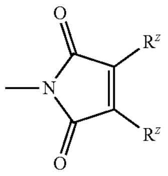

where $R^z$ is each independently a hydrogen atom, a fluorine atom, a chlorine atom, a bromine atom, an iodine atom, a methyl group, an ethyl group or a trifluoromethyl group;

$D^1$ and $D^2$ each independently represent a group selected from the following general formula (D-1):

General Formula (D-1)

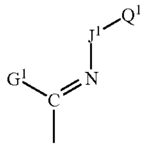

where:

$G^1$ represents a hydrogen atom or an alkyl group containing 1 to 6 carbon atoms, and the alkyl group is optionally unsubstituted or substituted by at least one substituent group E;

$Q^1$ represents a group selected from the following formulae (Q-1-1), (Q-7-1), (Q-7-2), (Q-7-7), (Q-8), (Q-10-2), (Q-10-3), (Q-10-4), (Q-10-5), (Q-10-6), (Q-10-7), (Q-10-8), (Q-10-9), (Q-11-2), (Q-11-3), (Q-11-4), (Q-11-5), (Q-11-6), (Q-11-7), (Q-11-8), (Q-11-9), (Q-11-10), (Q-11-11), (Q-11-12), (Q-21-1), (Q-21-2), (Q-22-1) and (Q-22-2) and is optionally unsubstituted or substituted by at least one substituent group E;

(Q-1-1)

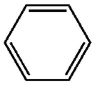

(Q-7-1)

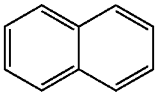

(Q-7-2)

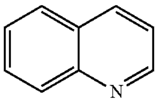

(Q-7-7)

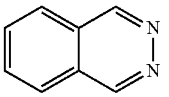

(Q-8)

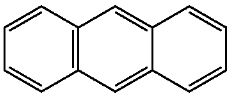

(Q-10-2)

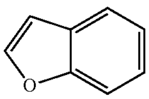

(Q-10-3)

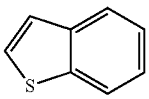

(Q-10-4)

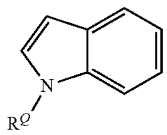

-continued (Q-10-5)

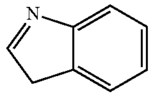

(Q-10-6)

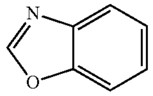

(Q-10-7)

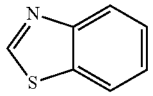

(Q-10-8)

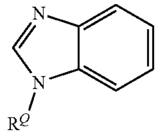

(Q-10-9)

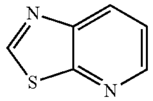

(Q-11-2)

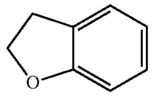

(Q-11-3)

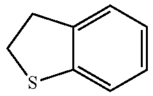

(Q-11-4)

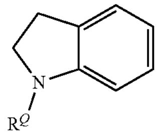

(Q-11-5)

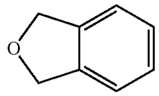

(Q-11-6)

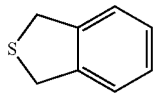

(Q-11-7)

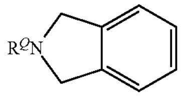

(Q-11-8)

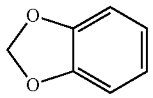

(Q-11-9)

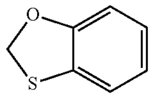

-continued (Q-11-10)

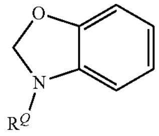

(Q-11-11)

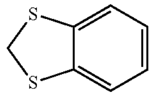

(Q-11-12)

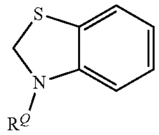

(Q-21-1)

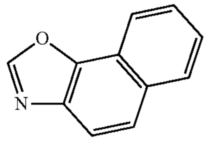

(Q-21-2)

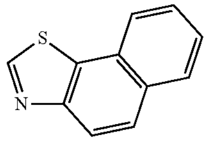

(Q-22-1)

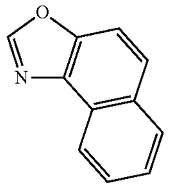

(Q-22-2)

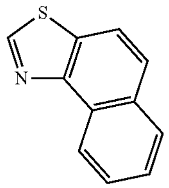

where $R^Q$ represents a hydrogen atom or an alkyl group containing 1 to 6 carbon atoms; and $J^1$ represents —O—, —S—, —COO—, —OCO—, —OCO—O—, —$NQ^2$-, —N═$CQ^2$-, —CO—$NQ^2$-, —OCO—$NQ^2$- or —O—$NQ^2$-, where:

$Q^2$ represents a hydrogen atom, an alkyl group containing 1 to 20 carbon atoms, a cycloalkyl group containing 3 to 12 carbon atoms, a cycloalkenyl group containing 3 to 12 carbon atoms, an organic group containing 2 to 30 carbon atoms and containing an aromatic hydrocarbon group (any carbon atom of the aromatic hydrocarbon group is optionally replaced by a heteroatom) or $-(L^6-A^5)_q-L^7-R^{sp2}—Z^2$; the alkyl group, the cycloalkyl group, the cycloalkenyl group and the aromatic hydrocarbon group are each optionally unsubstituted or substituted by at least one substituent group E; the alkyl group is optionally substituted by the cycloalkyl group or the cycloalkenyl group;

one $—CH_2—$ or two or more non-adjacent $—CH_2—$ in the alkyl group are each independently optionally replaced by —O—, —S—, —CO—, —COO—, —OCO—, —CO—S—, —S—CO—, $—SO_2—$, —O—CO—O—, —CO—NH—, —NH—CO—, —CH═CH—COO—, —CH═CH—OCO—, —COO—CH═CH—, —OCO—CH═CH—, —CH═CH—, —CF═CF— or —C≡C—; one $—CH_2—$ or two or more non-adjacent $—CH_2—$ in the cycloalkyl or cycloalkenyl group are each independently optionally replaced by —O—, —CO—, —COO—, —OCO— or —O—CO—O—; where:

$L^6$ represents —O—, —S—, —OCH2-, —CH2O—, —CH2CH2-, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH2-, —CH2S—, —CF2O—, —OCF2-, —CF2S—, —SCF2-, —CH═CH—COO—, —CH═CH—OCO—, —COO—CH═CH—, —OCO—CH═CH—, —COO—CH2CH2-, —OCO—CH2CH2-, —CH2CH2-COO—, —CH2CH2-OCO—, —COO—CH2-, —OCO—CH2-, —CH2-COO—, —CH2-OCO—, —CH═CH—, —N═N—, —CH═N—, —N═CH—, —CH═N—N═CH—, —CF═CF—, —C≡C— or a single bond;

$A^5$ represents a divalent alicyclic or aromatic hydrocarbon group containing 3 to 20 carbon atoms and optionally being unsubstituted or substituted by at least one substituent group E, and any carbon atom of the alicyclic or aromatic hydrocarbon group is optionally replaced by a heteroatom;

$L^7$ represents —O—, —S—, —OCH2-, —CH2O—, —CH2CH2-, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH2-, —CH2S—, —CF2O—, —OCF2-, —CF2S—, —SCF2-, —CH═CH—COO—, —CH═CH—OCO—, —COO—CH═CH—, —OCO—CH═CH—, —COO—CH2CH2-, —OCO—CH2CH2-, —CH2CH2-COO—, —CH2CH2-OCO—, —COO—CH2-, —OCO—CH2-, $—CH_2—COO—$, —CH2-OCO—, —CH═CH—, —N═N—, —CH═N—, —N═CH—, —CH═N—N═CH—, —CF═CF—, —C≡C— or a single bond;

$R^{sp2}$ represents a single bond or an alkylene group containing 1 to 20 carbon atoms, in which one —CH2- or two or more non-adjacent —CH2- are each independently optionally replaced by —O—, —COO—, —OCO—, —OCO—O—, —CO—NH—, —NH—CO—, —CH═CH— or —C≡C—; and $Z^2$ represents a polymerizable functional group selected from the following formulae (Z-1) to (Z-8);

(Z-1)

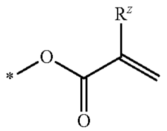

(Z-2)

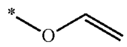

(Z-3)

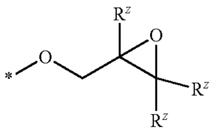

(Z-4)

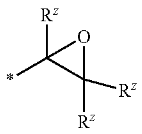

(Z-5)

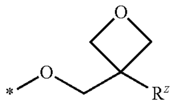

(Z-6)

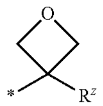

(Z-7)

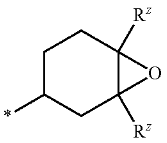

(Z-8)

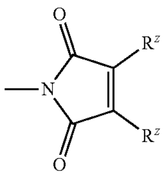

where $R^2$ is each independently a hydrogen atom, a fluorine atom, a chlorine atom, a bromine atom, an iodine atom, a methyl group, an ethyl group or a trifluoromethyl group;

q is an integer of 0 to 4; and when plural $L^6$s, as well as plural $A^5$s, are present, they are optionally the same or different from each other;

the substituent groups E, $E^1$ and $E^2$ each independently represent a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group containing 1 to 20 carbon atoms, in which one $—CH_2—$ or two or more non-adjacent $—CH_2—$ are each independently optionally replaced by —O—, —S—, —CO—, —COO—, —OCO—, —CO—S—, —S—CO—, —O—CO—O—, —CO—NH—, —NH—

CO—, —CH═CH—COO—, —CH═CH—OCO—, —COO—CH═CH—, —OCO—CH═CH—, —CH═CH—, —CF═CF— or —C≡C—, and any hydrogen atom in the alkyl group is optionally replaced by a fluorine atom, or the substituent groups E, $E^1$ and $E^2$ each independently represent a group represented by $-L^E-R^{spE}-Z^E$ where:

$L^E$ represents —O—, —S—, —OCH2-, —CH2O—, —CH2CH2-, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH2-, —CH2S—, —CF2O—, —OCF2-, —CF2S—, —SCF2-, —CH═CH—COO—, —CH═CH—OCO—, —COO—CH═CH—, —OCO—CH═CH—, —COO—CH2CH2-, —OCO—CH2CH2-, —CH2CH2-COO—, —CH2CH2-OCO—, —COO—CH2-, —OCO—CH2-, —CH2-COO—, $—CH_2—OCO—$, —CH═CH—, —N═N—, —CH═N—, —N═CH—, —CH═N—N═CH—, —CF═CF—, —C≡C— or a single bond;

$R^{spE}$ represents a single bond or an alkylene group containing 1 to 20 carbon atoms, in which one —CH2- or two or more non-adjacent —CH2- are each independently optionally replaced by —O—, —COO—, —OCO—, —OCO—O—, —CO—NH—, —NH—CO—, —CH═CH— or —C≡C—; and $Z^E$ represents a polymerizable functional group selected from the following formulae (Z-1) to (Z-8):

(Z-1)

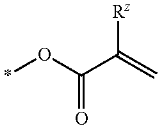

(Z-2)

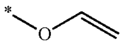

(Z-3)

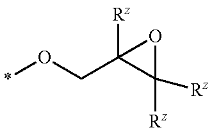

(Z-4)

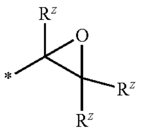

(Z-5)

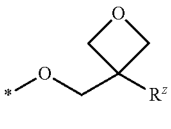

(Z-6)

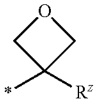

-continued (Z-7)

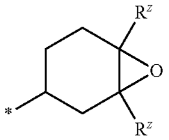

(Z-8)

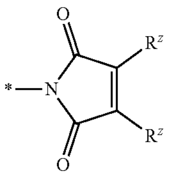

where $R^z$ is each independently a hydrogen atom, a fluorine atom, a chlorine atom, a bromine atom, an iodine atom, a methyl group, an ethyl group or a trifluoromethyl group;

when plural substituent groups Es, as well as plural substituent groups $E^1$s and plural substituent groups $E^2$s, are present in the compound, they are optionally the same or different from each other; and when plural $L^3$s, as well as plural $L^4$s, plural $A^3$s and plural $A^4$s, are present, they are optionally the same or different from each other;

m1 and m2 each independently represent an integer of 1 to 4; and n1 and n2 each independently represent an integer of from 0 to 3.

2. The polymerizable liquid crystal compound according to claim 1, wherein $D^1$ and $D^2$ each independently represent a group selected from the following general formulae (D-1) to (D-31) and (D-34) to (D-47):

(D-1)

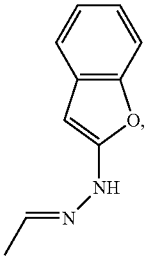

(D-2)

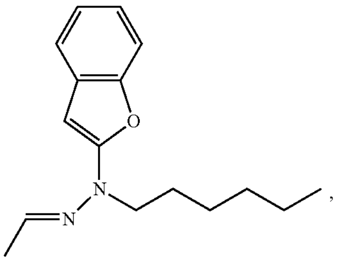

-continued
(D-3)
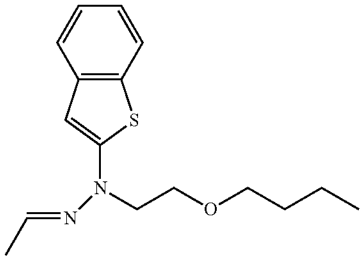
,
(D-4)
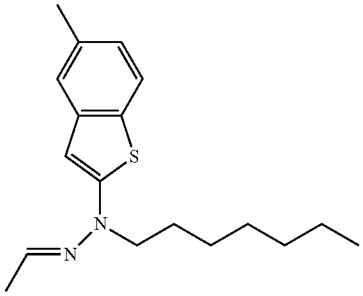
,
(D-5)
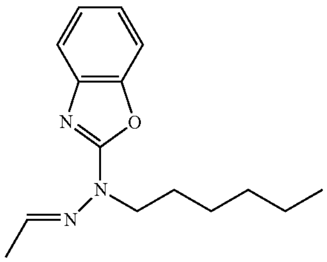
,
(D-6)
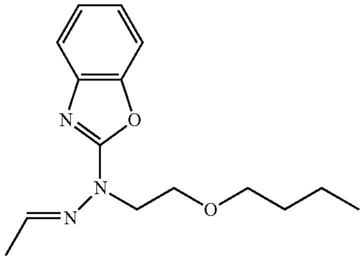
,
(D-7)
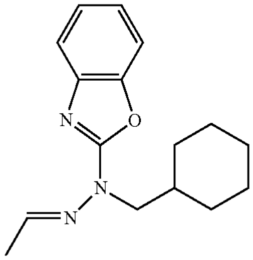
,
-continued
(D-8)
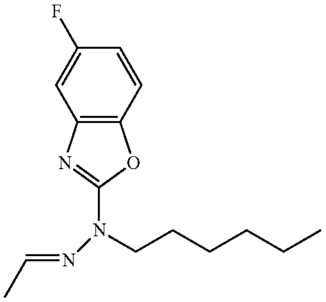
,
(D-9)
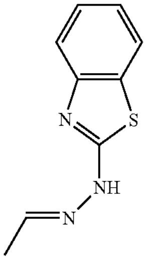
,
(D-10)
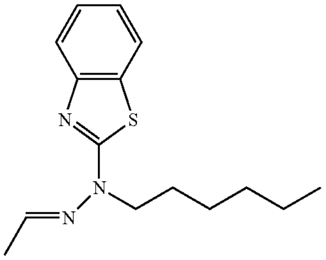
,
(D-11)
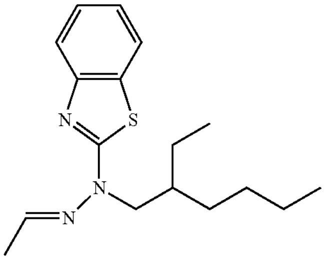
,
(D-12)
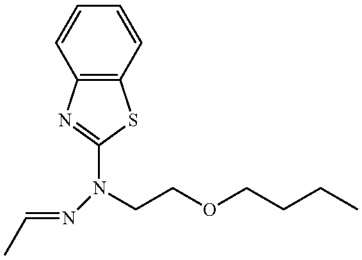
,
(D-13)
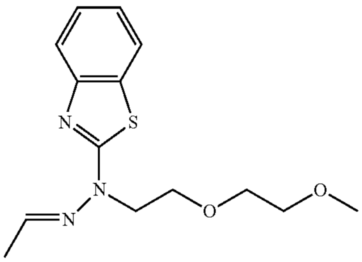
, -continued
(D-14)
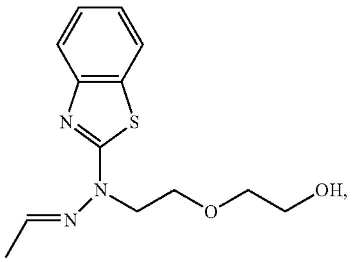
(D-15)
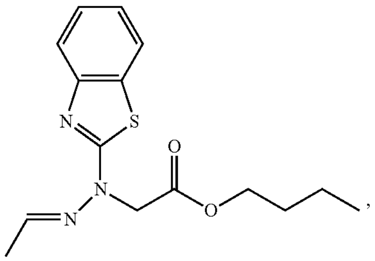
(D-16)
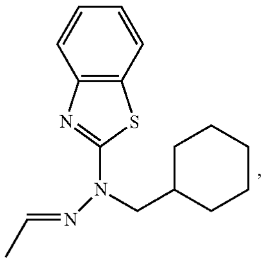
(D-17)
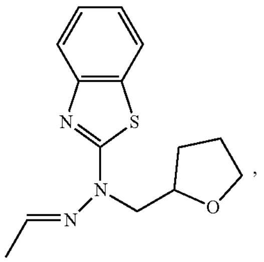
(D-18)
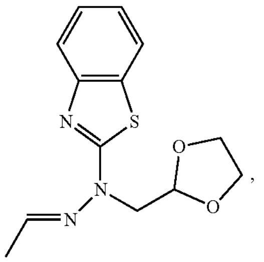
(D-19)
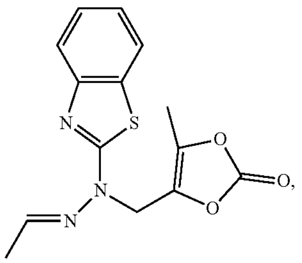
-continued
(D-20)
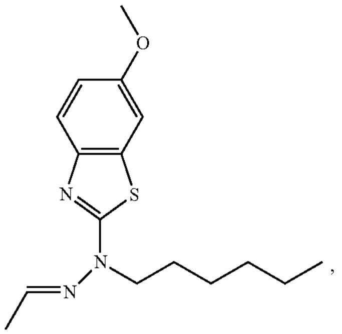
(D-21)
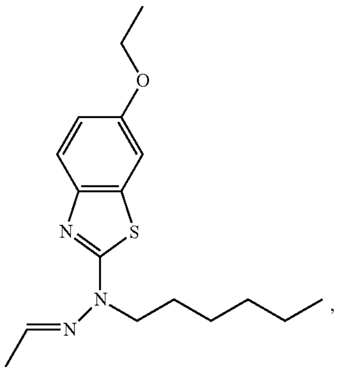
(D-22)
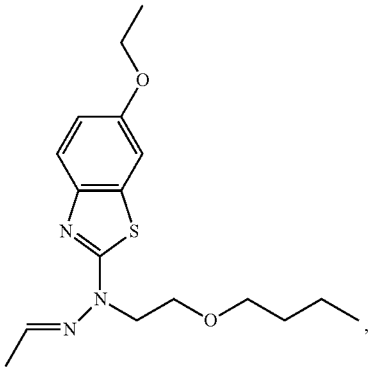
(D-23)
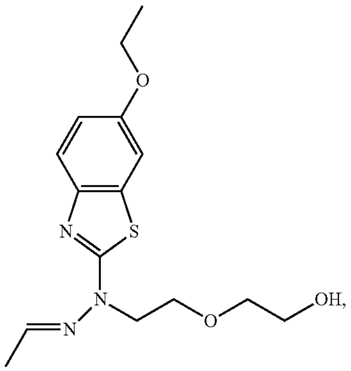

-continued
(D-24)
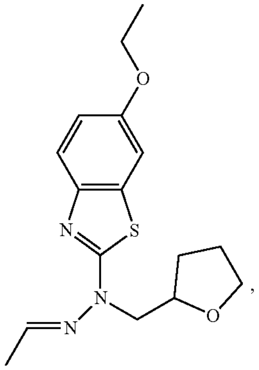
(D-25)
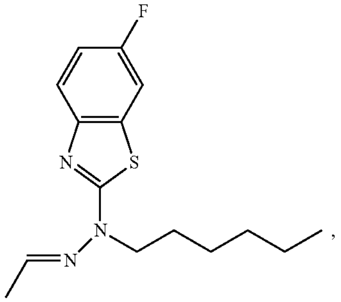
(D-26)
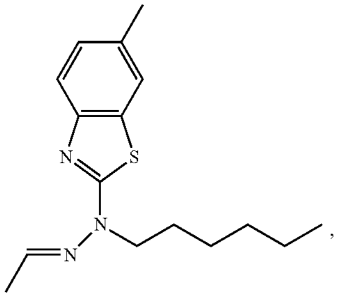
(D-27)
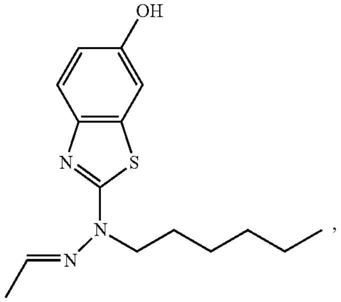
(D-28)
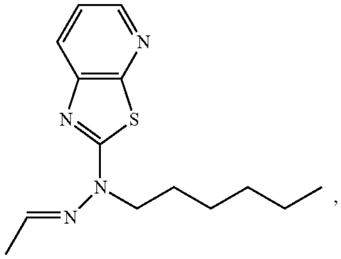
-continued
(D-29)
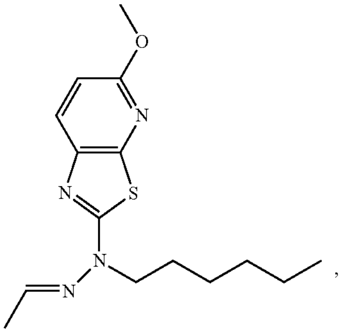
(D-30)
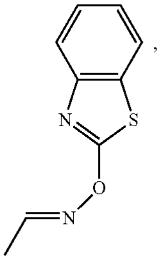
(D-31)
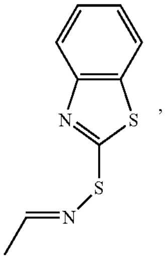
(D-34)
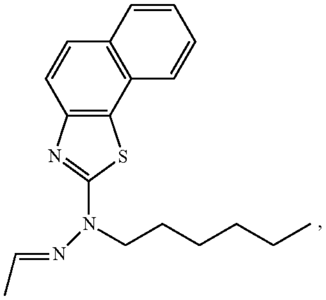
(D-35)
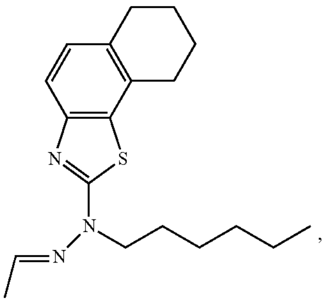

-continued
(D-36)
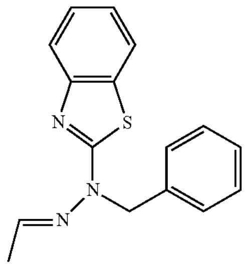
,
(D-37)
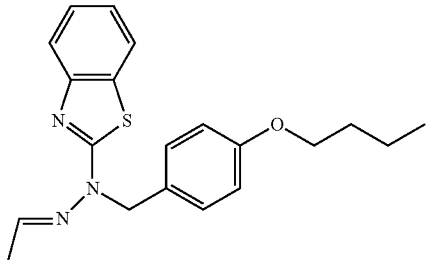
,
(D-38)
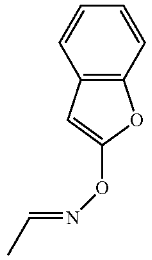
,
(D-39)
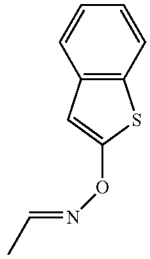
,
(D-40)
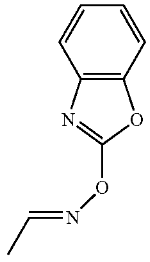
,
-continued
(D-41)
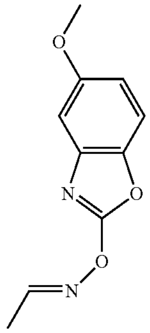
,
(D-42)
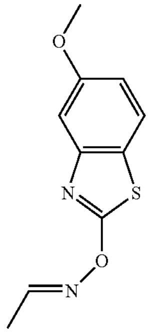
,
(D-43)
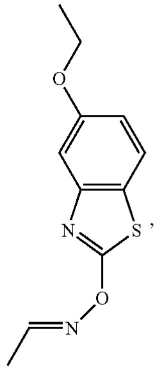
,
(D-44)
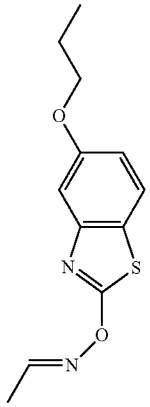
, -continued
(D-45)
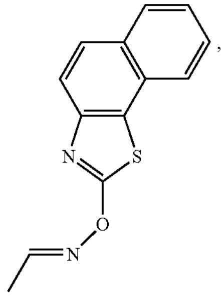
,
(D-46)
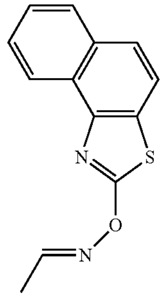
, and
-continued
(D-47)
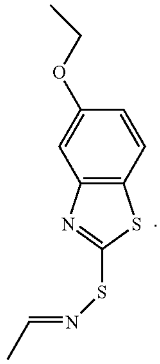
.
3. The polymerizable liquid crystal compound according claim 1, wherein the polymerizable liquid crystal compound is selected from the group consisting of compounds represented by the following chemical formulae:
(v)-1
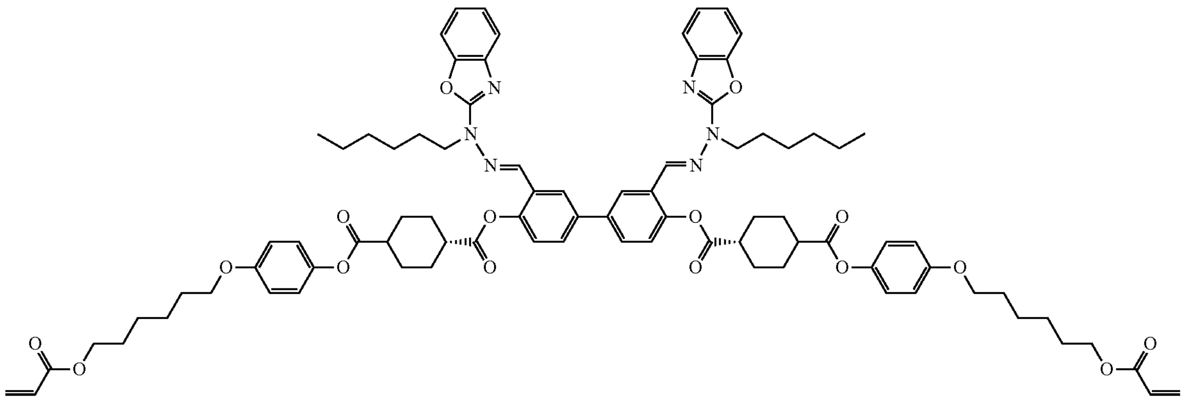
,
(vi)-1
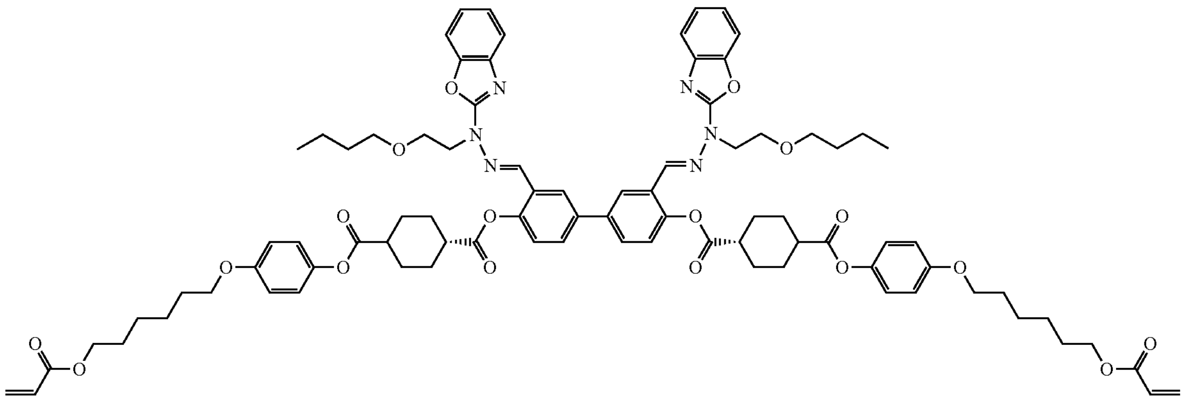
, -continued
(x)-1
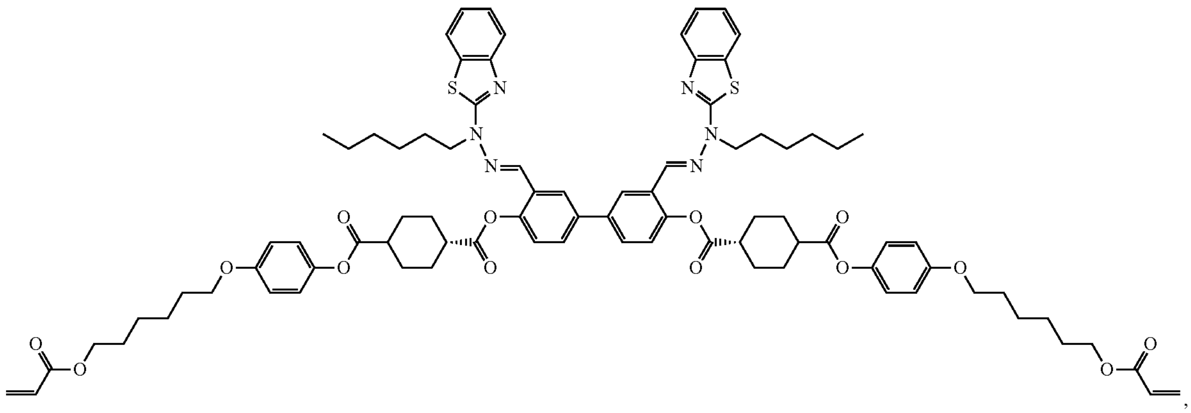
,
(xii)-1
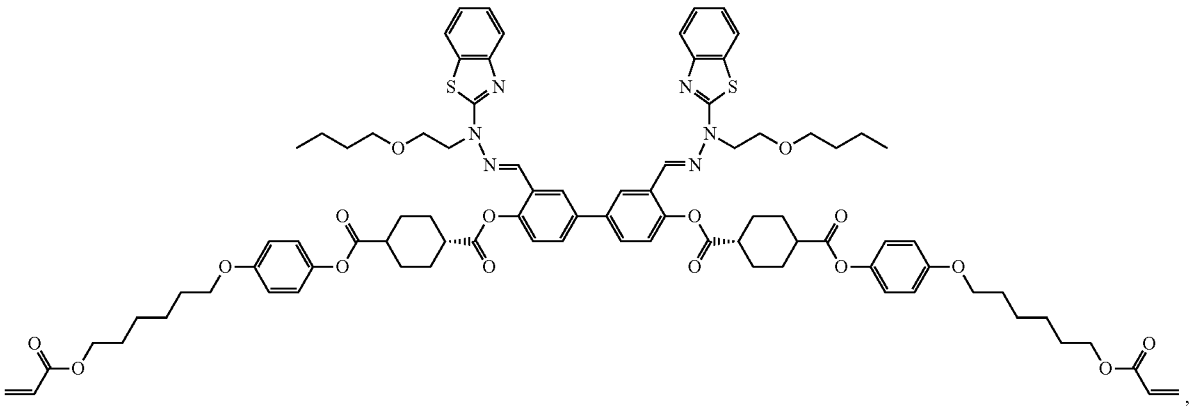
,
(xiii)-1
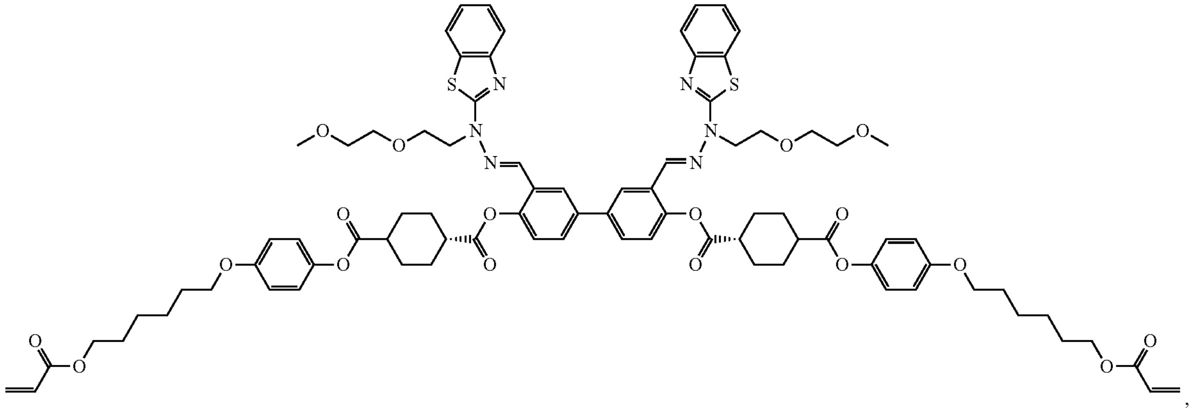
, -continued
(xiv)-1
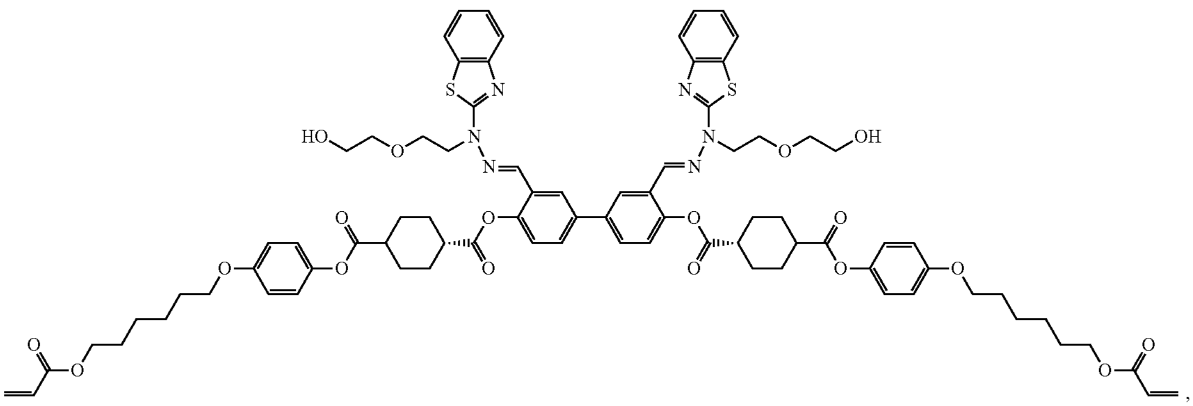
,
(xv)-1
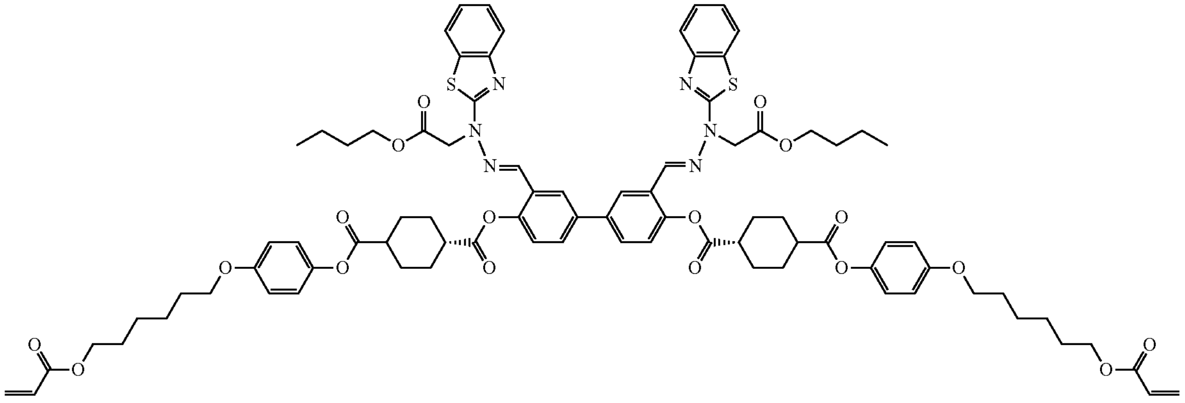
,
(xvi)-1
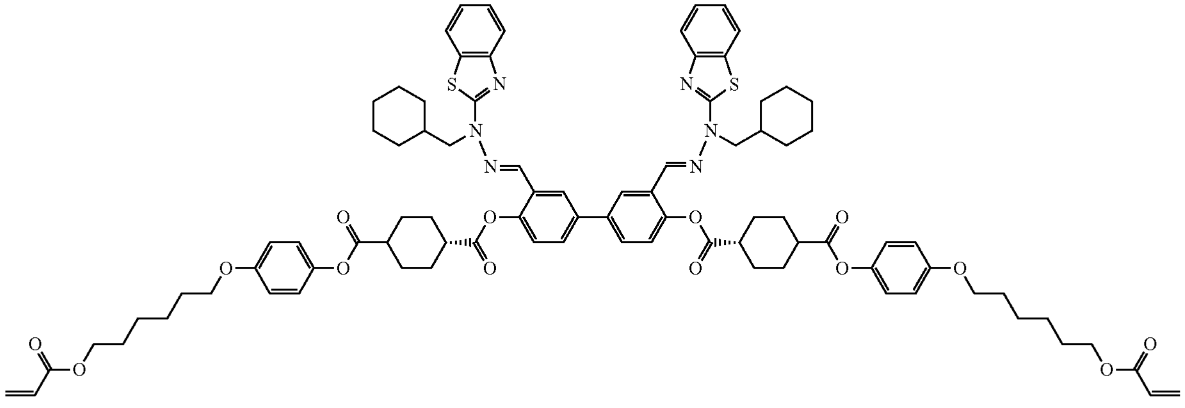
, -continued
(xvii)-1
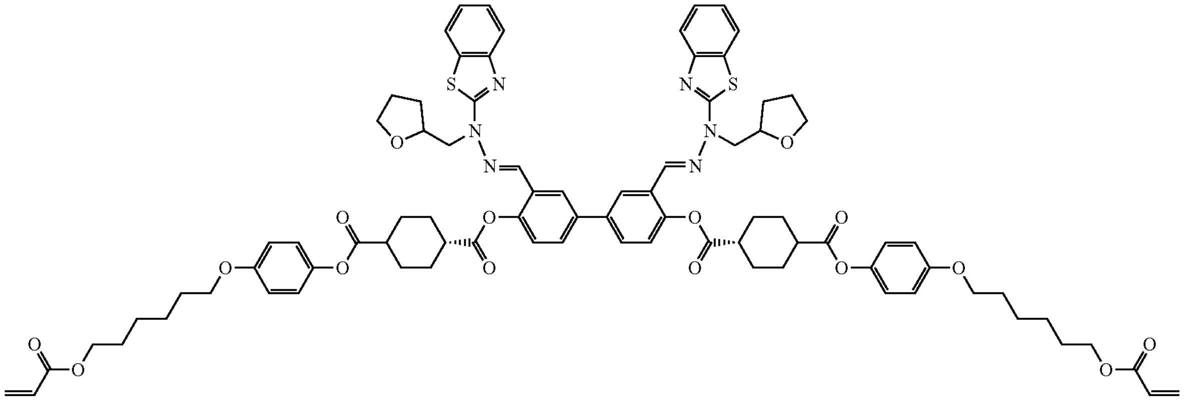
,
(xx)-1
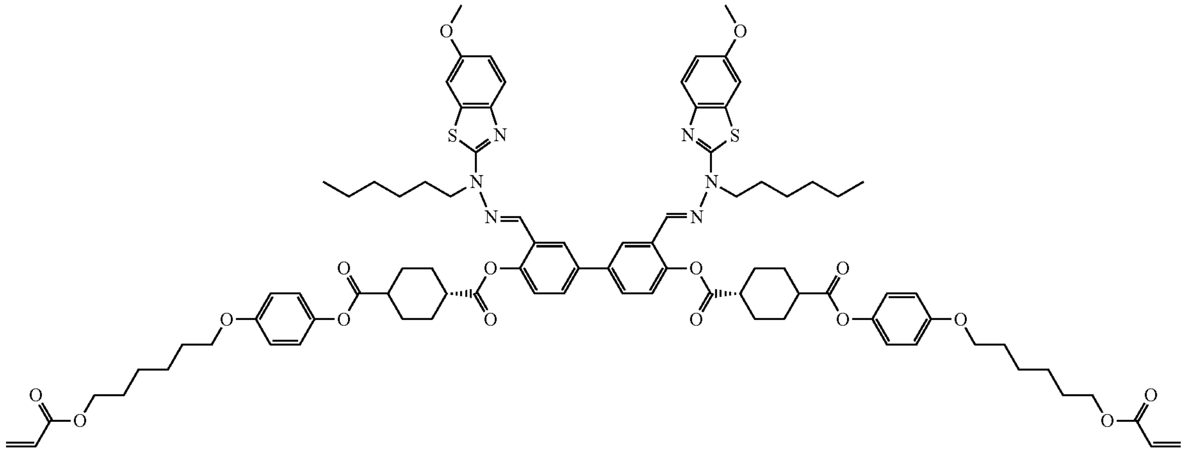
,
(xxi)-1
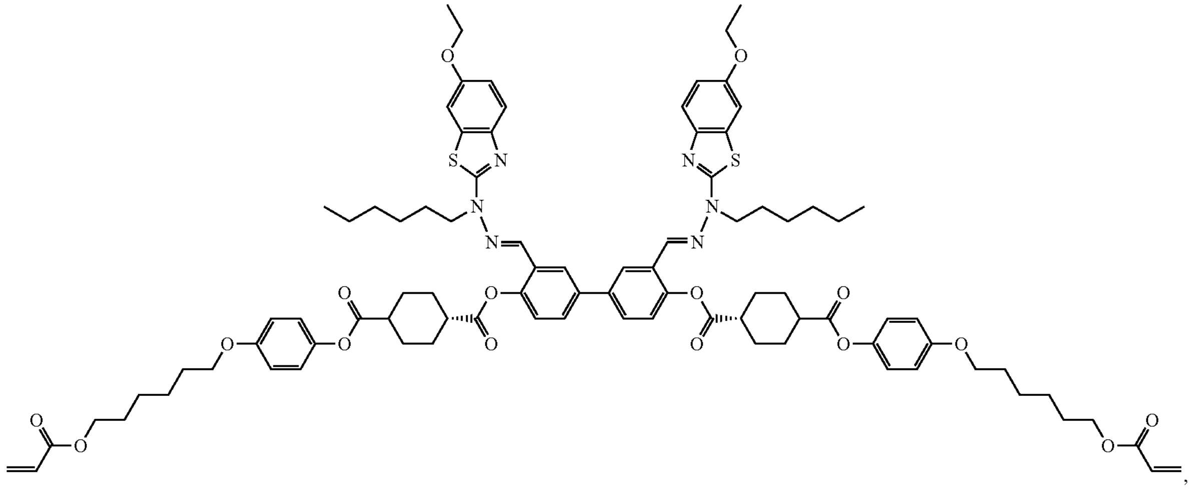
, -continued
(xxii)-1
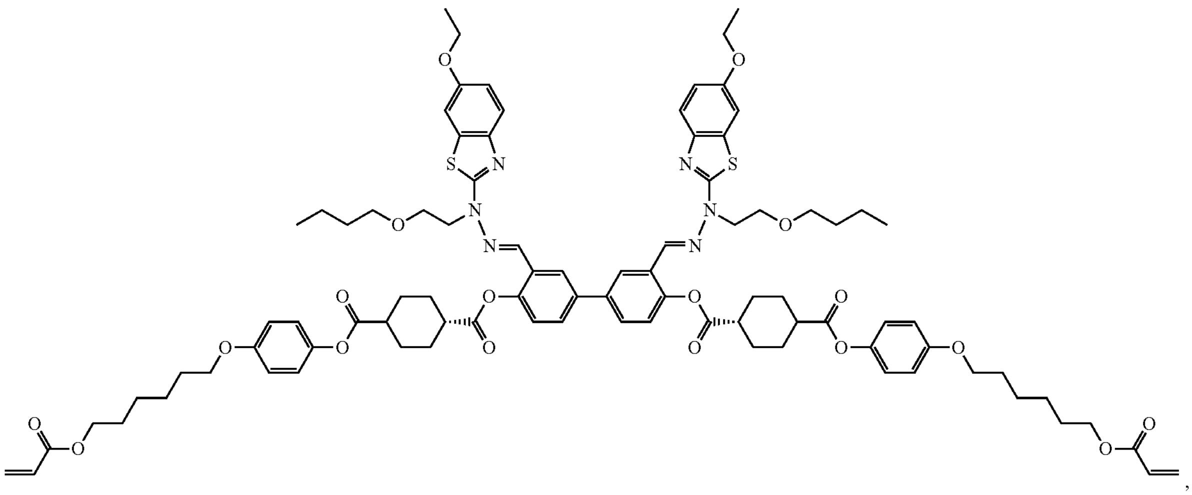
,
(xxv)-1
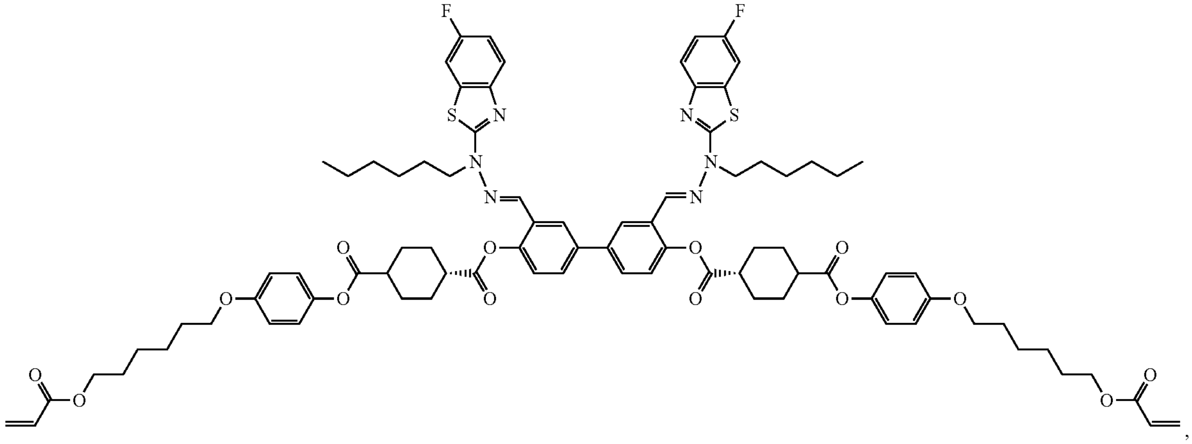
,
(xxvi)-1
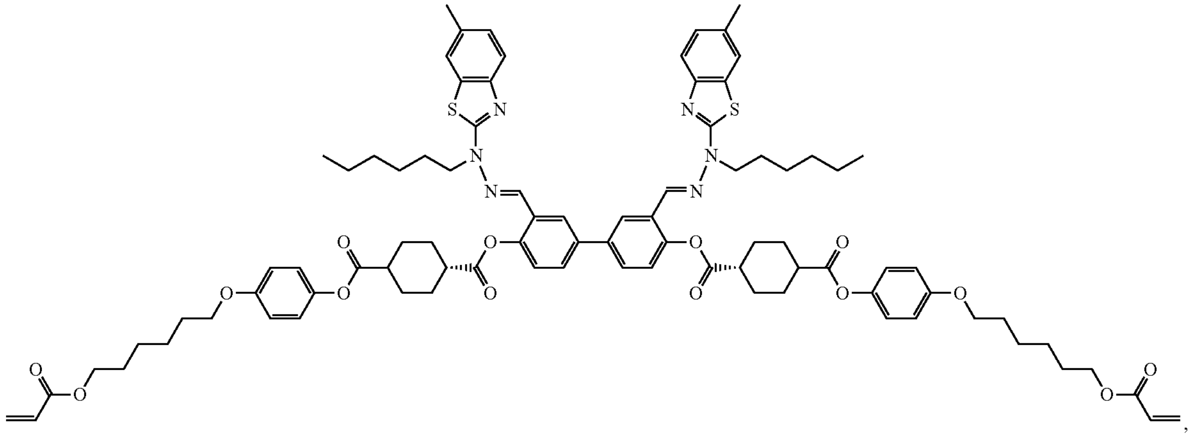
, -continued
(x)-2
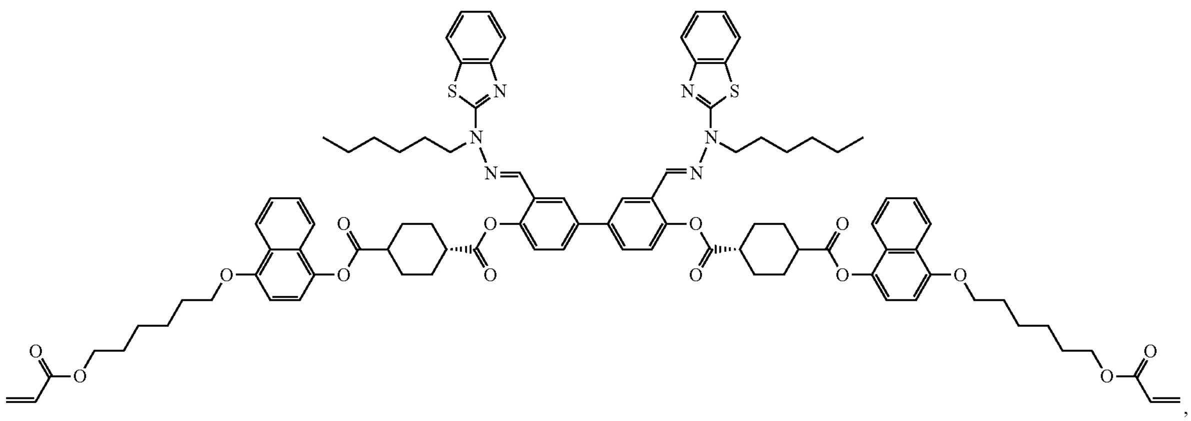
,
(x)-3
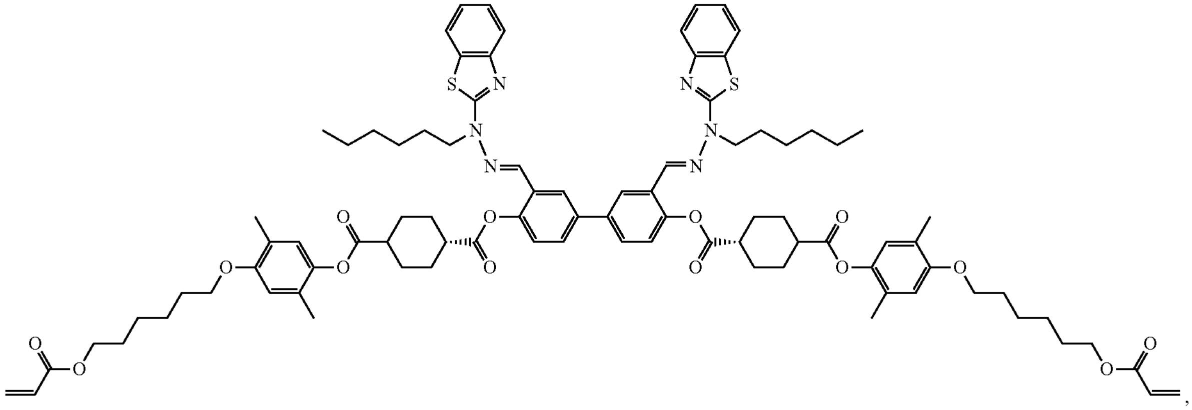
,
(x)-4
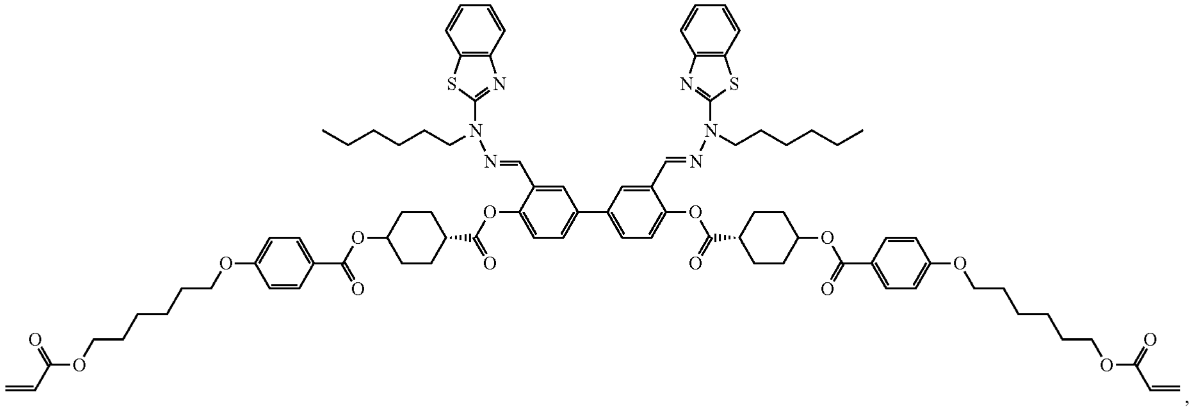
, -continued
(xxviii)-1
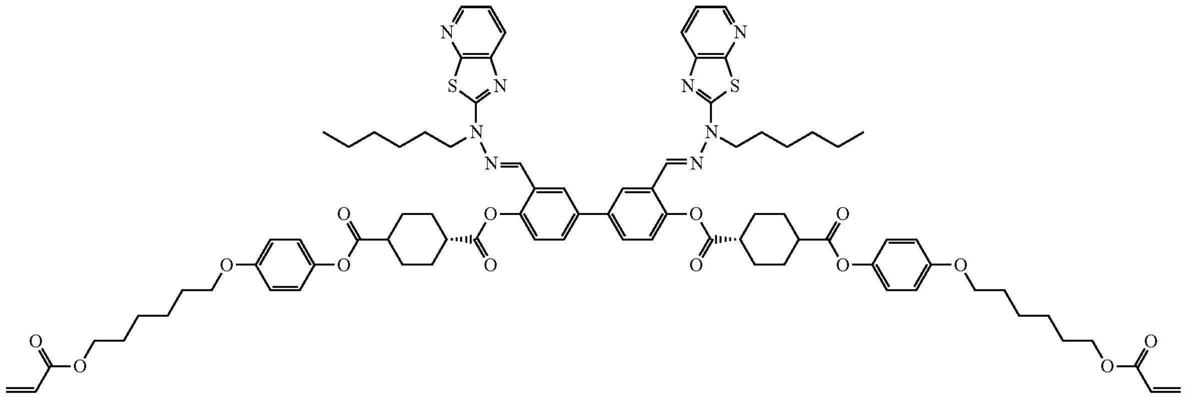
,
(lxx)-1
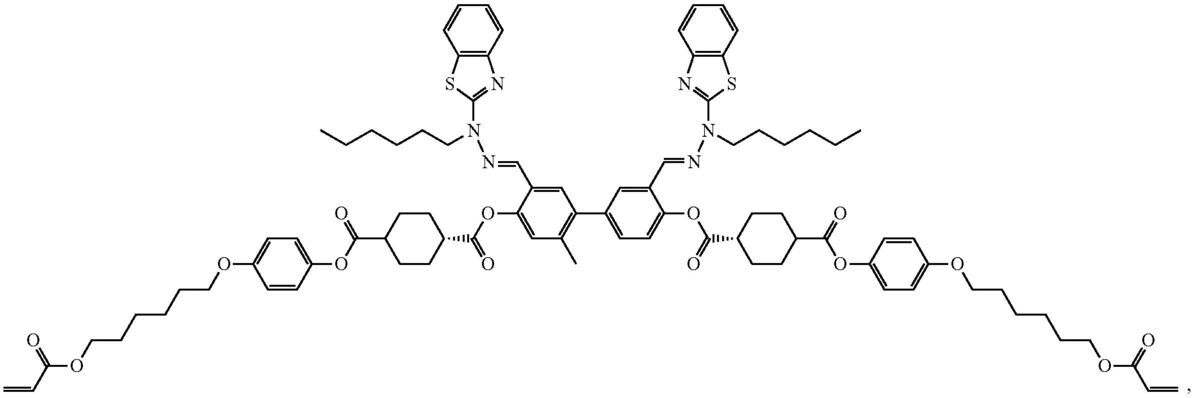
,
(lxxi)-1
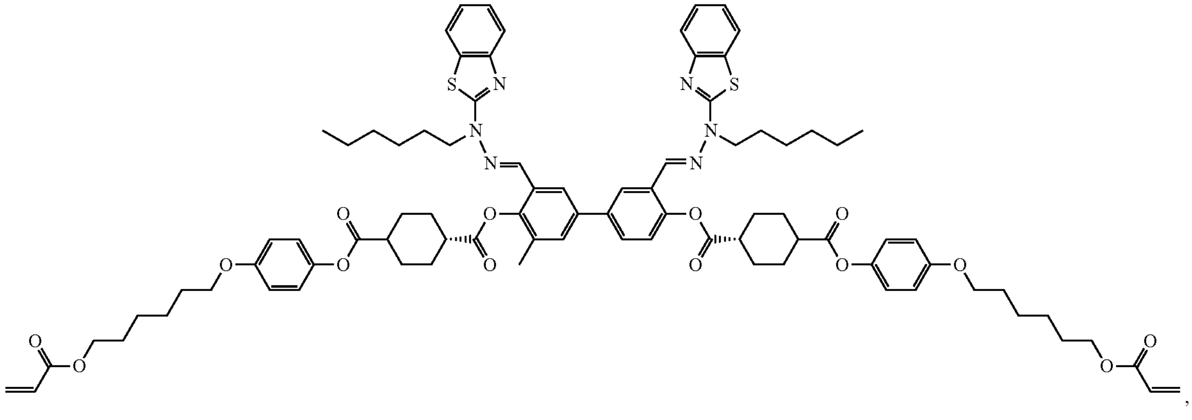
, -continued
(lxvii)-1
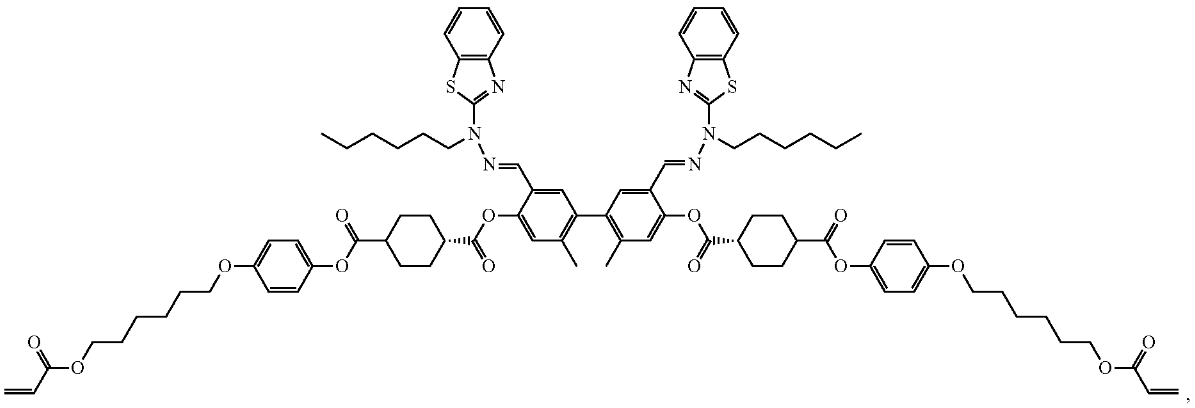
(lxxiii)-1
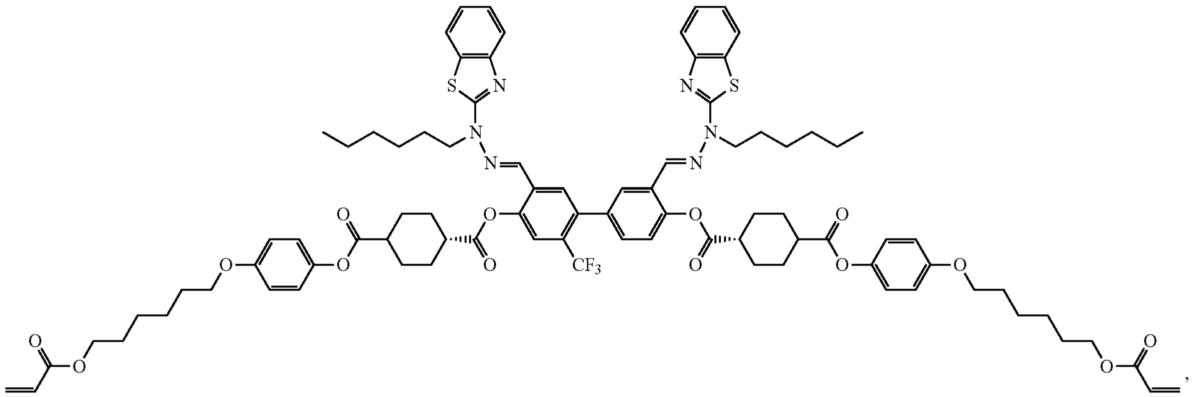
(xliii)-1
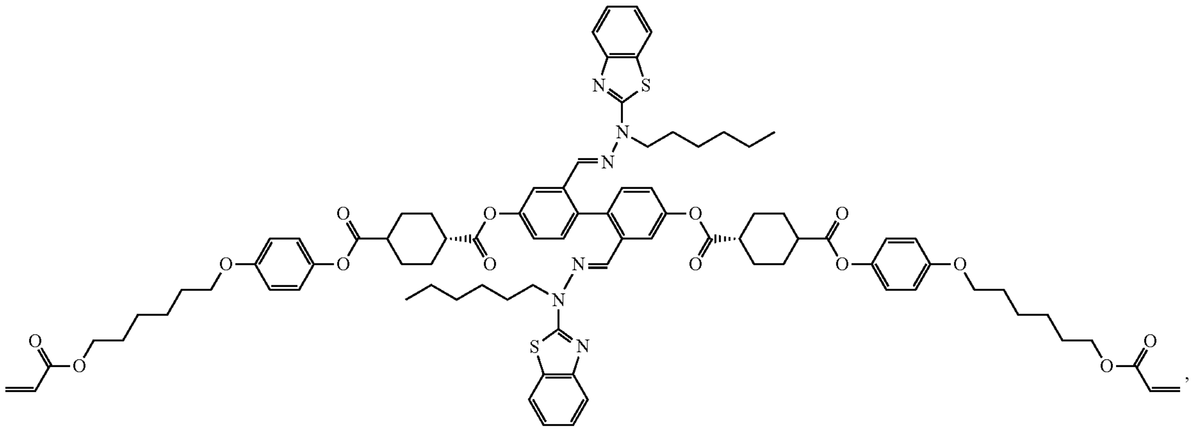

-continued
(xxxii)-1
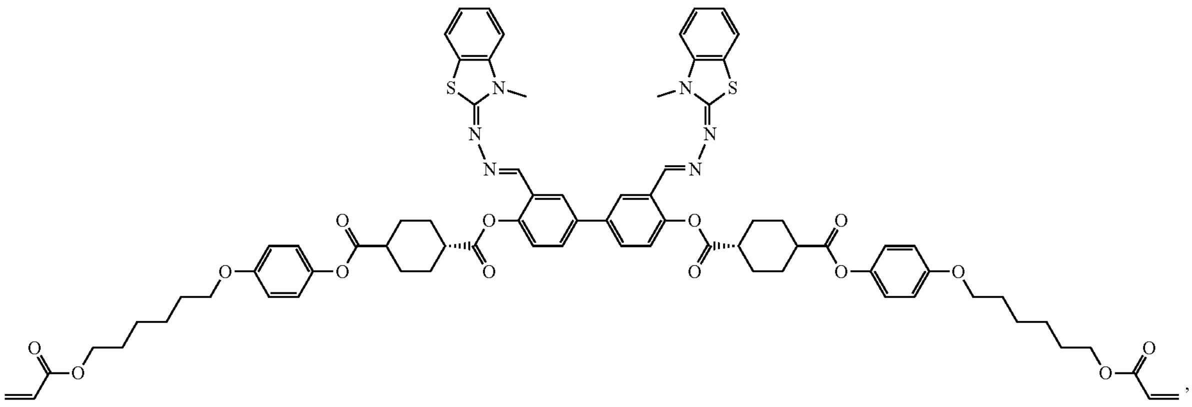
,
(xxx)-1
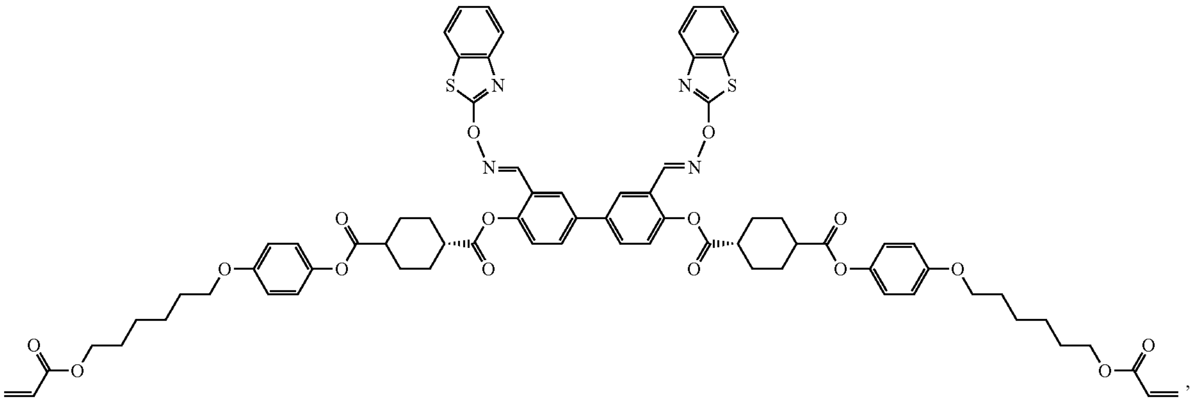
,
(lxxxvii)-1
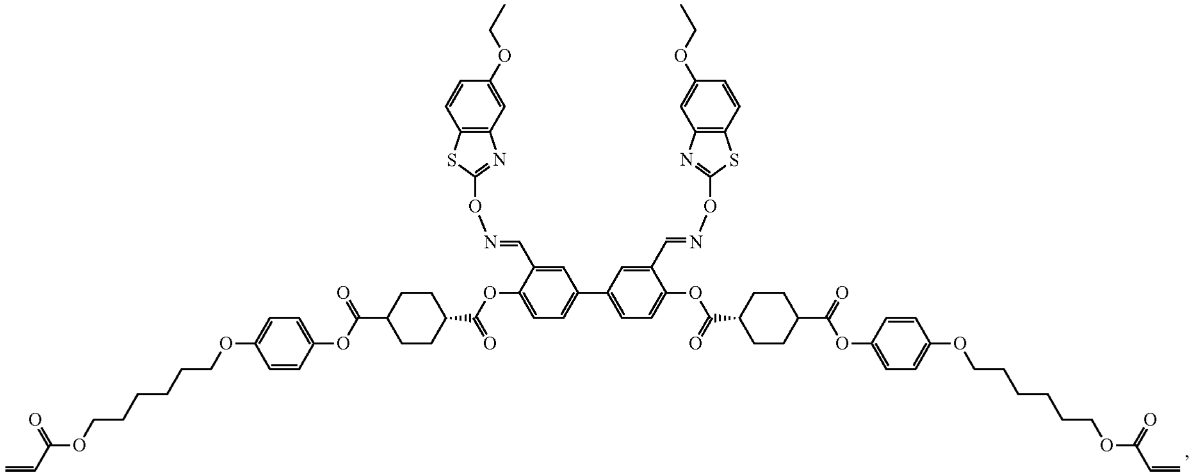
, -continued (xxxi)-1

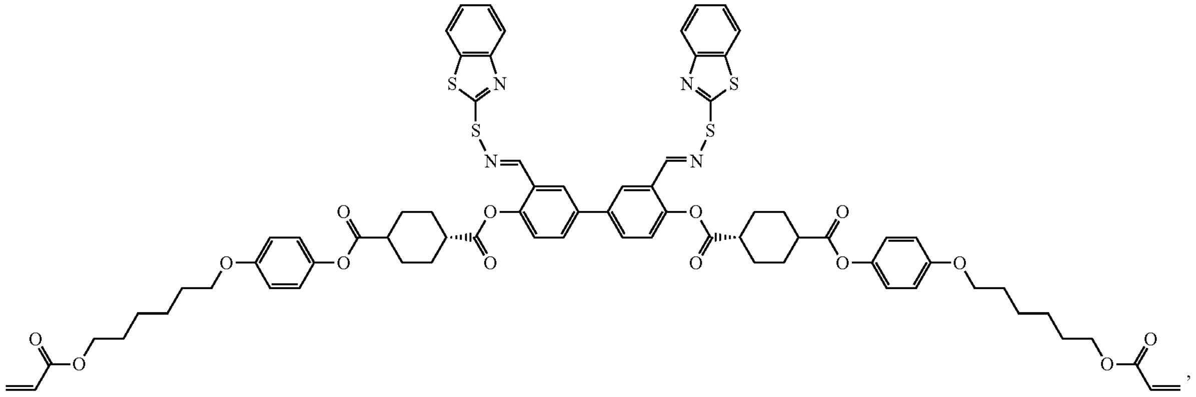

and (xci)-1

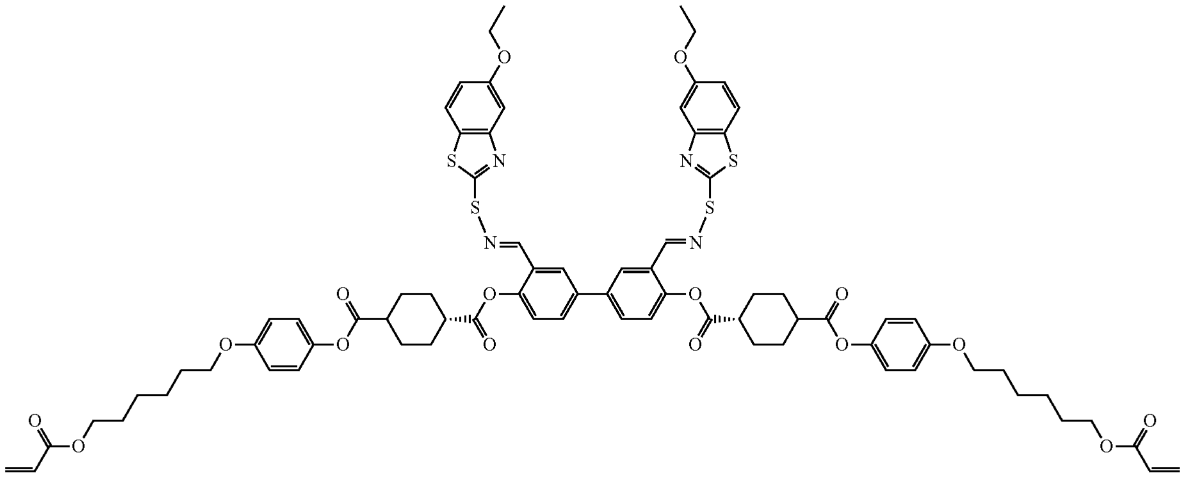

.

4. A polymerizable composition comprising:

the polymerizable liquid crystal compound defined by claim 1.

5. A polymerizable composition comprising:

the polymerizable liquid crystal compound defined by claim 1; and a polymerizable liquid crystal compound which is different from the polymerizable liquid crystal compound defined by claim 1.

6. A polymer obtained by polymerizing the polymerizable liquid crystal compound defined by claim 1.

7. A polymer obtained by polymerizing the polymerizable composition defined by claim 5.

8. A retardation film comprising:

a retardation layer containing a cured product of the polymerizable composition defined by claim 4.

9. A method for producing a retardation film, the method comprising:

forming, into a film, the polymerizable composition defined by claim 4;

aligning at least the polymerizable compound in the polymerizable composition formed into the film; and polymerizing at least the polymerizable compound after the aligning.

10. A transfer laminate configured to transfer a retardation layer, the transfer laminate comprising:

a retardation layer containing a cured product of the polymerizable composition defined by claim 4; and a support supporting the retardation layer in a removable manner.

11. An optical member comprising:

the retardation film defined by claim 8; and a polarizing plate disposed thereon.

12. A method for producing an optical member, the method comprising:

preparing a transfer laminate that comprises a retardation layer and a support supporting the retardation layer in a removable manner, wherein the retardation layer contains a cured product of the polymerizable composition defined by claim 4;

facing a transfer receiving object to the retardation layer of the transfer laminate, and transferring the transfer laminate onto the transfer receiving object; and removing the support from the transfer laminate transferred onto the transfer receiving object, wherein the transfer receiving object comprises a polarizing plate.

13. A display device comprising:

the retardation film defined by claim 8; or an optical member comprising the retardation film defined by claim 8 and a polarizing plate disposed thereon.

* * * * *